(12) United States Patent
De Groot et al.

(10) Patent No.: US 7,705,045 B2
(45) Date of Patent: Apr. 27, 2010

(54) PRODRUGS BUILT AS MULTIPLE SELF-ELIMINATION-RELEASE SPACERS

(75) Inventors: Franciscus Marinus Hendrikus De Groot, Nijmegen (NL); Patrick Henry Beusker, Nijmegen (NL); Johannes Wilhelm Scheeren, Malden (NL)

(73) Assignee: Syntarga, B.V., Nijmegen (NL)

( * ) Notice: Subject to any disclaimer, the term of this patent is extended or adjusted under 35 U.S.C. 154(b) by 490 days.

(21) Appl. No.: 10/534,777

(22) PCT Filed: Nov. 14, 2003

(86) PCT No.: PCT/NL03/00804

§ 371 (c)(1),
(2), (4) Date: Dec. 20, 2005

(87) PCT Pub. No.: WO2004/043493

PCT Pub. Date: May 27, 2004

(65) Prior Publication Data

US 2006/0116422 A1    Jun. 1, 2006

(51) Int. Cl.
*A61K 31/325* (2006.01)
*C07C 271/42* (2006.01)
(52) U.S. Cl. .......................... 514/483; 560/25
(58) Field of Classification Search .............. 514/483; 560/25
See application file for complete search history.

(56) References Cited

U.S. PATENT DOCUMENTS

| 5,965,566 A | 10/1999 | Greenwald et al. |
| 2004/0121940 A1 | 6/2004 | De Groot et al. |
| 2005/0271615 A1 | 12/2005 | Shabat et al. ............. 424/78.3 |

FOREIGN PATENT DOCUMENTS

EP          0 642 799          3/1995

(Continued)

OTHER PUBLICATIONS

Dubowchik G.M. et al, "Cathepsin B-Sensitive dipeptide prodrugs 1 . . . ", Bioorganic & Medicinal Chemistry Letters, Dec. 1, 1998, 3341-3346, vol. 8, No. 23, Oxford GB.
Dubowchik G.M. et al, "Cathepsin B-Sensitive dipeptide prodrugs 2 . . . ", Bioorganic & Medicinal Chemistry Letters, Dec. 1, 1998, 3347-3352, vol. 8, No. 23, Oxford GB.
De Groot F. et al., "Synthesis and Biological Evaluation . . . ", Journal of Medicinal Chemistry, American Chemical Society, 1999, 5277-5283, vol. 42 No. 25, Washington US.

(Continued)

*Primary Examiner*—Joseph R Kosack
(74) *Attorney, Agent, or Firm*—K&L Gates LLP

(57) ABSTRACT

This invention concerns multiple release spacers and spacer systems, which release multiple leaving groups following a single activation. It concerns compounds comprising a specifier linked to two or more of the same or different leaving groups (L in the figure) via a self-eliminating multiple release spacer or spacer system, which compounds upon a single activation step, in particular removal or transformation of the specifier, release at least two leaving groups.

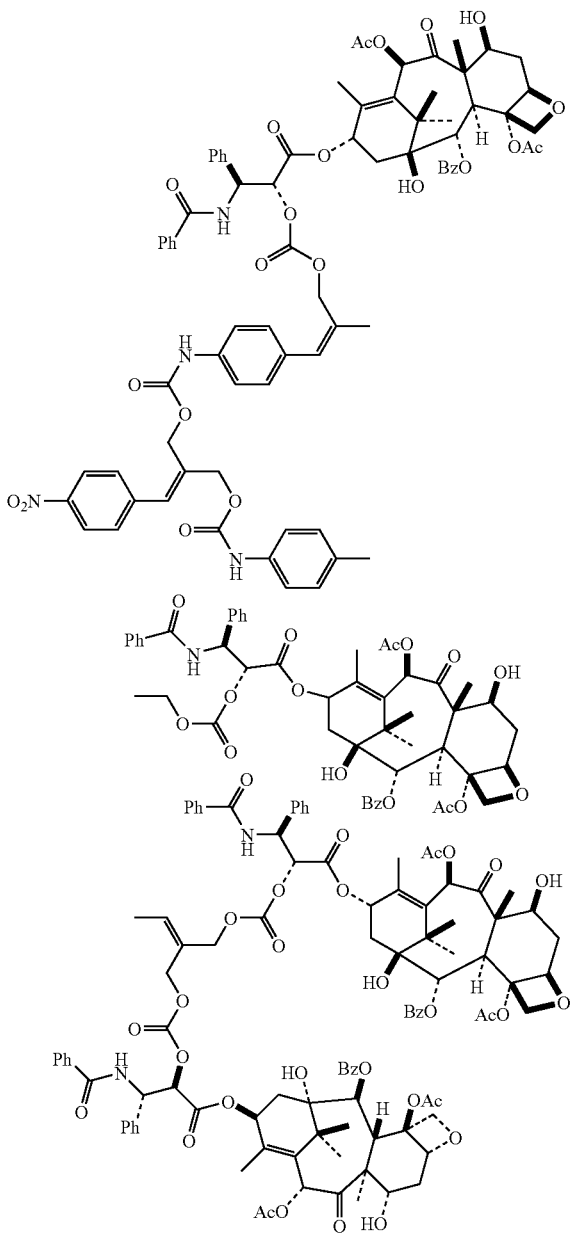

40 Claims, 23 Drawing Sheets

FOREIGN PATENT DOCUMENTS

| EP | 0 647 450 | 4/1995 |
|---|---|---|
| EP | 0 648 503 | 4/1995 |
| EP | 0 665 020 | 8/1995 |
| EP | 0 693 485 | 1/1996 |
| EP | 1 243 276 | 9/2002 |
| WO | 98/06875 | 2/1998 |
| WO | WO 98/13059 | 4/1998 |
| WO | WO 98/19705 | 5/1998 |
| WO | 98/43085 | 10/1998 |
| WO | WO 00/34231 | 6/2000 |
| WO | 00/64864 | 11/2000 |
| WO | WO 02/26220 | 4/2002 |

OTHER PUBLICATIONS

Appendino G. et al., "Synthesis of Paclitaxel . . . ", Tetrahedron, May 21, 1999, 6567-6576, vol. 55 No. 21, Elsevier Science Publishers, Amsterdam NL.

Kar, A. et al., "Synthesis and evaluation of daunorubicin . . . ", Bioorganic & Medicinal Chemistry Letters, Feb. 2000, 261-264, vol. 10, No. 3, Oxford GB.

De Groot F. et al., "Synthesis and Biological Evaluation of 2 . . . ", Journal of Medicinal Chemistry, American Chemical Society, 2000, 3093-3102, vol. 43, Washington US.

De Groot F. et al., "Elongated Multiple Electronic . . . ", Journal of Organic Chemistry, 2001, 8815-8830, vol. 66, Easton US.

De Groot F. et al., "Design, Synthesis, and Initial . . . ", Proceedings of the Annual Meeting of the American Association for Cancer Research, Mar. 2002, 144, vol. 43, NY US.

De Groot F. et al., "In Vivo Efficacy . . . ", Proceedings of the Annual Meeting of the American Association for Cancer Research, Mar. 2002, 415, vol. 43, NY US.

Battah et al., "Synthesis and Biological Studies of 5-Aminolevulinic Acid-Containing Dendrimers for Photodynamic Therapy," Bioconjugate Chem., 12:980-988 (2001).

Carl et al., "Communications to the Editor," Journal of Medicinal Chemistry, 24(5):479-480 (1981).

Choe et al., "Anticancer drug delivery systems: multi-loaded $N^4$-acyl poly(ethylene glycol) prodrugs of ara-C. II. Efficacy in ascites and solid tumors," Journal of Controlled Release, 79:55-70 (2002).

Damen et al., "Novel anthracycline prodrugs," Exp. Opin. Ther. Patents, 11(4):651-666 (2001).

de Groot et al., "Anticancer Prodrugs for Application in Monotherapy: Targeting Hypoxia, Tumor-Associated Enzymes, and Receptors," Current Medicinal Chemistry, 8:1093-1122 (2001).

De Jesús et al., "Polyester Dendritic Systems for Drug Delivery Applications: In Vitro and In Vivo Evaluation," Bioconjugate Chem., 13:453-461 (2002).

Dubowchik et al., "Doxorubicin Immunoconjugates Containing Bivalent, Lysosomally-Cleavable Dipeptide Linkages," Bioorganic & Medicinal Chemistry Letters, 12:1529-1532 (2002).

Dubowchik et al., "Receptor-mediated and enzyme-dependent targeting of cytotoxic anticancer drugs," Pharmacology & Therapeutics, 83:67-123 (1999).

Greenwald et al., "Controlled Release of Proteins from Their Poly(Ethylene Glycol) Conjugates: Drug Delivery Systems Employing 1,6-Elimination," Bioconjugate Chem., 14:395-403 (2003).

Göller et al., "Phosphorus dendrimers as new tools to deliver active substances," Tetrahedron Letters, 42:3587-3590 (2001).

Hay et al., "Structure-Activity Relationships for 4-Nitrobenzyl Carbamates of 5-Aminobenz[e]indoline Minor Groove Alkylating Agents as Prodrugs for GDEPT in Conjunction with E. coli Nitroreductase," J. Med. Chem. 46:2456-2466 (2003).

Huang et al., "Drug-targeting strategies in cancer therapy," Current Opinion in Genetics & Development, 11:104-110 (2001).

Ihre et al., Polyester Dendritic Systems for Drug Delivery Applications: Design, Synthesis, and Characterization, Bioconjugate Chem., 13:443-452 (2002).

King et al., "Monoclonal Antibody Conjugates of Doxorubicin Prepared with Branched Linkers: A Novel Method for Increasing the Potency of Doxorubicin Immunoconjugates," Bioconjugate Chem., 10:279-288 (1999).

Kovář et al., "Star Structure of Antibody-Targeted HPMA Copolymer-Bound Doxorubicin: A Novel Type of Polymeric Conjugate for Targeted Drug Delivery with Potent Antitumor Effect," Bioconjugate Chem., 13:206-215 (2002).

Krause et al., "Dendrimers in Diagnostics," Topics in Current Chemistry, 210:261-308 (2000).

Marriott et al., "Synthesis and Applications of Heterobifunctional Photocleavable Cross-Linking Reagents," Methods in Enzymology, 291:155-175.

Ottl et al., "Preparation and Photoactivation of Caged Fluorophores and Caged Proteins Using a New Class of Heterobifunctional, Photocleavable Cross-Linking Reagents," Bioconjugate Chemistry, 9(2):143-151 (1998).

Sideratou et al., "Quaternized Poly(propylene imine) Dendrimers as Novel pH-Sensitive Controlled-Release Systems," Langmuir, 16:1766-1769 (2000).

Smet et al., "Photolabile Dendrimers Using o-Nitrobenzyl Ether Linkages," Organic Letters, 2(4):511-513 (2000).

Sun et al., Syntheses of Dendritic Linkers Containing Chlorambucil Residues for the Preparation of Antibody-Multidrug Immunoconjugates, Bioorganic & Medicinal Chemistry Letters, 12:2213-2215 (2002).

Toki et al., "Protease-Mediated Fragmentation of p-Amidobenzyl Ethers: A New Strategy for the Activation of Anticancer Prodrugs," J. Org. Chem., 67:1866-1872 (2002).

Wang et al., "Synthesis of Starlike N-(2-Hydroxypropyl)methacrylamide Copolymers: Potential Drug Carriers," Biomacromolecules, 1:313-319 (2000).

SciFinder structural search results dated Jun. 18, 2009 (bibliographic information and abstract).

SciFinder structural search results dated Jun. 18, 2009 (structure and registry number).

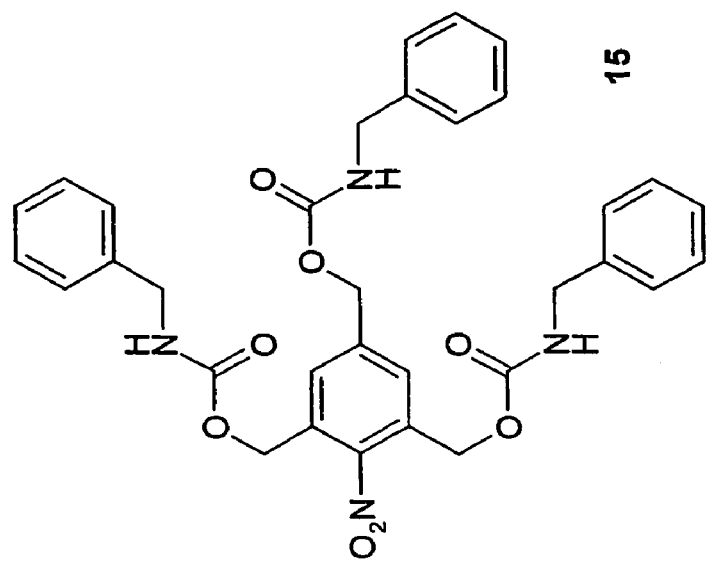
Fig. 10
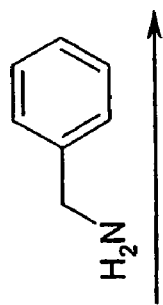
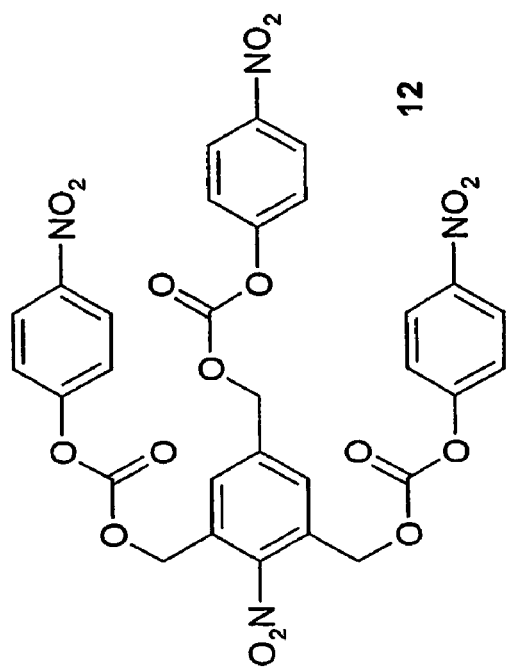

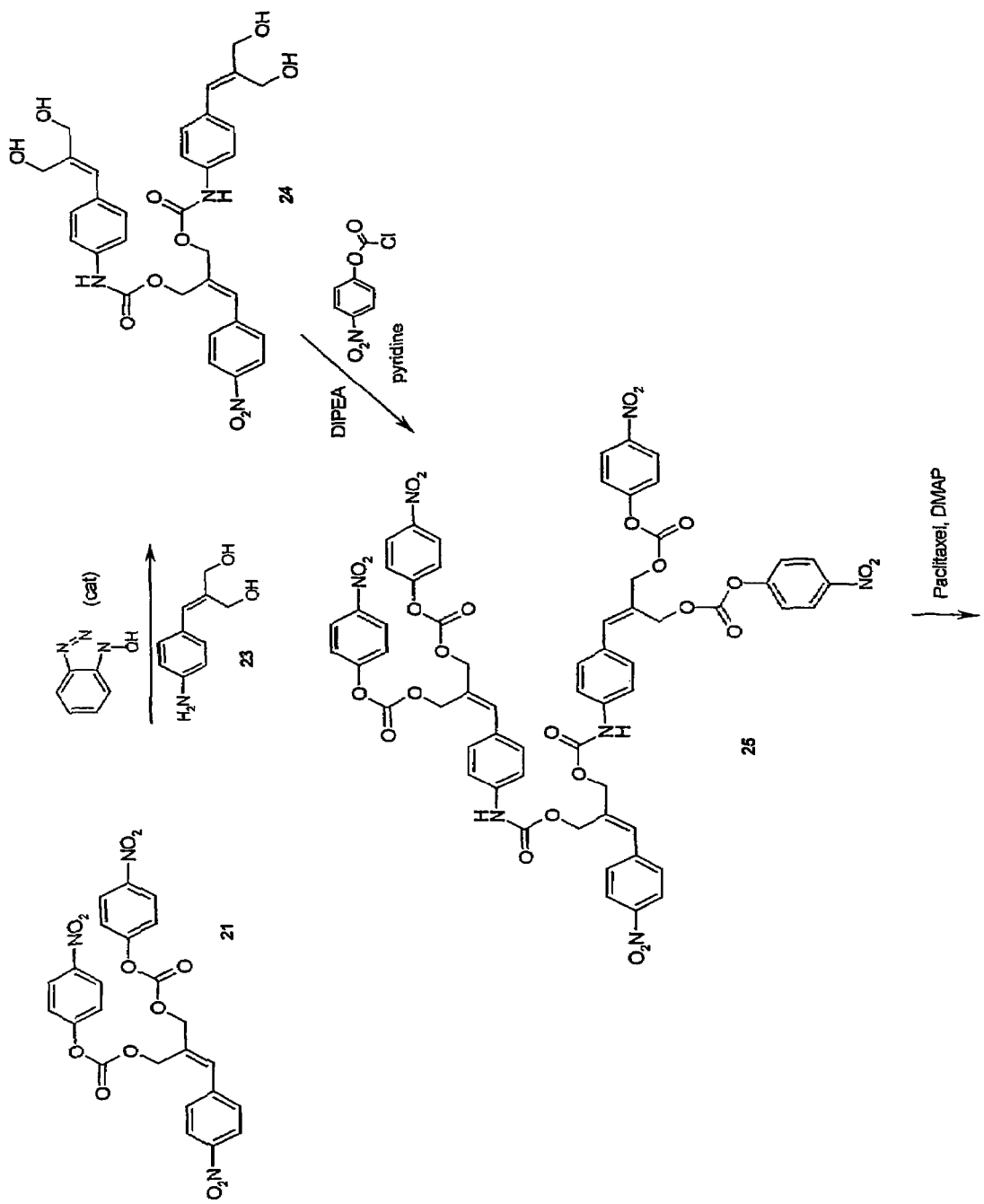
Fig13.1

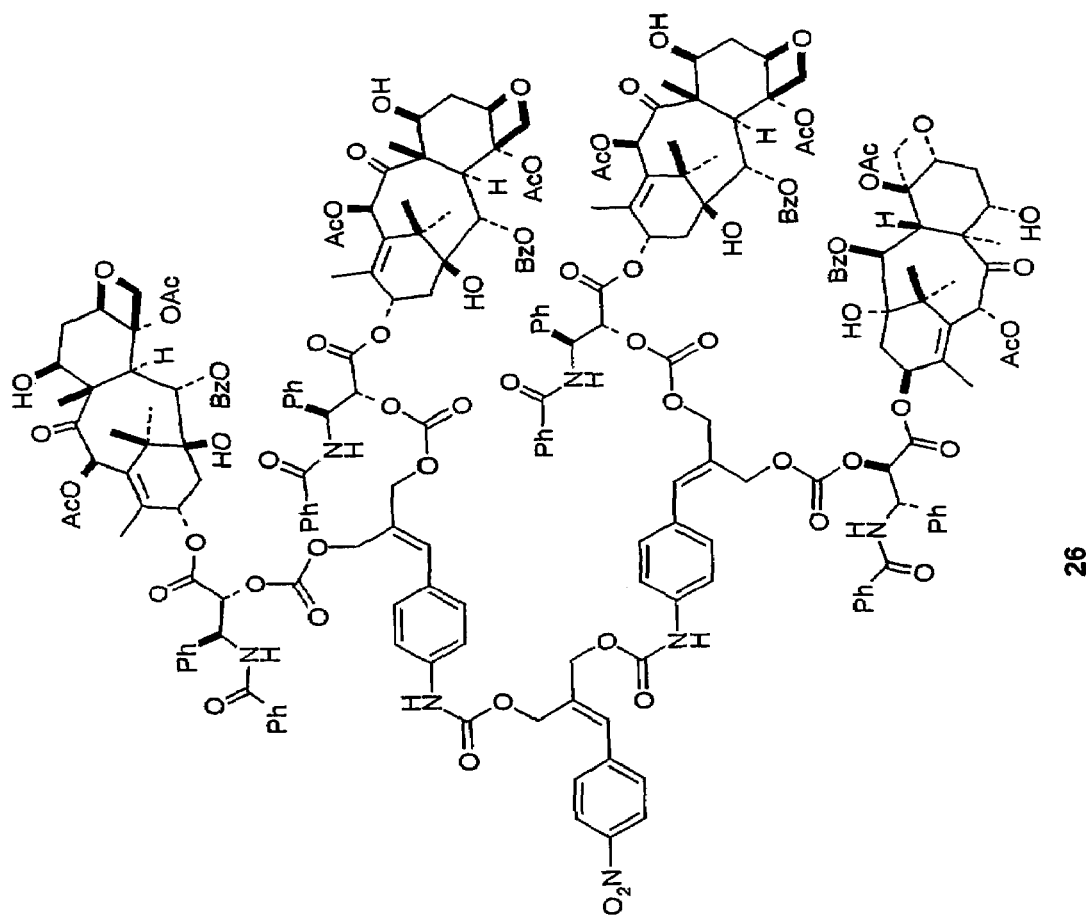
Fig13.2

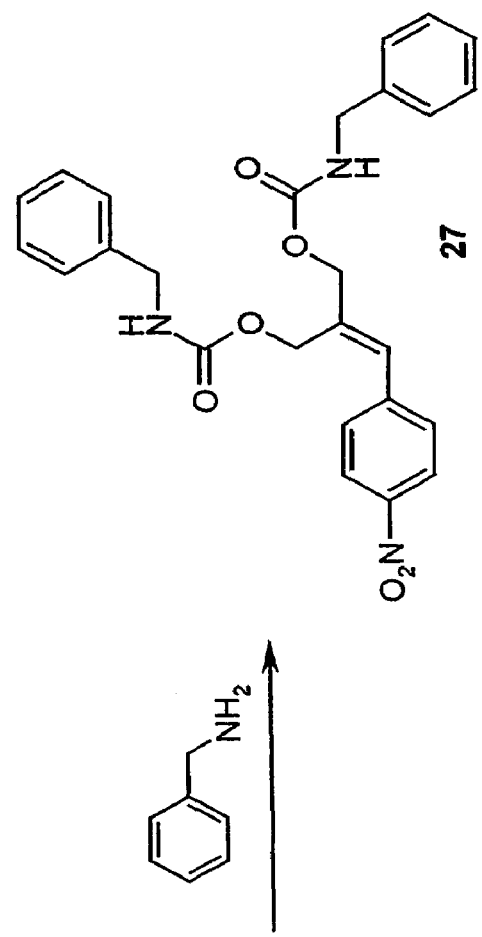
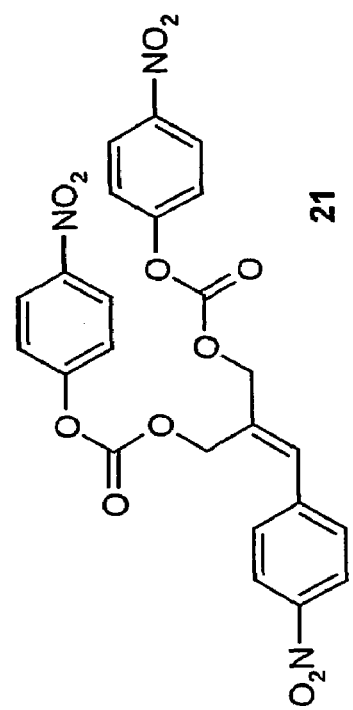
Fig. 14

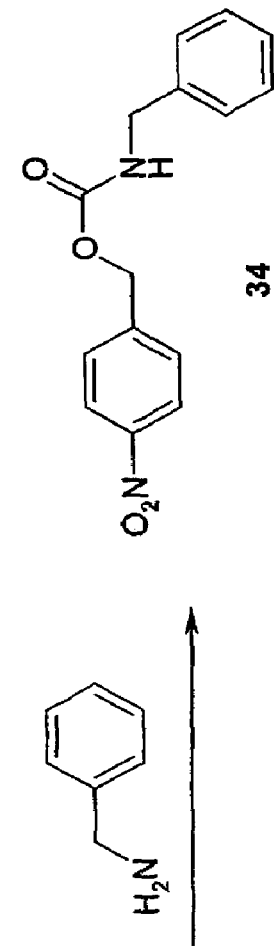
*Fig. 17*
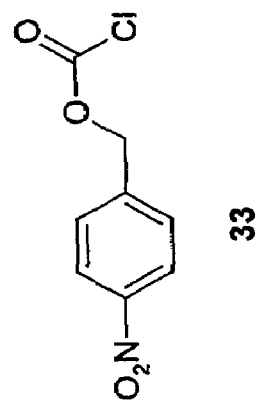
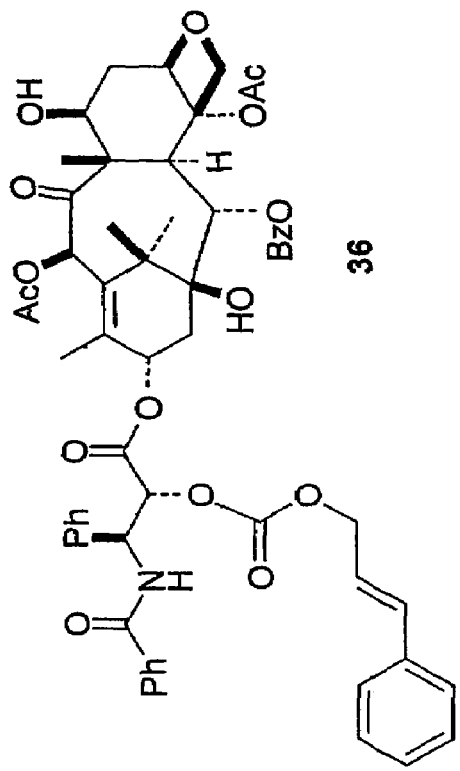
*Fig 18*
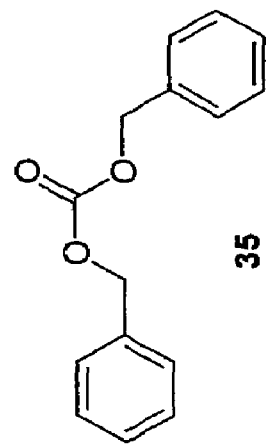

30 R = OMe
31 R = Cl

PRODRUGS BUILT AS MULTIPLE SELF-ELIMINATION-RELEASE SPACERS

CROSS-REFERENCE TO RELATED APPLICATIONS

This application is the national phase of International (PCT) Application No. PCT/NL03/00804, filed on Nov. 14, 2003, which claims foreign priority benefits under 35 U.S.C. §365(b) of International (PCT) Application No. PCT/NL02/00732, filed on Nov. 14, 2002.

FIELD OF THE INVENTION

This invention is directed to compounds or prodrugs comprising a multiple release spacer or spacer system. A multiple release spacer is defined as a self-elimination spacer that releases multiple leaving groups upon a single activation event. One or more (generations) of these multiple release spacers can be used for example to obtain conjugates or prodrugs which are activated by a single activation step at the preferred site of action in order to selectively deliver multiple therapeutic or diagnostic parent moieties to target cells or to a target site. In this invention preferably target cells are tumor cells.

BACKGROUND OF THE INVENTION

Lack of selectivity of chemotherapeutic agents is a major problem in cancer treatment. Because highly toxic compounds are used in cancer chemotherapy, it is typically associated with severe side effects. Drug concentrations that would completely eradicate the tumor cannot be reached because of dose-limiting side effects such as gastrointestinal tract and bone marrow toxicity. In addition, tumors can develop resistance against anticancer agents after prolonged treatment. In modern drug development, targeting of cytotoxic drugs to the tumor site can be considered one of the primary goals.

A promising approach to obtain selectivity for tumor cells or tumor tissue is to exploit the existence of tumor-associated enzymes. A relatively high level of tumor-specific enzyme can convert a pharmacologically inactive prodrug to the corresponding active parent drug in the vicinity of or inside the tumor. Via this concept a high concentration of toxic anticancer agent can be generated at the tumor site. All tumor cells may be killed if the dose is sufficiently high, which may decrease development of drug resistant tumor cells.

There are several enzymes that are present at elevated levels in certain tumor tissues. One example is the enzyme β-glucuronidase, which is liberated from certain necrotic tumor areas. Furthermore, several proteolytic enzymes have been shown to be associated with tumor invasion and metastasis. Several proteases, like for example the cathepsins and proteases from the urokinase-type plasminogen activator (u-PA) system are all involved in tumor metastasis. The serine protease plasmin plays a key role in tumor invasion and metastasis. The proteolytically active form of plasmin is formed from its inactive pro-enzyme form plasminogen by u-PA. The tumor-associated presence of plasmin can be exploited for targeting of plasmin-cleavable conjugates or prodrugs.

An enzyme can also be transported to the vicinity of or inside target cells or target tissue via antibody-directed enzyme prodrug therapy (ADEPT)[1], polymer-directed enzyme prodrug therapy (PDEPT) or macromolecular-directed enzyme prodrug therapy (MDEPT)[2], virus-directed enzyme prodrug therapy (VDEPT)[3] or gene-directed enzyme prodrug therapy (GDEPT)[4].

The technology of this invention relates to novel spacers (linkers) or spacer systems (linker systems) that can be inserted between a specifier (unit that can be cleaved or transformed) and leaving groups (for example parent drugs or detectable molecules). Furthermore, the invention relates to prodrugs and (bio)conjugates comprising a specifier, said novel spacers or spacer systems and multiple leaving groups, and to bifunctional linker systems comprising a (protected) specifier containing a reactive moiety that enables coupling to a targeting moiety on one side of the linker (system) and reactive moieties that enable coupling to multiple leaving groups (for example parent drugs or detectable molecules) on the other side of the linker (system). A great number of anticancer conjugates and prodiligs that have been developed in the past contain a self-eliminating connector or linker, also called self-elimination spacer. This spacer is incorporated between the specifier and the drug in order to facilitate enzymatic cleavage and so enhance the kinetics of drug release (as shown in FIG. 1). The specifier (which for example can be an oligopeptide substrate for a protease or for example a β-glucuronide substrate for β-glucuronidase) must be site-specifically removed or transformed, followed by a spontaneous spacer elimination to release the cytotoxic parent drug. Up to now self-elimination spacers have been implemented that release one drug molecule upon prodrug activation and subsequent spacer elimination. When the prodrugs and (bio-)conjugates containing multiple drug moieties are considered that have been reported thus far, an independent cleavage was necessary for each drug molecule to be released.

WO 98/13059 is a relevant disclosure describing a prodrug comprising an amino-terminal capped peptide covalently linked to a therapeutic drug through a self-eliminating spacer. In particular this document describes the use of p-aminobenzyl-oxycarbonyl (PABC) as self-elimninating spacer. The PABC electronic cascade spacer was already known for instance Carl et al., J. Med. Chem., 1981, vol. 24, 479-480. Specifically the anticancer drugs doxorubicin, mitomycin C, paclitaxel and camptothecin coupled to PABC are described. A second self-eliminating spacer that is described is p-aminobis(hydroxymethyl)styrene (BHMS), having the structure p-NH-Ph-CH=C(CH$_2$O—)$_2$, including the carbonyl groups the structure is p-NH-Ph-CH=C(CH$_2$OCO—)$_2$. It is noted that this spacer is described in this disclosure as a bis-carbamate, which teaches that two drug molecules are linked to this spacer via an amine functionality of the drug. The only drug moiety that is disclosed that is actually coupled to the BHMS spacer is doxorubicin. Doxorubicin is coupled via its sugar amino group resulting in a carbamate linkage between spacer and drug. Further it is stated that the spacer can bind two drug moieties. However, the document is silent on how many drug molecules are actually released.

Other systems that are loaded with multiple covalently bound bioactive molecules as end groups have been reported. Examples are systems that release doxorubicin after acidolysis of each hydrazone linker[5], starlike HPMA copolymers containing doxorubicin[6], or multi-loaded poly(ethylene glycol) prodrugs[7]. A doxorubicin-containing starlike HPMA copolymer with an antibody as the core has also been reported[8]. A number of recent publications have described the use of branched linkers in combination with antibody-containing prodrugs or bioconjugates with the aim of increasing the number of drugs bound per antibody[9]. However, to our knowledge, in each multi-loaded prodrug system reported so far, each single end group needs to be independently cleaved in order to release all end groups.

Thus there is a need for improved prodrugs or (bio-)conjugates in terms of (efficiency of) release of sufficient amounts of active drug in relation to the activation that is required at a desired site of action. In many cases, in prodrugs or (bio)conjugates, it is desirable to increase drug loading per targeting unit, in order to improve the efficacy of targeted compounds.

SUMMARY OF THE INVENTION

The present invention fulfills the above mentioned need with a compound comprising a specifier (V) linked to two or more of the same or different leaving groups (Z) via a self-eliminating multiple release spacer or spacer system, which compound upon a single activation step releases at least two leaving groups, said activation step being the removal or transformation of the specifier. Self-elimination spacers can also be coupled to one another, so that more than one spacer is incorporated between specifier and leaving group. Hereinbelow, also the term (self-elimination) spacer system is used, which comprises two or more spacers, being either self-eliminating multiple release or single release spacers, connected together. The present invention also describes bifunctional linker systems comprising a (protected) specifier containing a reactive moiety that enables coupling to a targeting moiety (which then together with the initial specifier becomes a functionalised specifier V) on one side of the spacer (system). Further, the bifunctional linker systems comprise reactive moieties that enable coupling to multiple leaving groups (for example parent drugs or detectable molecules).

BRIEF DESCRIPTION OF THE FIGURES

FIG. 10 shows the preparation of a model compound containing a triple release spacer and 3 benzylamine leaving groups.

FIG. 13 shows the preparation of a prodrug containing two generations of double release spacers and 4 paclitaxel moieties.

FIG. 14 shows the preparation of a model compound containing a double release spacer and 2 benzylamine leaving groups.

FIG. 17 shows the preparation of a model compound containing a single release spacer coupled to benzylamine.

FIG. 18 shows the reference compounds dibenzyl carbonate and 2'-O-cinnamyl oxycarbonylpaclitaxel.

DETAILED DESCRIPTION OF THE INVENTION

Figure 1:
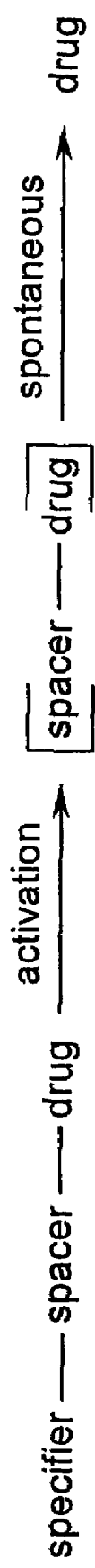
FIG. 1 shows schematically the conversion of a spacer containing prodrug into the parent drug.

In this invention a new technology is disclosed that can be used to induce release of more than one leaving group following a single activation step. It can be applied for example to prepare prodrugs or conjugates, which can for example be used for targeting drugs to disease-related or organ-specific tissue or cells, for example tumor-specific conjugates or prodrugs that are improved with respect to conjugates or prodrugs known thus far in that they release more than one parent moiety after a single activation step. This aims at a therapeutic advantage. The present invention is deemed to be applicable to all drugs that need to be delivered at a specific target site where a specific disease-related or specifically targeted biomolecule can convert the prodrug or conjugate into drugs or induce conversion of the prodrug or conjugate into drugs. This invention can furthermore find application in (non-specific) controlled release of compounds, with the aim of enhancing characteristics of parent moiety release.

In another aspect, this invention can find application in a diagnostic assay process. An enzyme can be detected by a compound of this invention containing a multiple release spacer or spacer system that is selectively activated by said enzyme to release multiple detectable molecules (leaving groups), thus increasing the sensitivity of the assay.

In this invention, self-elimination multiple release spacers are disclosed that enable release of multiple leaving group molecules upon a single activation event. These self-elimination multiple release spacers are applicable in conjugates or prodrugs, for example anticancer prodrugs, and significantly enhance the amount of drug molecules liberated per (enzymatic) activation, resulting in a potential therapeutic advantage.

In the generic structures throughout this description and in the claims letters are used to define structural elements. Some of these letters can be mistaken to represent an atom, such as C, N, O, P, B, F, S, V, W, I, Y. To avoid confusion whenever these letters do not represent an atom they are given in bold typeface.

In the structures throughout this description and in the claims molecular structures or parts thereof are drawn. As usual in such drawings bonds between atoms are represented by lines, in some cases, to indicate stereochemistry, by bold or broken or wedged lines. Usually a line ending in space (a "loose" end), i.e. at one end not having another line or specific atom connected to it represents a $CH_3$ group. This is correct for the drawings representing the preferred compounds according to the invention hereinbelow. However for those structures representing a structural element of the compounds according to the invention, in particular A, C, D, E, F, G, H, I, J. K, L, M, N, O, T, U and Y, a line ending in space indicates the position of attachment of another structural element of the compound or conjugate. This includes attachment to V, S or Z. Also for the drawings representing the preferred structural elements $(W—)_w(X—)_xC_c$, $(W—)_w(X—)_xC(D_d)_c$, $(W—)_w(X—)_xC(D(E_e)_d)_c$ and $(W—)_w(X—)_xC(D(E(F_f)_e)_d)_c$ a line ending in space indicates the position of attachment of another structural element of the compound or conjugate, including attachment to V, S or Z. An alternative drawing of a line representing a bond to another structural element would be a drawing of a line with a wavy line perpendicular at the "loose" end of the line.

Furthermore, the structures or parts thereof have been drawn, under the assumption that the structures are read from left to right, meaning that the specifier V is always located on the left side and the leaving groups Z or the reactive moieties S are always located on the right side of such structures.

According to the invention, two 'branched self-elimination spacers', herein also called 'multiple release spacers', have been developed that are able to release multiple moieties. Spacers that are able to release only a single moiety are called 'unbranched spacers' or 'single release spacers'.

Spacers, either branched or unbranched, which self-eliminate through a 1,(4+2n)-elimination (n=0,1,2,3,4,5,6,7,8,9 or 10) (for example 1,6-elimination, 1,8-elimination, or 1,10-elimination) are further called 'electronic cascade' spacers.

Figure 2:
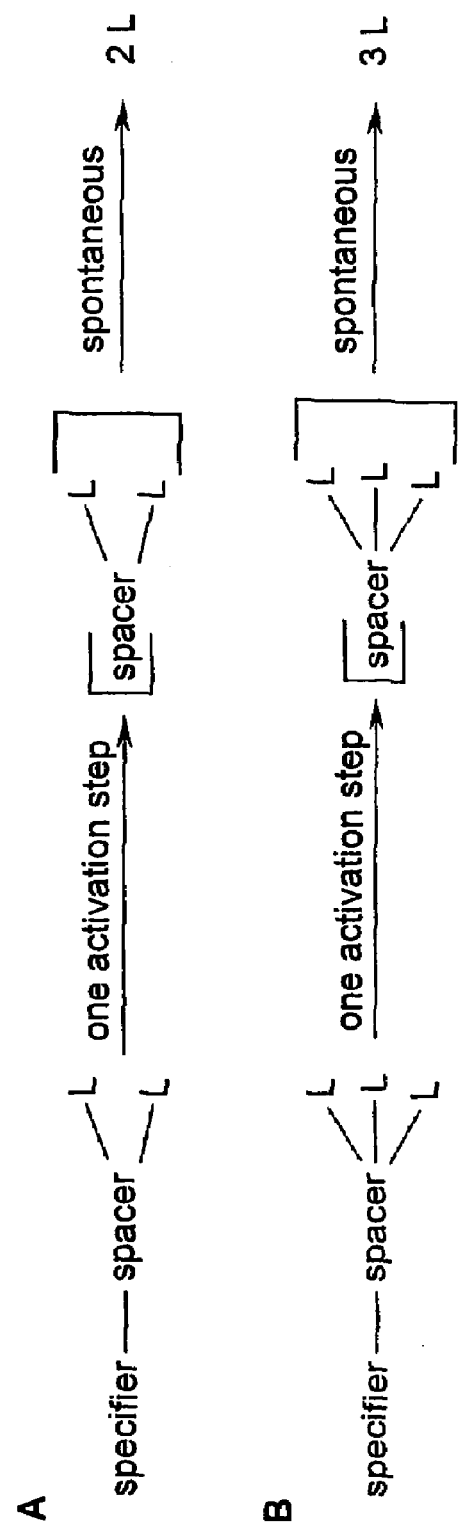
FIG. 2 shows schematically the liberation of multiple leaving group molecules from multiple release spacer containing compounds.

When a spacer able to release 2 leaving groups, hereinbelow called "double release spacer", is used between specifier and leaving groups, two leaving group molecules are released per (enzymatic) activation (FIG. 2a). When a spacer able to release 3 leaving groups, hereinbelow called "triple release spacer", is used, three leaving group molecules will be released per activated compound or prodrug (FIG. 2b).

When a spacer is connected to one or more other spacers via a direct bond, this combination of spacers is referred to as 'spacer system'. When at least one of these spacers is a multiple release spacer, it is called a 'multiple release spacer system'.

An aniline-based spacer is a multiple release or single release spacer that comprises an aromatic amino group on the lefthand side.

A phenol- or thiophenol-based spacer is a multiple release or single release spacer that comprises an aromatic hydroxy or thio group, respectively on the lefthand side. Lefthand side refers to the position in the molecule as shown in e.g. FIGS. 5, 6, 7 and 8.

Surprisingly it was found that it is required for more than one leaving group molecule to be released that the leaving groups are not aliphatic amine groups when only an aniline-based multiple release spacer is employed. In other words the leaving groups (Z) should not be coupled to the self-eliminating multiple release spacer via their aliphatic amine groups if the spacer is an aniline-based multiple release spacer. In the examples it is shown that if the leaving group Z is propylamine, p-methoxybenzylamine, benzylamine, or p-chlorobenzylamine, coupled via its primary amine group, maximally one of these leaving groups is actually released (see examples 22, 23, 26, 27, and 28/FIGS. 20, 21, 24, and 25).

When the spacer is a phenol-based or tiuophenol-based multiple release spacer or when the multiple release spacer is directly coupled to single release phenol- or thiophenol-based spacers or spacer systems, however, the leaving groups can also be coupled via their aliphatic amino group as all leaving groups are liberated upon activation.

Preferably the leaving groups Z are linked to the self-eliminating multiple release spacer via a group that possesses sufficient electron-withdrawing capacity, such as for example O, S, aromatic N, or aliphatic N. It is important to note that in the context of this invention with aromatic N is meant a nitrogen atom covalently bound to an aromatic group such as for instance a (substituted) phenyl ring or other (hetero)aromatic group, but also aromatic N can mean a nitrogen in an aromatic ring such as for instance in a pyrrole ring or in an imidazole ring. As disclosed in this invention, the leaving groups must possess better leaving group capabilities than aliphatic anines when the multiple release spacer is an aniline-based spacer. Propylamine, p-methoxybenzylamine, benzylamine, and even p-chlorobenzylamine did not possess sufficient electron-withdrawing capacity to induce complete release of all end groups when the spacer is an aniline-based spacer. In contrast, benzyl alcohol, phenethyl alcohol, paclitaxel, and certain para-substituted aniline derivatives all showed to be completely released from double and triple release spacers disclosed in this invention. For example in case of the herein disclosed double release spacers, when the para-substituted aniline derivative was $NH—C_6H_4—CH_2—O—CO—NH—CH_2—R$, multiple release did not take place. In contrast, when the para-substituted aniline derivative was $NH—C_6H_4—CH=C(CH_2—O—CO—2'—O\text{-paclitaxel})_2$, multiple release did tale place. When the multiple release spacer is a phenol- or thiophenol-based multiple release spacer or when the multiple release spacer is coupled to single release phenol- or thiophenol-based spacers, aliphatic amines are also suitable leaving groups and release of all aliphatic amine leaving groups does occur. This can be reasoned based on the above as aliphatic alcohols prove to be suitable leaving groups (e.g., from $H_2N—C_6H_4—CH=C(CH_2—O—CO—2'—O\text{-paclitaxel})_2$ two molecules of paclitaxel are released) and therefore release of phenol-based spacers, to which an aliphatic amine leaving group is connected, from a multiple release spacer (e.g., $H_2N—C_6H_4—CH=C(CH_2—O—C(O)O—C_6H_4—CH_2OC(O)NR^1R^2)_2$) should occur by virtue of their increased leaving capability with respect to aliphatic alcohols. As elimination of aliphatic amines from hydroxybenzyl-based spacer-aliphatic amine conjugates is known[10], release of aliphatic amines from spacer systems in which the aliphatic amine is directly connected to a phenol-based spacer takes place as well.

The above shows that subtle changes can determine whether multiple release occurs or not. With all aliphatic amines, and even with certain para-substituted aniline derivatives tested, release of more than one leaving group did not take place when the spacer is an aniline-based spacer, but occurs when the spacer is a phenol- or thiophenol-based spacer, whereas with certain other para-substituted aniline derivatives, and with all hydroxyl leaving groups tested, complete elimination of all end groups did occur independent of the type of spacer used.

For at least two molecules to leave the compound according to the invention the leaving group should be coupled via its oxygen, such as for example its primary, secondary or tertiary alcohol, its phenol, or its phosphate, its sulphur, or its aromatic amine. In order for at least two leaving groups that are coupled via their aliphatic amino group to leave from a conjugate comprising one multiple release spacer, the spacer should be a phenol- or thiophenol-based multiple release spacer or the spacer system comprising one aniline-based multiple release spacer should also comprise single release phenol- or thiophenol-based spacers directly connected to this multiple release spacer. The linkage between self-eliminating multiple release spacer (system) and leaving group can be described as carbonate, alkyl phosphate, oxycarbonylthio, carbaniate, or N-aryl-carbamate. In some cases, for example in case of an aromatic alcohol leaving group coupled to a single release self-elimination spacer via an aryl ether linkage[11], the leaving group can also be linked to the spacer without an oxycarbonyl unit without compromising self-elimination.

In one embodiment the compound comprises one self-eliminating multiple release spacer. In a further embodiment the compound comprises two or more self-eliminating multiple release spacers. In yet a further embodiment the compound comprises three or more self-eliminating multiple release spacers.

Figure 3:
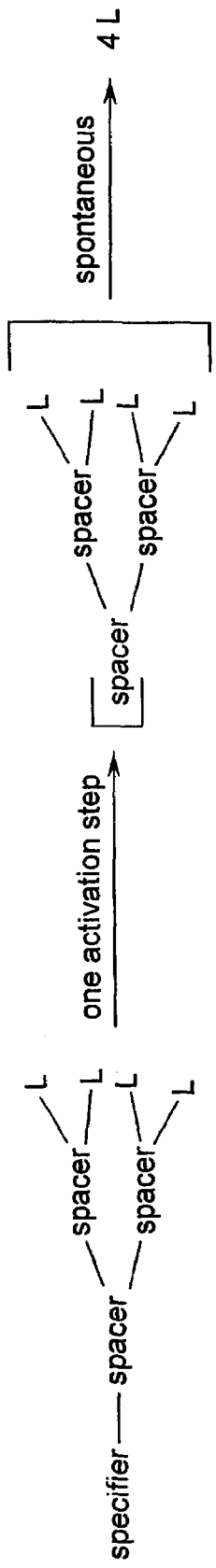
FIG. 3 shows schematically the liberation of 4 leaving group molecules from a compound containing 2 generations of double release spacers.
Figure 4:
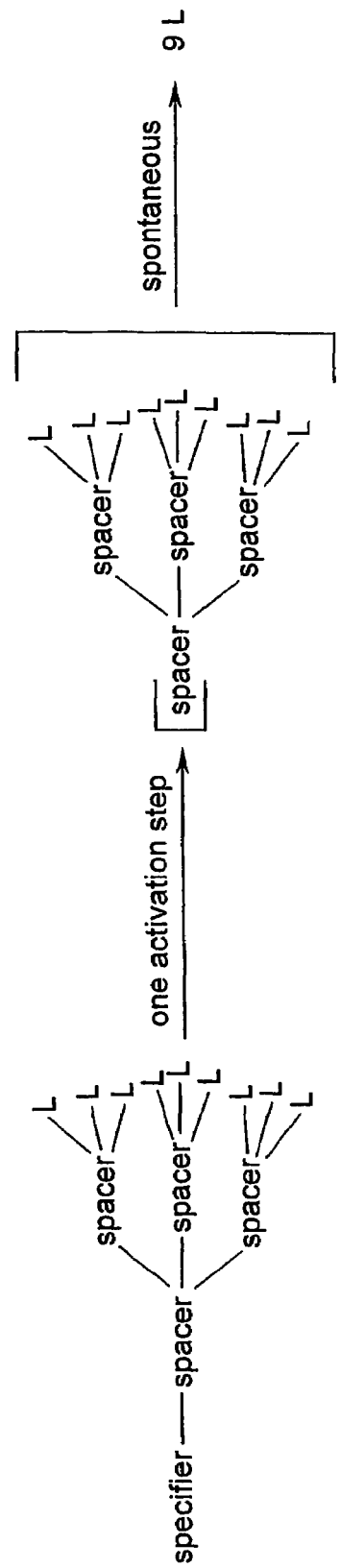
FIG. 4 shows schematically the liberation of 9 leaving group molecules from a compound containing 2 generations of triple release spacers.

The self-elimination multiple release spacers can also be coupled to one another (FIGS. 3 and 4). In this case compounds are obtained that contain multiple generations of multiple release spacers. If one multiple release spacer is incorporated in the spacer system of the compound according to the invention, the compound contains one generation of multiple release spacer. If two or more self-elimiating multiple release spacers are coupled to a first self-eliminating multiple release spacer, the resulting compound contains two generations of multiple release spacers (second generation). If two or more self-eliminating multiple release spacers are coupled to two or more multiple release spacers that constitute the second generation self-eliminating multiple release spacers, the resulting compound contains three generations of multiple release spacers (third generation). If a compound according to the invention contains two or more generations of self-eliminating multiple release spacers, the compound possesses a dendritic (or dendrimeric) structure and can be called a dendrimer. In one embodiment of the invention the compound comprises one self-eliminating multiple release spacer. In a further embodiment of the invention the compound comprises two or more generations of self-eliminating multiple release spacers. In yet a further embodiment the compound comprises three or more generations of self-eliminating multiple release spacers. For instance by coupling two self-elimination double release spacers to a first self-elimination double release spacer and optionally again coupling of four self-elimination double release spacers to the second two self-elimination double release spacers, a dendritic structure is constructed. The number of leaving group molecules, for example drug molecules, that can be bound per specifier is multiplied with every generation of self-elimination multiple release spacers incorporated. Each new generation of self-elimination multiple release spacers that is coupled to the preceding generation multiplies the number of leaving group molecules that can eventually be present in the compound or conjugate by a factor that is equal to the number of leaving groups that can be bound to the multiple release spacer of the generation that is newly incorporated. The final compound or prodrug (or bioconjugate) that is obtained is a dendrimer.

Thus in a further embodiment of the invention the compound comprises a self-eliminating multiple release spacer system in the form of a dendritic structure.

For at least two molecules to leave such a dendritic multiple release spacer system, the leaving groups should be coupled via their oxygen, such as for example their primary, secondary or tertiary alcohol, their phenol, or their phosphate, their sulphur, or their aromatic amine. In order for at least two leaving groups that are coupled via their aliphatic amino group to leave, at least one generation of the dendritic multiple release spacer system should comprise phenol- or thiophenol-based multiple release spacers or should be coupled to the next generation of multiple release spacers or to the leaving groups via single release phenol- or thiophenol-based spacers. Preferably the highest generation of multiple release spacers or spacer systems should be phenol- or thiophenol-based.

In a preferred embodiment, when an aniline-, phenol- or thiophenol-based multiple release spacer (system) is used, the leaving groups are not aliphatic amines, but preferably for example O, S or aromatic N.

Dendrimers, also known as starburst polymers, are well-defined highly branched tree-like macromolecules with a large number of end groups[12]. One application of dendrimeric (or dendritic) structures that has been explored is drug delivery[13]. In the emerging field of dendrimeric drug delivery, biologically active substances can be covalently linked to dendrimeric end groups, or can be encapsulated inside dendrimers. In the examples of the first case that have been reported thus far, each drug molecule must be independently liberated via a chemical or biological cleavage step[14]. In the second case, specific physiological conditions need to change the folding and/or tertiary structure of the dendrimer, thereby releasing encapsulated material. Release of active substances from dendrimers can be induced by pH[15], incorporation of photosensitive units[16], or by enzymatic cleavage[17].

The novel self-elimination multiple release spacers disclosed herein enable complete release of multiple leaving groups, for example biologically active substances, that are covalently linked to the dendrimeric end groups in such a way that a single activation is sufficient to release all end groups (FIGS. 3 and 4). A single chemical or biological activating event should lead to a cascade of self-elimination reactions thereby releasing multiple leaving groups. Dendrimers with these properties may be useful for several applications, and are considered particularly useful in the area of diagnostics and the area of drug delivery, for example in anticancer therapy, where tumor-selective degradation of the dendrimeric material is desired. Multiple drug molecules can be site-specifically released by employment of only one targeting or drug delivery device. Compounds that contain two or more generations of multiple release self-elimination spacers, optionally connected to each other via single release spacers or spacer systems are further called 'cascade dendrimers'.

Several applications are imaginable for the multiple release spacers or spacer systems or cascade dendrimers of this invention. Firstly, bioactive compounds can be site-specifically delivered. The concept can be applied to anticancer agents, but also antibiotics can be incorporated as end groups in a cascade dendrimer that is activated for example by bacterial enzymes, such as for example β-lactamase. In addition, cascade dendrimers may be applicable in the agrochemical field for release of pesticides[18]. Through sophisticated synthesis, cascade dendrimers may be prepared that contain two or more different parent compounds. This may be interesting when it is considered that combination therapy emerges as a clinically important mode of treatment for diseases such as cancer, bacterial diseases, and HIV.

Furthermore, biodegradable dendrimers might be interesting for the production of biodegradable materials such as plastics, or may be used as devices that enable the controlled or slow release of drugs by incorporation of, for example, an enzymatically degradable sequence. In addition, cascade dendrimers may be used for diagnostic purposes[19]. They could serve as an amplification mechanism in diagnostic assays, see hereinbelow.

Several strategies have evolved to improve the specificity of anticancer drugs, the prodrug concept being one of them[20,21]. A prodrug is an inactive derivative of an active drug, which is site-specifically activated to release the active parent drug. Prodrugs that are activated by tumor-specific or tumor-targeted enzymes have shown promising results[22]. Alternatively, prodrugs of antitumor agents coupled to polymers, as already reported by Ringsdorf[23], provide another targeting principle. Polymers, including dendrimers, can passively lead to tumnor-specificity, due to the enhanced permeability and retention effect (EPR)[24]. This effect retains polymeric material with an approximate molecular weight >40 kD inside tumor tissue due to discontinuous (leaky) and poorly formed tumor endothelium and poor lymphatic drainage. Frequently used polymeric carriers for drug delivery are poly[N-(2-hydroxypropyl)methacrylamide](poly-HPMA)[25], poly-glutamic acid, for example poly-L-glutamic acid (PG), and poly(ethylene) glycol (PEG)[26]. Application of dendrimers in drug delivery can be preferred to other polymers because, by definition, dendrimers are not as polydisperse as conventional polymers. In general, they can be obtained as homogeneous compounds more easily than polymers, a fact that may facilitate approval of dendrimeric material for medicinal purposes.

An important advantage of cascade dendrimers over conventional dendrimers or polymers would be that they would be selectively degradable, thus clearable from the body. Clearance of polymers from the body is a limiting factor in current polymeric drug delivery systems, as the maximum molecular weight of synthetic macromolecules that can be cleared from the body ranges from 25 to 45 kD[27]. Cascade dendrimers as disclosed herein can be considered as an alternative for self-assembling dendrimeric systems[28] that also possess these desirable properties of degradability.

Thus, the multiple release dendrimeric conjugates and prodrugs of this invention containing covalently bound anticancer drug molecules as end groups and activated by a specific enzyme that is localized in the tumor environment or by any other specific chemical or biological event would combine a number of desirable properties for a tumor-selective anticancer compound.

More specifically the invention relates to compounds of the formulas $$V-(W-)_w(X-)_xC((A\text{-})_aZ)_c,$$

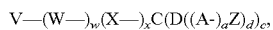

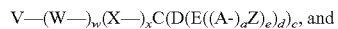

wherein:

V is selected from [O] and a specifier which is removed or transformed by a chemical, photochemical, physical, biological, or enzymatic activation, optionally after prior binding to a receptor;

$$(W-)_w(X-)_xC((A\text{-})_a)_c,$$

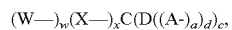

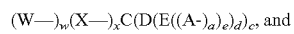

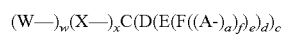

are self-eliminating multiple release spacers or spacer systems;

W and X are each a single release 1,(4+2n) electronic cascade spacer, being the same or different;

A is a cyclization elimination spacer;

C, D, E, and F are each a self-eliminating multiple release spacer or spacer system that upon activation can maximally release c, d, e, and f leaving groups, respectively;

each Z is independently a leaving group or H or OH or a reactive moiety;

a is 0 or 1;

c, d, e, and f are independently an integer from 2 (included) to 24 (included);

w and x are independently an integer from 0 (included) to 5 (included);

n is an integer of 0 (included) to 10 (included).

In a further embodiment, the invention relates to compounds of the formulas $$V-(W-)_w(X-)_xC((A\text{-})_aS)_c,$$

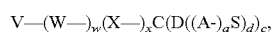

wherein:

V, W, X, C, D, E, F, A, w, x, c, d, e, f, and a are as defined above and each S independently has no meaning or is H, OH, or a reactive moiety that allows for coupling the multiple release spacer system to leaving groups Z, which may be the same or different, to afford compounds $$V-(W-)_w(X-)_xC((A\text{-})_aZ)_c,$$

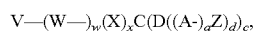

, respectively.

A compound or prodrug (or (bio)conjugate) according to this invention comprises a specifier V, which is meant to consist of a group that can be site specifically removed or transformed and that is covalently attached to at least two therapeutic or diagnostic moieties Z or to at least two reactive moieties S via the novel self-eliminating multiple release spacer or spacer system $(W-)_w(X)_xC((A\text{-})_a)_c$ or $(W-)_w(X-)_xC(D((A\text{-})_a)_d)_c$ or $(W-)_w(X-)_xC(D(E((A\text{-})_a)_e)_d)_c$ or $(W-)_w(X-)_xC(D(E(F((A\text{-})_a)_f)_e)_d)_c$. These self-eliminating multiple release spacers or spacer systems possess multiple sites for attachment of moieties Z or moieties S.

According to a preferred embodiment of the invention, the self-elimination multiple release spacers or spacer systems C, D, E, and F are independently selected from compounds having the formula

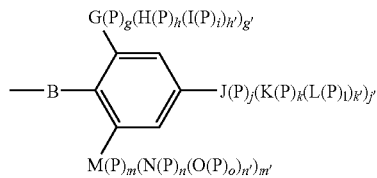

wherein
B is selected from $NR^1$, O, and S;
P is $C(R^2)(R^3)Q-(W-)_w(X-)_x$;
Q has no meaning or is —O—CO—;
W and X are each a single release 1,(4+2n) electronic cascade spacer, being the same or different;
G, H, I, J, K, L, M, N, and O are independently selected from compounds having the formula:

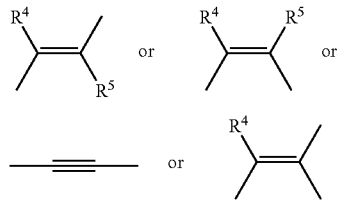

wherein $R^1$, $R^2$, $R^3$, $R^4$, and $R^5$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$), di-substituted amino ($NR_x^1R_x^2$) nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are independently selected from a $C_{1-6}$ alkyl group, a $C_{3-20}$ heterocyclyl group or a $C_{5-20}$ aryl group, two or more of the substituents $R^1$, $R^2$, $R^3$, $R^4$, and $R^5$ optionally being connected to one another to form one or more aliphatic or aromatic cyclic structures, or
G, J, and M may also be selected from the group of P and hydrogen with the proviso that if two of G, J, and M are hydrogen, the remaining group must be

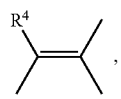

or be

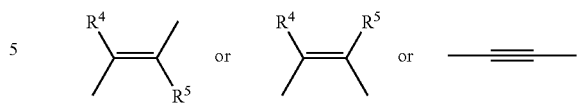

and at the same time be conjugated to

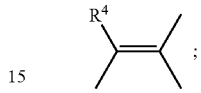

g, h, i, j, k, l, m, n, o, h', g', k', j', n', m' are independently 0, 1, or 2 with the provisos that
if G=hydrogen or P, g, h, i, h', and g' all equal 0;
if J=hydrogen or P, j, k, l, k', and j' all equal 0;
if M=hydrogen or P, m, n, o, n', and m' all equal 0;
if G, H, I, J, K, L, M, N, or O is

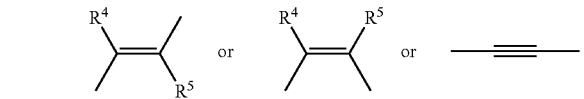

then g+g'=1, h+h'=1, i=1, j+j'=1, k+k'=1, l=1, m+m'=1, n+n'=1, or o=1, respectively;
if G, H, I, J, K, L, M, N, or O is

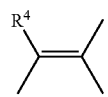

then g+g'=2, h+h'=2, i=2, j+j'=2, k+k'=2, l=2, m+m'=2, n+n'=2, or o=1, respectively;
if g'=0 and G is not hydrogen or P, then h, h', and i equal 0 and g>0;
if g=0 and G is not hydrogen or P, then g'>0;
if g'>0 and h'=0, then i=0 and h>0;
if g'>0 and h=0, then h'>0 and i>0;
if j'=0 and J is not hydrogen or P, then k, k', and 1 equal 0 and j>0;
if j=0 and J is not hydrogen or P, then j'>0;
if j'>0 and k'=0, then l=0 and k>0;
if j'>0 and k=0, then k'>0 and l>0;
if m'=0 and M is not hydrogen or P, then n, n', and o equal 0 and m>0;
if m=0 and M is not hydrogen or P, then m'>0;
if m'>0 and n'=0, then o=0 and n>0;
if m'>0 and n=0, then n'>0 and o>0;
w and x are independently an integer from 0 (included) to 5 (included);
with the proviso that
if the compound contains only C and no D, no E, and no F are present, and B=$NR^1$, and G and M are H, and g, h, i, h', g', k, l, k', l', m, n, o, n', and m' are 0, and J=

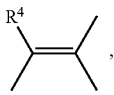

and j=2, and Q=—O—CO—, and w and x are 0, and $R^1$, $R^2$, $R^3$, and $R^4$ are H, then at least one of the leaving groups Z is not connected to Q via an aliphatic amino group.

According to another preferred embodiment of the invention the 1,(4+2n) electronic cascade spacers W and X are independently selected from compounds having the formula

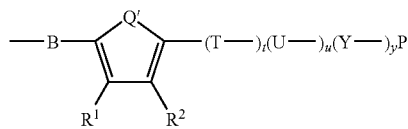

$Q'$=—$R^5C$=$CR^6$—, S, O, $NR^5$, —$R^5C$=N—, or —N=$CR^5$—

B=$NR^7$, O, S

P=C($R^3$)($R^4$)Q wherein
Q has no meaning or is —O—CO—;
t, u, and y are independently an integer of 0 to 5;
T, U, and Y are independently selected from compounds having the formula:

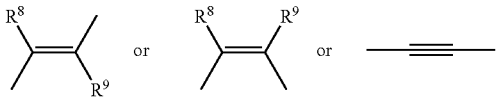

wherein $R^1$, $R^2$, $R^3$, $R^4$, $R^5$, $R^6$, $R^7$, $R^8$, and $R^9$ independently represent H, $C_{1-6}$ alkyl, $C_{3-20}$ heterocyclyl, $C_{5-20}$ aryl, $C_{1-6}$ alkoxy, hydroxy (OH), amino ($NH_2$), mono-substituted amino ($NR_xH$) di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy (S(=O)$_2$OH), sulphonate (S(=O)$_2OR_x$), sulphonyl (S(=O)$_2R_x$), sulphixy (S(=O)OH), sulphinate (S(=O)$OR_x$), sulphinyl (S(=O)$R_x$), phosphonooxy (OP(=O)(OH)$_2$), and phosphate (OP(=O)(OR_x)$_2$), where $R_x$, $R_x^1$ and $R_x^2$ are independently selected from a $C_{1-6}$ alkyl group, a $C_{3-20}$ heterocyclyl group or a $C_{5-20}$ aryl group, two or more of the substituents $R^1$, $R^2$, $R^3$, $R^4$, $R^5$, $R^6$, $R^7$, $R^8$, or $R^9$ optionally being connected to one another to form one or more aliphatic or aromatic cyclic structures.

In a preferred embodiment leaving groups Z are linked to the self-eliminating multiple release spacer or spacer system via an O, S or aromatic N of the leaving group.

In order to further clarify the above mentioned formulae, compound 26 depicted in FIG. 13 will serve as an example. This compound is a compound of the formula V—(W—)$_w$(X—)$_x$C(D((A-)$_a$Z)$_d$)$_c$. It contains two generations of double release spacers, to which 4 end groups Z have been coupled. The specifier V is [O], which means that V—B is an oxidized form of B (part of C). Reduction of this functionality induces self-elimination. Such moiety V—B can be chemically reduced, but it can also be reduced under physiological conditions under hypoxic conditions, or by a nitroreductase. Z is paclitaxel. No single release spacer is incorporated in between the specifier [O] and the multiple release spacers, which means that w=x=0. C is the double release spacer containing the benzylidene-propane-1,3-bis-oxycarbonyl unit, which eliminates according to the principle depicted in FIG. 8. No cyclization elimination spacer is present, which means that a=0. Because two double release spacers have been coupled to the first double release spacer, d=c=2.

In general, multiple release spacers disclosed in this invention possess multiple release characteristics because they are branched on two levels; i) branching on the aromatic ring where both ortho and para-substituents with respect to the location of the specifier can be introduced, and ii) branching by incorporation of additional conjugated double bonds at para and/or ortho positions of the aromatic rings, where the terminal C-atom of the double bond provides a branching point where two leaving groups can be attached. Theoretically, these two elements for branching self-eliminating spacers to obtain multiple release spacers or spacer systems can be infinitely extended.

In addition to incorporation of one or more (generations of) self-eliminating multiple release spacers, it may also be desirable to incorporate a single release, also called unbranched, self-eliminating spacer or spacer system in between the specifier and the first multiple release spacer. This may facilitate the activation step. This single release self-eliminating spacer or spacer system is described by —(W—)$_w$(X—)$_x$. Furthermore, it may be desirable to add single release self-eliminating spacers or spacer systems to a previous generation, coupled to a next generation of multiple release spacers (thus obtaining a previous generation of multiple release spacer systems), or to the highest generation of multiple release spacer(s) before leaving groups Z in order to increase the surface area of the final conjugate. This may increase the number of end groups that can be accommodated and it may also increase the final size of the conjugate, which may go together with certain advantages, such as for example benefiting from the Enhanced Permeability and Retention (EPR) effect. Furthermore, when only aniline-based multiple release spacers are used, connection of single release phenol- or thiophenol-based spacers to a generation of multiple release spacers or, preferably, to the highest generation of multiple release spacers before leaving groups Z enables the release of two or more leaving groups Z that are coupled with their aliphatic amino group to the multiple release spacer system.

When only aniline-based multiple release spacers are used and no single release phenol- or thiophenol-based spacers are incorporated into the multiple release spacer system to which leaving groups Z are coupled with their aliphatic amino group only 1 Z group will be released. This is also true for incorporation of single release aniline-based spacer(s) in the multiple release spacer system to which leaving groups Z are coupled with their aliphatic amino group. Single release spacers that are added to a generation of multiple release spacers, or to the highest generation of multiple release spacer(s) before leaving groups Z or reactive moieties S are represented in the above formulae by —(W—)$_w$(X—)$_x$ in P, which is a part of C, D, E, and F.

In general, aniline-based single release or multiple release spacers are preferred over phenol- or thiophenol-based single release or multiple release spacers. The above shows, however that it might sometimes be beneficial to include phenol- or thiophenol-based single release spacer in the multiple release spacer system. For the same reason, it is sometimes beneficial to include phenol- or thiophenol-based multiple release spacers. In general, to release two or more Z groups that are connected to the multiple release spacer or spacer system via an aliphatic amino group, at least one, preferably all, multiple release spacers or spacer systems of either generation C, D (if present), E (if present), or F (if present), preferably the one(s) connected to either A, Z, or S, have to be phenol- or thiophenol-based multiple release spacers or spacer systems, meaning that i) B=O or S for at least one, preferably all, multiple release spacers in that generation, or ii) when B=N for all multiple release spacers in said generation, at least one single release spacer is connected to at least two branches of at least one, preferably all, multiple release spacer in said generation, and B=O or S for at least two of those single release spacers.

In the formulae above, Q is preferably O—CO, but it may also have no meaning. For example, a compound with an aryl ether linkage between self-elimination spacer and leaving group, where the oxycarbonyl function is lacking (Q has no meaning), has been reported to undergo self-eliniation as well[11].

Figure 5:
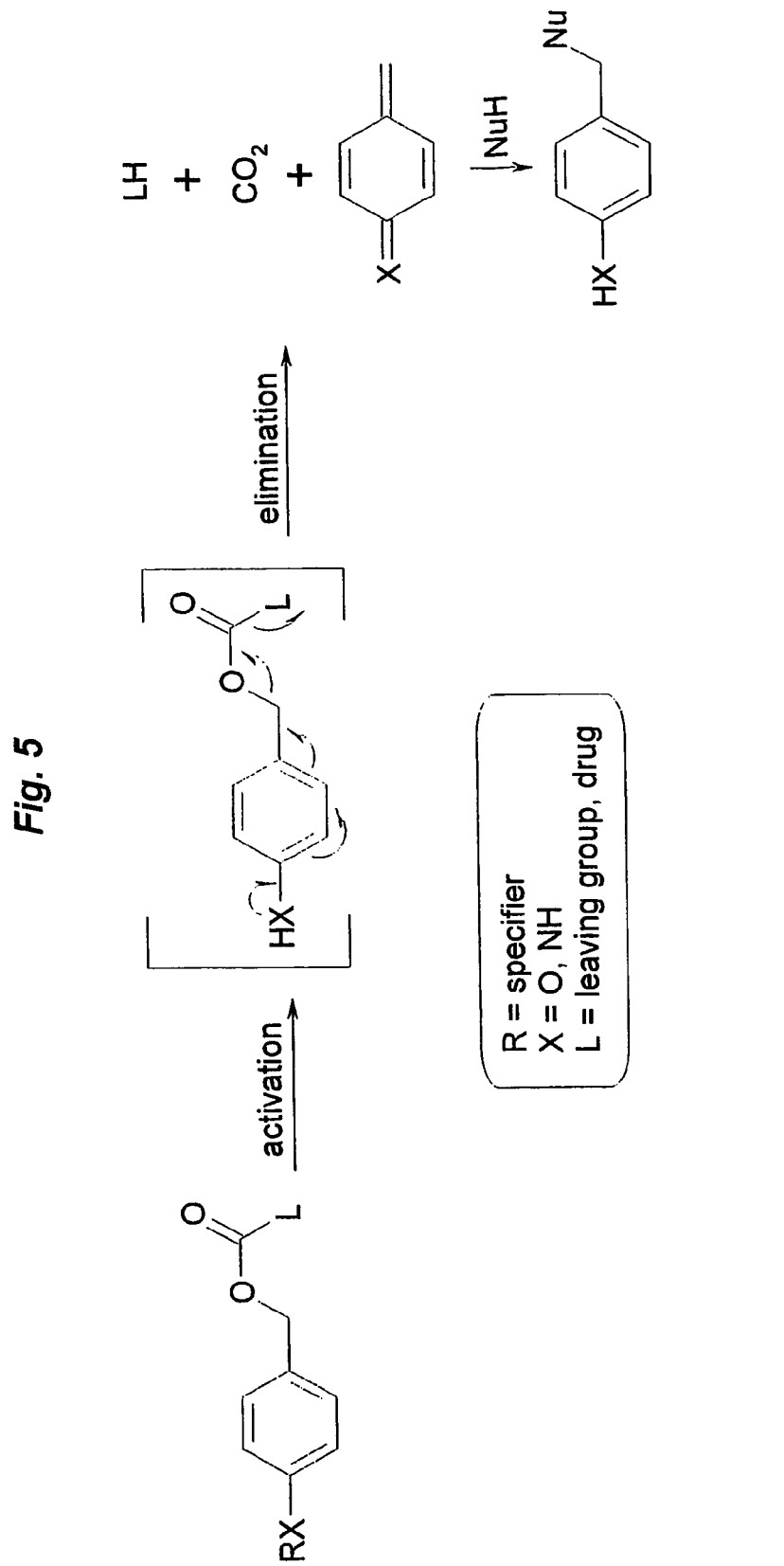
FIG. 5 shows the principle of 1,6-elimination.
Figure 6:
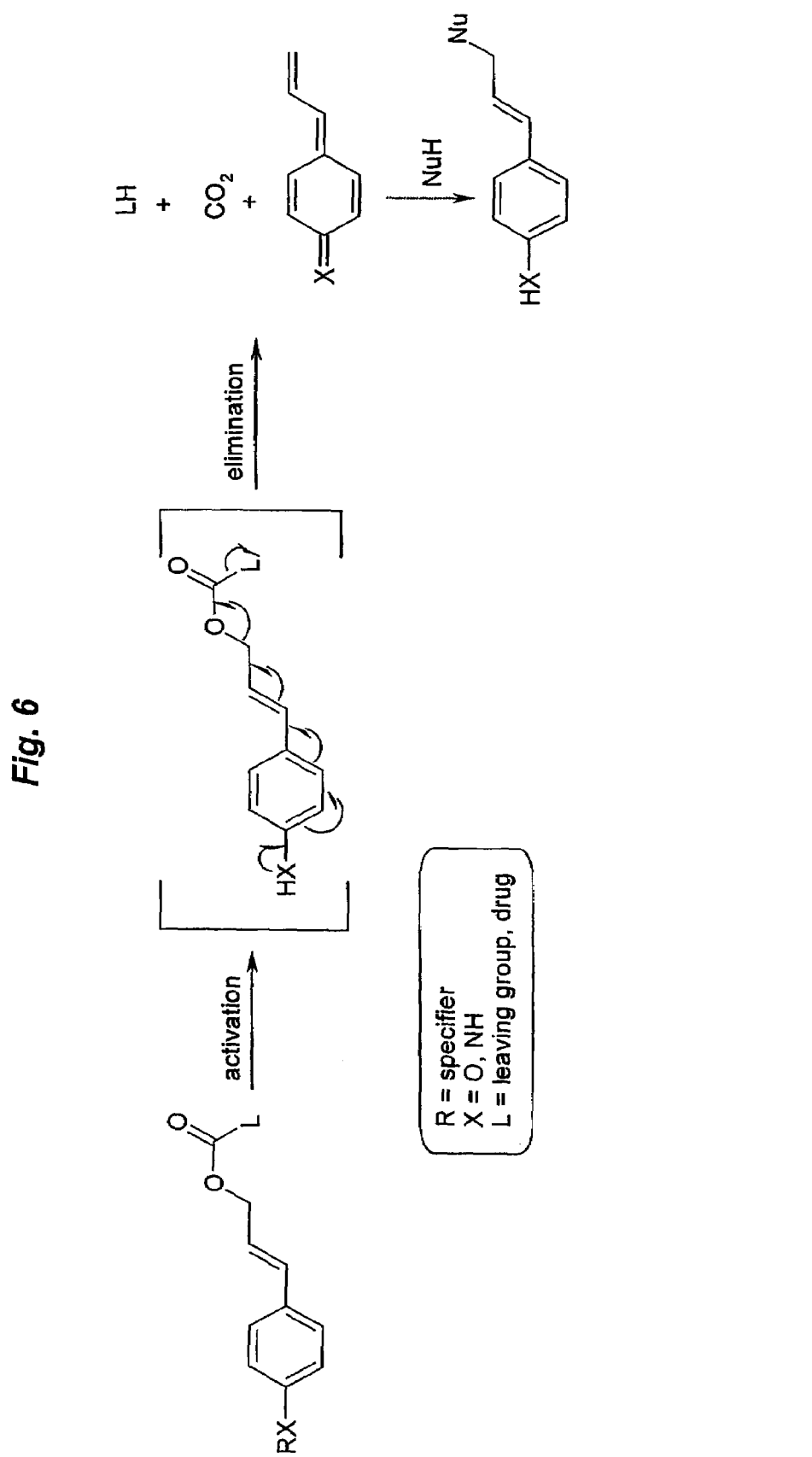
FIG. 6 shows the principle of 1,8-elimination.

The principle of 1,6-elimination, as such developed by Carl et al. in 1981, can be considered one of the most versatile self-elinination principles that can be used in prodrug design. According to this principle, spacer elimination proceeds via the mechanism depicted in FIG. 5. This particular elimination process has proven to be very successful when applied in the prodrug concept. Spacers that self-eliminate through an electronic cascade sequence as indicated in FIGS. 5 and 6 generally show much faster half-lives of elimination than do spacers that eliminate via a cyclization reaction. This is a significant difference between cyclization spacers and electronic cascade spacers.

Elongated self-elimination spacers can be incorporated between a cleavable moiety and leaving group, for example between specifier and drug as disclosed in WO 02/083180 (see also ref. 29). Increasing the length of self-elimination spacers may have (an) additional advantage(s). Self-elimination spacers with increased length may increase the rate and/or efficiency of activation of conjugate or prodrug. As a result, drug release characteristics may be enhanced through long spacers. The self-elimination spacers or spacer systems of the present invention can also be longer than conventional self-elimination spacers, such as for example the 1,6-elimination spacer, because they are elongated themselves or because multiple self-elimination linkers are combined within one multiple release spacer system. Thus, the spacers or spacer systems of the present invention can be branched, but in addition they can be elongated. Both factors (length and degree of branching) of a spacer or spacer system must be carefully considered when designing conjugates or prodrugs. A high degree of branching may be disadvantageous for the efficiency of activation of the conjugate or prodrug, especially when the branching points are in close proximity to the site of activation. When a high degree of branching is desirable in order to accommodate many leaving groups Z, it may be beneficial to incorporate single release self-elimination spacers in between the specifier V and the branching point(s). It may increase the efficiency of activation.

Connection of single release spacer(s) to generations of multiple release spacers may enable an increase of the total number of end groups that can be incorporated because the surface of the outer sphere is increased by incorporation of additional single release spacer(s), and as a result more end groups (for example drugs) can be accommodated. To obtain a conjugate or prodrug that possesses the desired properties, a considered choice of a specific multiple release spacer or spacer system optionally including one or more single release self-elimination spacers, must be made.

The novel self-eliminating multiple release spacers disclosed in this invention may be coupled to one another to yield multiple release spacer systems in which the spacers are coupled through aryl-carbamate functions, by employing hydroxybenzotriazole as a catalyst to couple an aromatic amine to a p-nitrophenyl carbonate.

The invention is in another aspect related to compounds of the above-mentioned formulas wherein A is a cyclization spacer, further called ω-amino aminocarbonyl cyclization spacer having a formula selected from

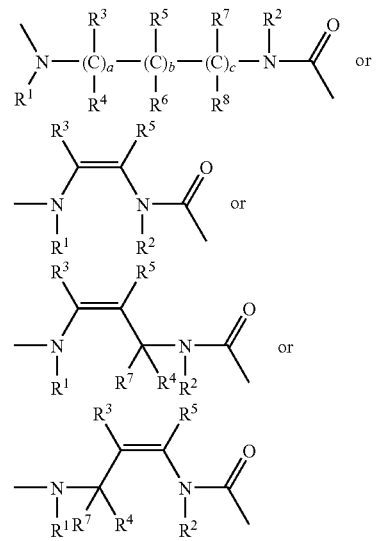

wherein:
a is an integer of 0 or 1; and
b is an integer of 0 or 1; and
c is an integer of 0 or 1; provided that
a+b+c=2 or 3;
and wherein $R^1$ and $R^2$ independently represent H, $C_{1-6}$ alkyl, said alkyl being optionally substituted with one or more of the following groups: hydroxy (OH), ether ($OR_x$), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether ($SR_x$), tetrazole, carboxy (COOH), carboxylate ($COOR_x$), sulphoxy ($S(=O)_2OH$), sulphonate ($S(=O)_2OR_x$), sulphonyl ($S(=O)_2R_x$), sulphixy ($S(=O)OH$), sulphinate ($S(=O)OR_x$), sulphinyl ($S(=O)R_x$), phosphonooxy ($OP(=O)(OH)_2$), and phosphate ($OP(=O)(OR_x)_2$), where $R_x$, $R_x^1$ and $R_x^2$ are selected from a $C_{1-6}$ alkyl group, a $C_{3-20}$ heterocyclyl group or a $C_{5-20}$ aryl group;

$R^2$ has no meaning when S has no meaning, which means that a double bond is present between the rightmost nitrogen atom and the carbonyl group (N=C=O); and $R^3$, $R^4$, $R^5$, $R^6$, $R^7$, and $R^8$ independently represent H, $C_{1-6}$ alkyl, $C_{3-20}$ heterocyclyl, $C_{5-20}$ aryl, $C_{1-6}$ allkoxy, hydroxy (OH), amino ($NH_2$), mono-substituted amino ($NR_xH$), di-substituted amino ($NR_x^1R_x^2$), nitro ($NO_2$), halogen, $CF_3$, CN, $CONH_2$, $SO_2Me$, CONHMe, cyclic $C_{1-5}$ alkylamino, imidazolyl, $C_{1-6}$ alkylpiperazinyl, morpholino, thiol (SH), thioether (SR$_x$), tetrazole, carboxy (COOH), carboxylate (COOR$_x$), sulphoxy (S(=O)$_2$OH), sulphonate (S(=O)$_2$OR$_x$), sulphonyl (S(=O)$_2$R$_x$), sulphixy (S(=O)OH), sulphinate (S(=O)OR$_x$), sulphinyl (S(=O)R$_x$), phosphonooxy (OP(=O)(OH)$_2$), and phosphate (OP(=O)(OR$_x$)$_2$), where R$_x$, R$_x^1$ and R$_x^2$ are selected from a C$_{1-6}$ alkyl group, a C$_{3-20}$ heterocyclyl group or a C$_{5-20}$ aryl group; and wherein R$^1$, R$^2$, R$^3$, R$^4$, R$^5$, R$^6$, R$^7$, and R$^8$ can be a part of one or more aliphatic or aromatic cyclic structures, two or more of the substituents R$^1$, R$^2$, R$^3$, R$^4$, R$^5$, R$^6$, R$^7$, or R$^8$ optionally being connected to one another to form one or more aliphatic or aromatic cyclic structures.

The ω-amino group of the ω-amino aninocarbonyl cyclization spacer A does not need to be in close proximity to a particular electron-withdrawing substituent nor does it need to be an aromatic nitrogen, when it is connected to a multiple release spacer system that contains phenol- or thiophenol-based spacers in one generation, preferably in the highest generation (which is the one connected to A, Z, or S).

The ω-amino group of the ω-amino aminocarbonyl cyclization spacer should possess sufficient leaving group ability. In a preferred embodiment the ω-amino group of the ω-amino aminocarbonyl cyclization spacer is an N-aryl or an aliphatic N wherein the N is positioned in proximity of an electron-withdrawing group, such that the electron-withdrawing group can properly exert its electron-withdrawing property so that the leaving group ability of the ω-amino group is increased. The nucleophilicity of the leaving amino group should however be sufficient to allow for a sufficiently fast cyclization reaction.

In a further embodiment the invention relates to a compound, wherein group A is an ω-amino aminocarbonyl cyclization spacer, and Z is a moiety coupled via its hydroxyl group to A.

Preferred compounds according to the invention are those wherein (W—)$_w$(X—)$_x$C$_c$, (W—)$_w$(X—)$_x$C(D$_d$)$_c$, (W—)$_w$(X—)$_x$C(D(E$_e$)$_d$)$_c$ or (W—)$_w$(X—)$_x$C(D(E(F$_f$)$_e$)$_d$)$_c$ is selected from the group consisting of

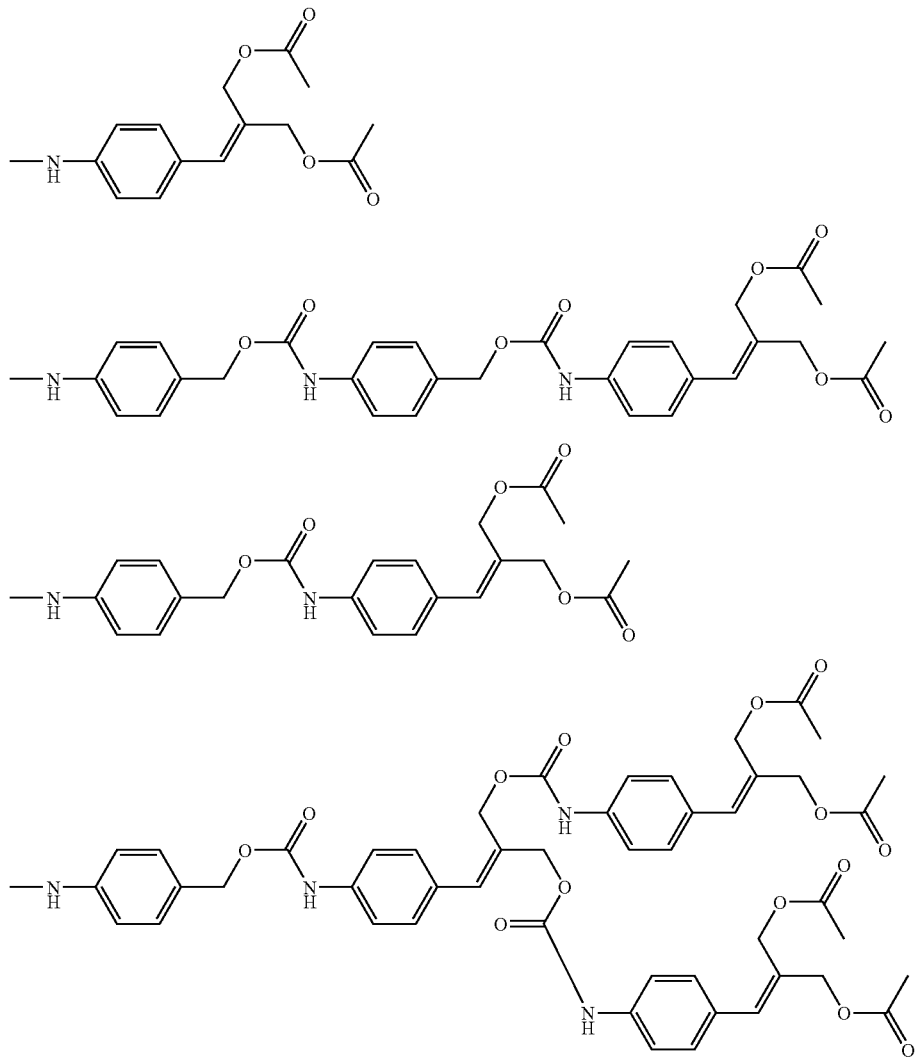

-continued
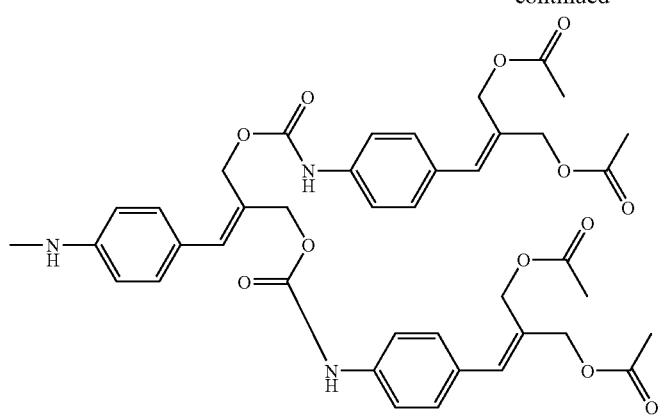
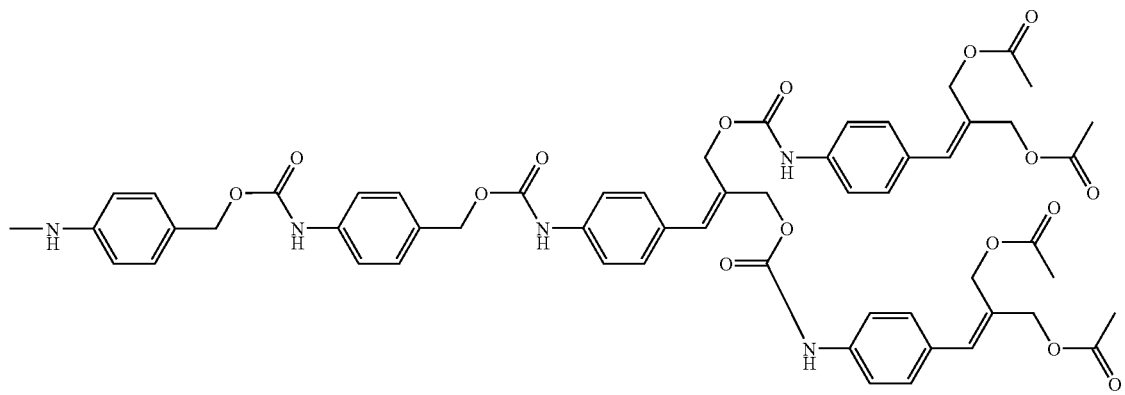
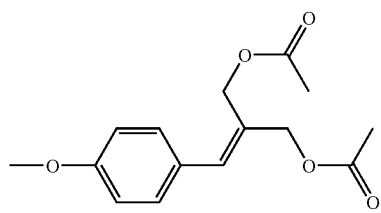
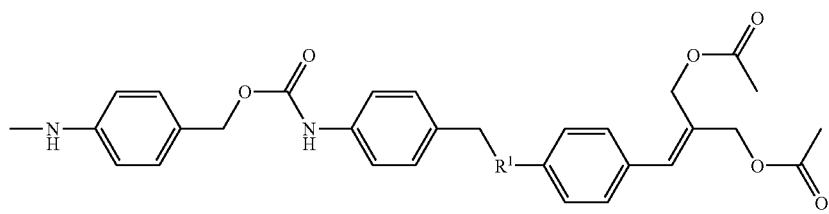
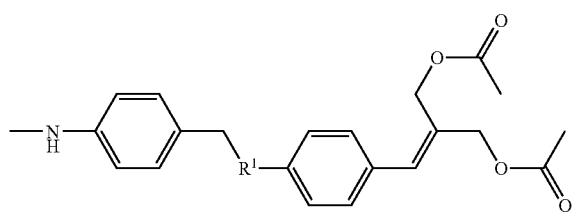

-continued
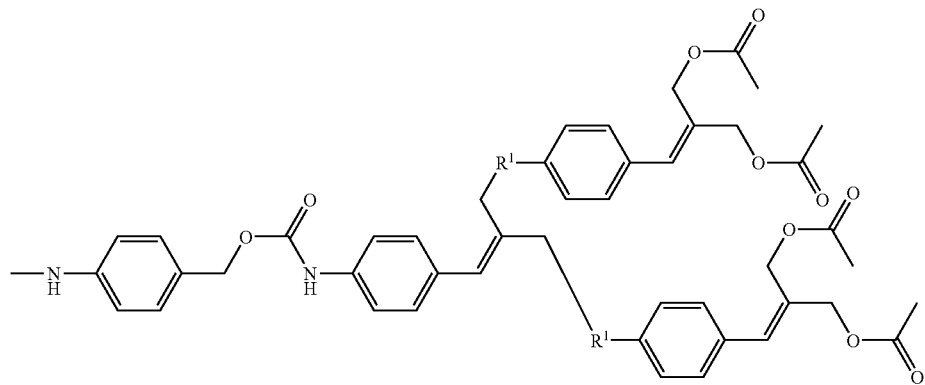
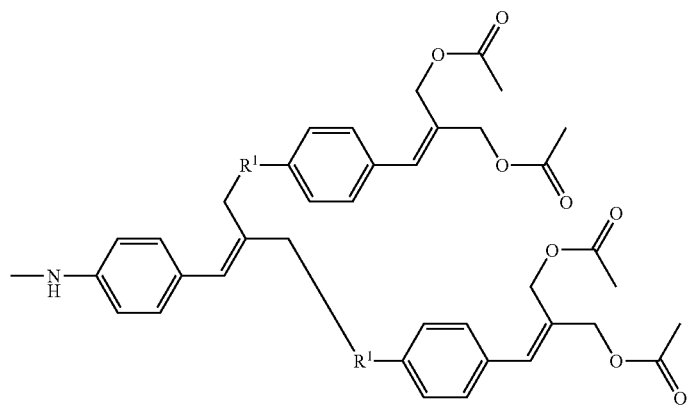
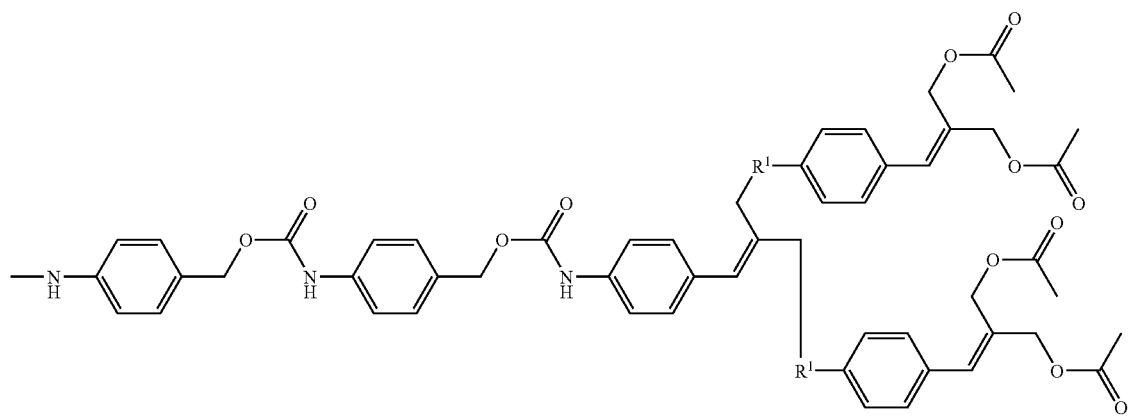
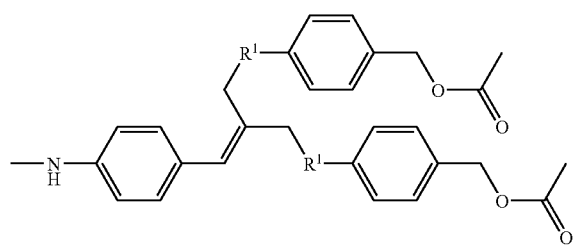

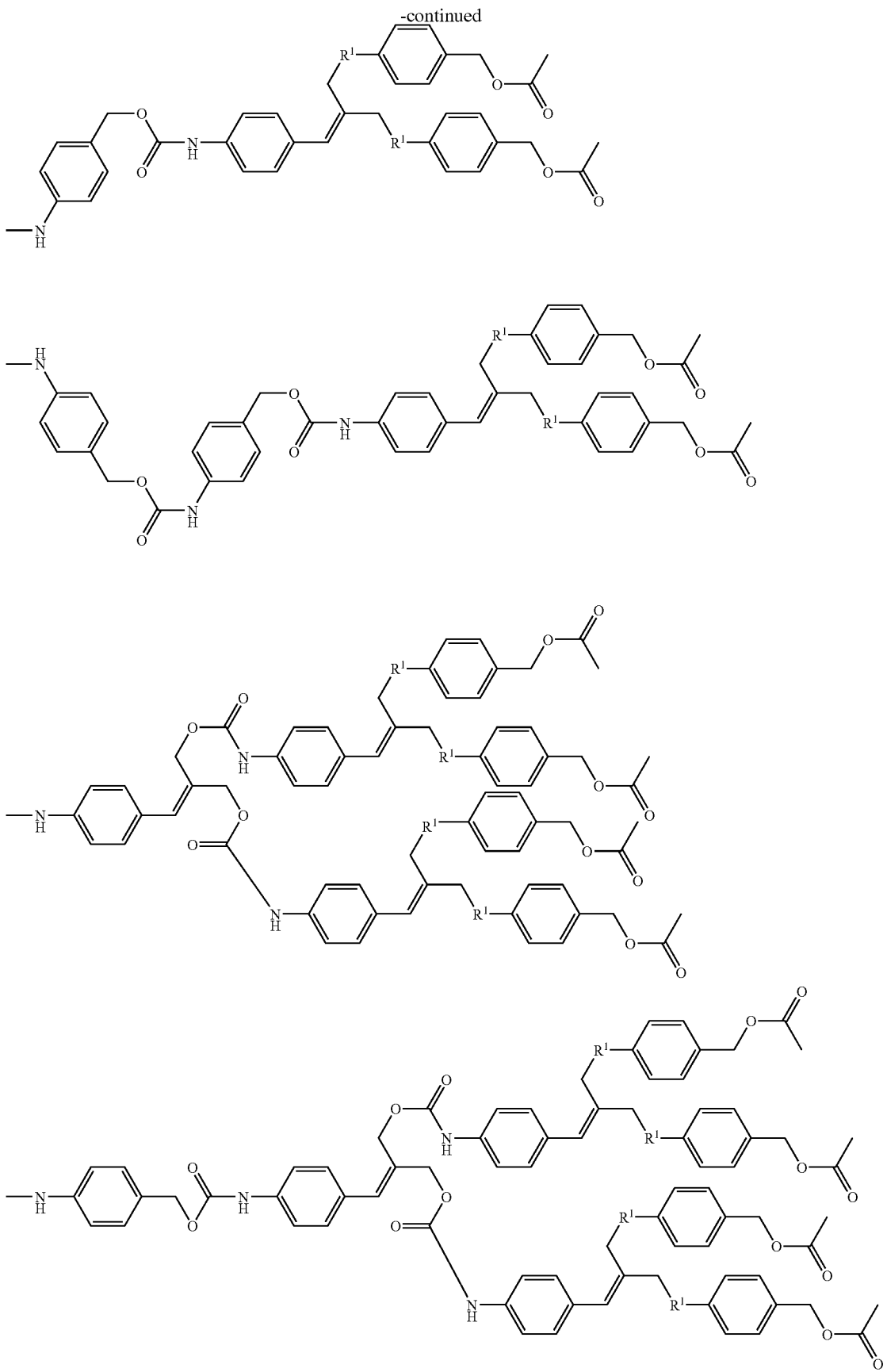

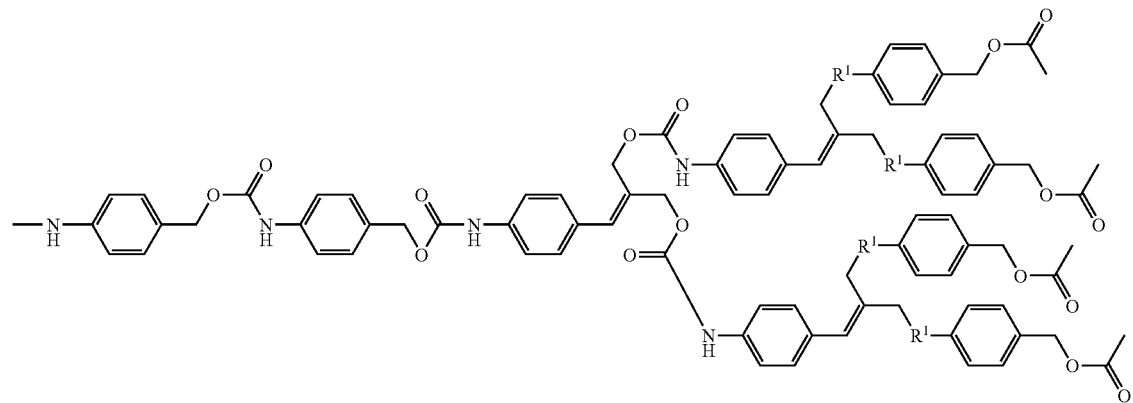
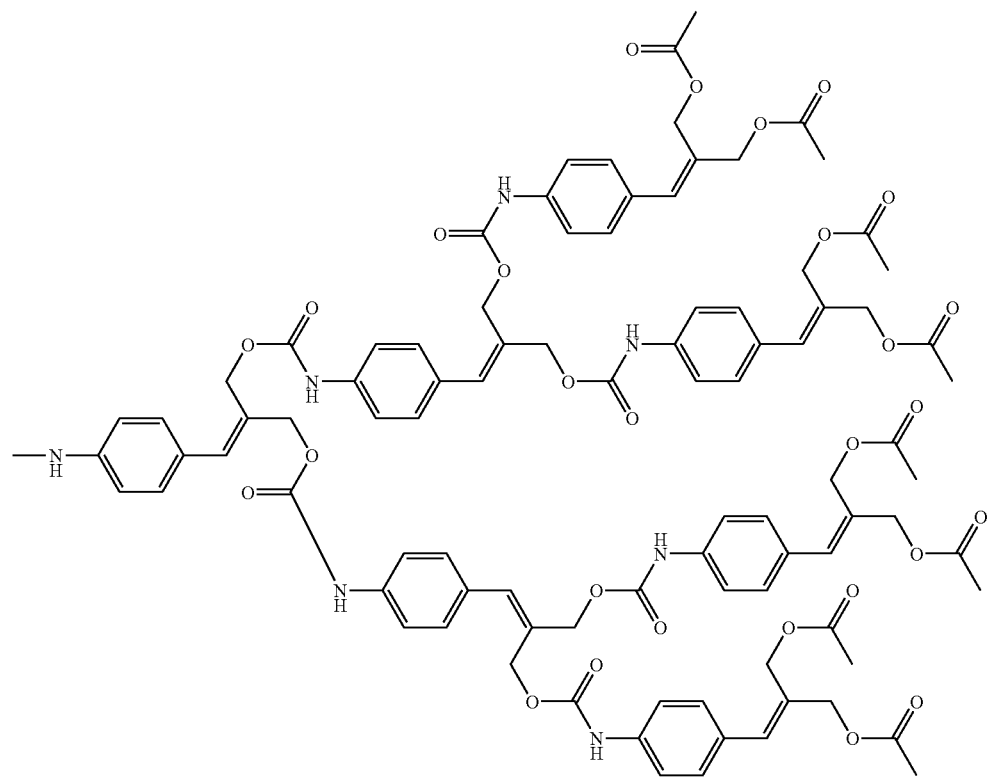

-continued
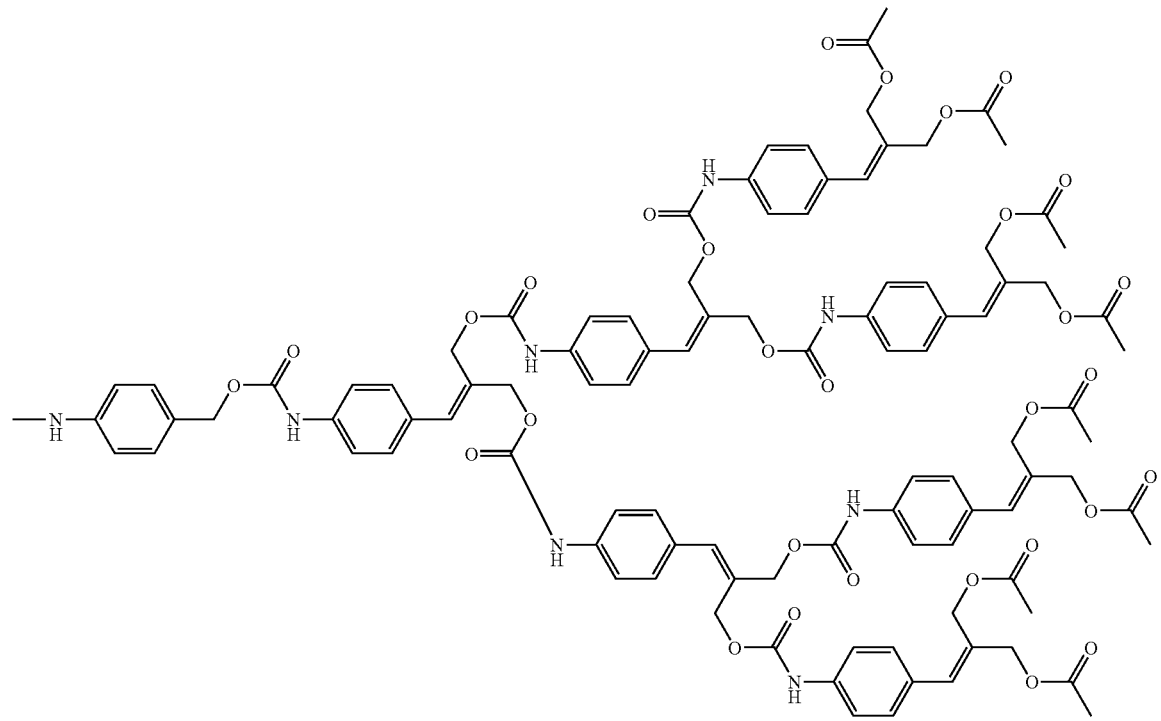
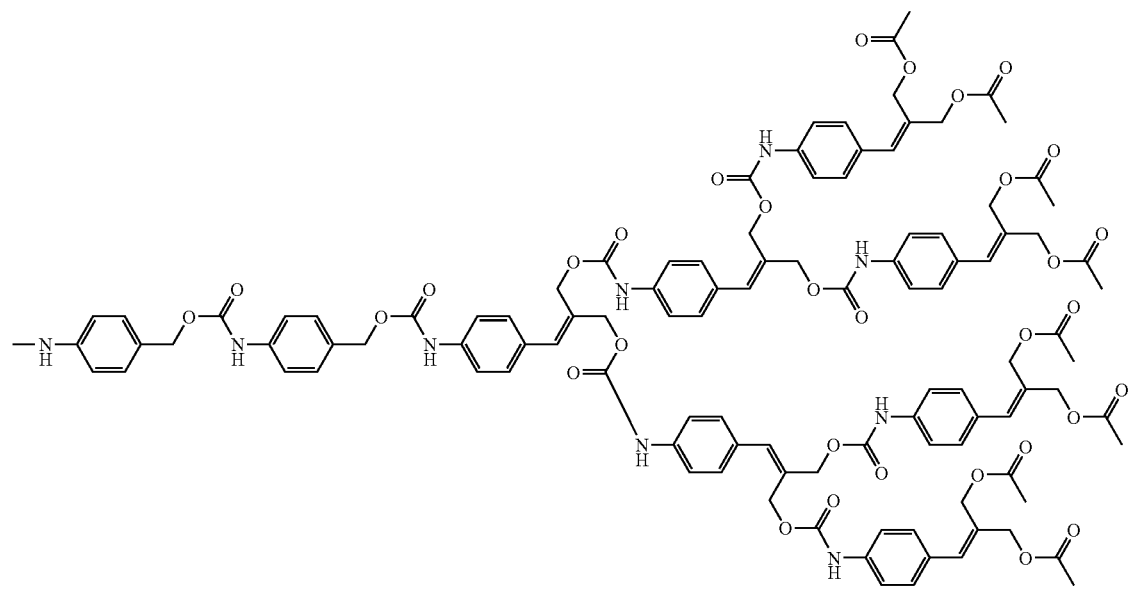

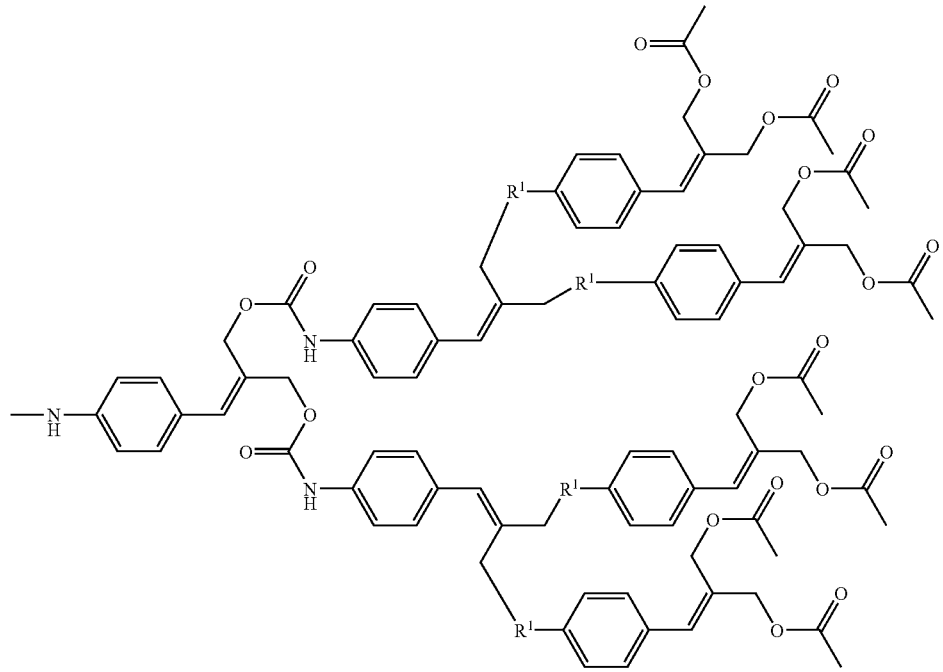
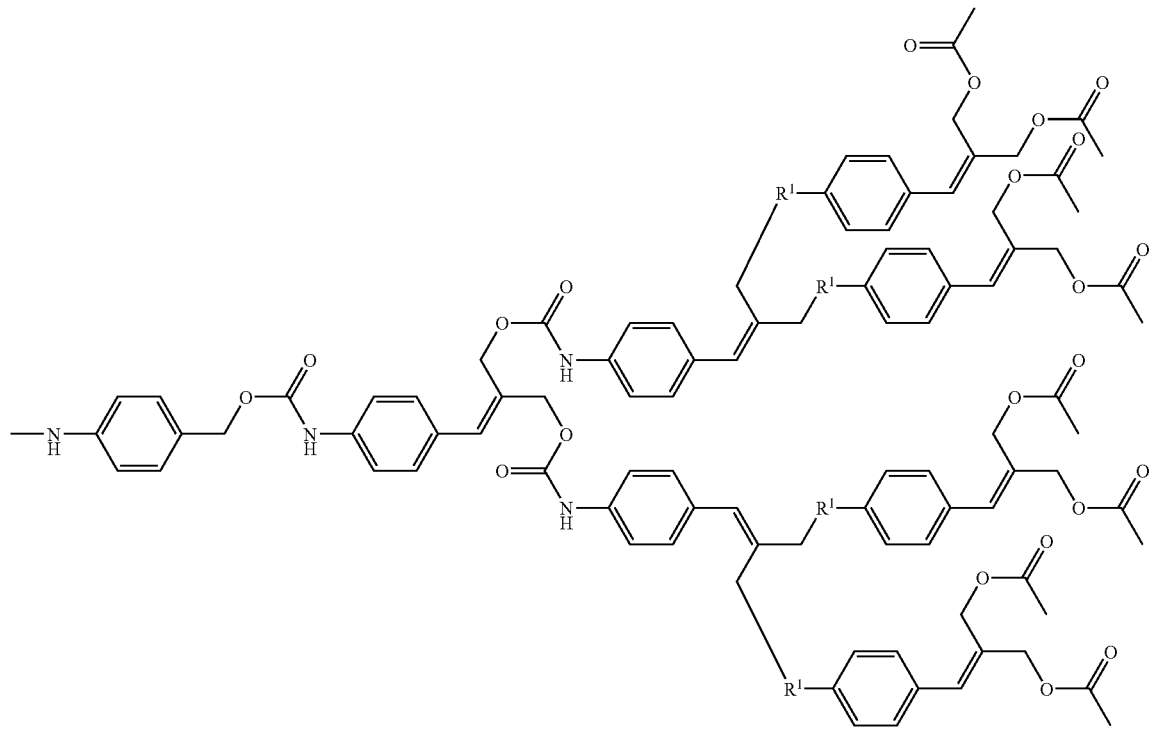

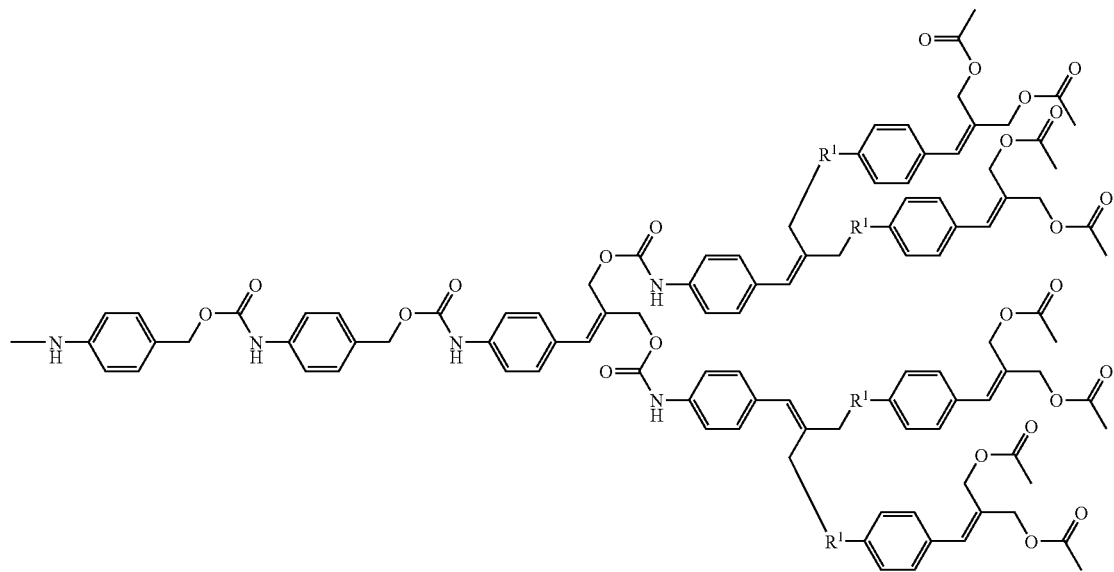
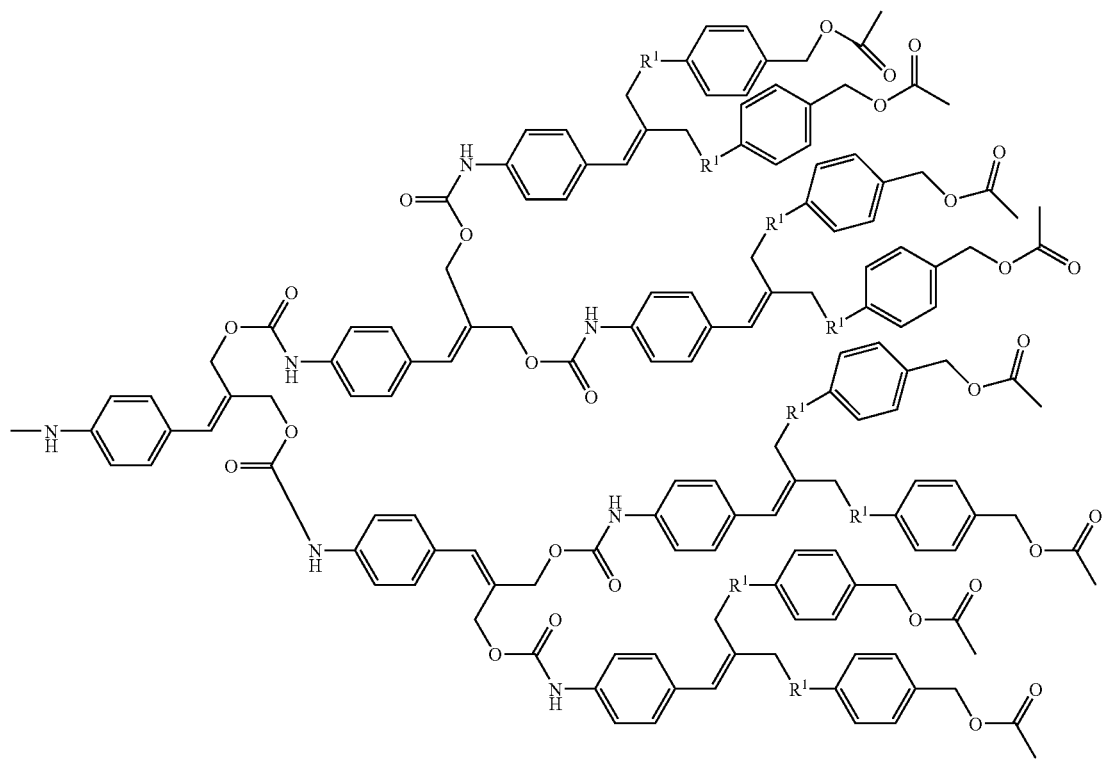

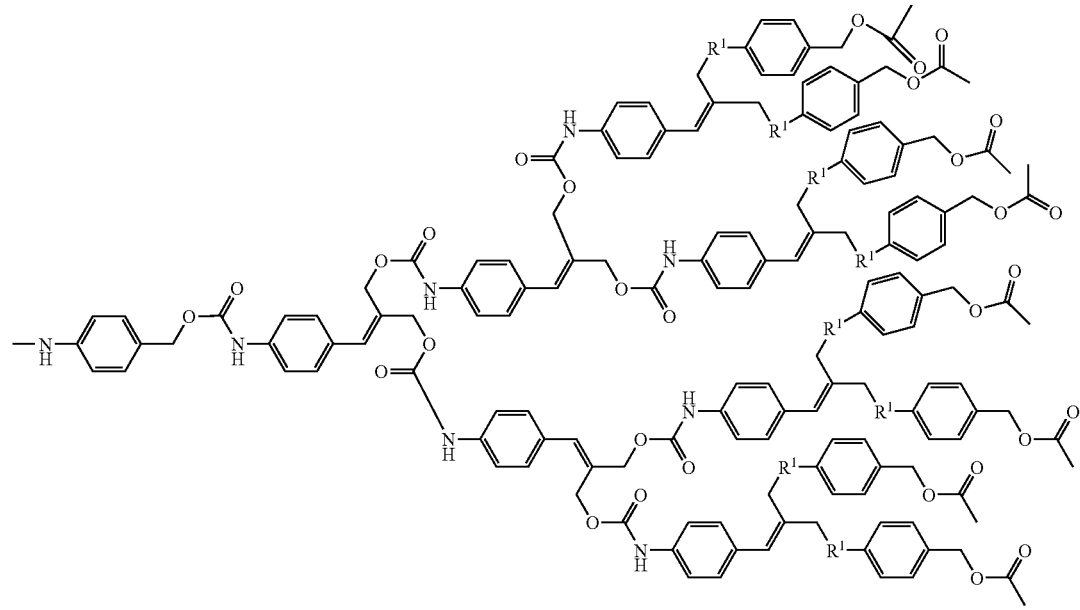
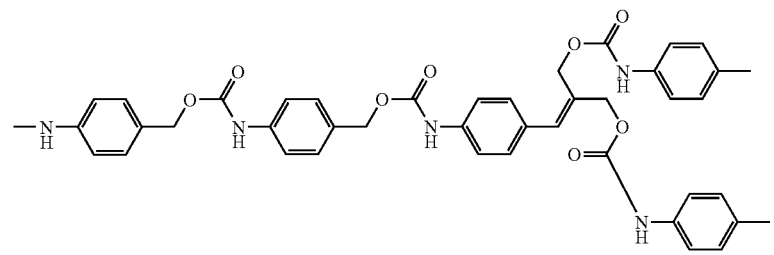
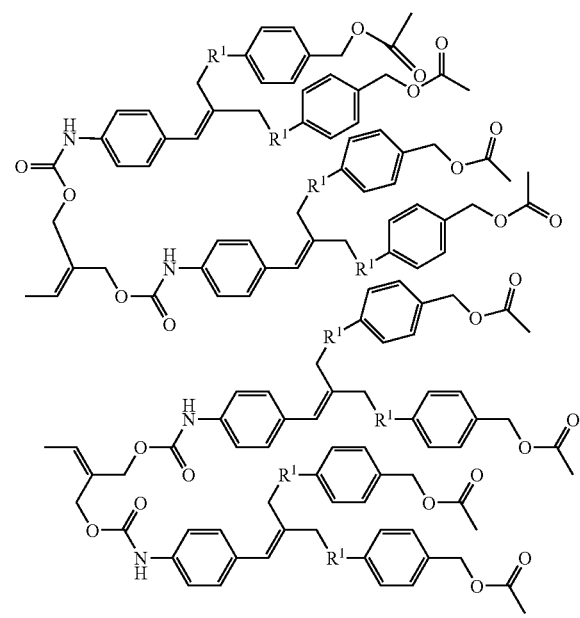

-continued
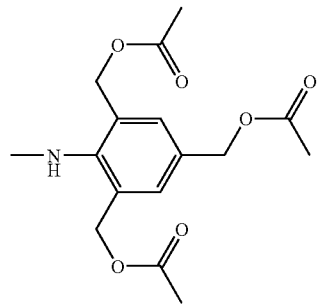
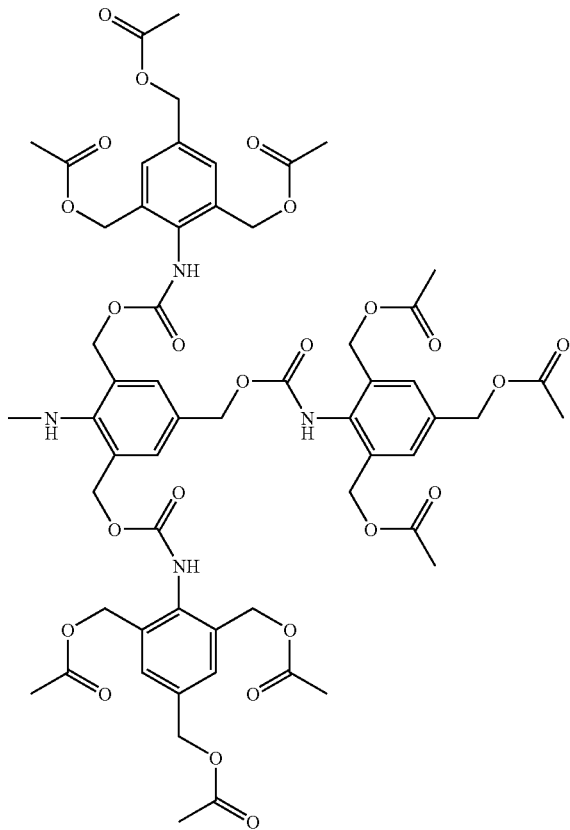
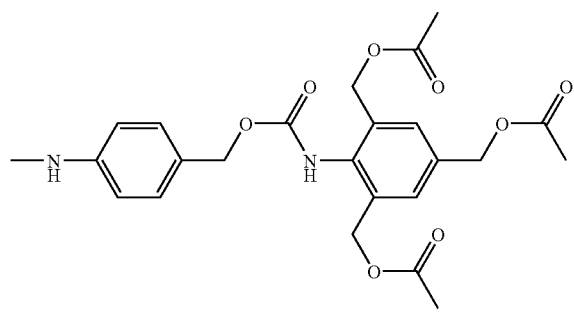
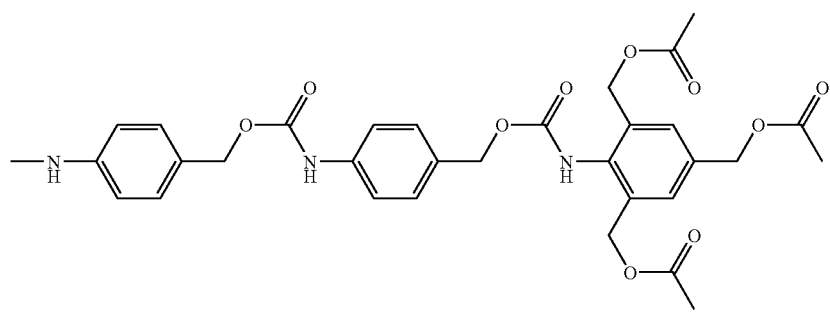

-continued
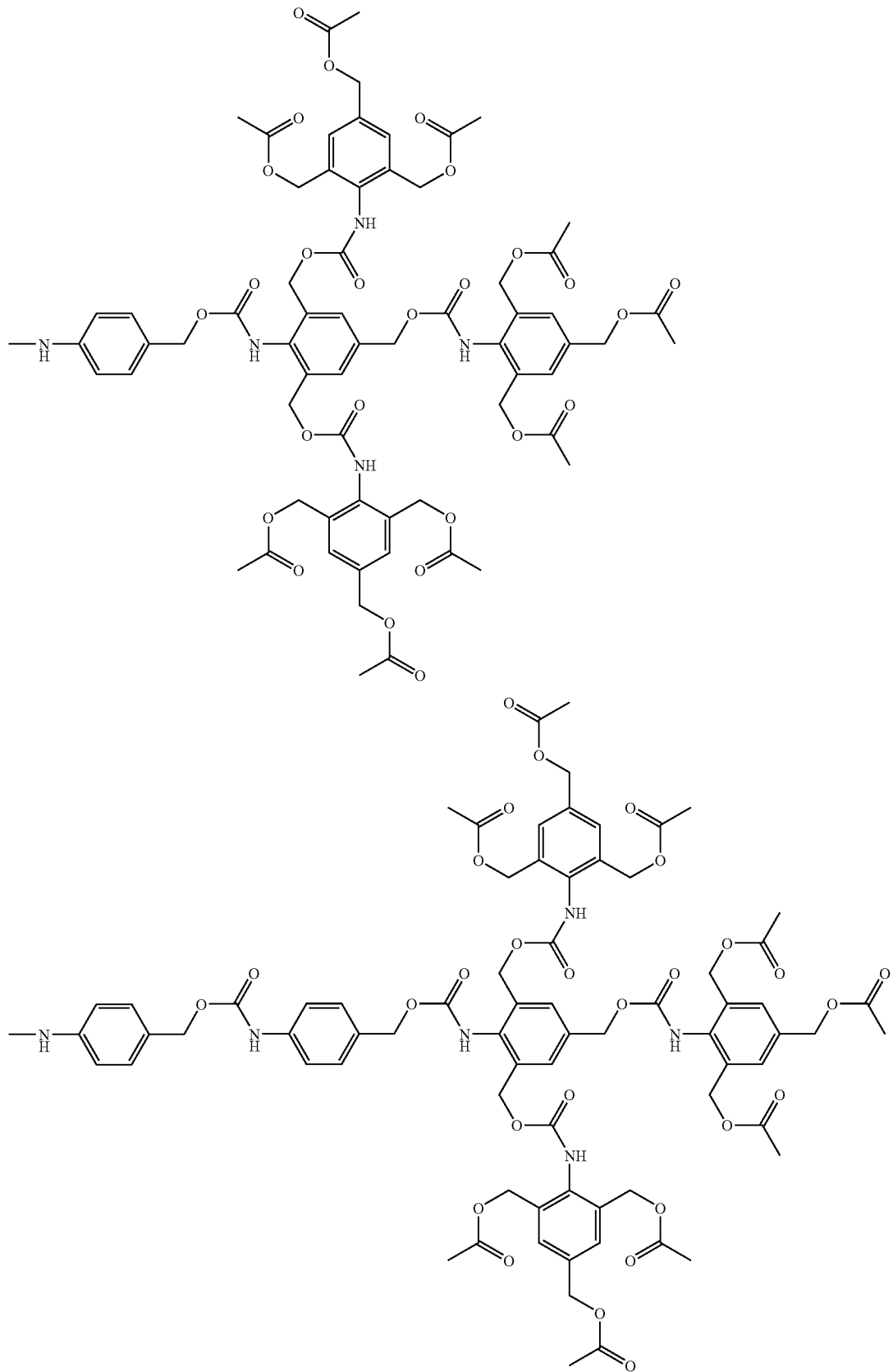

-continued
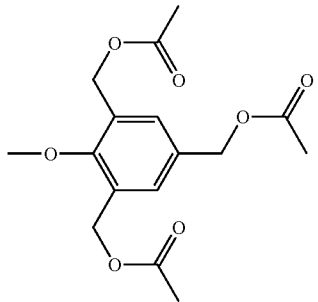
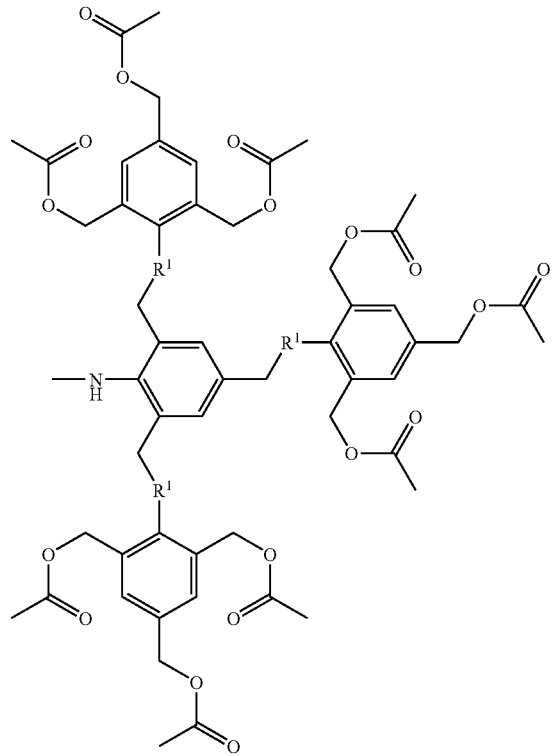
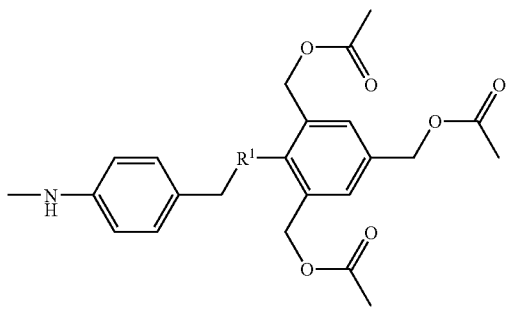
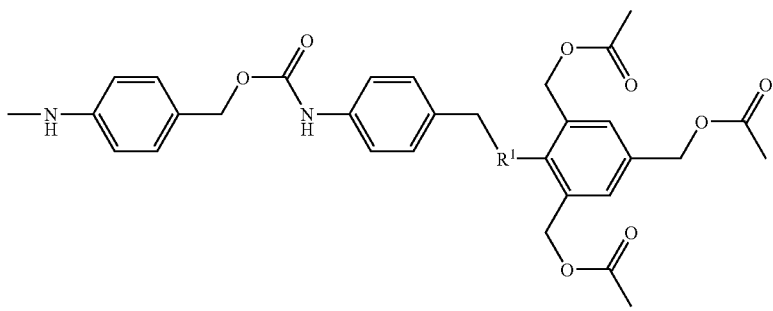

-continued
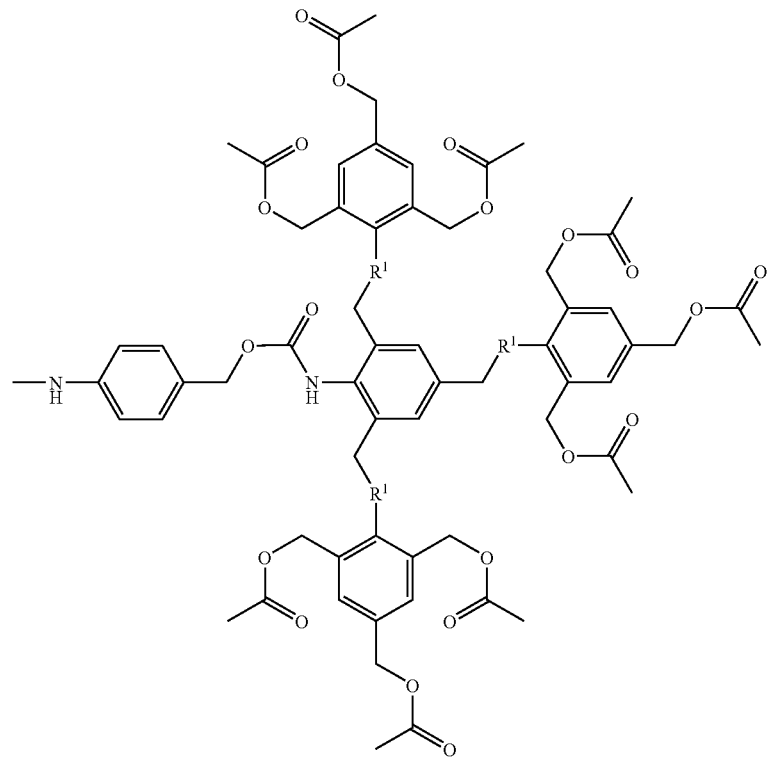
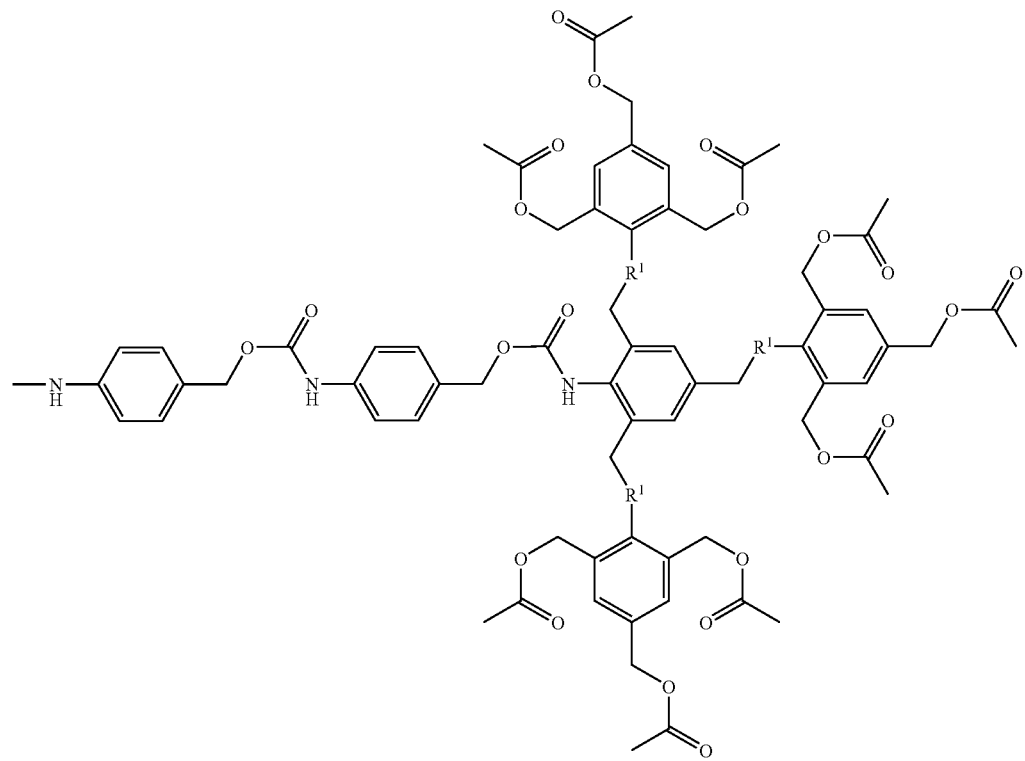

-continued
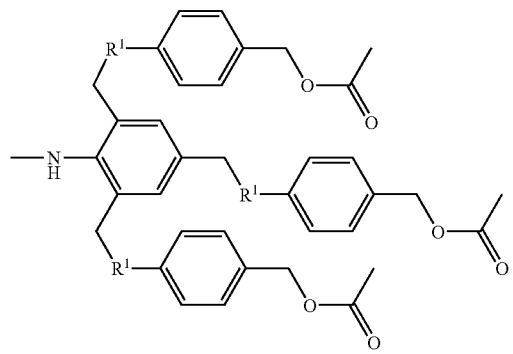
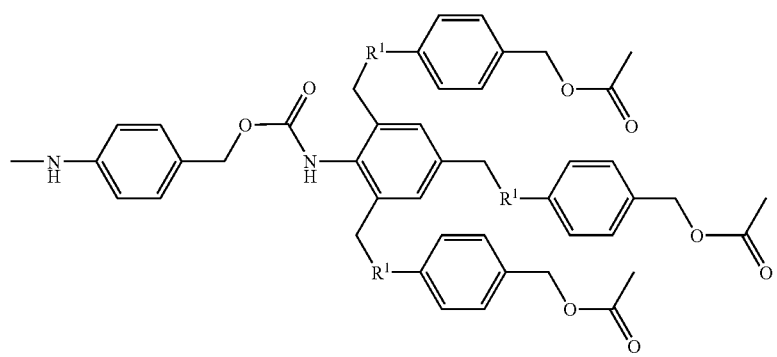
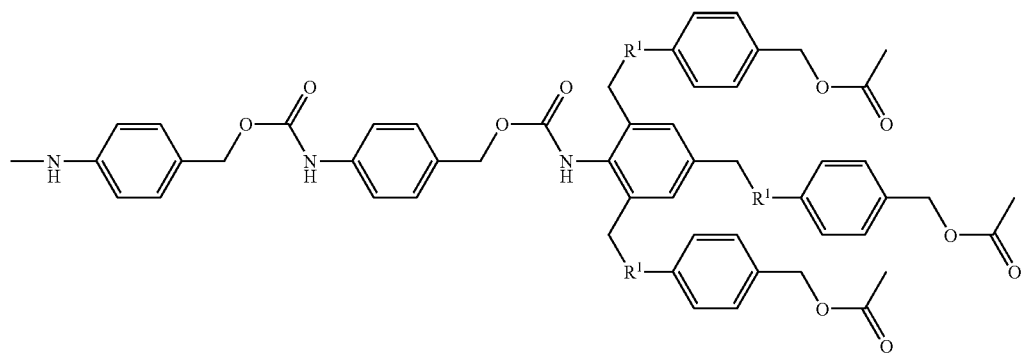

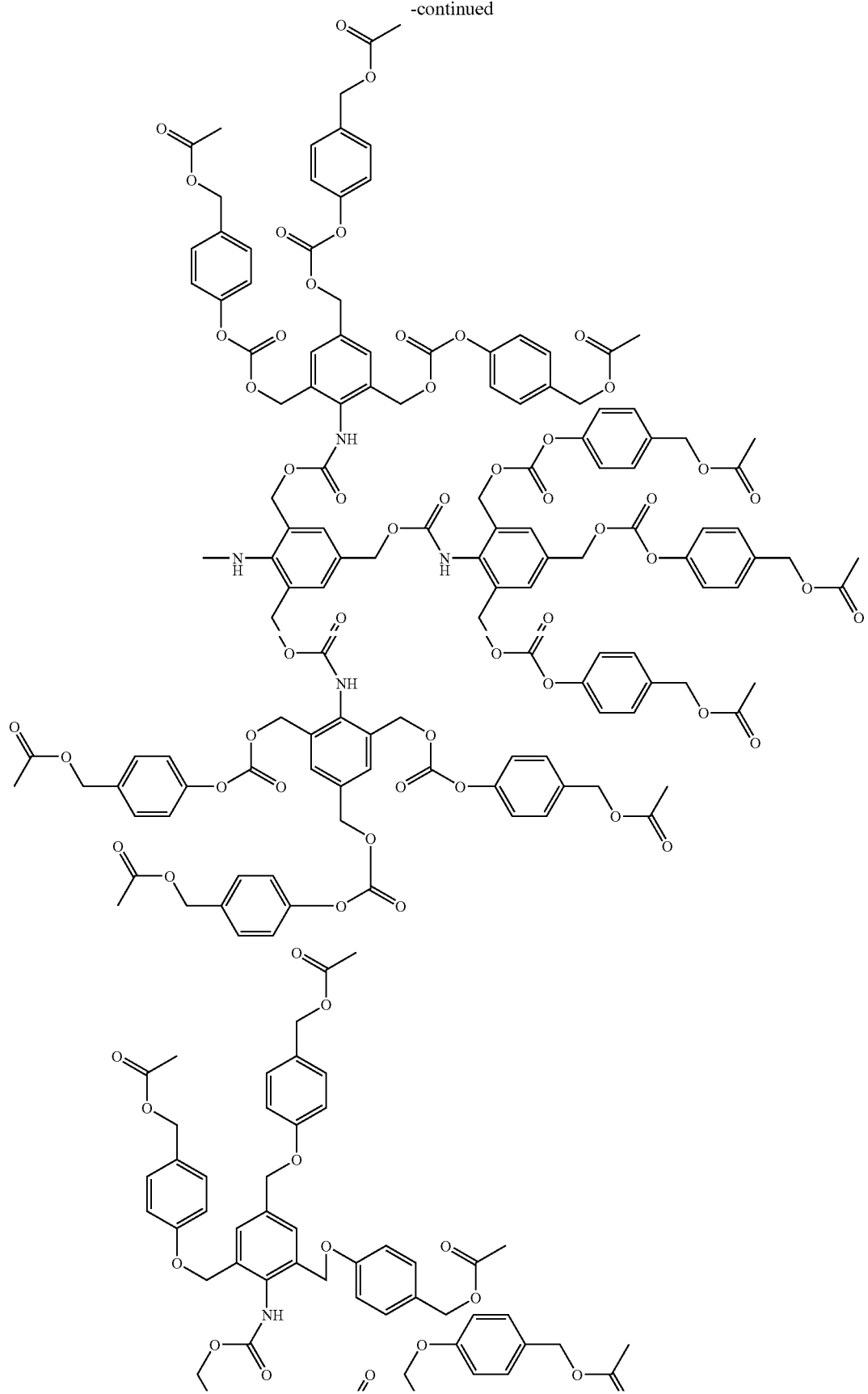

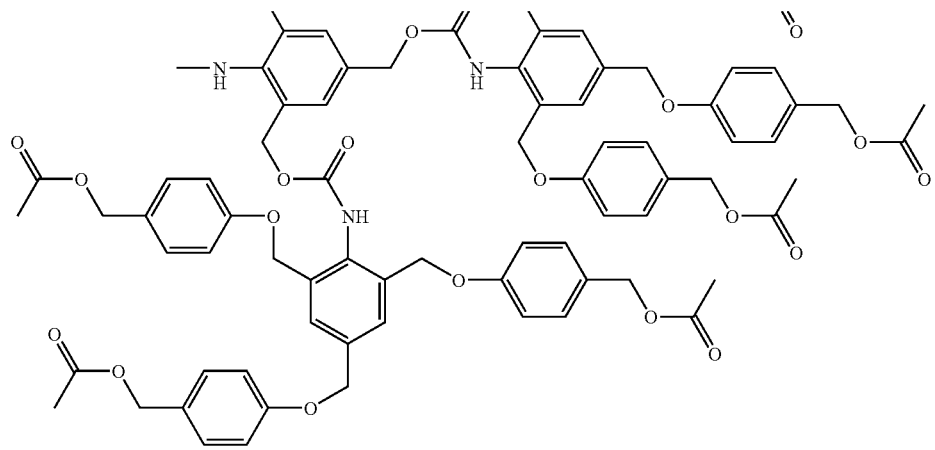
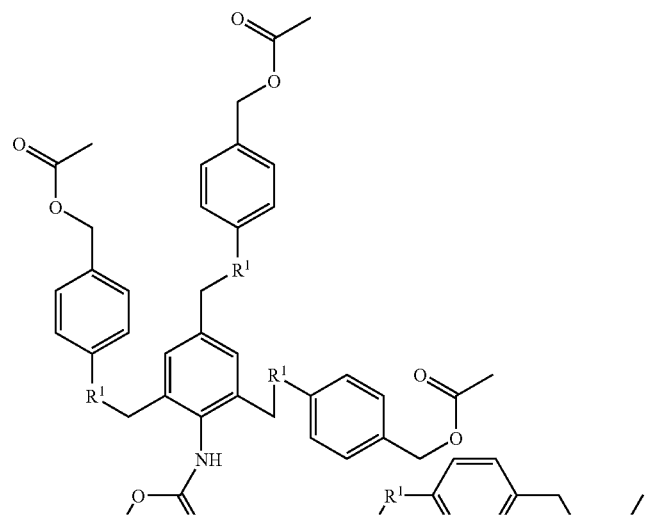
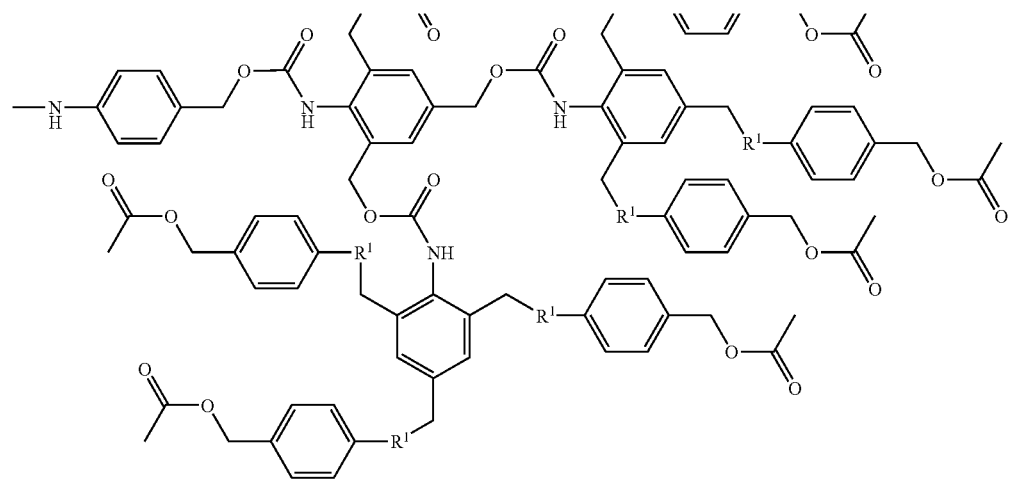

-continued
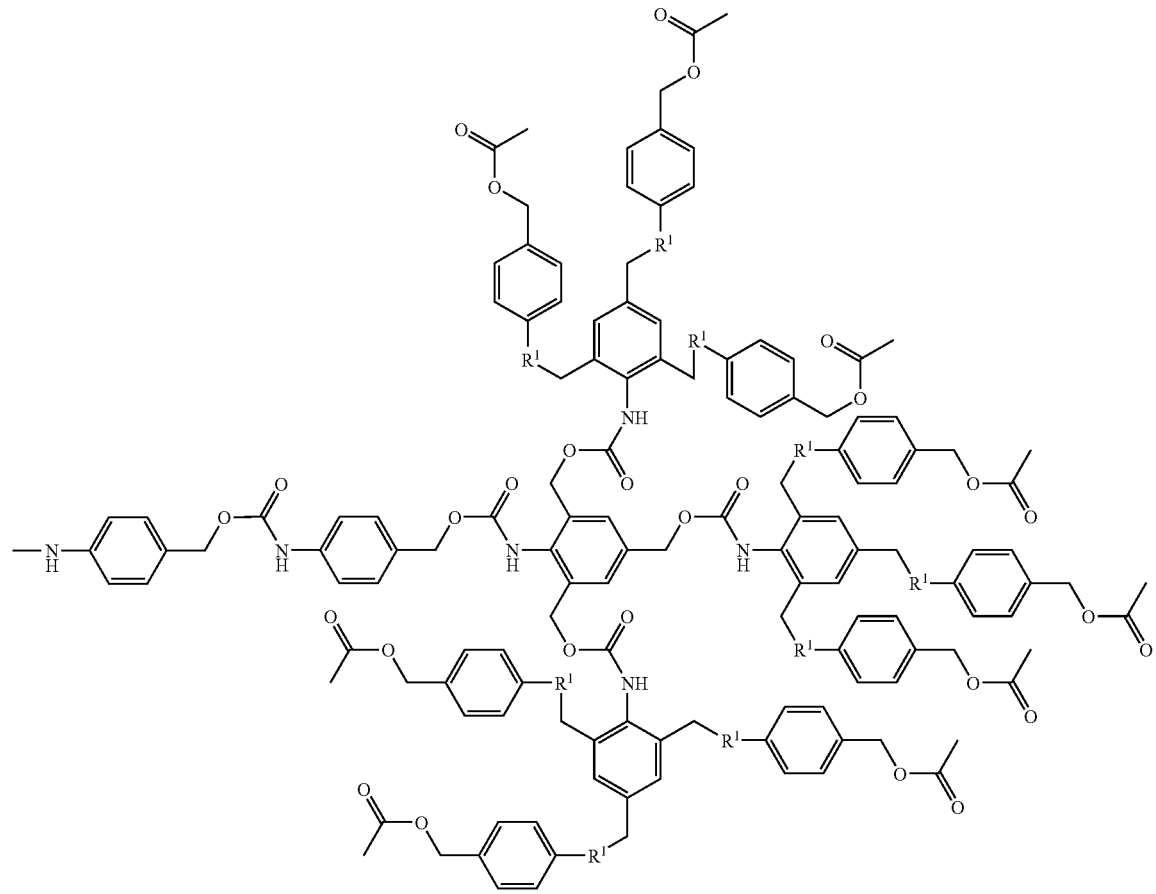
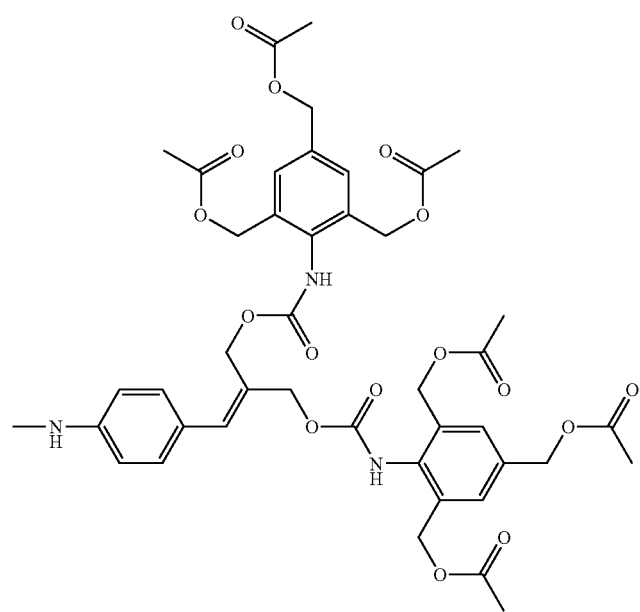

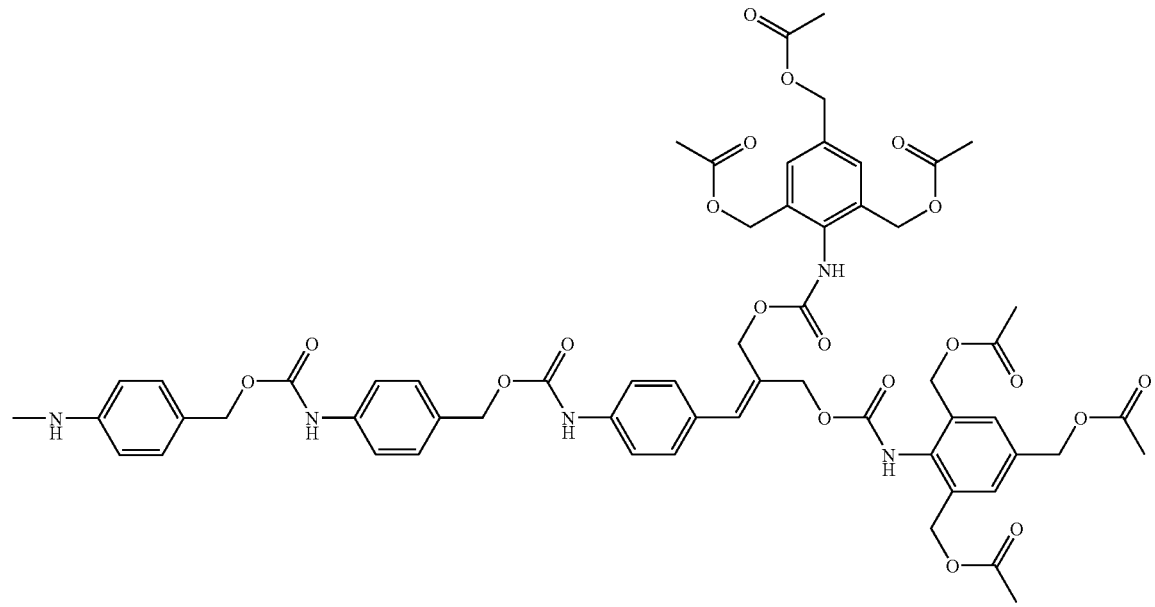
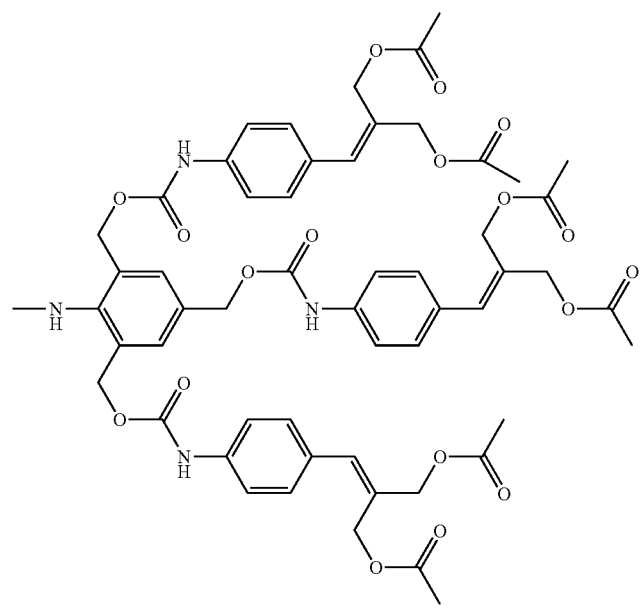

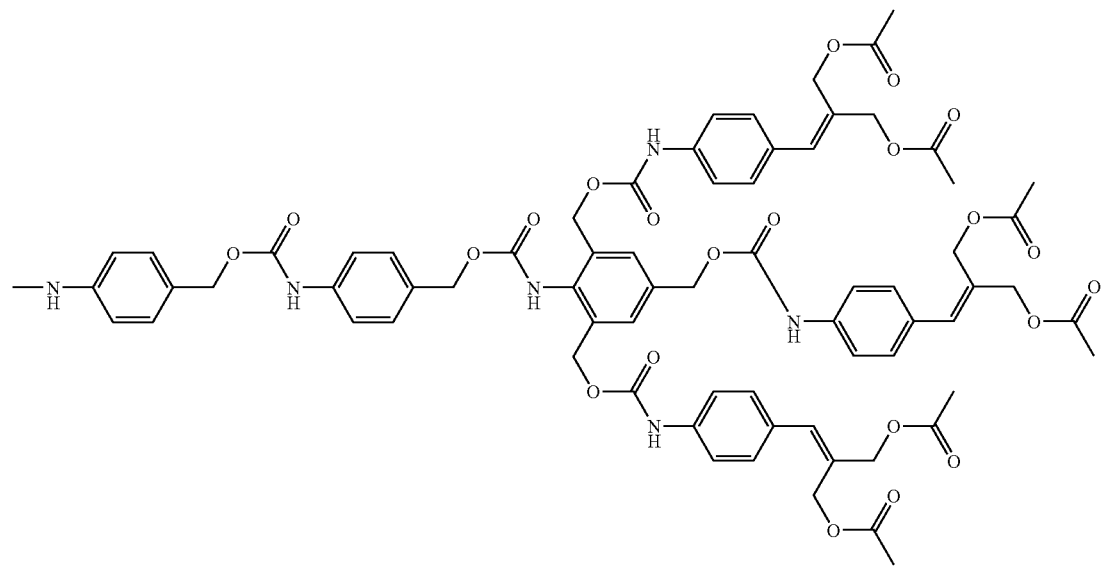
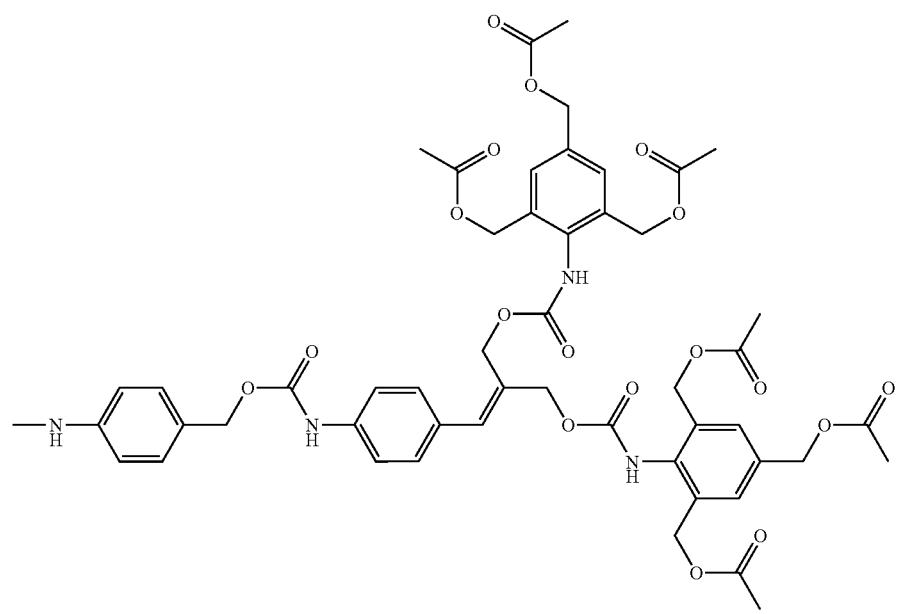

-continued
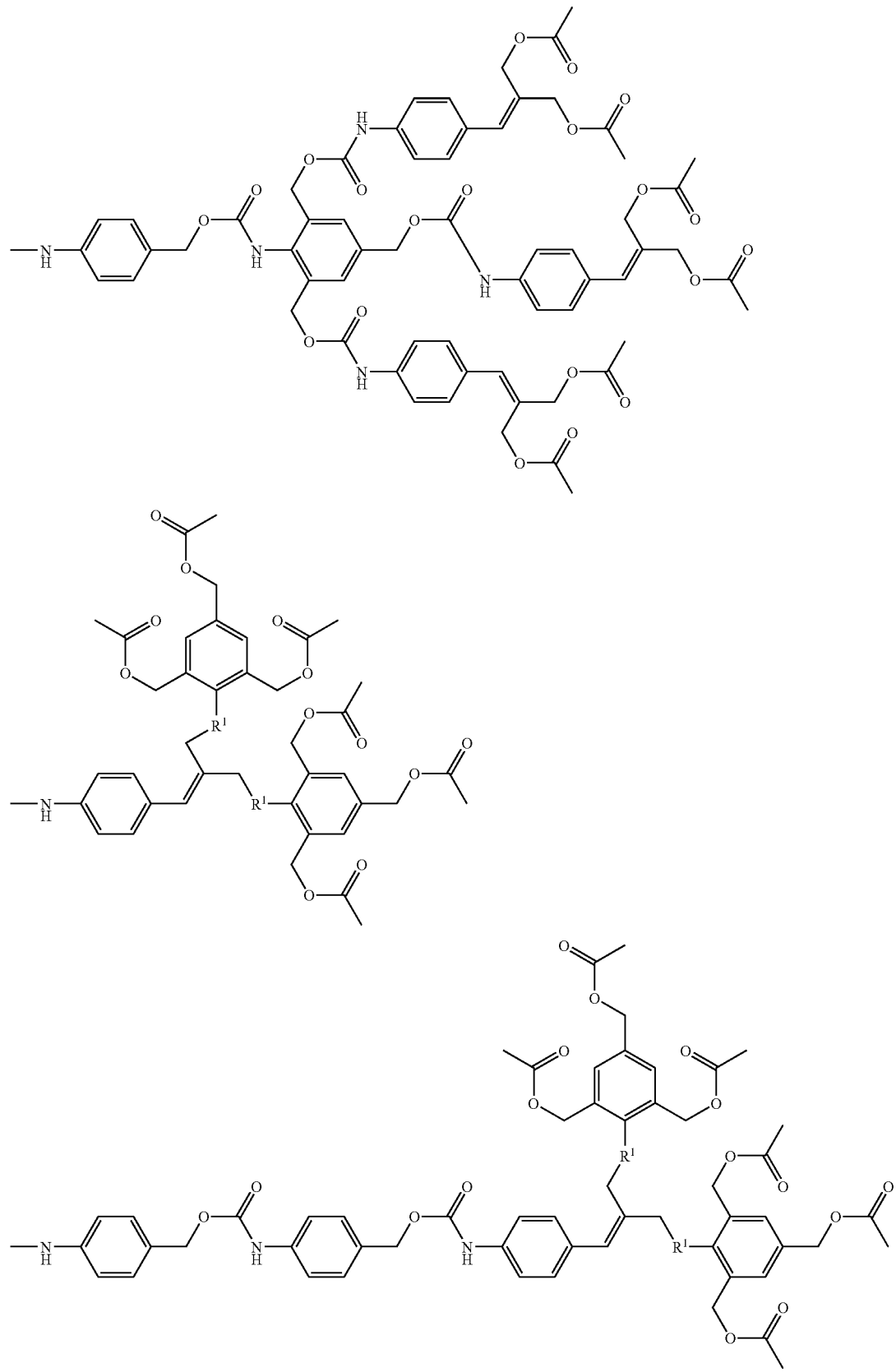

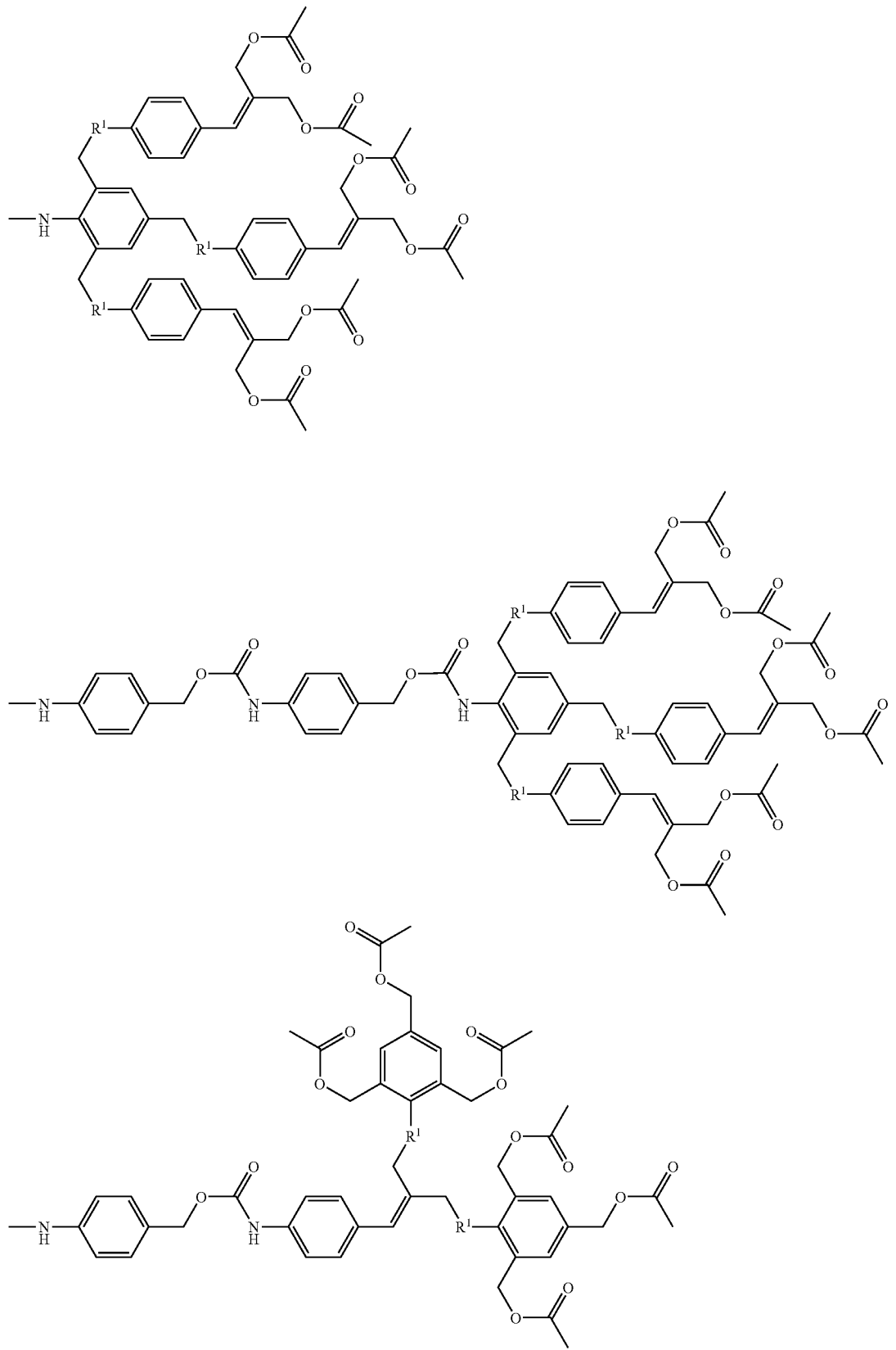

-continued
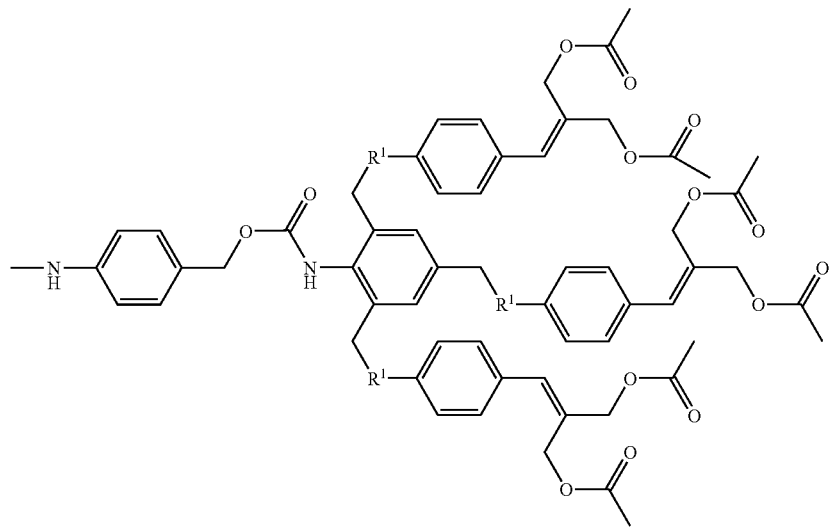
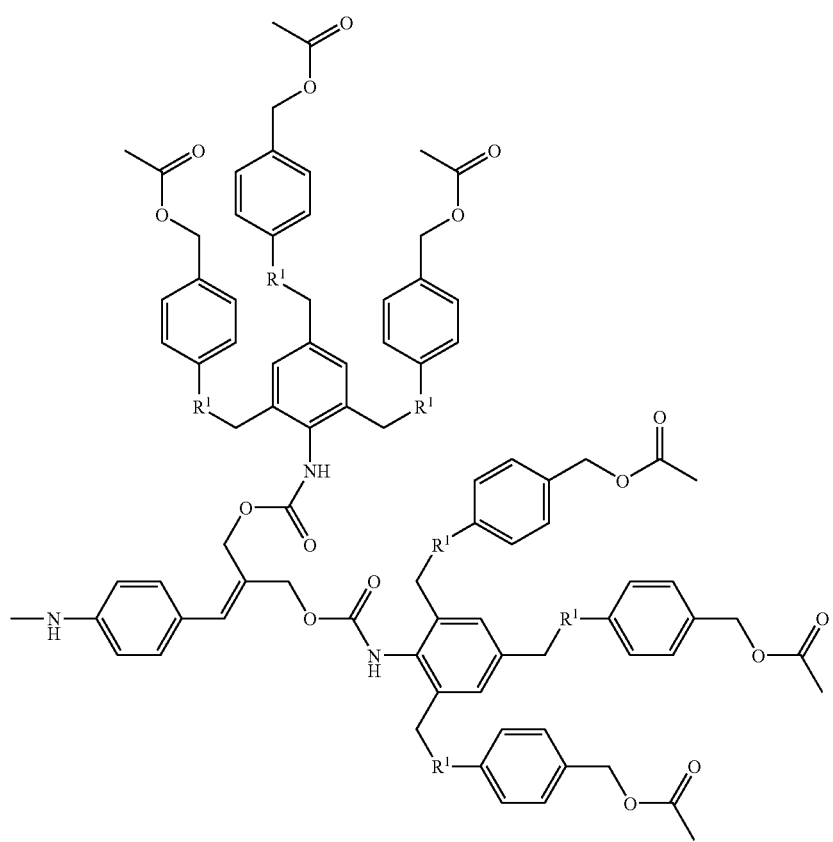

-continued
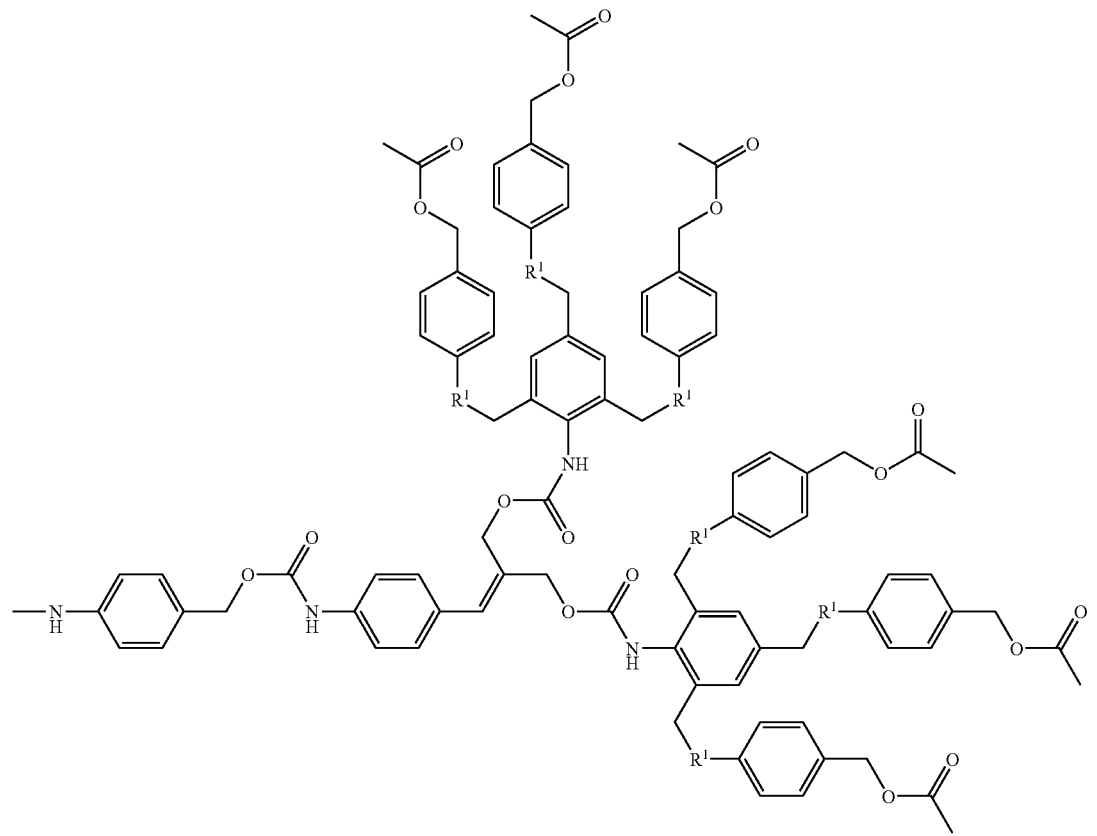
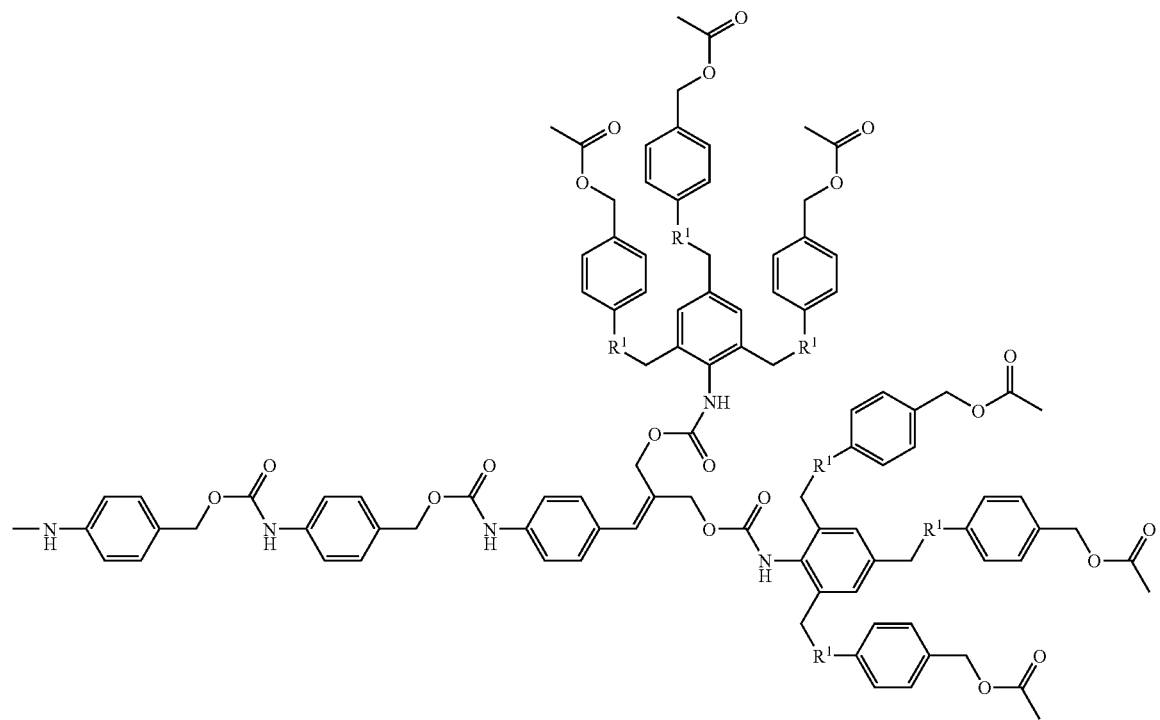

-continued
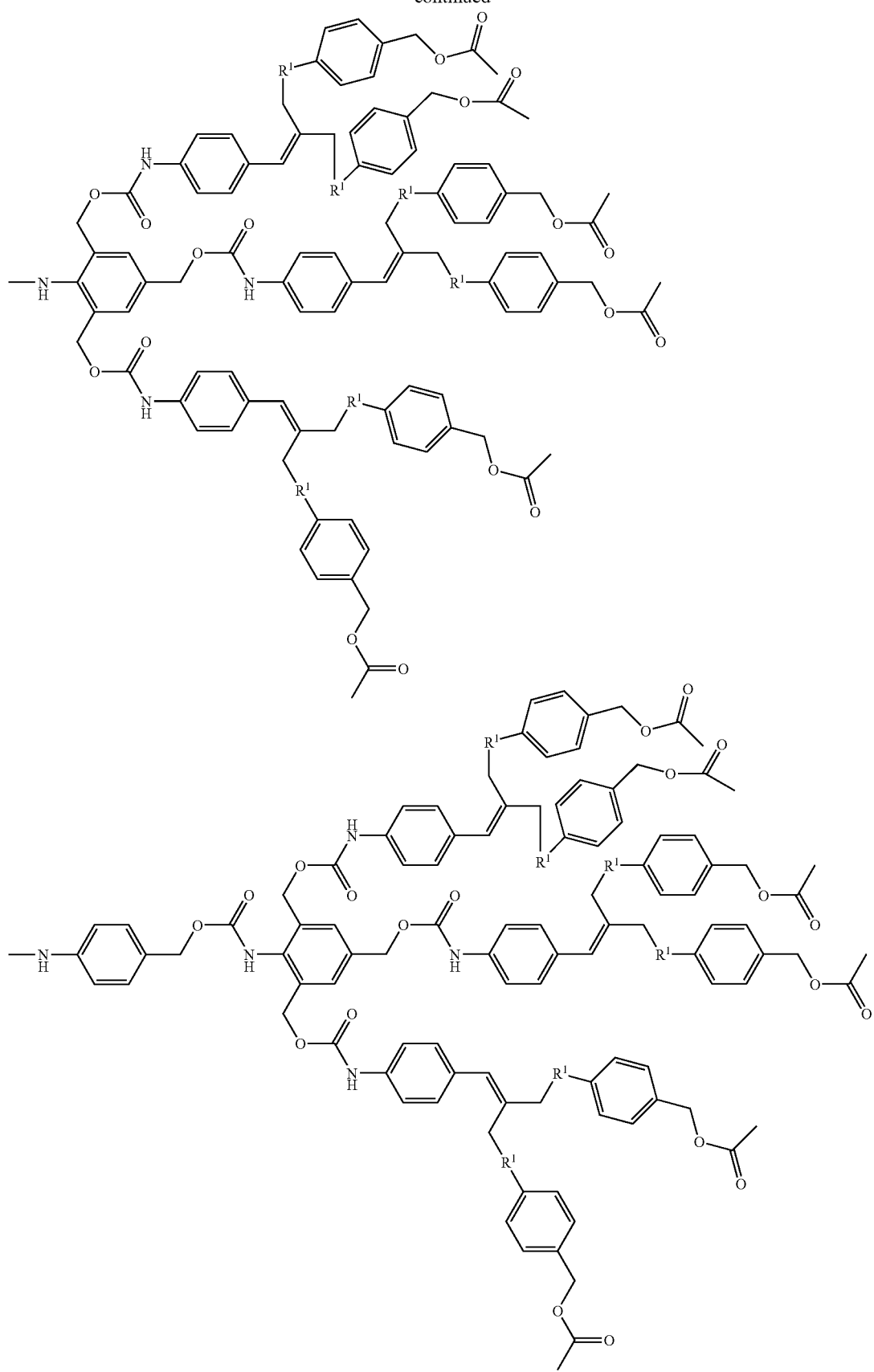

-continued

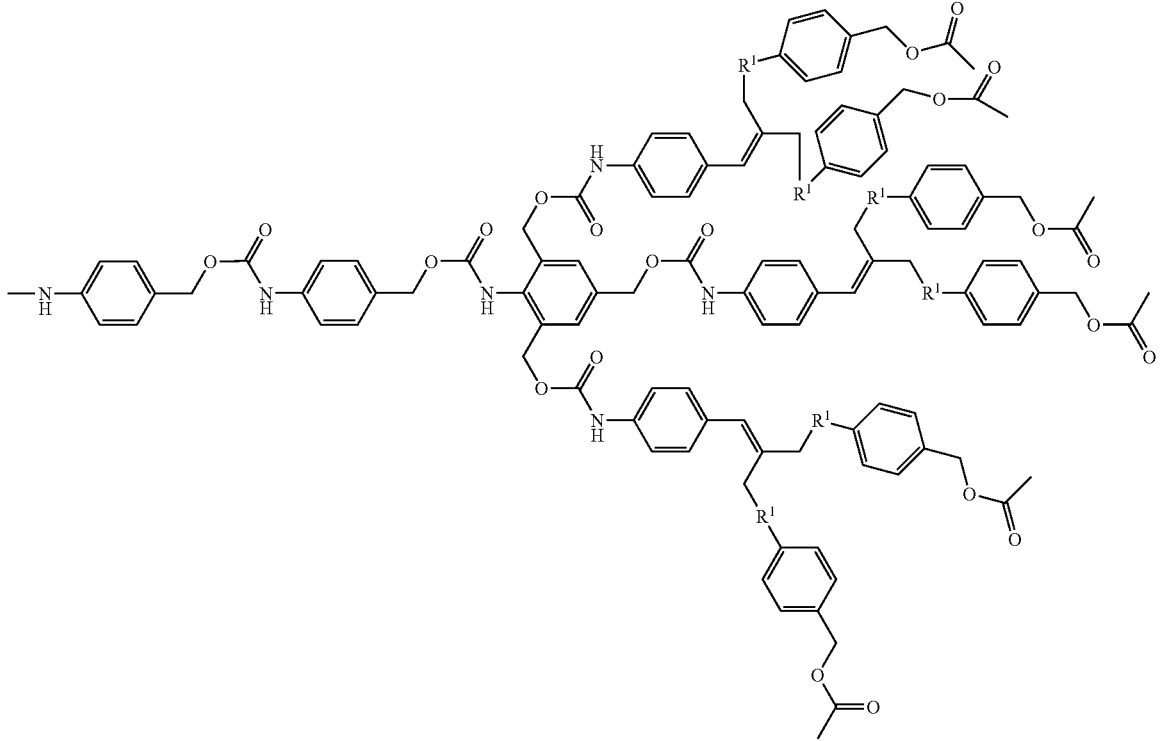

R¹ = O or OC(O)O and from the compounds depicted above wherein single release 1,6-elimination p-aminobenzyloxycarbonyl spacer(s) are replaced by single release 1,8-elimination p-aminocinnamyloxycarbonyl spacer(s).

In a further embodiment the compounds depicted in the previous paragraph further comprise ω-amino aminocarbonyl cyclization spacers A.

The invention also relates to the self-eliminating multiple release spacers or spacer systems per se as described in this invention. The invention thus relates to compounds as defined above without specifier V and with Z or S is H or OH, exemplified by for instance aminotriol 16 (FIG. 11) and aminodiol 23 (FIG. 13), extending to spacer systems comprising more than one spacer.

Also the invention relates to derivatives of the self-eliminating multiple release spacers or spacer systems per se that can be used for facilitating coupling with specifiers, leaving groups, reactive moieties or spacers. For instance an amino group may be derivatized as its isocyanate and an alcohol group may be derivatized as its p-nitrophenyl carbonate. Other derivatizations are well within the knowledge of the skilled person.

One end of the spacer or spacer system must be able to react with the specifier, for example the tripeptide that is a substrate for plasmin. Typically, this end of the spacer or spacer system is an amino group or a hydroxyl group, but it can also be another functionality. The functionalities at the other end of the linker or linker system must be able to react with the leaving group Z (the drug). Typically, these ends of the multiple release spacer or spacer system are hydroxyl groups, but they can also be other functionalities. In one embodiment, these functionalities react with the hydroxyl group of the drug to form for example carbonate linkages between linker and drug. In another embodiment, these functionalities react with the aromatic amino group of the drug to form for example N-aryl carbamate linkages between linker and drug. In again another embodiment, these functionalities react with the sulfhydryl group of the drug to form for example oxycarbonylthio linkages between linker and drug. In again another embodiment these functionalities react with the carboxylic acid group of the drug. If spacers A are included in the spacer system, typically the hydroxyl group of the drug is reacted with A to form carbamate linkages between A and Z.

In the compounds of the invention the specifier V typically contains a substrate molecule that is specifically cleaved by an enzyme present in the vicinity of or inside the target cells, for example tumor cells. More preferably, the specifier V contains a substrate that is specifically cleaved by an enzyme present at elevated levels in the vicinity of or inside the target cells as compared to other parts of the body, and most preferably the enzyme is present only in the vicinity of or inside the target cells. In an embodiment suitably the specifier V constitutes a targeting moiety in order to target the compounds to specific cells.

In the compounds of the invention, the specifier V may also contain a reactive moiety that can react with a targeting moiety that can target the resulting compounds to the target site by selective binding to a receptor or other receptive moiety associated with a given target cell population or by causing accumulation of the compounds of the invention in the vicinity of or inside the target cells by another mechanism. In case these compounds contain two or more reactive moieties S, the compounds are from hereon called "bifunctional linkers". When the compounds comprise two or more moieties Z, the compounds are from hereon called "monofunctional spacer-leaving group conjugates". Both bifunctional linkers and monofunctional spacer-leaving group conjugates can be used to prepare prodrugs of the present invention that contain a specifier with a targeting group as well as a substrate specifically cleavable at the target site, a multiple release spacer system and two or more leaving groups Z. Although in this invention spacers and spacer systems are described that are able to release multiple leaving groups, it is obvious that monofunctional spacer-leaving group conjugates and bifunctional linkers can also be designed that contain single release spacers and spacer systems, such as for example described in WO 02/83180 and EP 1243276, which are incorporated by reference.

In an aspect of the invention, the reactive moiety in V is reacted with a nucleophilic group on a targeting moiety, e.g., a thiol group, an amino group, or an aldehyde group, to form a new specifier V that contains a targeting moiety.

In a preferred aspect of the invention, the reactive moiety in V is reacted with a nucleophilic group on a protein or protein fragment, e.g., a thiol group, an amino group, or an aldehyde group, to form a new specifier V that contains a protein or a protein fragment as the targeting moiety.

In a more preferred aspect of the invention, the reactive moiety in V is reacted with a nucleophilic group on an antibody or antibody fragment, e.g., a thiol group, an amino group, or an aldehyde group, to form a new specifier V that contains an antibody or antibody fragment as the targeting moiety.

In another more preferred aspect of the invention, the reactive moiety in V is reacted with a nucleophilic group on a peptide vector or receptor-binding moiety, e.g., a thiol group, an amino group, or an aldehyde group, to form a new specifier V that contains a peptide vector or receptor-binding moiety as the targeting moiety.

In a preferred embodiment the reactive moiety in V is, without limitation,

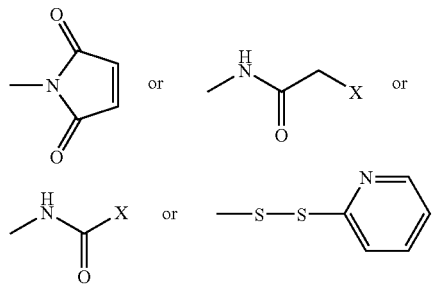

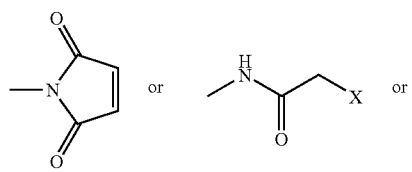

wherein X is een leaving group. These reactive moieties can be used to couple a targeting moiety having a nucleophilic group, e.g., a thiol group, to the specifier V having such a reactive moiety to form a new specifier V that contains a targeting moiety.

In a more preferred embodiment of the invention, the reactive moiety in V is, without limitation,

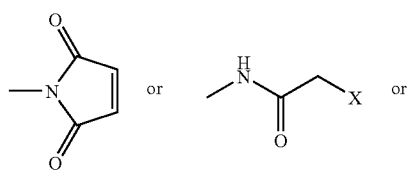

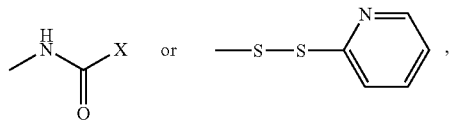

and is reacted with a nucleophilic group on a protein or protein fragment, e.g., a thiol group, to form a new specifier V that contains a protein or a protein fragment as the targeting moiety.

In another more preferred embodiment of the invention, the reactive moiety in V is, without limitation,

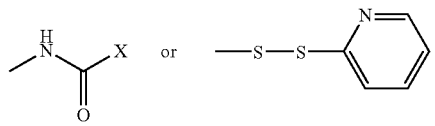

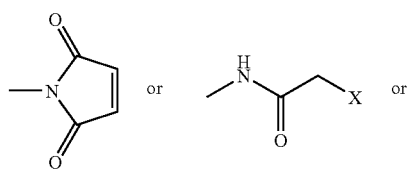

and is reacted with a nucleophilic group on an antibody or antibody fragment, e.g., a thiol group, to form a new specifier V that contains an antibody or antibody fragment as the targeting moiety.

In another more preferred embodiment of the invention, the reactive moiety in V is, without limitation,

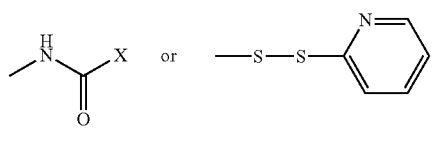

and is reacted with a nucleophilic group on a peptide vector or receptor-binding moiety, e.g., a thiol group, to form a new specifier V that contains a peptide vector or a receptor-binding moiety as the targeting moiety.

In another preferred embodiment, the reactive moiety in V is, without limitation, an activated ester such as a N-hydroxysuccinimide ester, a p-nitrophenyl ester, a pentafluorophenyl ester, and further an isothiocyanate, isocyanate, anhydride, acid chloride, sulfonyl chloride, or aldehyde. These reactive moieties can be used to couple a targeting moiety having a nucleophilic group, e.g., an amino group, to the specifier V having such a reactive moiety to form a new specifier V that contains a targeting moiety.

In a more preferred embodiment of the invention, the reactive moiety in V is, without limitation, an activated ester such as a N-hydroxysuccinimide ester, a p-nitrophenyl ester, a pentafluorophenyl ester, and further an isothiocyanate, isocyanate, anhydride, acid chloride, sulfonyl chloride, or aldehyde, and is reacted with a nucleophilic group on a protein or protein fragment, e.g., an amino group, to form a new specifier V that contains a protein or a protein fragment as the targeting moiety.

In another more preferred embodiment of the invention, the reactive moiety in V is, without limitation, an activated ester such as a N-hydroxysuccinimide ester, a p-nitrophenyl ester, a pentafluorophenyl ester, and further an isothiocyanate, isocyanate, anhydride, acid chloride, sulfonyl chloride, or aldehyde, and is reacted with a nucleophilic group on an antibody or antibody fragment, e.g., an amino group, to form a new specifier V that contains an antibody or antibody fragment as the targeting moiety.

In another more preferred embodiment of the invention, the reactive moiety in V is, without limitation, an activated ester such as a N-hydroxysuccinimide ester, a p-nitrophenyl ester, a pentafluorophenyl ester, and further an isothiocyanate, isocyanate, anhydride, acid chloride, sulfonyl chloride, or aldehyde, and is reacted with a nucleophilic group on a peptide vector or receptor-binding moiety, e.g., an amino group, to form a new specifier V that contains a peptide vector or a receptor-binding moiety as the targeting moiety.

In another preferred embodiment, the reactive moiety in V is, without limitation, an amino group or a hydrazine group. These reactive moieties can be used to couple a targeting moiety having a nucleophilic group, e.g., an aldehyde group, to the specifier V having such a reactive moiety to form a new specifier V that contains a targeting moiety.

In a more preferred embodiment of the invention, the reactive moiety in V is, without limitation, an amino group or a hydrazine group, and is reacted with a nucleophilic group on a protein or protein fragment, e.g., an aldehyde group, to form a new specifier V that contains a protein or protein fragment as the targeting moiety.

In another more preferred embodiment of the invention, the reactive moiety in V is, without limitation, an amino group or a hydrazine group, and is reacted with a nucleophilic group on an antibody or antibody fragment, e.g., an aldehyde group, to form a new specifier V that contains an antibody or antibody fragment as the targeting moiety.

In another more preferred embodiment of the invention, the reactive moiety in V is, without limitation, an amino group or a hydrazine group, and is reacted with a nucleophilic group on a peptide vector or receptor-binding moiety, e.g., an aldehyde group, to form a new specifier V that contains a peptide vector or a receptor-binding moiety as the targeting moiety.

The specifier V may also contain a moiety that targets the compounds of the invention to the target site by selective binding to a receptor or other receptive moiety associated with a given target cell population or by causing accumulation of the compounds of the invention in the vicinity of or inside the target cells by another mechanism. This targeting moiety may, for example, be bombesin, transferrin, gastrin, gastrin-releasing peptide, a molecule that specifically binds $\alpha_v\beta_3$ and/or $\alpha_v\beta_5$-integrin receptors, such as RGD-containing peptides, platelet-derived growth factor, IL-2, IL-6, a tumor growth factor, vaccinia growth factor, insulin and insulin-like growth factors I en II, an antigen-recognizing immunoglobulin or an antigen-recognizing fragment thereof, or a carbohydrate. Preferably, that antigen recognized by the immunoglobulin (or fragment thereof) is specific for the target cells, e.g. a tumor-specific antigen.

In one embodiment, the specifier V contains a di-, tri-, or oligopeptide which consists of an amino acid sequence specifically recognized and thus cleavable by a protease, for example plasmin, a cathepsin, cathepsin B, prostate-specific antigen (PSA), urokinase-type plasminogen activator (u-PA), or a member of the family of matrix metalloproteinases, present in the vicinity of or inside the target cells, for example tumor cells. Typically, the specifier V contains a substrate for the serine protease plasmin.

In another embodiment, V contains a substrate for one or more of the cathepsins, typically cathepsin B. In again another embodiment, V contains a β-glucuronide that is specifically recognized by β-glucuronidase present in the vicinity of or inside tumor cells. In again another embodiment the specifier is [O], yielding for example a nitro group that can be reduced under hypoxic conditions or by nitroreductases. In another embodiment V is a nitro-(hetero)aromatic moiety, for example nitrobenzyloxycarbonyl. After reduction of the nitro group or removal of the nitro-aromatic specifier, elimination of the spacers or spacer systems described in this invention leads to drug release. It can be understood that any specifier that is specifically cleaved following recognition by a disease-specific and/or organ-specific and/or specifically targeted enzynme and/or receptor can be incorporated into conjugates and prodrugs that contain the spacers or spacer systems claimed in this invention.

In one embodiment the invention relates to a compound wherein the specifier V contains a tripeptide. Preferably the tripeptide is linked via its C-terminus to the self-eliminating multiple release spacer or spacer system. More preferably the C-terminal amino acid residue of the tripeptide is selected from arginine and lysine, the middle amino acid residue of the tripeptide is selected from alanine, valine, leucine, isoleucine, methionine, phenylalanine, cyclohexylglycine, tryptophan and proline, and the N-terminal amino acid residue of the tripeptide is selected from a D-amino acid residue and a protected L-amino acid residue including protected glycine.

In a further embodiment the specifier V is selected from D-alanylphenylalanyllysine, D-valylleucyllysine, D-alanylleucyllysine, D-valylphenylalanyllysine, D-valyltryptophanyllysine and D-alanyltryptophanyllysine.

It should be noted that specifier V, either in the form of a di-, tri-or oligopeptide, or in any other form, may contain protective groups. Such compounds comprising protected specifier V may not, when contacted with for instance specifier specific enzymes, release the leaving groups. However, when deprotected and suitably activated such compounds will release leaving groups and thus such compounds comprising protected specifier V also fall under the scope of this invention. In particular the above can be envisaged in relation to the bifunctional or monofunctional compounds V—(W—)$_w$(X—)$_x$C((A-)$_a$S)$_c$, V—(W—)$_w$(X—)$_x$C(D((A-)$_a$S)$_d$)$_c$, V—(W—)$_w$(X—)$_x$C(D(E((A-)$_a$S)$_e$)$_d$)$_c$, V—(W—)$_w$(X—)$_x$C(D(E(F((A-)$_a$S)$_f$)$_e$)$_d$)$_c$ V—(W—)$_w$(X—)$_x$C((A-)$_a$Z)$_c$, V—(W—)$_w$(X—)$_x$C(D((A-)$_a$Z)$_d$)$_c$, V—(W—)$_w$(X—)$_x$C(D(E((A-)$_a$Z)$_e$)$_d$)$_c$, and V—(W—)$_w$(X—)$_x$C(D(E(F((A-)$_a$Z)$_f$)$_e$)$_d$)$_c$ mentioned earlier. Suitable protective groups for chemical functional groups, in particular for amino acids, are well known to the organic chemist and may for example be found in T. W. Greene, Protective Groups in Organic Synthesis, John Wiley & Sons, New York, 1981.

In yet a further embodiment the invention relates to a compound wherein the specifier V is an amino-terminal capped peptide covalently linked via the C-terminus to the self-eliminating multiple release spacer or spacer system. Preferably the specifier V is selected from benzyloxycarbonylphenylalanyllysine, benzyloxycarbonylvalyllysine, D-phenylalanylphenylalanyllysine, benzyloxycarbonylvalylcitrulline, tert-butyloxycarbonylphenylalanyllysine, benzyloxycarbonylalanylarginylarginine, benzyloxycarbonylphenylalanyl-N-tosylarginine, 2-aminoethylthiosuccinimidopropionylvalinylcitrulline, 2-aminoethylthiosuccinimidopropionyllysylphenylalanyllysine, acetylphenylalanyllysine, and benzyloxycarbonylphenylalanyl-O-benzoylthreonine.

The moiety Z is preferably a therapeutic or diagnostic moiety, but it can also be a hydrogen or OH group or a reactive moiety. A H or OH group or a reactive moiety may be accidentally introduced in a final conjugate during its synthesis, in case final coupling of leaving groups to the multiple release spacer or spacer system does not proceed completely. H or OH groups will not act as leaving group, but are not expected to inhibit elimination of leaving groups Z.

Z can for instance be an anticancer drug, an antibiotic, an anti-inflammatory agent, or an anti-viral agent. Typically, the moiety Z is an anticancer drug. Preferably the anticancer drug is the hydroxyl containing etoposide, camptothecin, irinotecan (CPT-11), SN-38, topotecan, 9-aminocamptothecin, 9-nitrocamptothecin, 10-hydroxycamptothecin, GG211, lurtotecan, combrestatin, paclitaxel, docetaxel, esperamycin, 1,8-dihydroxy-bicyclo[7.3.1]trideca-4-ene-2,6-diyne-13-one, anguidine, doxorubicin, morpholine-doxorubicin, N-(5, 5-diacetoxypentyl) doxorubicin, daunorubicin, epirubicin, idarubicin, mitoxantrone, vincristine, vinblastine, tallysomycin, bleomycin, 4-bis(2-chloroethyl)aminophenol, 4-bis(2-fluoroethyl)aminophenol, and derivatives thereof.

The anticancer drug can also be the sulfhydryl containing esperamicin, 6-mercaptopurine, or derivatives thereof. The anticancer drug can also be the carboxyl containing methotrexate, aminopterin, camptothecin (ring-opened form of the lactone), chlorambucil, melphalan, butyric acid and retinoic acid, and derivatives thereof. The anticancer drug can also be the aziridine amino containing or aromatic amino containing mitomycin C, nitomycin A, an anthracycline derivative containing an amine functionality with sufficient leaving group ability, mitoxantrone, 9-aminocamptothecin, methotrexate, aminopterin, tallysomycin, bleomycin, actinomycin, N,N-bis (2-chloroethyl)-p-phenylenediaamine, N,N-bis(2-fluoroethyl)-p-phenylenediamine, deoxycytidine, cytosine arabinoside, gemcitabine, and derivatives thereof.

The anticancer drug can also be the aliphatic amino-containing daunorubicin, doxorubicin, epirubicin, idarubicin, N-(5,5-diacetoxypentyl)doxorubicin, an anthracycline, N$^8$-acetyl spermidine, 1-(2-chloroethyl)-1,2-dimethanesulfonyl hydrazine, or derivatives thereof.

In one embodiment Z is selected from paclitaxel, docetaxel, or a derivative thereof, which is coupled to the self-eliminating multiple release spacer or spacer system via its 2'-hydroxyl group. In a further embodiment Z is selected from camptothecin, irinotecan (CPT-11), SN-38, topotecan, 9-aminocamptothecin, 9-nitrocamptothecin, 10-hydroxycamptothecin, GG211, lurtotecan, or a derivative thereof, which is coupled to the self-eliminating multiple release spacer or spacer system via its 20-hydroxyl group. In yet a further embodiment Z is selected from SN-38, topotecan, 10-hydroxycamptothecin, etoposide, 4-bis(2-chloroethyl) aminophenol, 4-bis(2-fluoroethyl)aminophenol, combrestatin, or a derivative thereof, which is coupled to the self-eliminating multiple release spacer or spacer system via its phenolic hydroxyl group. In a further embodiment Z is selected from 9-amminocamptothecin, N,N-bis(2-chloroethyl)-p-phenylenediamine, N,N-bis(2-fluoroethyl)-p-phenylenediamine, or a derivative thereof, which is coupled to the self-eliminating multiple release spacer or spacer system via its aromatic primary amine group. In yet a further embodiment Z is selected from doxorubicin, daunorubicin, epirubicin, idarubicin, or a derivative thereof, which is coupled to the self-elimination multiple release spacer (system) via its aliphatic amino group, provided that at least one generation of the multiple release spacer system, preferably the highest generation, contains phenol- or thiophenol based spacers.

The moiety S is a reactive moiety that enables coupling of moieties Z to the multiple release spacer (system). When the moiety S is connected via a carbonyl group to the multiple release spacer or spacer system, suitable S moieties include, without limitation, N-succinimidyl-N-oxide, p-nitrophenoxide, pentafluorophenoxide, carboxylates, halides, and sulfonates. When the moiety S is directly connected to the methylene group of the multiple release spacer system, suitable S moieties include, without limitation, halides and sulfonates. The moiety S may also be H or OH, in which case coupling to Z occurs by in situ conversion of S to a reactive moiety which is then substituted by Z in the same reaction mixture.

The compounds of the invention that contain two or more moieties S can be used to prepare the compounds of the invention that contain two or more moieties Z. When the compounds of the invention that contain two or more moieties S contain a specifier V that also contains a reactive moiety, the compounds have been named bifunctional linkers. When the compounds of the invention that contain two or more moieties S contain a specifier V that does not contain a reactive moiety, the compounds are from hereon called "monofiuctional specifier-spacer conjugates". Although in this invention spacers and spacer systems are described that are able to release multiple leaving groups, it is obvious that monofunctional specifier-spacer conjugates and bifunctional linkers can also be designed that contain single release spacers and spacer systems, such as for example described in WO 02/83180 and EP 1243276, which are incorporated by reference.

Preferred compounds according to the invention are those selected from the group consisting of

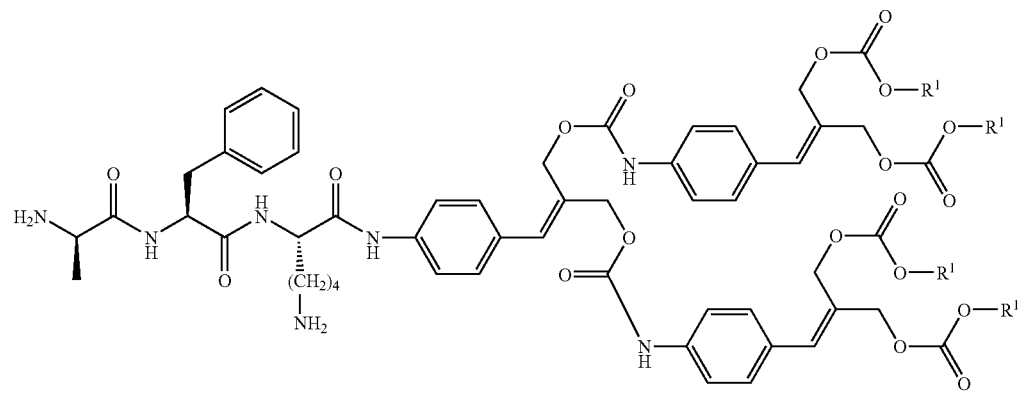
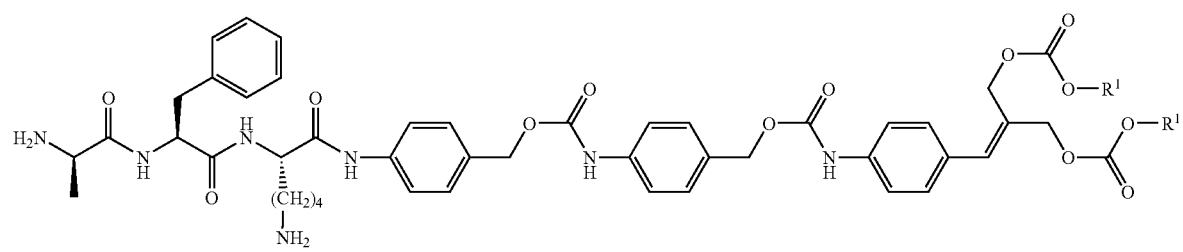
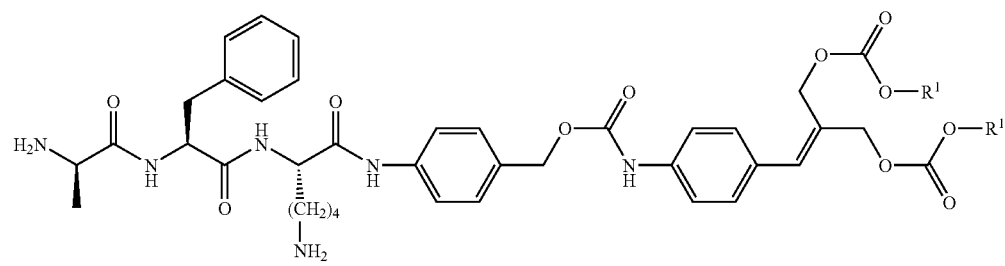
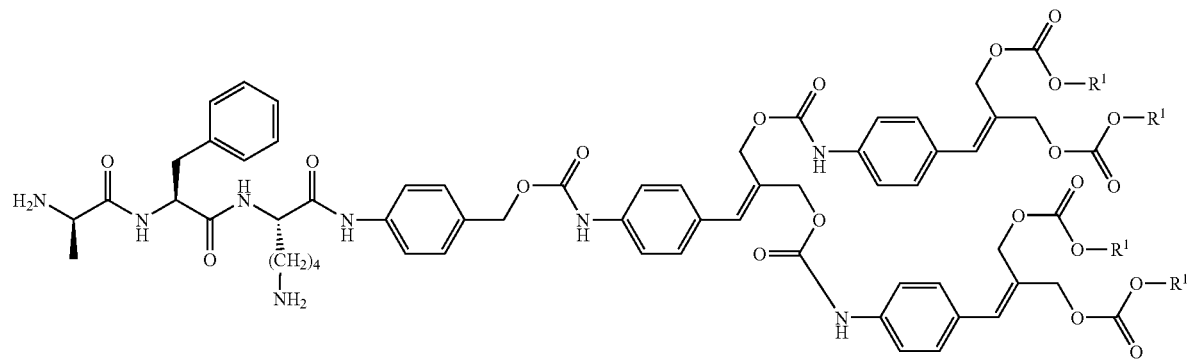
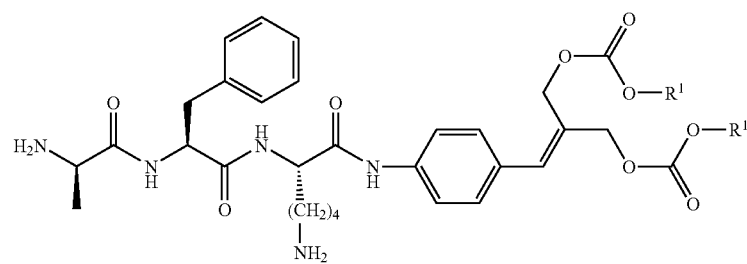

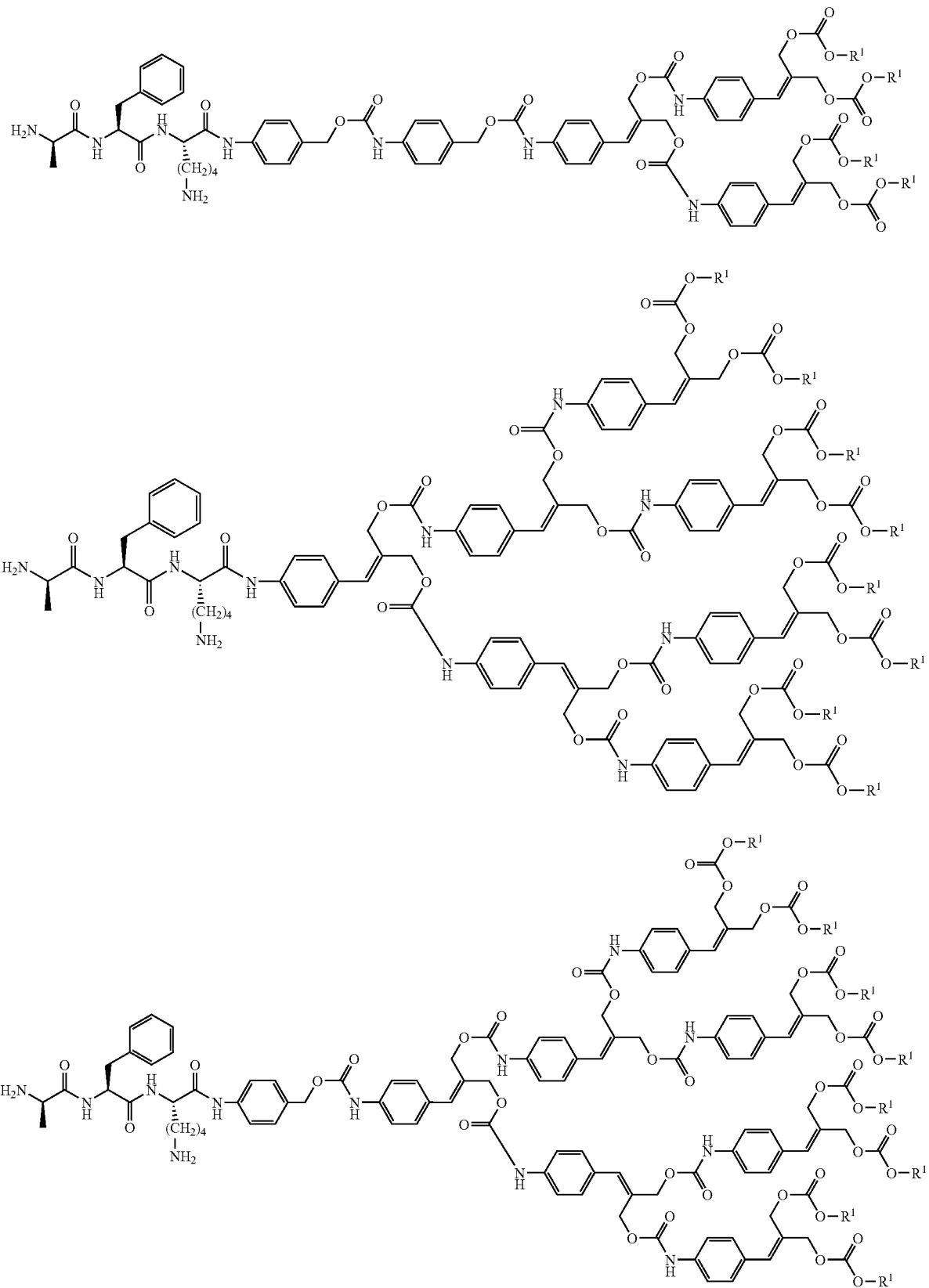

-continued
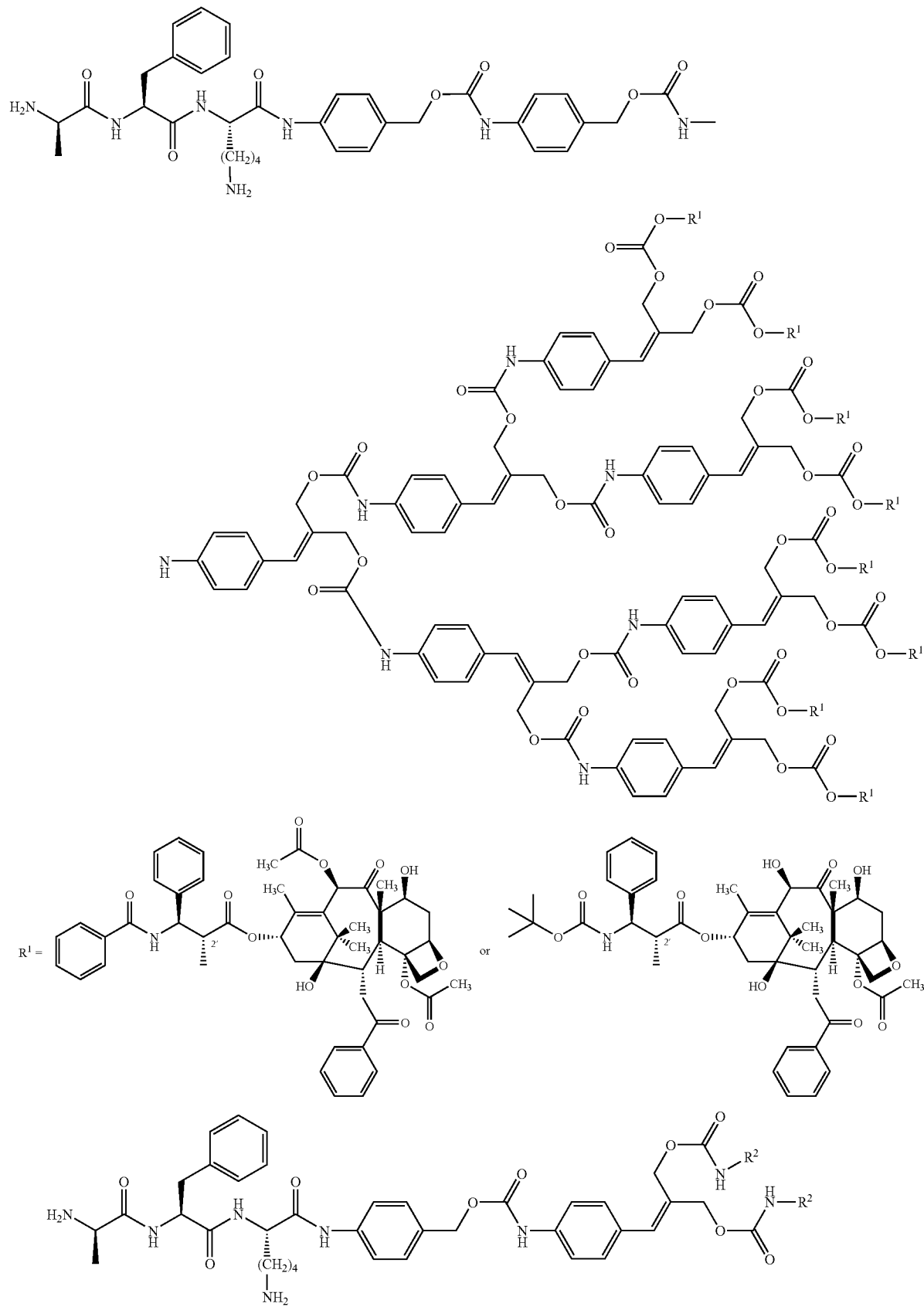

-continued
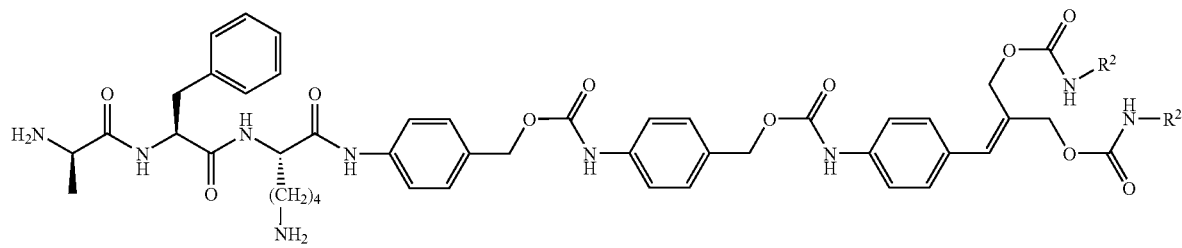
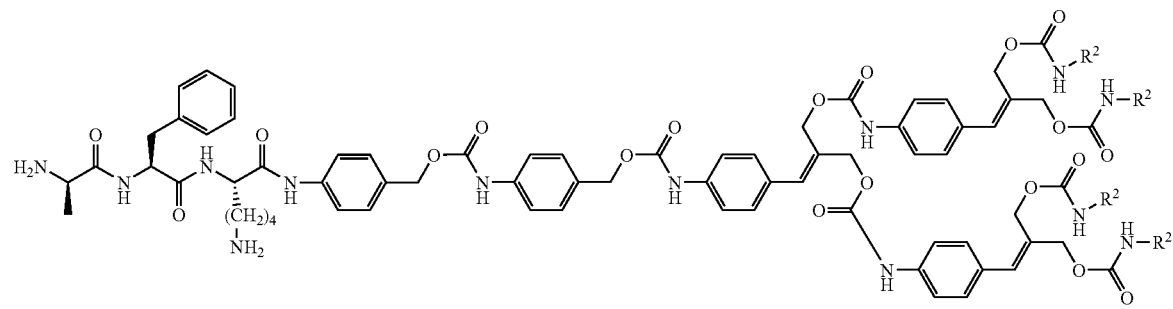
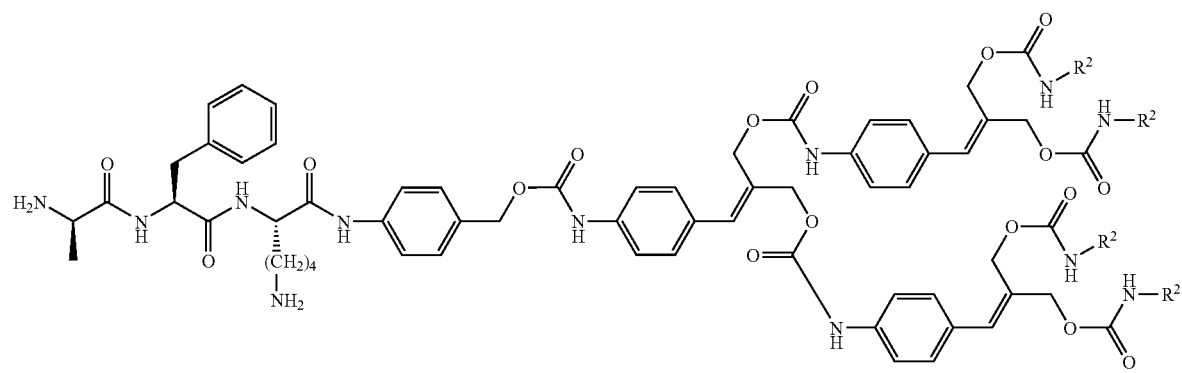
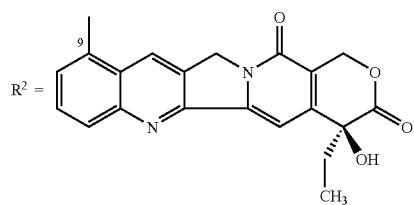
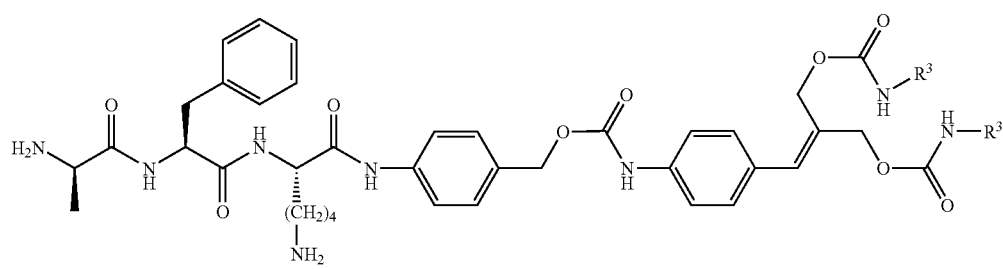
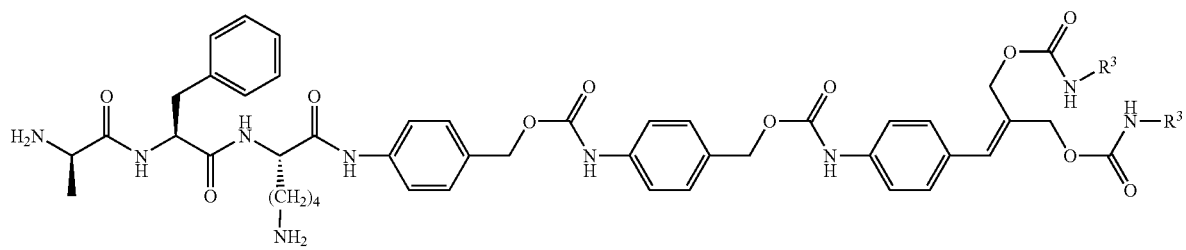

-continued
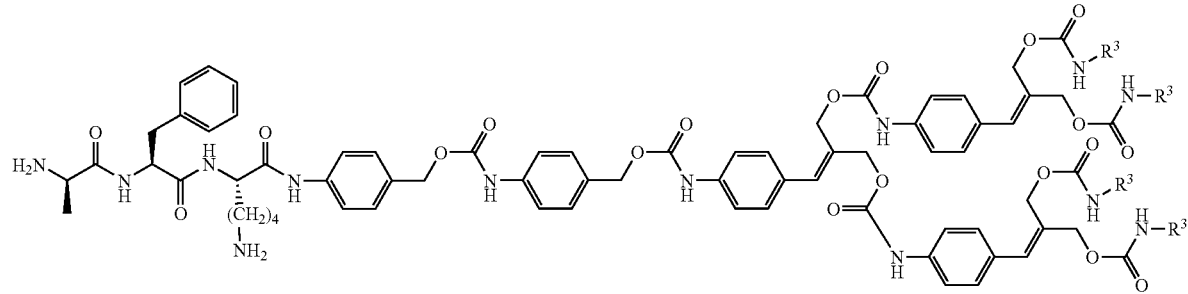
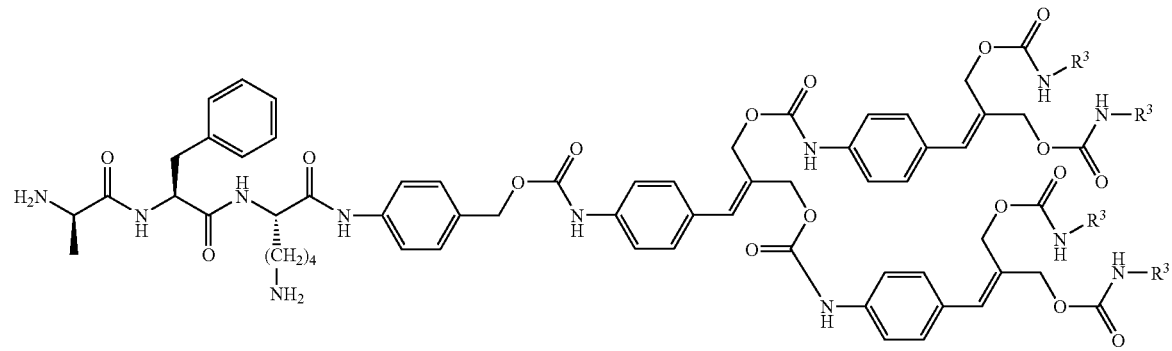
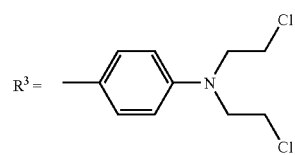
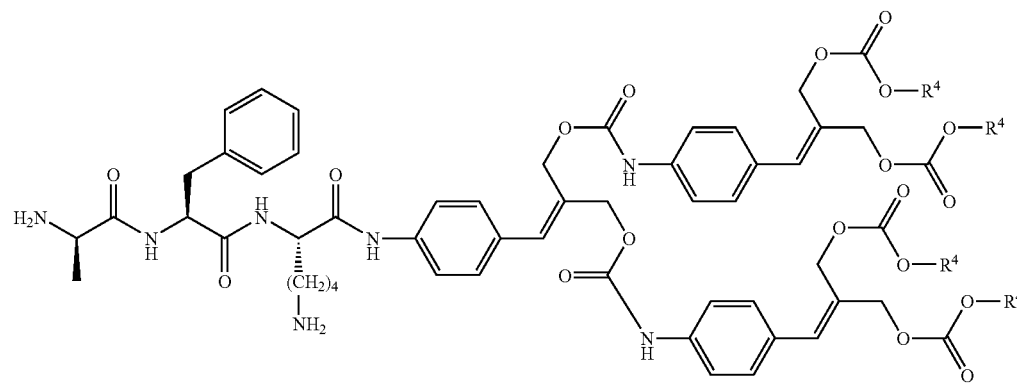
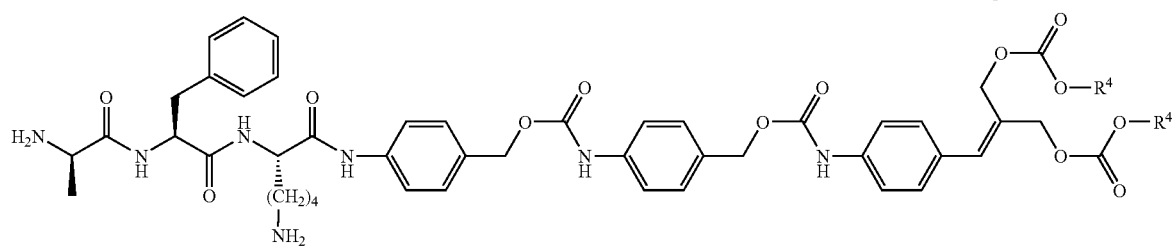
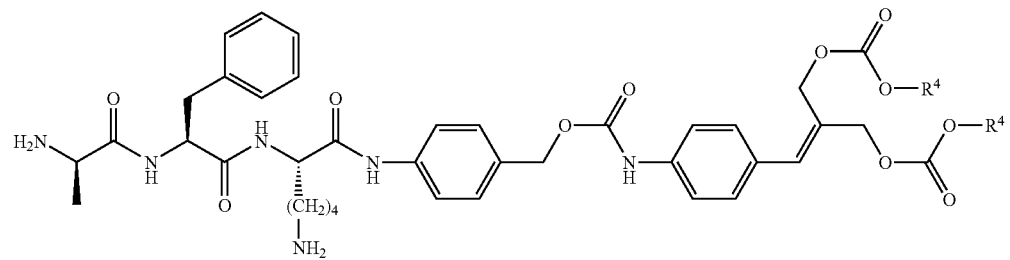

-continued
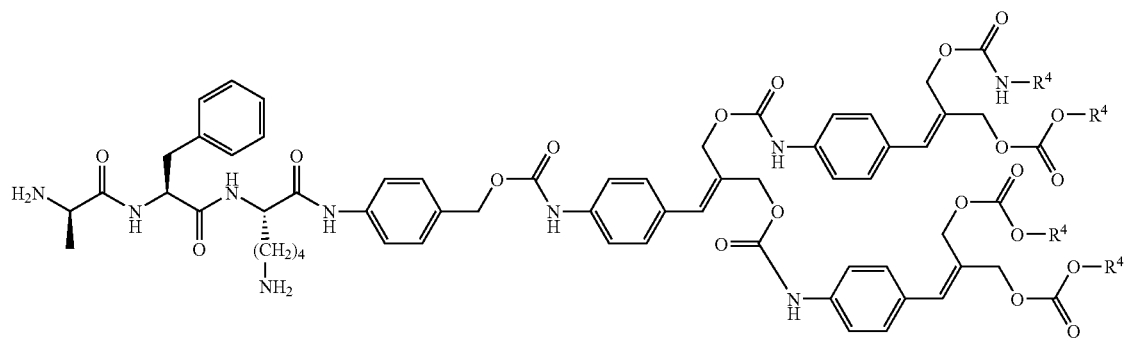
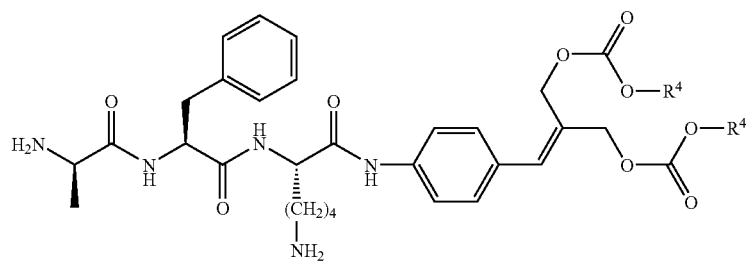
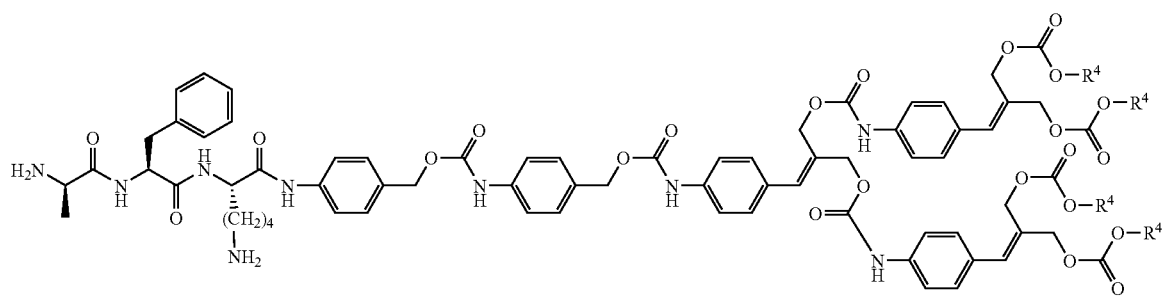
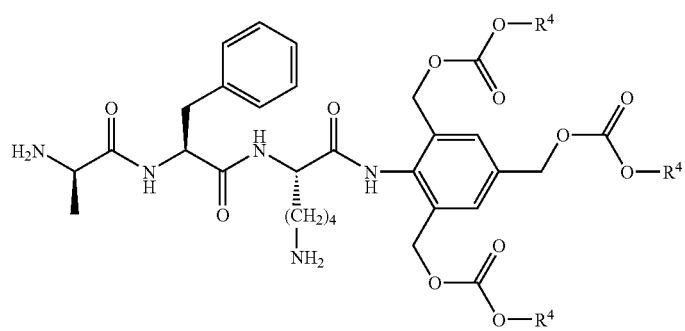
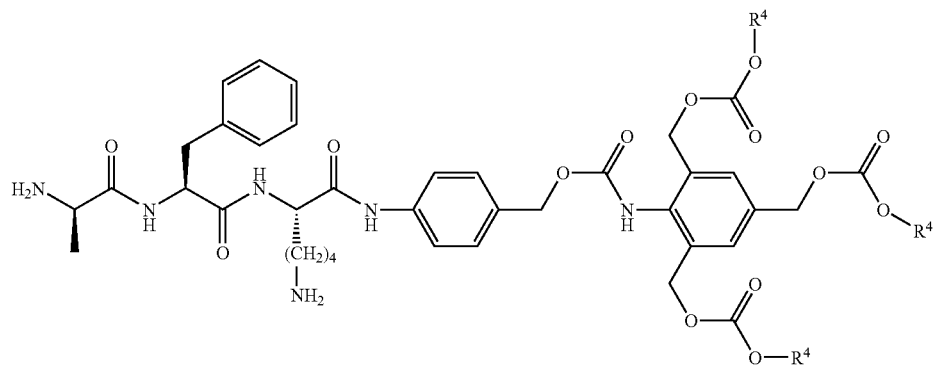

-continued
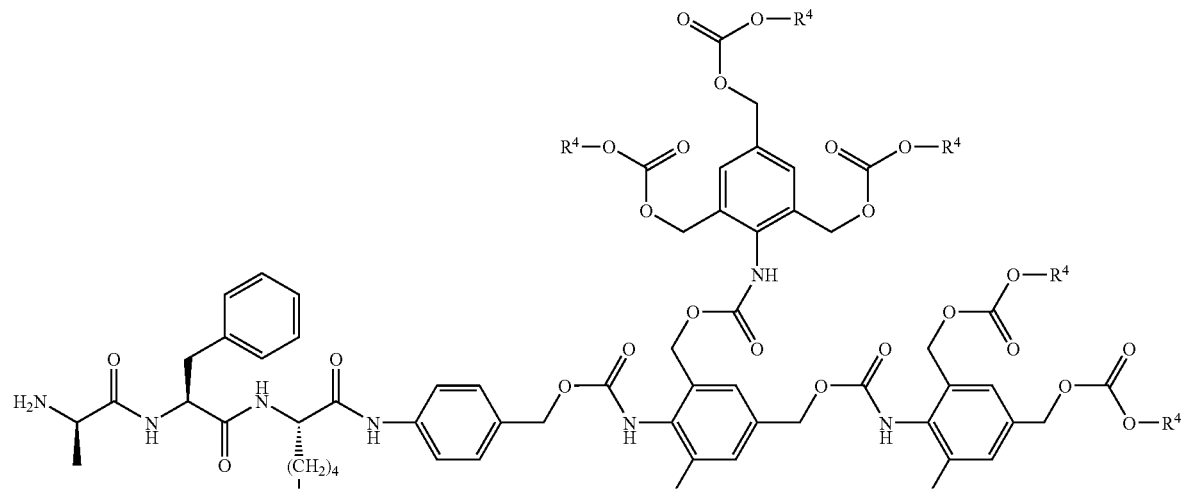
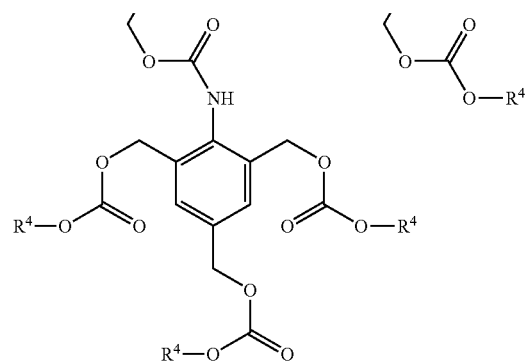
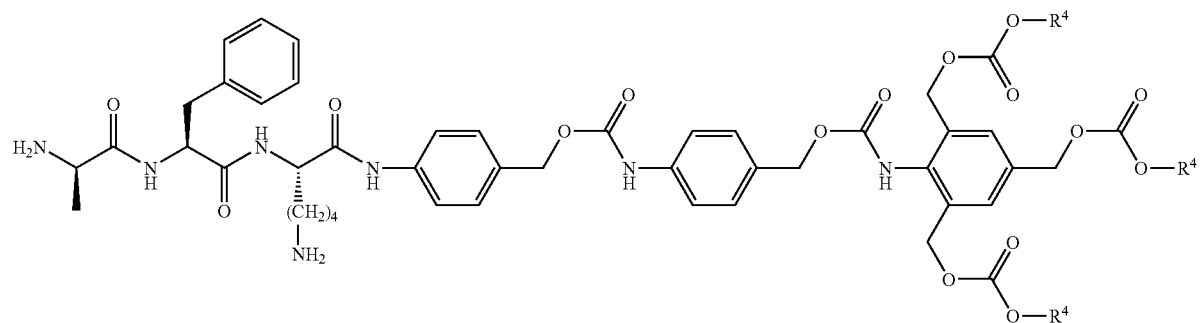

-continued
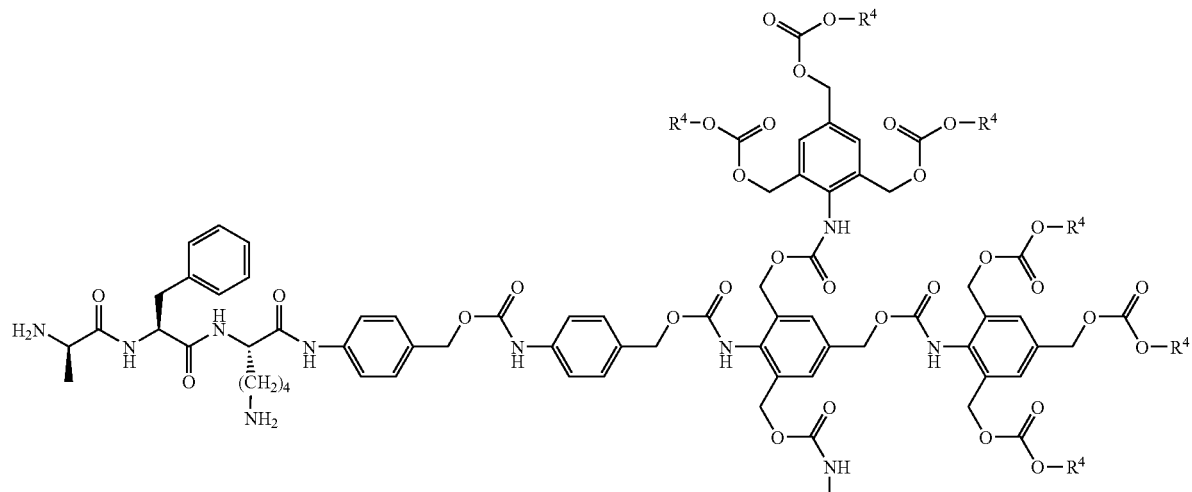
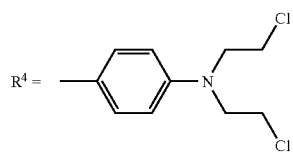
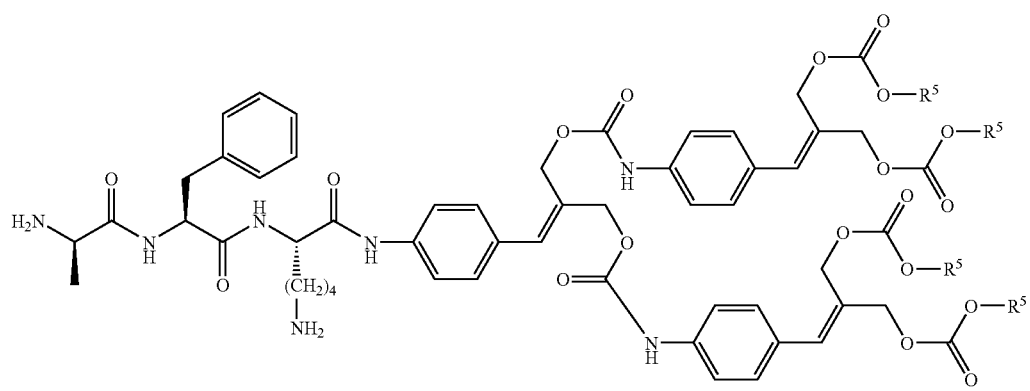
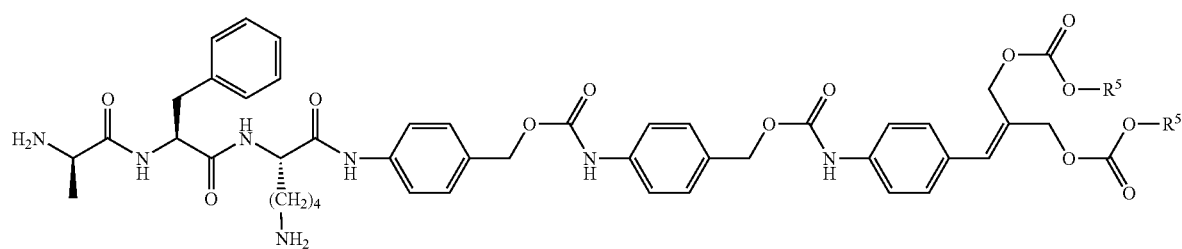

-continued
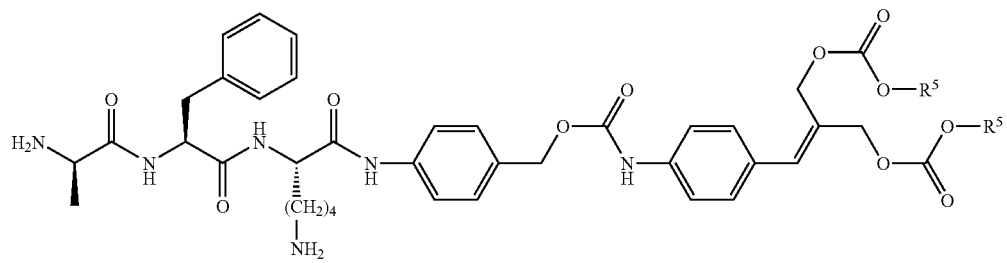
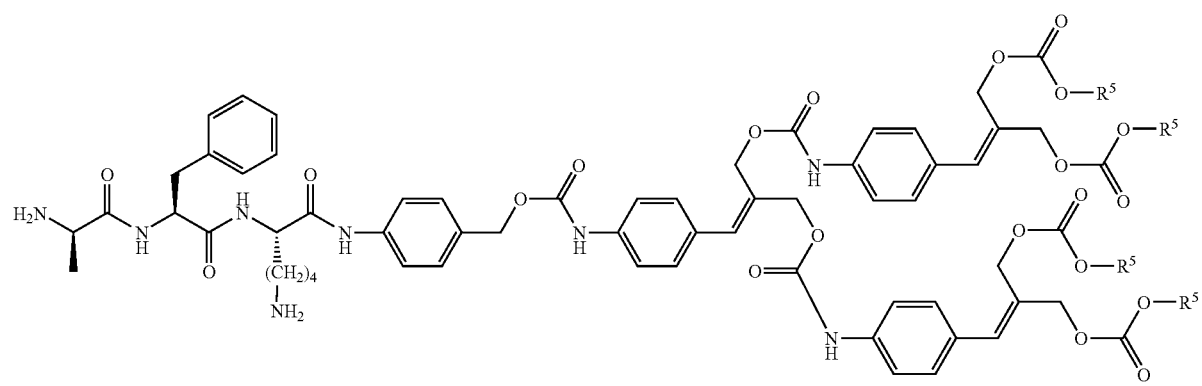
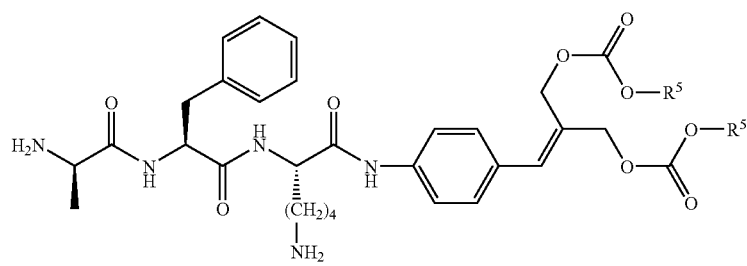
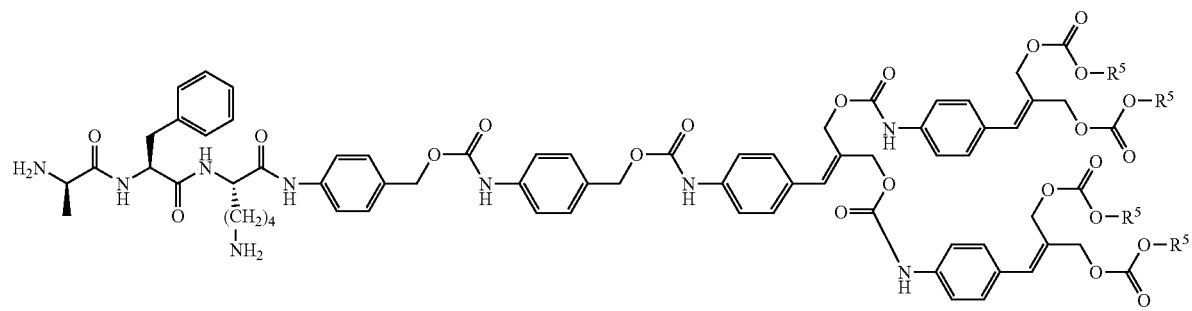
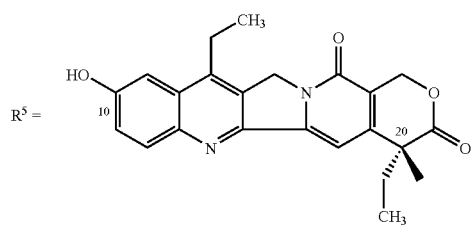

-continued
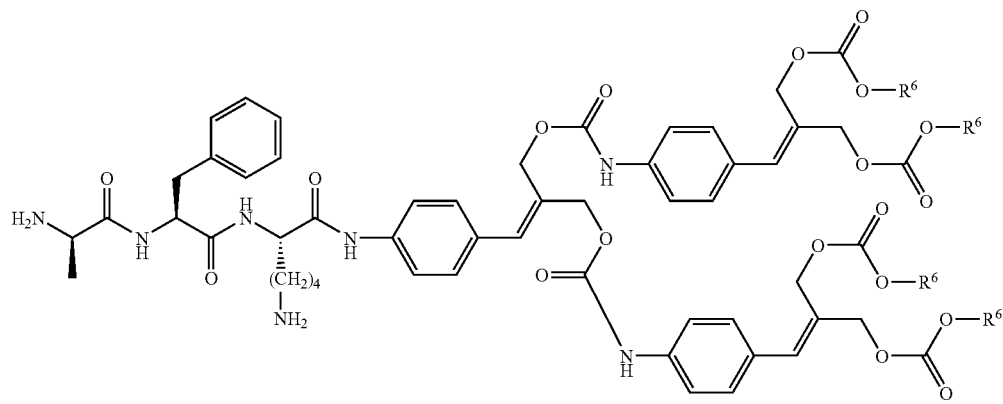
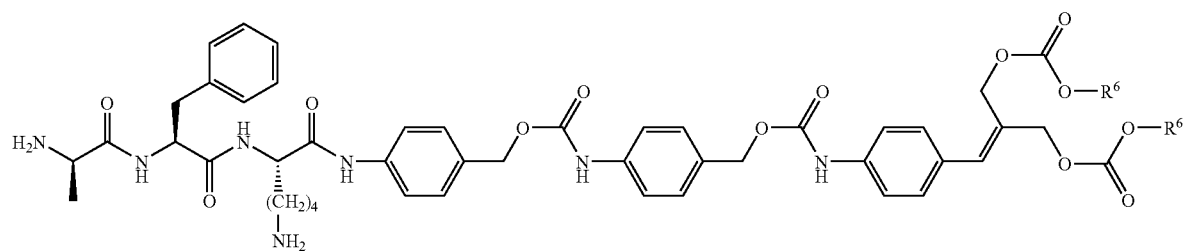
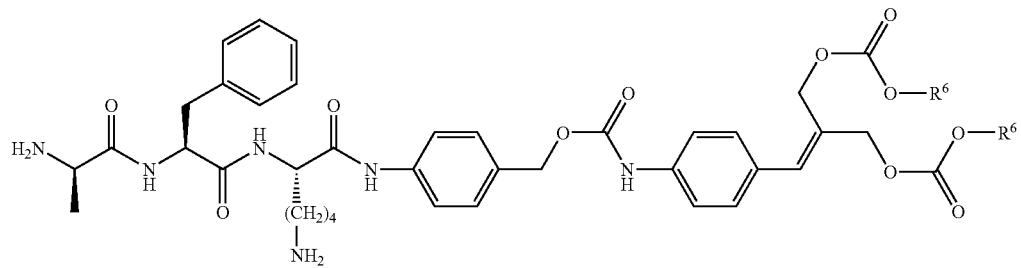
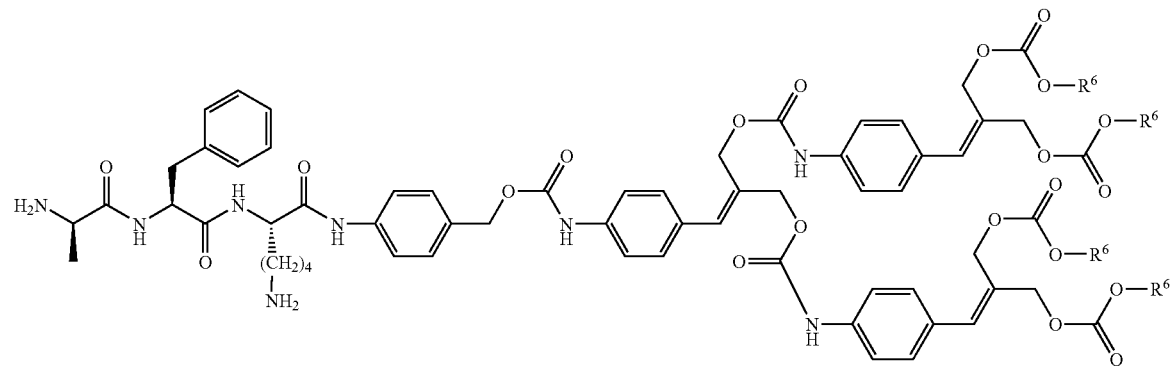
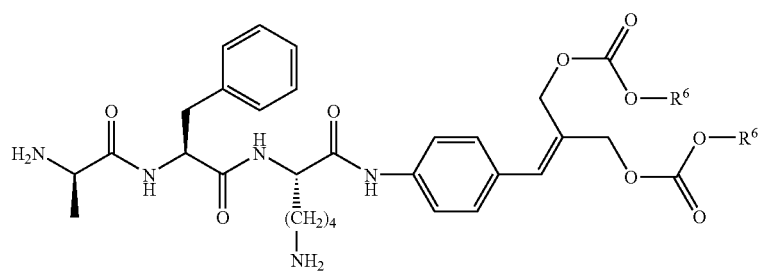

-continued
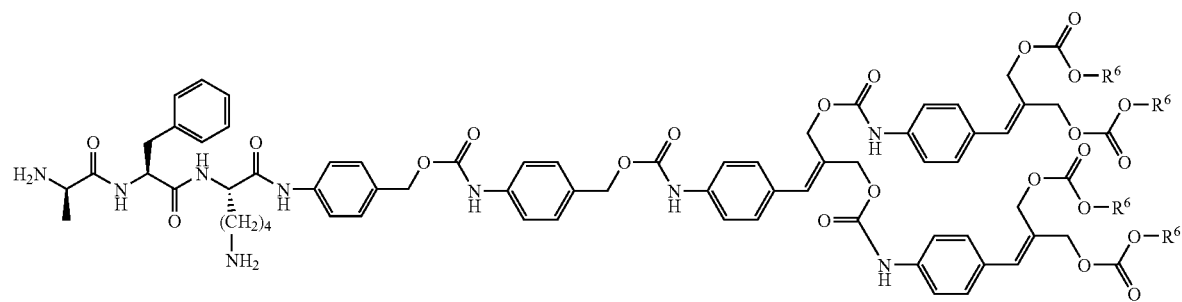
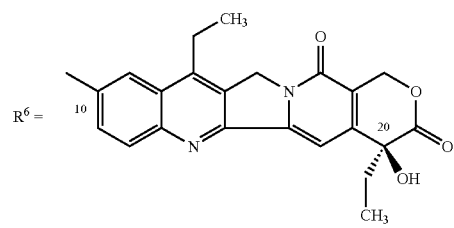
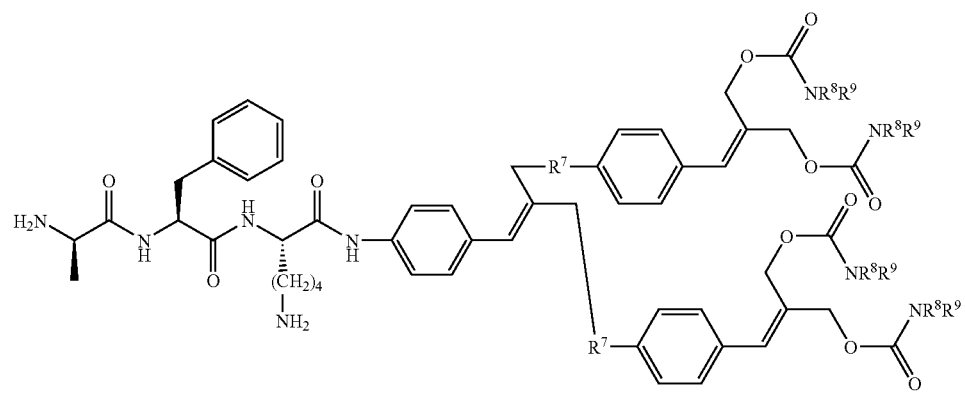
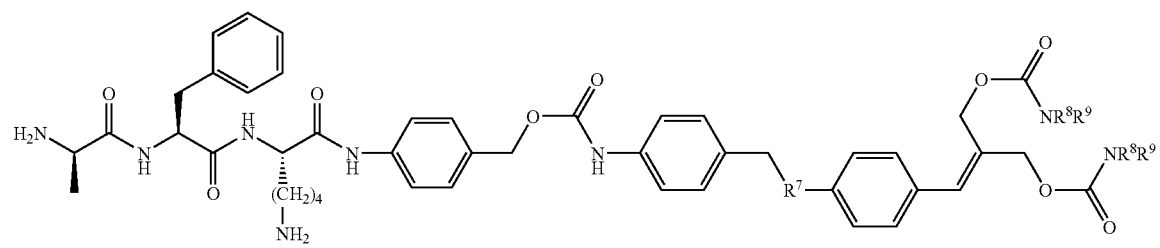
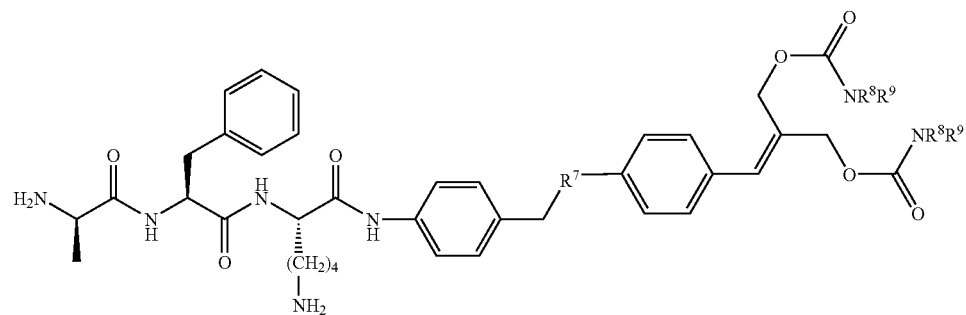

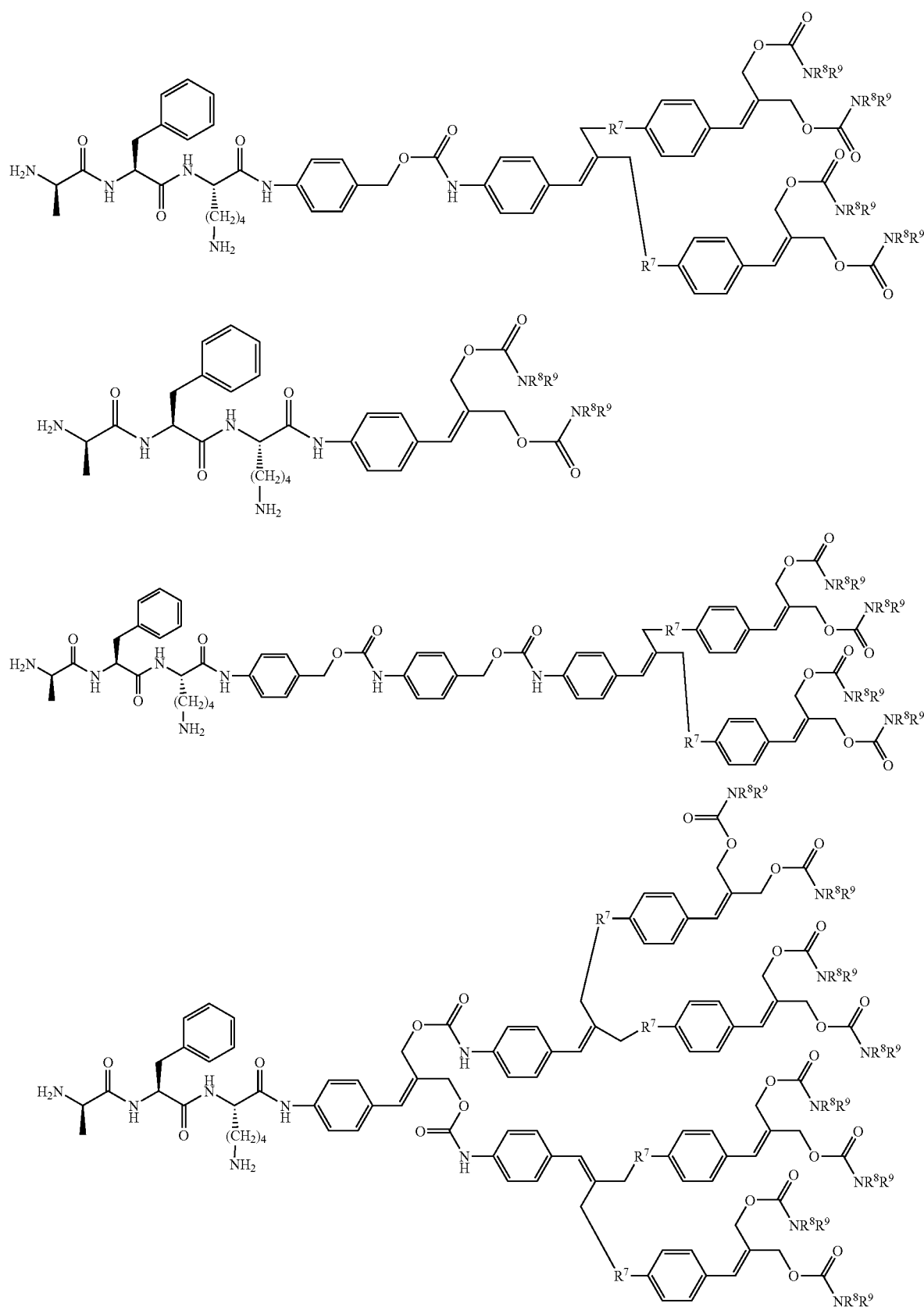

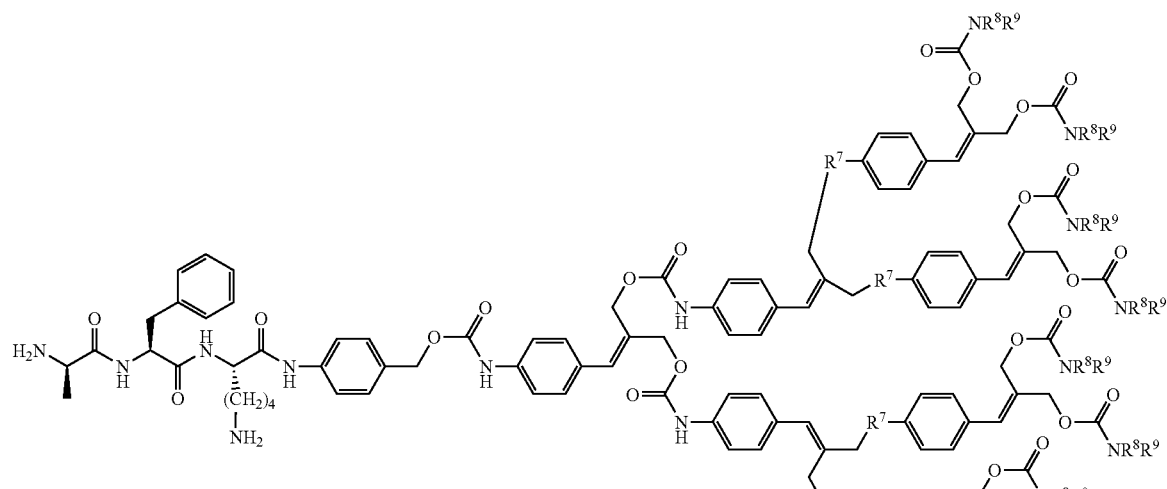
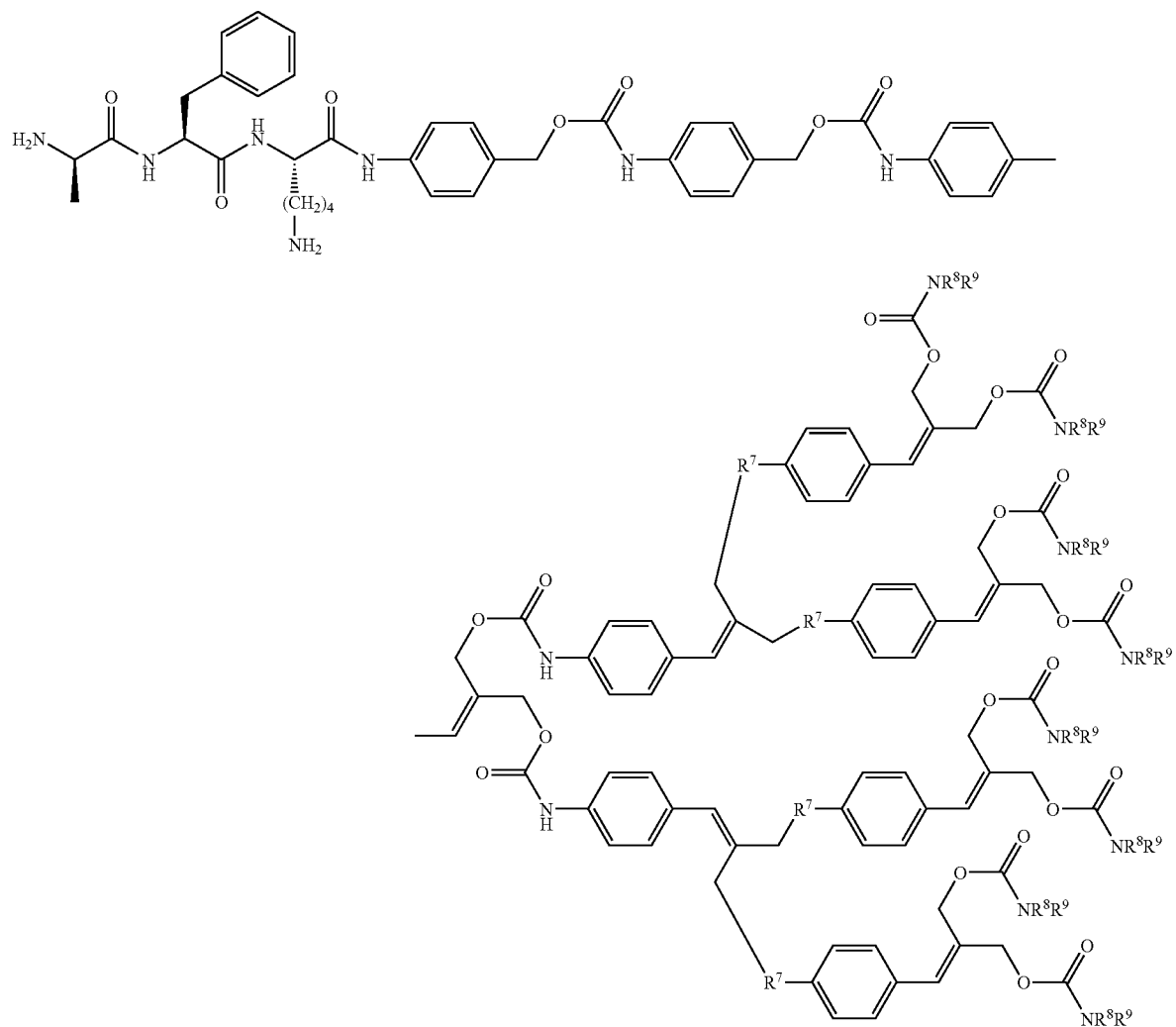

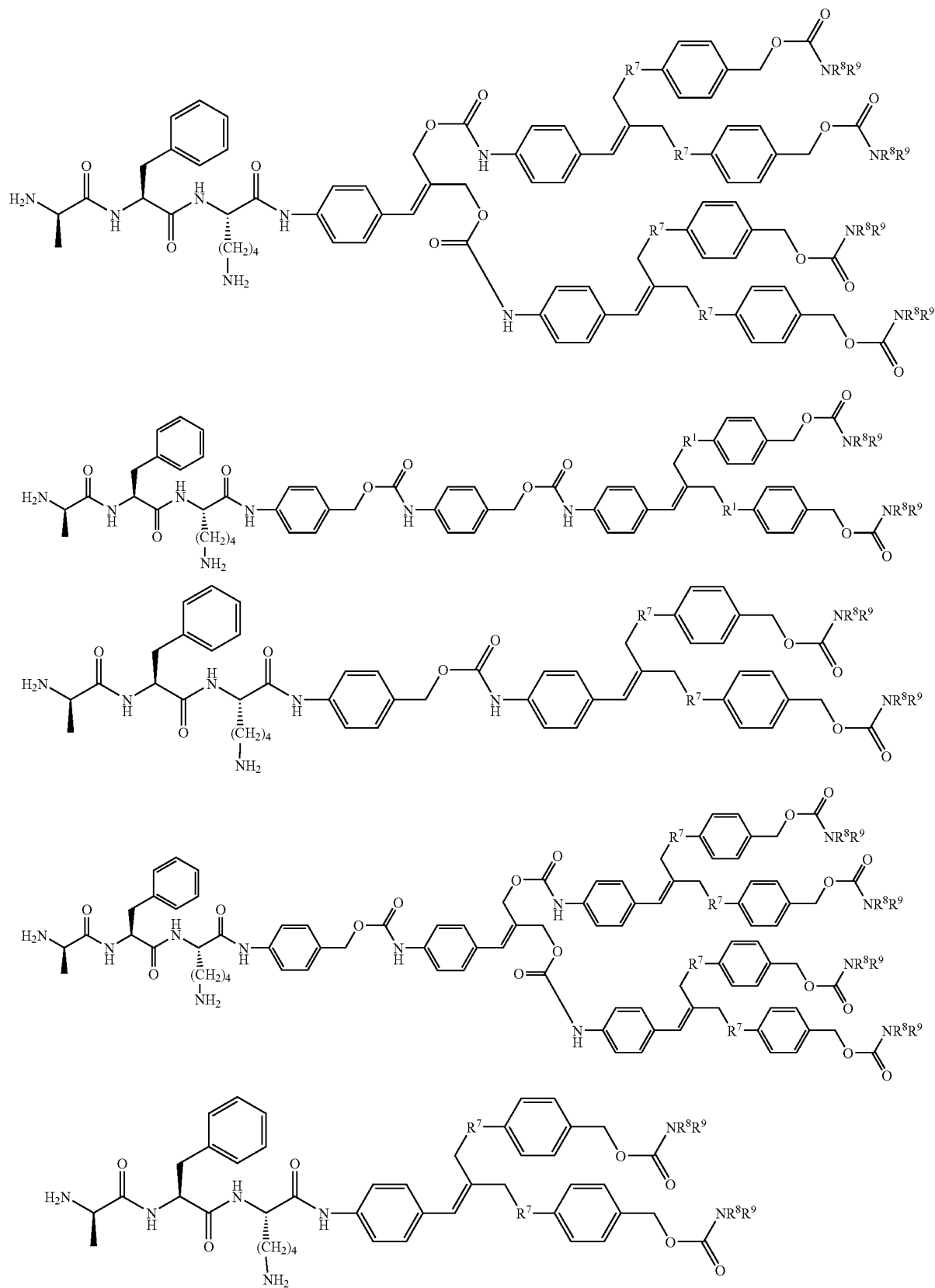

-continued
101
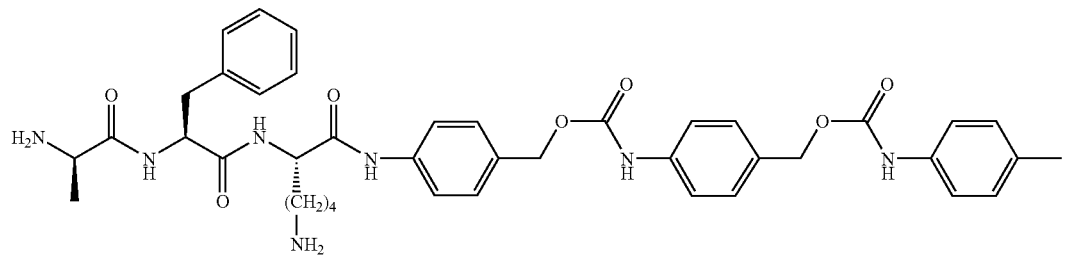
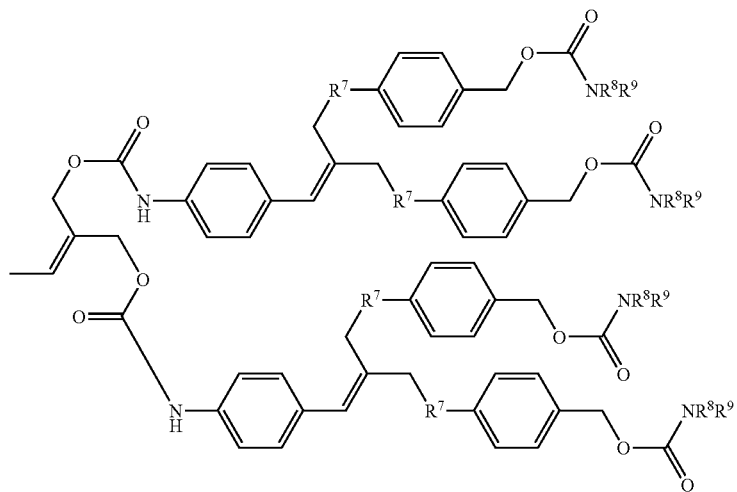
102
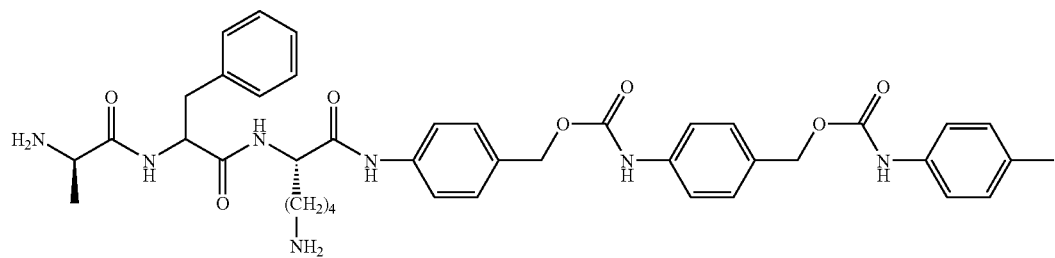
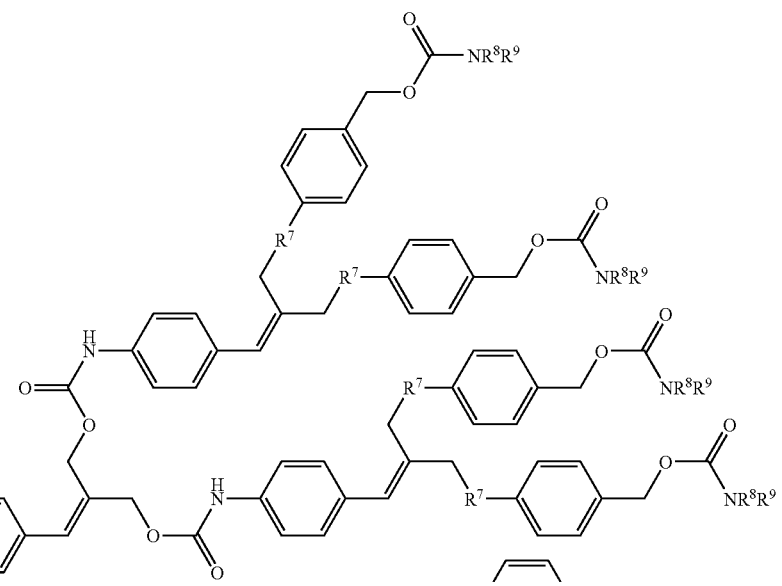

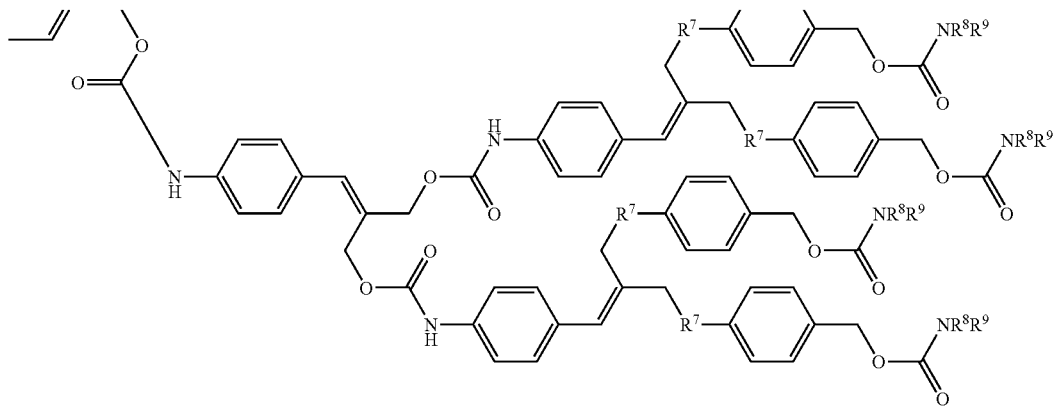
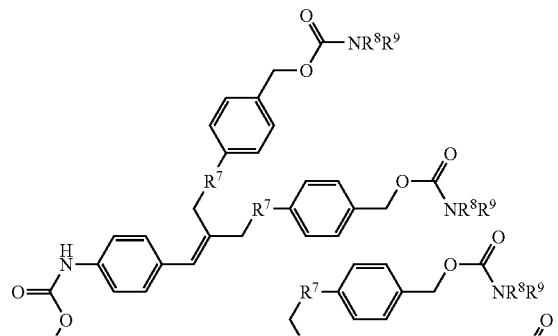
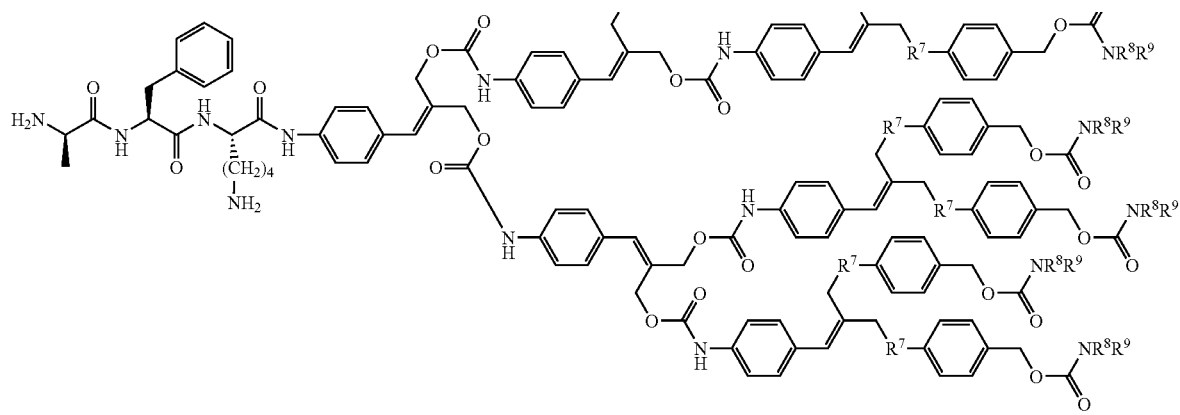
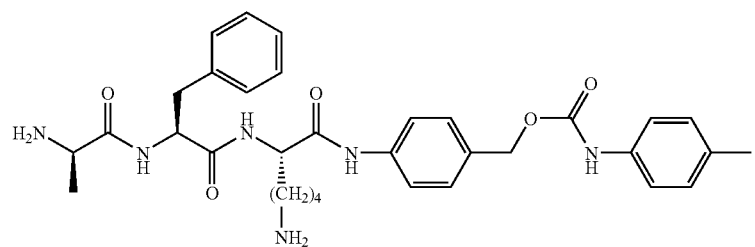

-continued
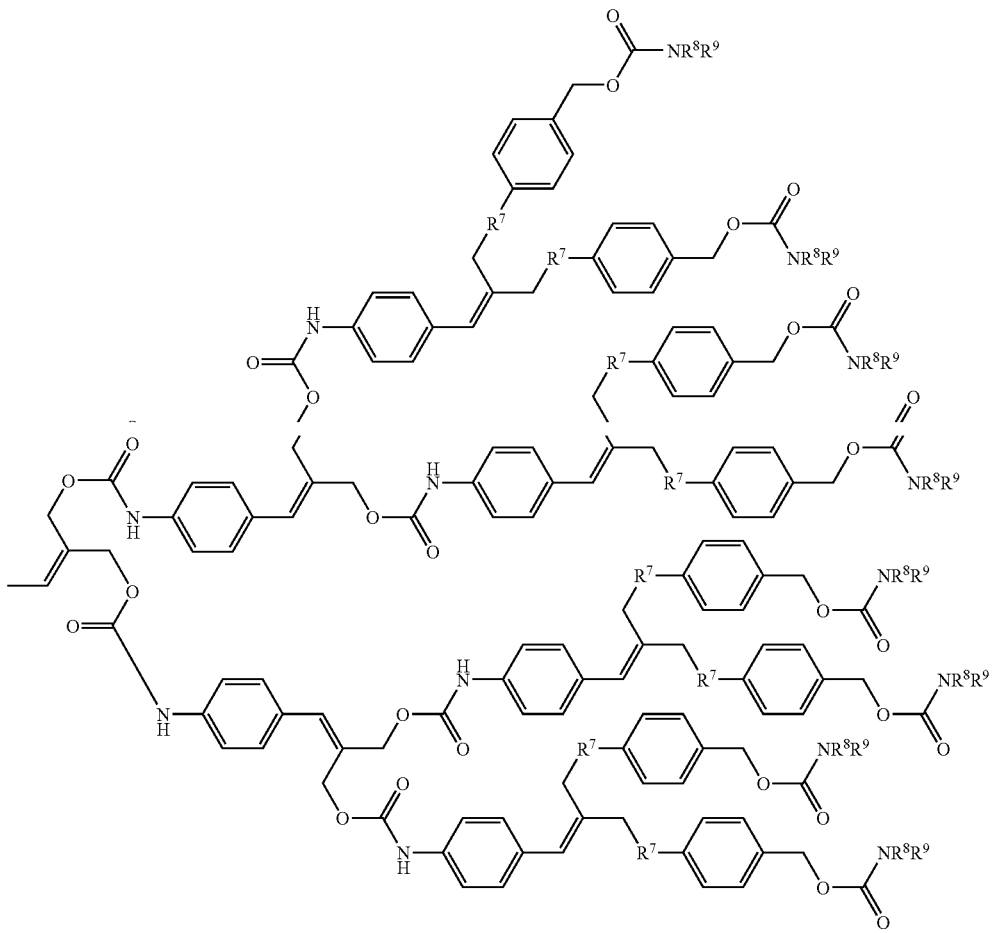
$R^7$ = O or OC(O)O, $R^8$ = 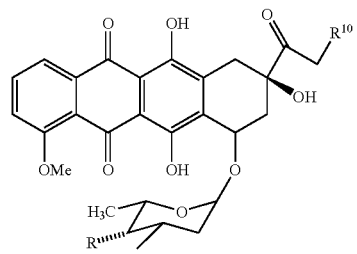 and $R^9$ = H, or
$R^{10}$ = CH & $R^{11}$ = α-OH or
$R^{10}$ = H or $R^{11}$ = α-OH or
$R^{10}$ = OH & $R^{11}$ = β-OH
$R^8$ = 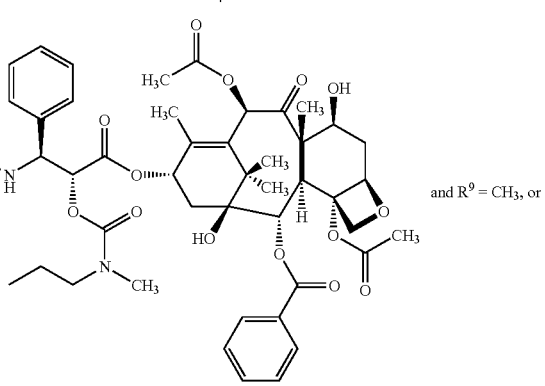 and $R^9$ = CH$_3$, or -continued

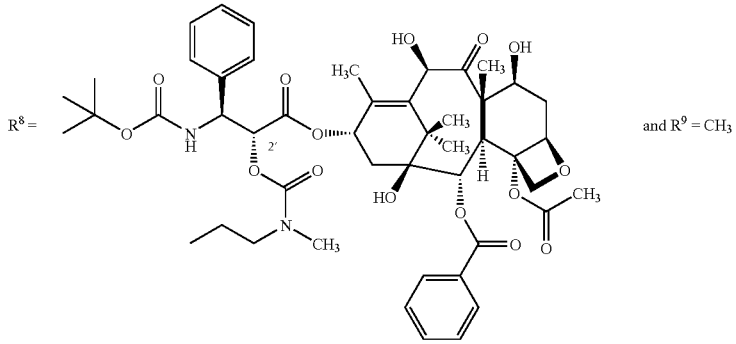

and salts thereof.

A compound consisting of an amino-terminal capped peptide covalently linked via one single p-NH-Ph-CH=C(CH$_2$OCO—)$_2$ spacer to two doxorubicin molecules is excluded from the scope of this invention. Further compounds consisting of an amino-terminal capped peptide covalently linked via one single p-NH-Ph-CH=C(CH$_2$OCO—)$_2$ spacer to two anticancer drug molecules may or may not be excluded from the scope of this invention.

When an enzyme needs to be quantitatively detected, incorporation of a multiple release spacer or spacer system into a compound or conjugate that is enzymatically cleaved by said enzyme increases the sensitivity of such an assay as one enzymatic cleavage can liberate numerous detectable molecules.

Detection or determination of an enzyme, for example a protease, in a sample can be performed by incubating the sample with a compound containing a multiple release spacer or spacer system according to this invention, which is a substrate for the (proteolytic) enzyme, and observing (proteolytic) cleavage of said substrate. The phrase "determining an enzyme" means both qualitative analysis, i.e. detecting the presence of the enzyme, determining whether it is present, and quantitative analysis, i.e. quantifying the enzyme, determining the enzyme activity present in the sample.

For many proteases chromogenic or fluorogenic peptide substrates have been devised which are often commercially available. In many cases, for example in case of serine proteases, the enzymes do not recognize the sequence which is C-terminal to the hydrolyzed bond. This part can be replaced by a chromogenic or fluorogenic leaving group like p-nitroaniline or β-naphtylamine. Such chromogenic or fluorogenic compounds can serve as leaving group Z in compounds of the present invention. The multiple release spacer or spacer system may increase the sensitivity that can be obtained for detection and quantification of physiological concentrations of enzymes in biological fluids or tissue-extracts.

An enzyme can also be indirectly determined via its pro-enzyme containing a recognition site, e.g., an activation site, cleavable by said enzyme to be determined. Cleavage of the pro-enzyme can in such case be detected by observing the resulting activity using a suitable substrate of the activated pro-enzyme, the substrate containing a multiple release spacer or spacer system of the present invention.

In one embodiment the invention relates to a diagnostic assay process in which a compound according to the invention is used.

In a further embodiment the invention relates to a process in which the presence or amount of an enzyme is determined by using a compound according to the invention.

In yet a further embodiment the invention relates to a process in which the presence or amount of a protease is determined by using a compound according to the invention.

In a further embodiment the invention relates to a process in which the compound according to the invention that is used comprises a substrate for said protease and leaving group Z is detected.

In yet a further embodiment the invention relates to a process in which the compound according to the invention that is used comprises a substrate for an enzyme, which is the product of cleavage of its pro-enzyme precursor by said protease and leaving group Z is detected.

The specifier V may also comprise a polymer, such as for example poly[N-(2-hydroxy-propyl)methacrylamide] (poly-HPMA), poly-glutamic acid (poly-L-glutamic acid (PG)), or poly(ethylene) glycol (PEG), which causes accumulation of compounds of the invention in the vicinity of or inside the target cells, e.g. tumor cells, because of the Enhanced Permeability and Retention (EPR) effect. These polymers may as such be regarded as a targeting moiety. Two or more molecules of the invention may also be coupled to a central (core) monomeric or polymeric molecule to obtain a larger structure that could accumulate as a result of the EPR effect, in addition to other mechanisms of accumulation. Suitable polymers are for example poly[N-(2-hydroxy-propyl)methacrylamide] (poly-HPMA), poly-glutamic acid (poly-L-glutamic acid (PG)), or poly(ethylene) glycol (PEG). Thus the invention also relates to a composite structure comprising two or more compounds according to the invention, connected with a polymeric structure.

Figure 7:
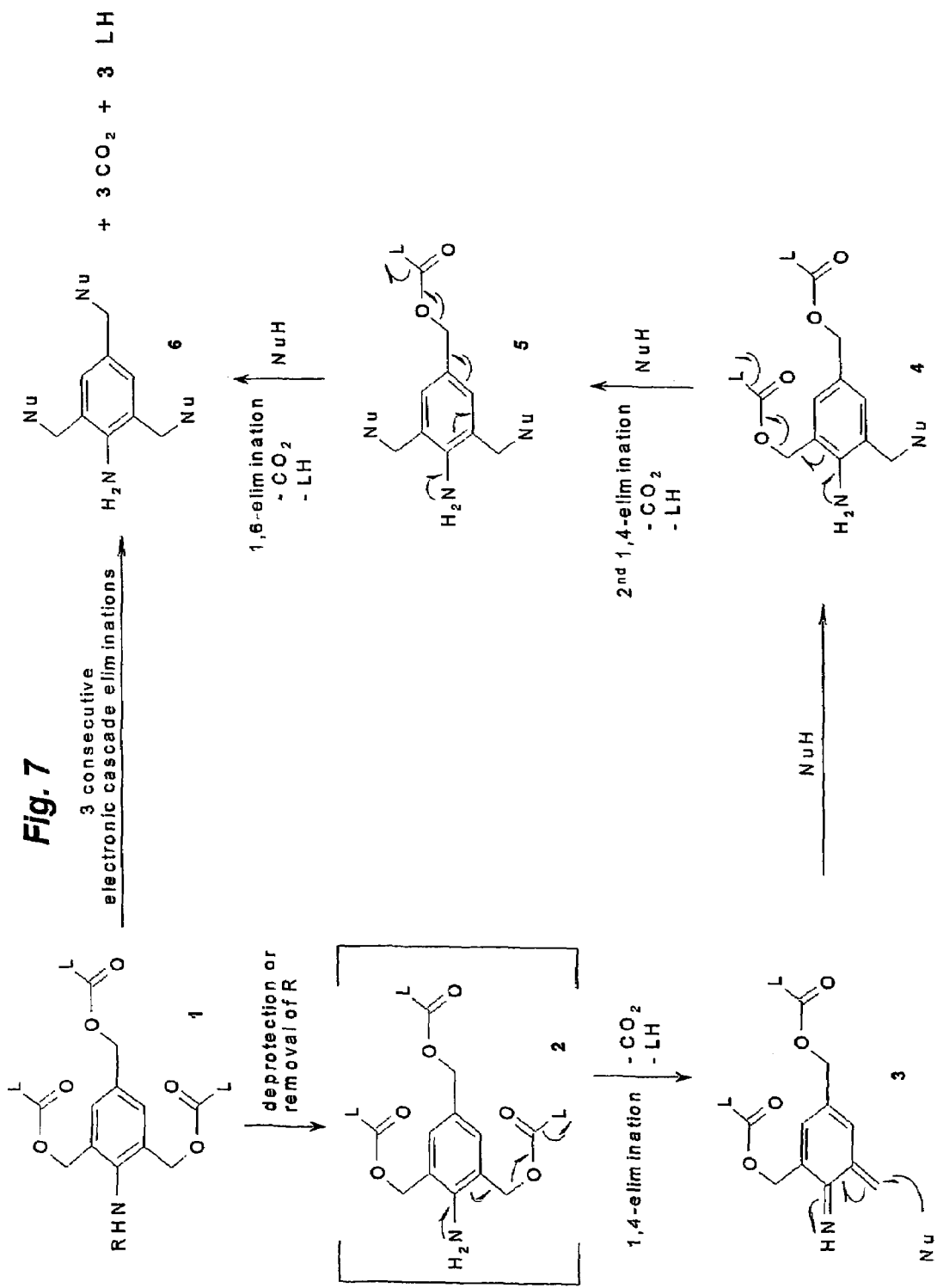
FIG. 7 shows the proposed principle of elimination of 3 leaving groups from a triple release spacer.

Structures of multiple release spacers are disclosed that can serve as suitable monomers to construct the multiple release dendrimeric prodrugs or (bio)conjugates. A suitable monomer is able to release 2 or more leaving groups after activation. One herein disclosed structure of such multiple release monomer is depicted in FIG. 7. Triple release from this monomer, as depicted in FIG. 7, is based on the principles of unbranched 1,4- and 1,6-elimination spacers[30]. After unmasking of the amine of 1 (FIG. 7), 2 can undergo an electronic cascade reaction, after which the reactive non-aromatic species 3 is immediately trapped by a nucleophile, such as for example water, to regenerate the aromatic amine function in 4. This process of self-elimination and trapping is repeated two more times, after which three leaving groups L—H have been liberated. The sequence in which the three electronic cascade elimination reactions take place as depicted in FIG. 7 was chosen randomly. In fact, the three fragmentations (two 1,4-eliminations and one 1,6-elimination) may occur in any random order. Employing n generations of this monomer, cascade dendrimers can potentially be constructed that contain $3^n$ end groups.

Figure 8:
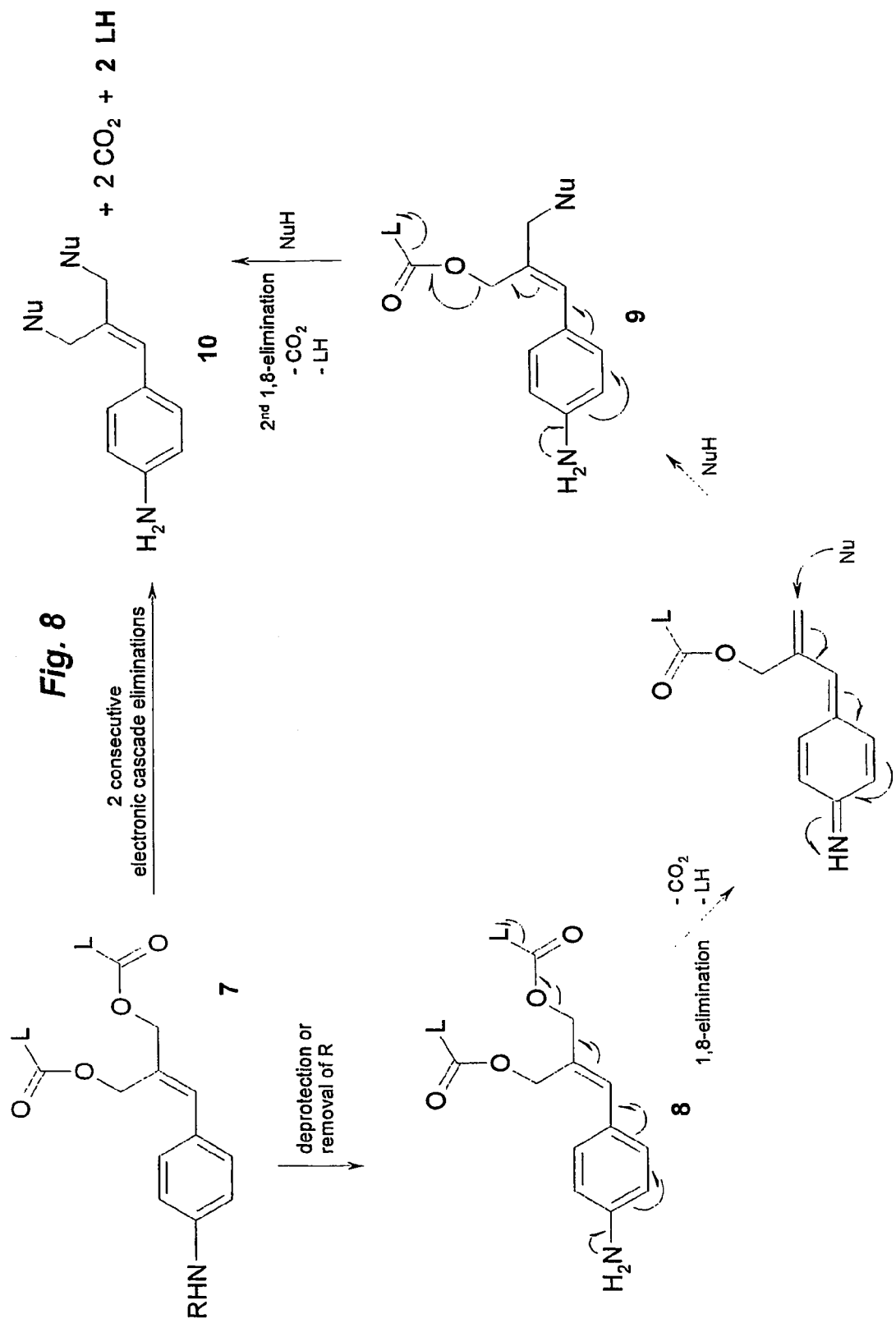
FIG. 8 shows the proposed principle of elimination of 2 leaving groups from a double release spacer.

FIG. 8 depicts the principle of drug release from a double release spacer. Self-elimination of this double release spacer is based on 1,8-elimination. Deprotection of the amino group in 7, affording 8, sets the stage for 2 1,8-elinination reactions releasing 2 leaving groups L-H.

An amine or hydroxylamine can be generated from a masked amine through reduction of a nitro function to the corresponding hydroxylamine or amine function. Both the hydroxylamine and the amine derivatives induce self-elimination of the spacer.

To deliver proof of principle for multiple release of leaving groups from conjugates and prodrugs containing a multiple release spacer or spacer system as disclosed herein, compounds were synthezised that contain multiple leaving groups coupled as end groups to one or two generations of multiple release spacers. These compounds were to release the leaving groups upon reduction of the nitro group attached to the aromatic ring at the center of the multiple release linker or linker system. Reduction of the nitro group to the corresponding hydroxylamine or amine should trigger the multiple release cascade and simultaneously liberate all leaving groups. Alternatively, removal of an Aloc protecting group to unmask the amine can trigger self-elimination. In addition to serving as compounds to deliver proof of principle, the synthesized nitroaromatic compounds that contain antitumor drugs, such as paclitaxel, as leaving groups can be considered for application in selective drug targeting to hypoxic areas in tumors, where the nitro group will be reduced. Alternatively, these compounds can be used as conjugates and prodrugs that are activated by nitroreductases which are targeted to tumor cells through one of the directed enzyme prodrug therapy (DEPT) approaches. The synthesis of these compounds is disclosed.

The triple release building blocks nitrotriol 11 (FIG. 9) and aminotriol 16 (FIG. 11) can be synthesized following a number of routes. Several approaches to obtain the corresponding amino-tri-methylester or amino-tri-carboxylic acid have been reported starting from for example nitromesitylene[31].

Synthesis of the double release building block nitrodiol 20 (FIG. 12) has been reported in the literature[32]. The double release building block aininodiol 23 (FIG. 13) can be synthesized by reduction of the nitro group of 2-p-nitrobenzylidene propane-1,3-diol 20.

Proof of principle of triple release should be delivered with a monomeric model compound with a structure similar to 1 (FIG. 7). To obtain such a compound, nitrotriol 11 was activated with excess p-nitrophenyl chloroformate in the presence of diisopropylethylamine (DIPEA) and pyridine to yield triply activated compound 12 (FIG. 9).[33] Triply activated 12 was subsequently reacted with benzyl alcohol to yield model compound 13, or with phenethyl alcohol to yield model compound 14. Triply activated 12 was also reacted with benzylamine to obtain model compound 15 (FIG. 10).

In order to obtain model compound 19 (FIG. 11), aminotriol 16 was N-protected with an Aloc group to yield 17, subsequently triply activated with p-nitrophenyl chloroformate to yield 18, and coupled with propylamine.

Figure 12:
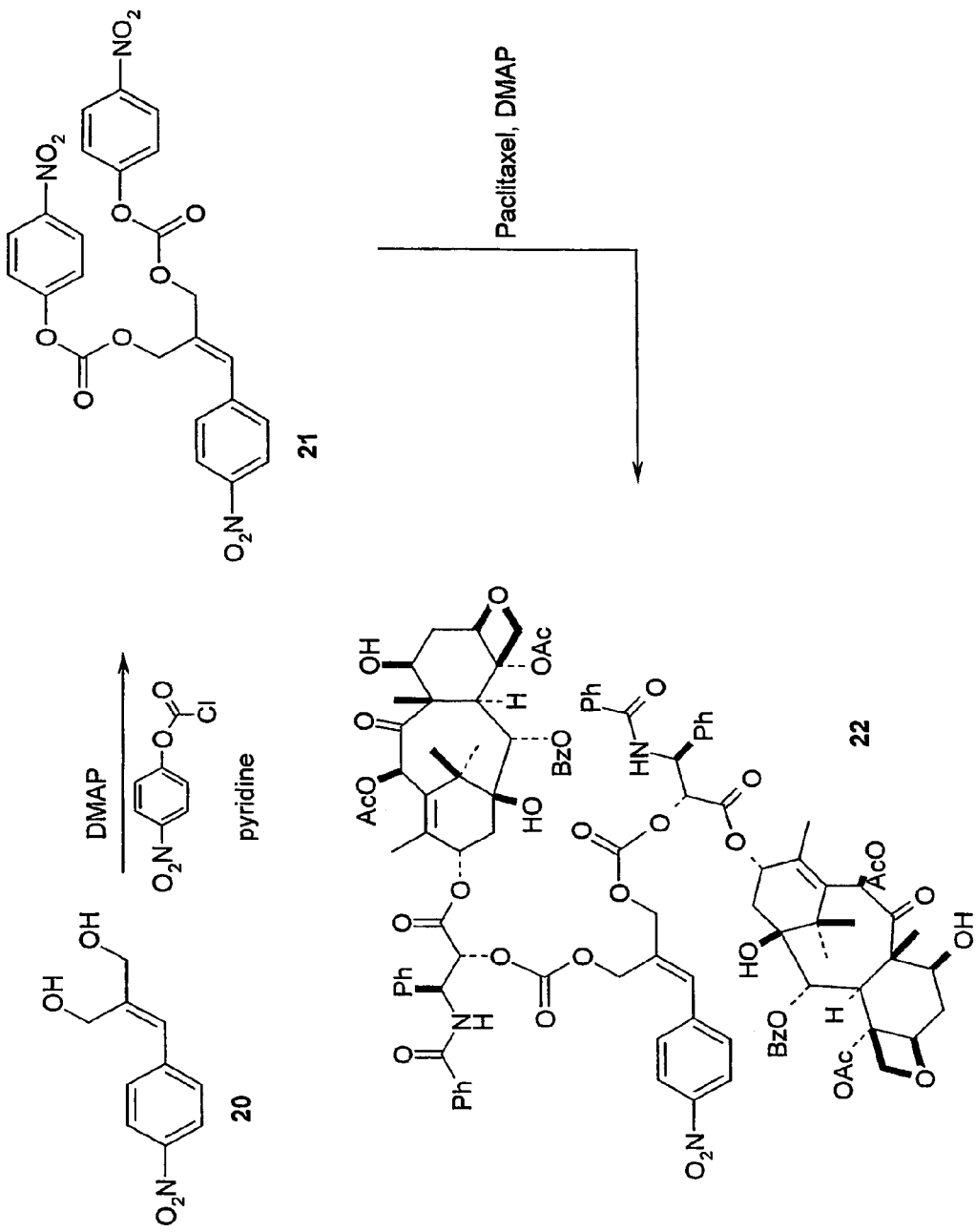
FIG. 12 shows the preparation of a prodrug containing a double release spacer and 2 paclitaxel moieties.

Proof of principle for the fact that the dual release spacer with a structure similar to 10 (FIG. 8) can indeed release both leaving groups is also disclosed in this invention. For this purpose, nitrodiol 20 was doubly activated with excess p-nitrophenyl chloroformate in the presence of diisopropylethylamine (DIPEA) and pyridine to yield doubly activated compound 21 (FIG. 12). Doubly activated 21 was subsequently reacted with paclitaxel to yield the desired model compound 22.

In addition to delivering proof of principle for double release from a spacer with a structure similar to 10 (FIG. 8), a model compound was synthesized for delivering proof of principle for release of 4 leaving groups from a multiple release prodrug or (bio)conjugate containing 2 generations of double release spacers. For this purpose, two molecules of aminodiol 23 were coupled to doubly activated 21 using HOBt as a catalyst to yield tetraol 24 (FIG. 13). Tetraol 24 was quadruply activated with excess p-nitrophenyl chloroformate in the presence of diisopropylethylamine (DIPEA) and pyridine to yield quadruply activated compound 25. Quadruply activated 25 was subsequently reacted with paclitaxel to yield the desired model compound 26.

Doubly activated 21 was also reacted with benzylamine to yield model compound 27 (FIG. 14). To synthesize additional model compounds, doubly activated 21 was also reacted with the single release 1,6-elimination spacer to yield 28 (FIG. 15), which was subsequently activated using p-nitrophenyl chloroformate to yield 29. Doubly activated 29 was reacted with p-methoxybenzylamine, p-chlorobenzylamine, or phenethyl alcohol, to yield model compounds 30, 31, and 32, respectively (FIG. 16).

To obtain a reference compound for demonstration of single 1,6-elimination, p-nitrobenzyl chloroformate 33 was reacted with benzylamine to yield model compound 34 (FIG. 17).

Two other reference compounds were also prepared (FIG. 18). Dibenzyl carbonate 35 and 2'-O-cinnamyloxycarbonylpaclitaxel 36 were synthesized as reference compounds to demonstrate that these compounds remain intact upon treatment with conditions that are necessary for reduction of the nitro function of the model compounds described above.

Although the conjugates, test compounds, and reference compounds are based on aniline-based spacers, it is obvious to one skilled in the art that similar compounds containing one or more phenol- or thiophenol-based spacers can be prepared analogously.

Figure 19:
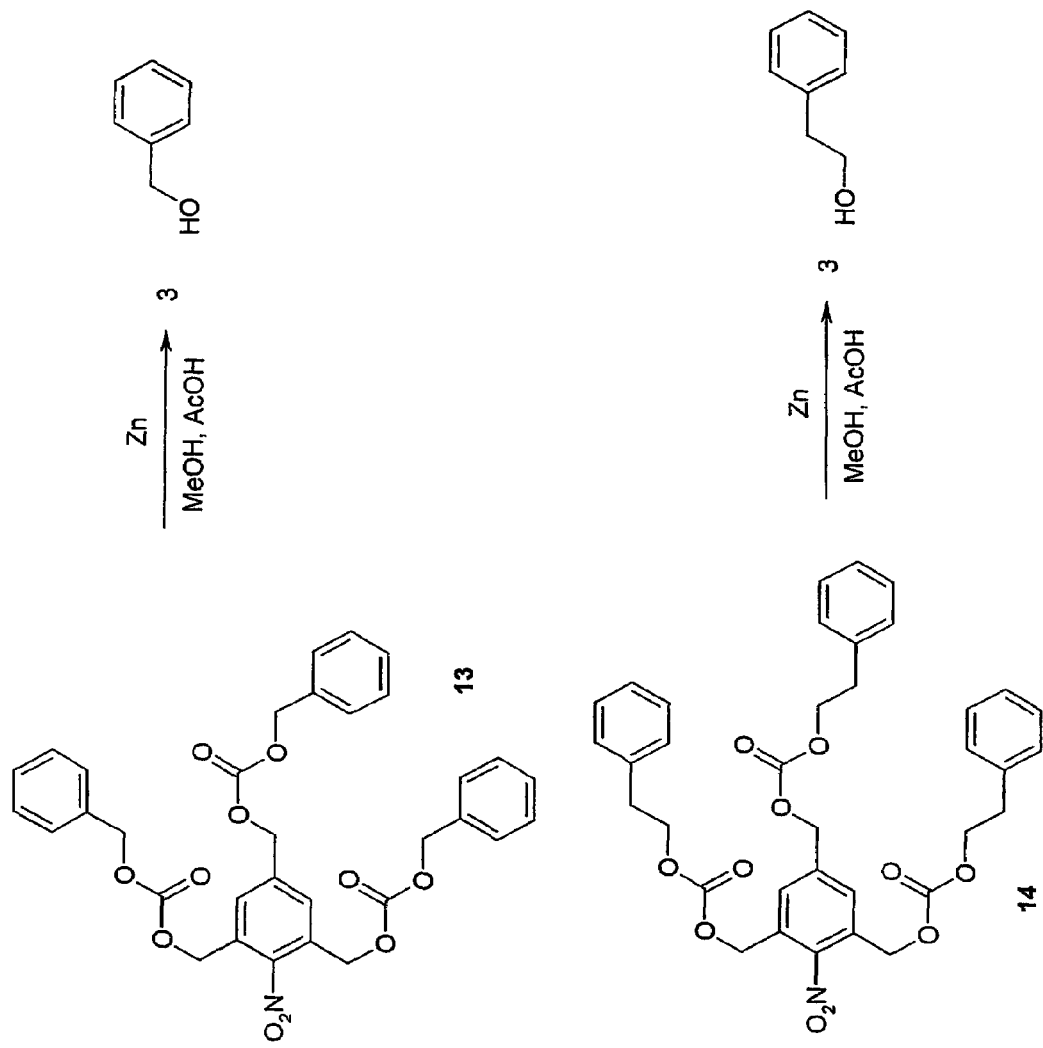
FIG. 19 shows the reduction of the nitro group in the 2 model compounds containing 3 benzyl alcohol or 3 phenethyl alcohol leaving groups with the concomitant liberation of all leaving groups.
Figure 20:
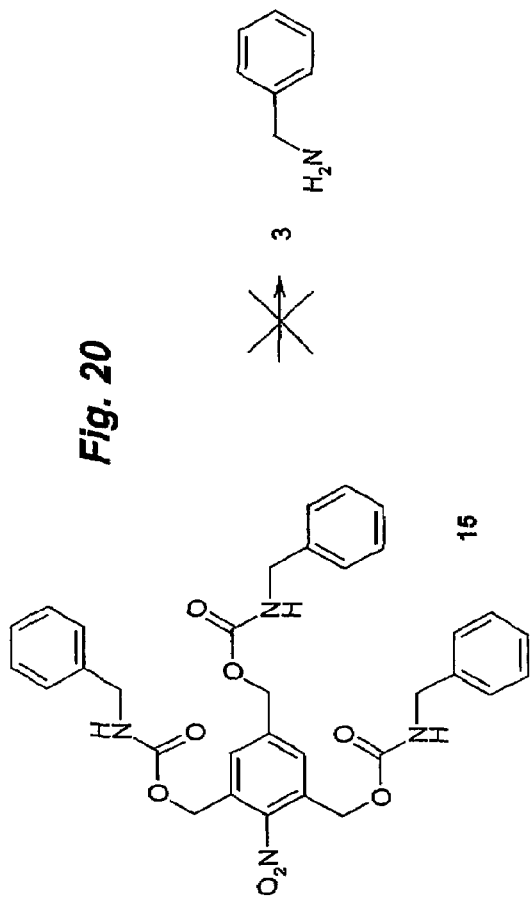
FIG. 20 shows the reduction of the nitro group in the model compound containing 3 benzylamine leaving groups.
Figure 21:
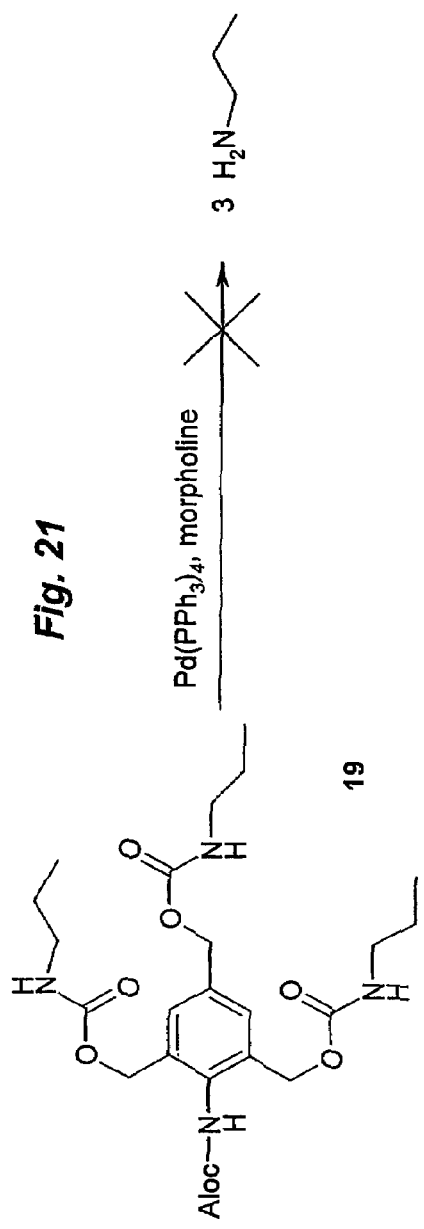
FIG. 21 shows the removal of the Aloc group from the model compound containing 3 propylamine leaving groups.

In order to deliver proof of principle for release of all three leaving groups, 13 and 14 were unmasked by reduction of the nitro group using zinc in the presence of acetic acid (FIG. 19). Within one hour thin layer chromatography indicated complete disappearance of starting compound and formation of a substantial amount of benzyl alcohol or phenethyl alcohol. NMR spectra of the products indicated complete formation of free benzyl alcohol or phenethyl alcohol, no signals from benzyl carbonate or phenethyl carbonate protons being present.

When the nitro function of model compound 15 was reduced (FIG. 20), thin layer chromatography indicated formation of a single product. However, formation of benzylamine was not or hardly observed. According to NMR, maximally 33 percent of benzylamine was released from 15.

Treatment of the model compound 19 (FIG. 21) with palladiumtetrakistriphenylphosphine and morpholine resulted in disappearance of starting compound within one hour. However, again no complete release of propylamine was observed.

Figure 22:
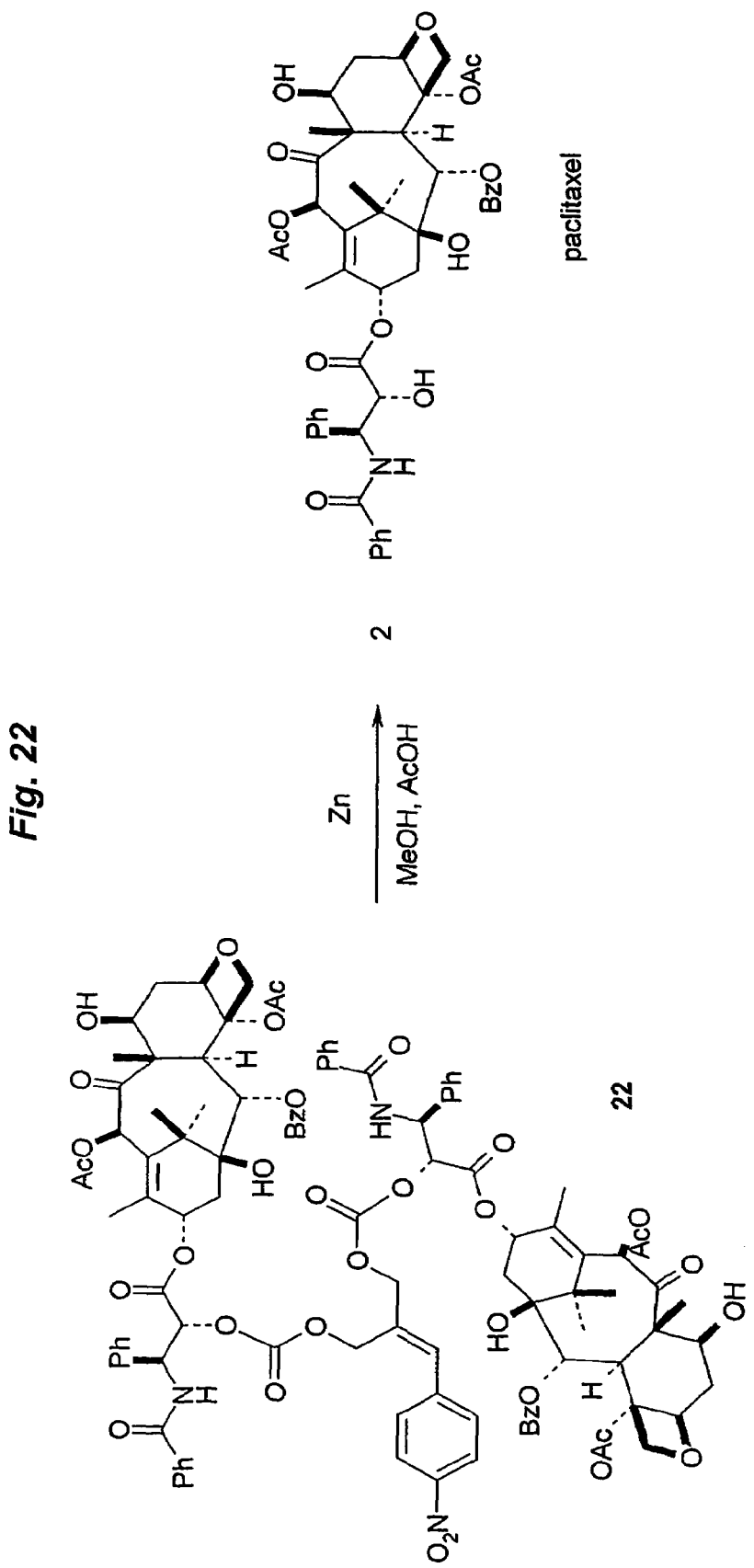
FIG. 22 shows the reduction of the nitro group in the prodrug containing 2 paclitaxel moieties with the concomitant liberation of 2 molecules of paclitaxel.

In order to deliver proof of principle for release of both paclitaxel leaving groups, 22 was unmasked by reduction of the nitro group using zinc in the presence of acetic acid (FIG. 22). Within 30 minutes thin layer chromatography indicated complete disappearance of starting compound and formation of a substantial amount of paclitaxel. An NMR spectrum of the product indicated complete formation of free paclitaxel, no signals from paclitaxel-2'-carbonate protons were present.

Figure 23:
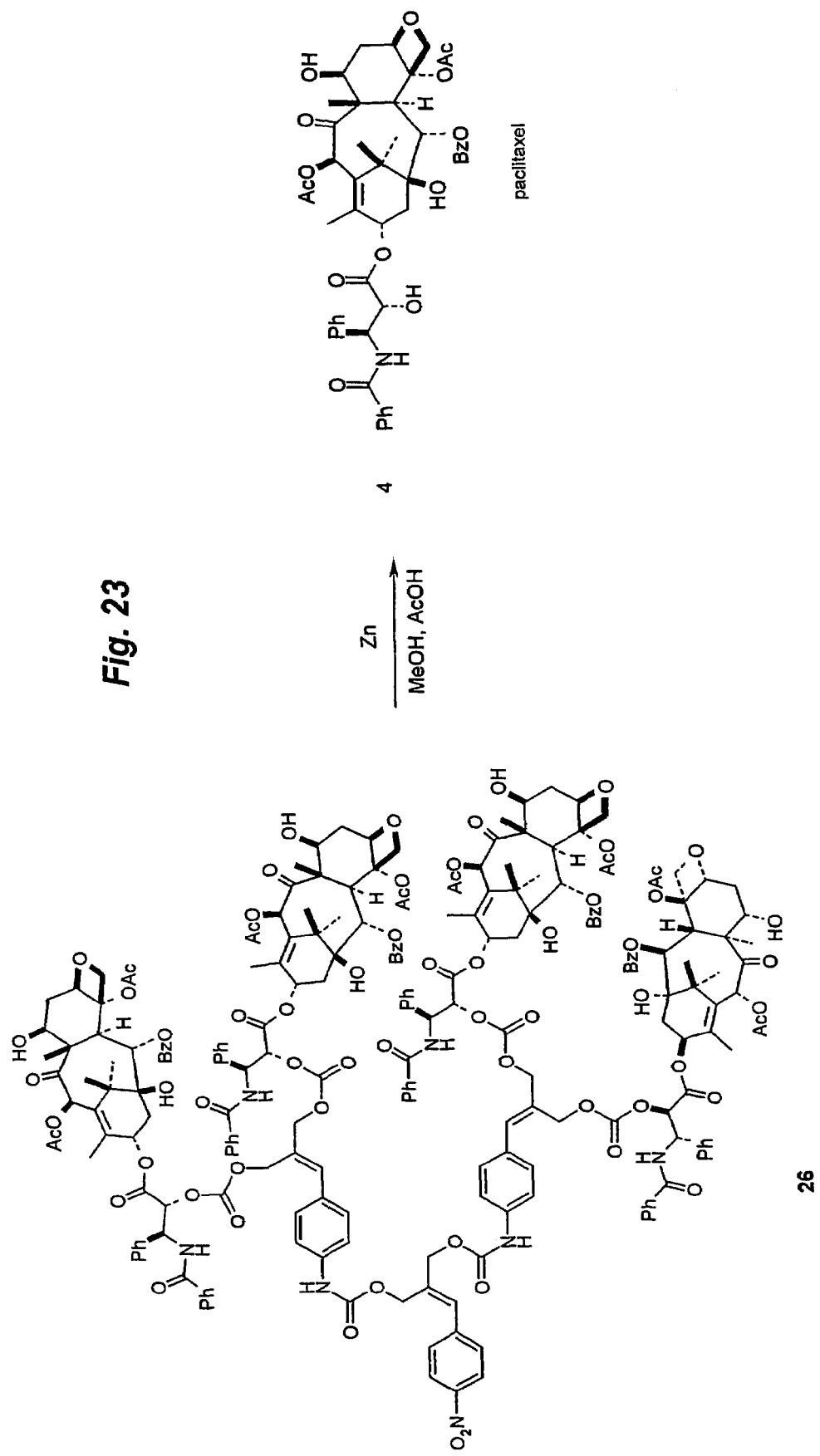
FIG. 23 shows the reduction of the nitro group in the prodrug containing 4 paclitaxel moieties with the concomitant liberation of 4 molecules of paclitaxel.
Figure 24:
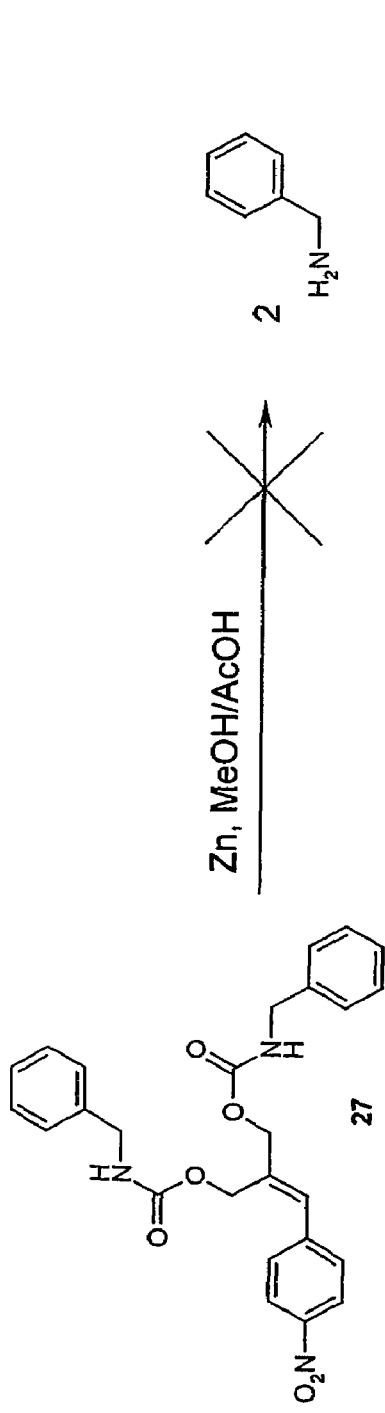
FIG. 24 shows the reduction of the nitro group in the model compound containing 2 benzylamine leaving groups.
Figure 25:
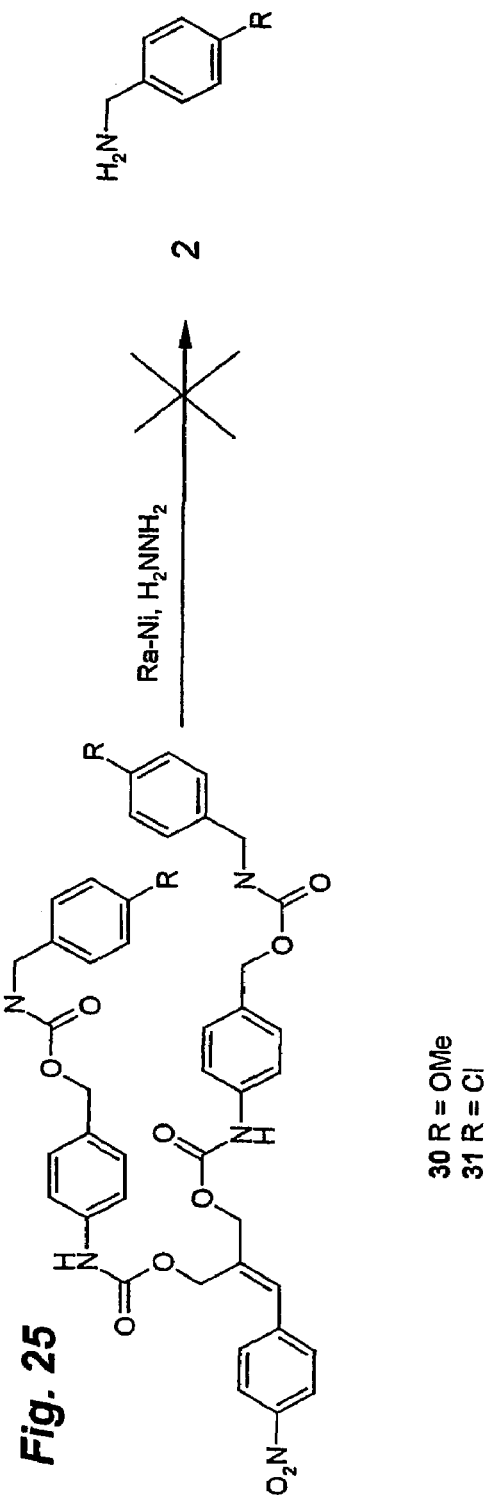
FIG. 25 shows the reduction of the nitro group in the 2 model compounds containing 2 p-methoxybenzylamine or 2 p-chlorobenzylamine leaving groups.
Figure 26:
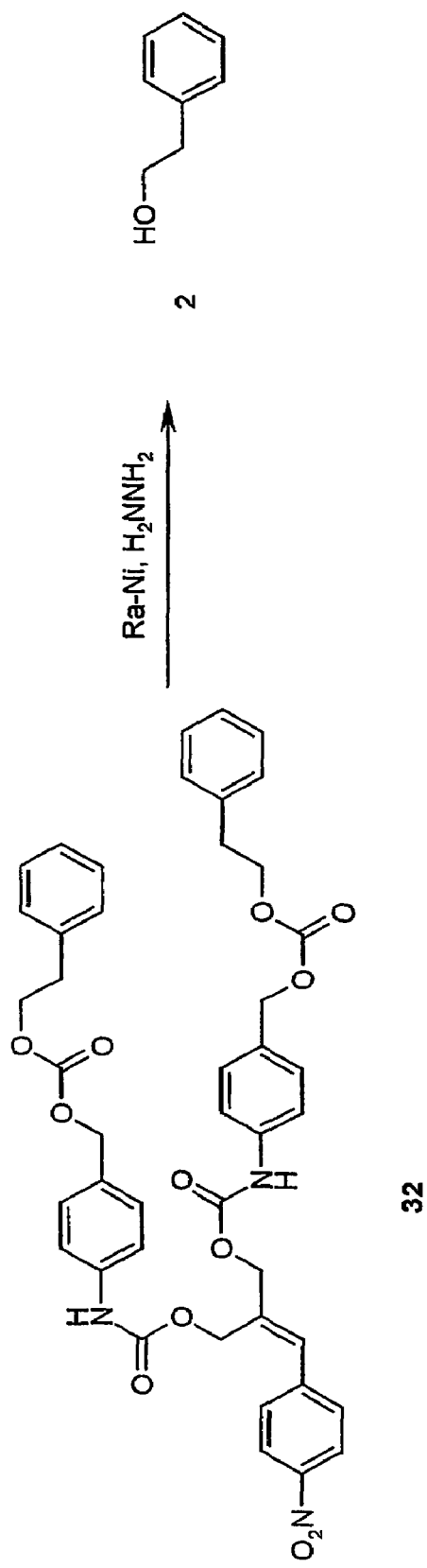
FIG. 26 shows the reduction of the nitro group in the model compound containing 2 phenethyl alcohol moieties with the concomitant liberation of 2 molecules of phenethyl alcohol.

A similar reduction of the nitro group of the model compound 26, containing 2 generations of multiple release spacers and containing 4 paclitaxel units, led to complete disappearance of starting material within 30 minutes and a substantial amount of paclitaxel was formed according to thin layer chromatography (FIG. 23). Also in this case, an NMR spectrum of the product indicated complete formation of free paclitaxel.

Treatment of model compound 27, containing benzylarnine as leaving groups (FIG. 24), with zinc showed disappearance of starting compound. However, again no complete release of benzylamine was observed.

Also model compounds 30 and 31, containing aliphatic amine leaving groups (p-methoxybenzylamine or p-chlorobenzylamine), were reduced. In both cases, within 30 min, the starting compound was converted into a single product, however, again no free amine was formed.

When the phenethyl alcohol leaving group containing compound 32 was reduced under the same conditions, the product showed to be completely converted into free phenethyl alcohol, as observed by $^1$H-NMR.

To verify whether the single release single release 1,6-elimination spacer self-eliminates when the leaving group is an aliphatic amine, compound 34 was reduced. NMR indicated complete release of benzylamine.

Figure 28:
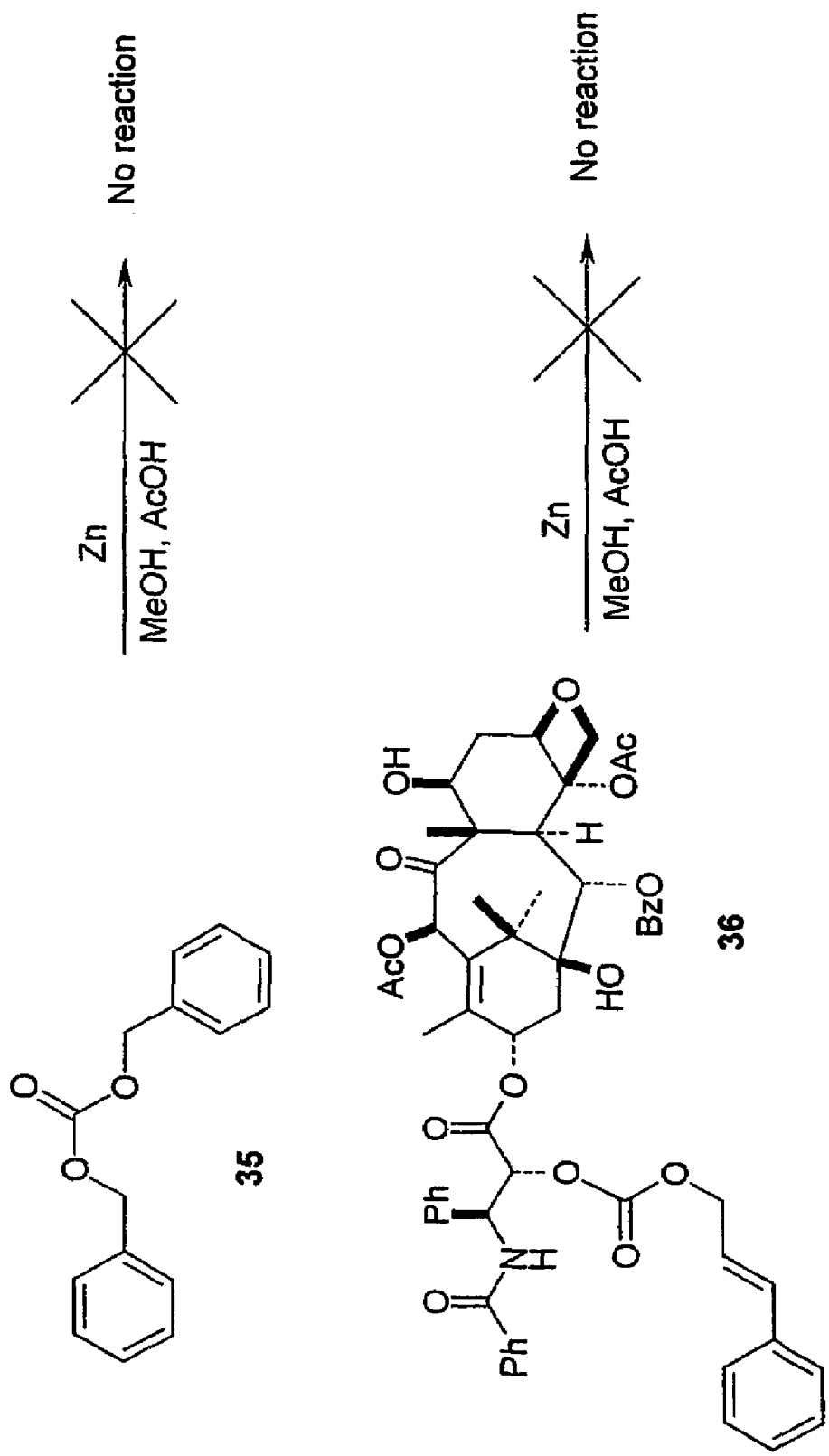
FIG. 28 shows the treatment of two reference compounds with zinc and acetic acid, which does not lead to any degradation of starting material.

The reference compounds 35 and 36 were also treated with zinc and acetic acid (FIG. 28). According to $^1$H-NMR both compounds did not show any degradation, which demonstrates that the liberation of leaving groups from the nitro-containing model compounds is not due to unwanted side reactions.

From some reduction products of aliphatic amine leaving group containing model compounds, NMR or thin layer chromatography showed in some cases after 1-3 months following nitro reduction or Aloc deprotection, that percentages of liberated leaving group remained unchanged. In each case, no more than one equivalent of aliphatic amine was released. Both the herein disclosed double and triple release aniline-based multiple release spacers are not able to release more than one leaving group, if the leaving group is an aliphatic amine. The multiple release structures as depicted in FIGS. 7 and 8 have been shown in this invention to possess multiple release characteristics when the leaving group is an aromatic amine or an oxygen (hydroxyl). Apparently, the extent of electron-withdrawing capacity of the leaving groups determines whether more than one leaving group can be liberated from the herein disclosed spacers. When the multiple release spacer is a phenol- or thiophenol-based multiple release spacer or when the multiple release spacer is coupled to single release phenol- or thiophenol-based spacers, aliphatic amines are also suitable leaving groups and release of all aliphatic amine leaving groups does occur. Aliphatic alcohols prove to be suitable leaving groups (e.g., from $H_2N-C_6H_4-CH=C(CH_2-O-CO-2'-O-paclitaxel)_2$ two molecules of paclitaxel are released) and therefore release of phenol-based spacers, to which an aliphatic amine leaving group is connected, from a multiple release spacer (e.g., $H_2N-C_6H_4-CH=C(CH_2-O-C(O)O-C_6H_4-CH_2OC(O)NR^1R^2)_2$) occurs by virtue of their increased leaving capability with respect to aliphatic alcohols. As elimination of aliphatic amines from hydroxybenzyl-based spacer-aliphatic amine conjugates is known[10], release of aliphatic amines from spacer systems in which the aliphatic amine is directly connected to a phenol-based spacer takes place as well.

Upon removal or transformation of the specifier V in the compounds or prodrugs disclosed in this invention, thus upon unmasking of B of the branched spacer or spacer system coupled to V, under physiological conditions, the reactive intemiediate(s) formed after self-elimination is (are) likely to be trapped by water, thereby regenerating molecules like aminodiol 23 and/or aminotriol 16. When a multiple release conjugate or prodrug constructed with one of the monomers disclosed in this invention is used for drug delivery purposes, the degradation products of the prodrug or (bio)conjugate after the multiple self-elimination cascade must be non-toxic (except from drugs to be released in tumor targeting approaches). Therefore, we have tested the aminotriol monomer 16 and aminodiol monomer 23 for their cytotoxicity in a panel of seven weul-characterized human tumor cell lines. Both compounds turned out to be non-toxic (see example 33).

The total attainable number of end groups (e.g., drug moieties) per dendrimeric prodrug or conjugate may be restricted by steric conditions. When incorporation of multiple large bioactive end groups is desired, it is likely that only several generations of multiple release monomeric spacers can be used. The number of end groups that can be incorporated may be increased by addition of additional unbranched self-elimination spacer(s) (systems) to a generation of multiple release spacers or to the highest generation of multiple release spacer(s) before leaving groups Z in order to enlarge the outer sphere surface, thereby enabling attachment of more end groups.

The electronic cascade self-elimination process of 4-aminobenzyl alcohol 1,6-elimination spacers is known to proceed with a short half-live. This is an important factor in drug delivery applications of self-elimination spacers, as fast drug release after site-specific activation is required. When a slower release of leaving groups is desired, the spacer monomer may be tuned such that the spacer elimination process is retarded. This can be of use when the functional multiple release spacers or spacer systems of this invention are used for controlled release purposes.

Unbranched and branched monomeric aminobenzyloxycarbonyl and related electronic cascade spacers or spacer systems can be coupled to a next generation of monomeric spacers via carbamate bonds, which are presumably more stable under physiological conditions than ester or carbonate bonds[34].

In the present invention, the synthesis and application of new multiple release spacers and spacer systems is described. In one embodiment, the dual or triple release monomer(s) employed in the multiple release prodrug or (bio)conjugate release the end groups (drugs) through several consecutive 1,4-, 1,6-, or 1,8-eliminations. Proof of principle of double or triple self-elimination was delivered upon chemical reduction of the nitrobenzyl or nitrocinnamyl derivatives containing benzyl alcohol, phenethyl alcohol, or paclitaxel as leaving groups (FIGS. 19, 22, 23, 26). Complete release was observed by thin layer chromatography, and was unambiguously confirmed by NMR. Also the compound containing 2 generations of double release monomers and 4 paclitaxel moieties was shown to release all end groups following reduction of the nitro group (FIG. 23).

Obviously, unbranched self-elimination spacers may be incorporated in between the specifier and the multiple release spacers. This may be beneficial for the enzymatic removal or transformation of the specifier. A branched multiple release moiety directly coupled to the specifier may increase steric crowding around the specifier-spacer bond to be cleaved; additional single release self-elimination spacers may provide a solution here.

Thus, for efficient removal or transformation of the specifier, in some cases it is particularly preferred to incorporate one or more single release self-elimination spacers in between specifier and one or more generation(s) of a multiple release spacer. This means that in compounds of formula

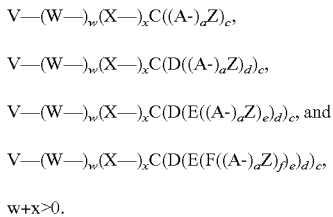

w+x>0.

In addition, single release self-elimination spacers may be added to the highest generation of the multiple release spacer(s) before leaving groups Z. This may be beneficial for enhanced release of Z, depending on the chemical nature of the function with which Z, preferably a drug, is attached to the spacer. Incorporation of single release self-elimination spacers before Z (for example drug moieties) may be beneficial for the stability of the final product. If, for example, a self-elimination ω-amino aminocarbonyl cyclization spacer is incorporated in between the single release or multiple release electronic cascade spacer and a leaving group that is connected through its hydroxyl group, the stability of the final product may be increased when used under physiological conditions. Furthermore, when only aniline-based multiple release spacers are used, addition of single release phenol- or thiophenol-based spacers to a generation of multiple release spacers or, preferably, to the highest generation of multiple release spacer(s) before leaving groups Z enables the release of two or more leaving groups Z that are coupled with their aliphatic amino group to the multiple release spacer system.

When only aniline-based multiple release spacers are used and no single release phenol- or thiophenol-based spacers are incorporated into the multiple release spacer system to which leaving groups Z are coupled with their aliphatic amino group only 1 Z group will be released.

In yet another aspect the invention relates to the use of any of the compounds defined above for the manufacture of a pharmaceutical preparation for the treatment of a mammal being in need thereof. The invention also relates to methods of treating a mammal being in need thereof, whereby the method comprises the administration of a pharmaceutical composition to the mammal in a therapeutically effective dose.

In a further aspect the invention relates to a process for preparing a pharmaceutical composition containing a compound as defined above, to provide a solid or a liquid formulation for administration orally, topically or by injection. Such a process at least comprises the step of mixing the compound with a pharmaceutically acceptable carrier.

The invention also relates to pharmaceutical compositions comprising the compounds of the invention as defined above. The compounds of the invention may be administered in purified form together with a pharmaceutical carrier as a pharmaceutical composition. The preferred form depends on the intended mode of administration and therapeutic or diagnostic application. The pharmaceutical carrier can be any compatible, nontoxic substance suitable to deliver the compounds of the invention to the patient. Pharmaceutically acceptable carriers are well known in the art and include, for example, aqueous solutions such as (sterile) water or physiologically buffered saline or other solvents or vehicles such as glycols, glycerol, oils such as olive oil or injectable organic esters, alcohol, fats, waxes, and inert solids may be used as the carrier. A pharmaceutically acceptable carrier may further contain physiologically acceptable compounds that act, e.g. to stabilize or to increase the absorption of the compounds of the invention. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the composition. Pharmaceutically acceptable adjuvants, buffering agents, dispersing agents, and the like, may also be incorporated into the pharmaceutical compositions.

For oral administration, the active ingredient can be administered in solid dosage forms, such as capsules, tablets, and powders, or in liquid dosage forms, such as elixirs, syrups, and suspensions. Active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The compounds of the invention are however preferably administered parenterally. Preparations of the compounds of the invention for parenteral administration must be sterile. Sterilization is readily accomplished by filtration through sterile filtration membranes, optionally prior to or following lyophilization and reconstitution. The parenteral route for administration of compounds of the invention is in accord with known methods, e.g. injection or infusion by intravenous, intraperitoneal, intramuscular, intraarterial, or intralesional routes. The compounds of the invention may be administered continuously by infusion or by bolus injection. A typical composition for intravenous infusion could be made up to contain 100 to 500 ml of sterile 0.9% NaCl or 5% glucose optionally supplemented with a 20% albumin solution and 1 mg to 10 g of the compound of the invention, depending on the particular type of compound of the invention and its required dosing regime. Methods for preparing parenterally admninistrable compositions are well known in the art and described in more detail in various sources, including, for example, Remington's Pharmaceutical Science[35].

The invention also relates to compounds as defined above, wherein the specifier V is removed or transformed by an enzyme that is transported to the vicinity of or inside target cells or target tissue via antibody-directed enzyme prodrug therapy (ADEPT)[1], polymer-directed enzyme prodrug therapy (PDEPT) or macromolecular-directed enzyme prodrug therapy (MDEPT)[2], virus-directed enzyme prodrug therapy (VDEPT)[3] or gene-directed enzyme prodrug therapy (GDEPT)[4].

The invention is further exemplified by the following Examples. These examples are for illustrative purposes and are not intended to limit the scope of the invention.

EXAMPLES

Example 1

Activation of nitrotriol 11 to give triply activated 12 (see FIG. 9). 100 mg (0.47 nmmol) of nitrotriol 11 was dissolved in 6 mL of dry THF under an argon atmosphere. The solution was added dropwise to a solution of 4-nitrophenyl chloroformate (1.42 g, 15 equiv) and pyridine (569 μL, 15 equiv) in 5 mL dry THF. The reaction mixture was stirred for 1 h, dichloromethane was added, and the organic layer was washed with 10% citric acid and brine. The organic layer was dried over anhydrous sodium sulfate and evaporated to dryness. The product was purified by means of column chromatography (EtOAc/heptane 3/5) to afford 139 mg (42%) of triply activated 12. $^1$H-NMR (300 MHz, CDCl$_3$) δ 5.41 (s, 2H, CH$_2$), 5.47 (s, 4H, CH$_2$), 7.37-7.42 (m, 6H, aromatic), 7.76 (s, 2H, aromatic), 8.26-8.30 (m, 6H, aromatic) ppm; FAB-MS m/e 709 (M+H)$^+$, 731 (M+Na)$^+$; Anal. (C$_{30}$H$_{20}$O$_{17}$N$_4$) calculated C 50.86%, H 2.85%, N 7.91%, measured C 51.09%, H 3.13%, N 7.54%.

Example 2

Figure 9:
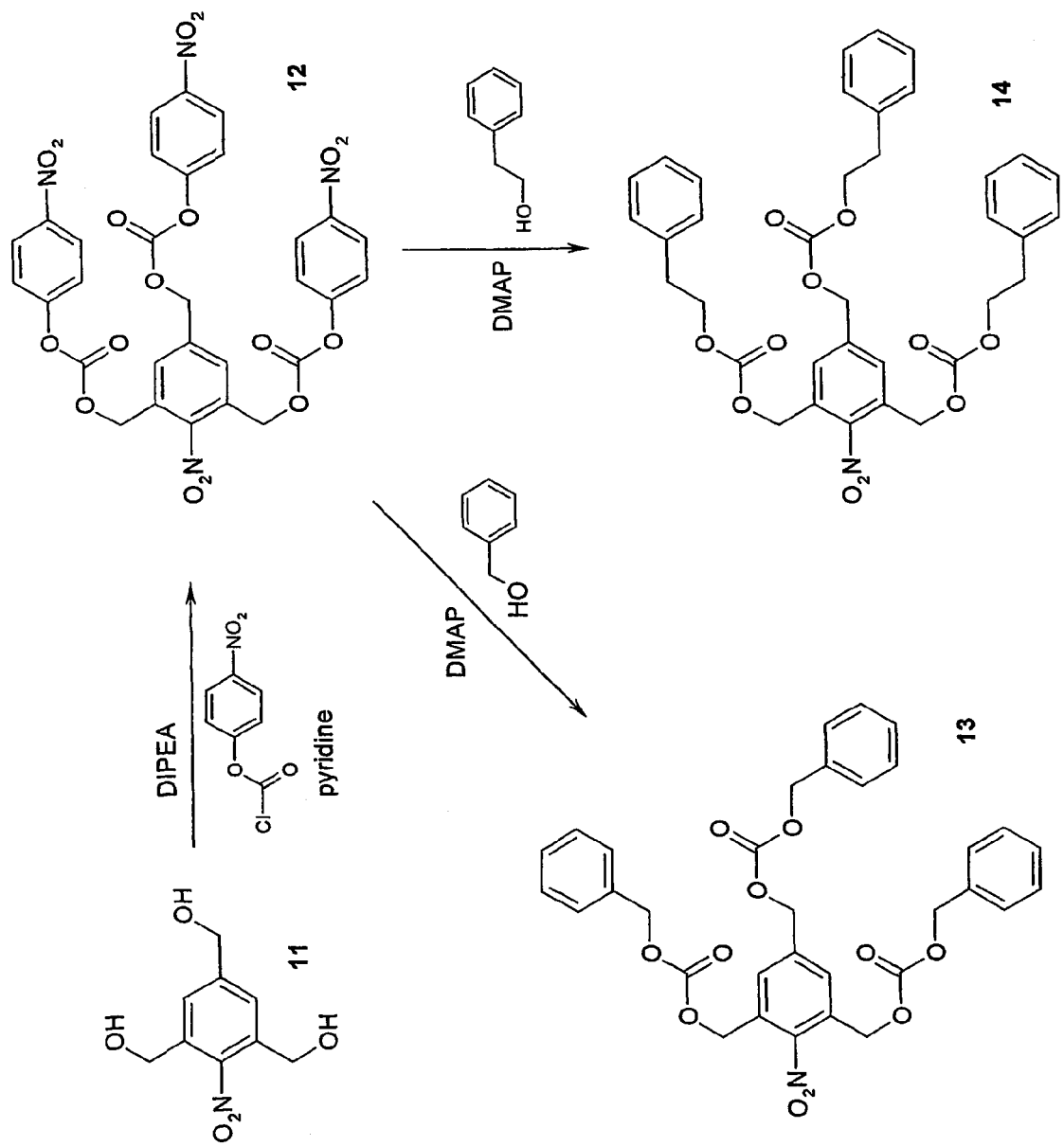
FIG. 9 shows the preparation of 2 model compounds containing a triple release spacer and 3 benzyl alcohol or phenethyl alcohol leaving groups.

Coupling of benzyl alcohol to triply activated 12 to give 13 (see FIG. 9). Triply activated 12 (29.5 mg, 0.042 mmol) was dissolved in dry dichloromethane. Benzyl alcohol (13 μL, 3.1 equiv) and DMAP (17 mg, 3.3 equiv) were added and the reaction mixture was stirred for 64 h. Dichloromethane was added and the organic layer was washed with saturated sodium bicarbonate, 10% citric acid, and brine, and dried over sodium sulfate. The product was purified by means of column chromatography (EtOAc/heptane 3/5) to afford 15 mg (59%) of desired product 13. $^1$H-NMR (300 MHz, CDCl$_3$) δ 5.15-5.18 (m, 8H, benzylic), 5.27 (s, 4H, benzylic), 7.33-7.39 (m, 15H, aromatic benzyl alcohol), 7.52 (s, 2H, aromatic spacer) ppm.

Example 3

Coupling of phenethyl alcohol to triply activated 12 to give 14 (see FIG. 9). Triply activated 12 (27 mg, 0.038 mmol) was dissolved in dry dichloromethane and the solution was cooled to 0° C. Phenethyl alcohol (16 μL, 3.5 equiv) and DMAP (16 mg, 3.5 equiv) were added and the reaction mixture was allowed to reach Rt and was stirred for 40 h. Dichloromethane was added and the organic layer was washed with saturated sodium bicarbonate, 10% citric acid, and brine, and dried over sodium sulfate. The product was purified by means of column chromatography (EtOAc/heptane 1/1) to afford 14 mg (57%) of desired product 14. $^1$H-NMR (300 MHz, DMSO-D$_6$/CDCl$_3$/CD$_3$OD) δ 2.91 (m, 6H, CH$_2$C$\underline{H}_2$Ph), 4.30 (m, 6H, C$\underline{H}_2$CH$_2$Ph), 5.18 (m, 6H, OC$\underline{H}_2$Ph), 7.14-7.28 (m, 15H, aromatic), 7.58 (s, 2H, aromatic) ppm; ESI-MS m/e 680 (M+Na)$^+$.

Example 4

Coupling of benzylamine to triply activated 12 to give 15 (see FIG. 10). To a solution of 12 (523 mg, 0.738 mmol) in dichloromethane were added benzylamine (403 μL, 3.69 mmol) and Et$_3$N (514 μL, 3.69 mmol). The reaction mixture was stirred at room temperature for 4 h. Dichlorormethane was added and the resulting mixture was washed with 10% citric acid, saturated sodium bicarbonate and brine, dried with anhydrous sodium sulfate, and concentrated under reduced pressure. Column chromatography (CH$_2$Cl$_2$/MeOH 25/1) gave 15 (406 mg, 90%) as a solid. $^1$H-NMR (300 MHz, CDCl$_3$) δ 4.31-4.36 (m, 6H, benzylic benzylamine), 5.13 (s, 2H, benzylic spacer), 5.20 (s, 4H, benzylic spacer), 7.23-7.34 (m, 17 H, aromatic) ppm.

Example 5

Figure 11:
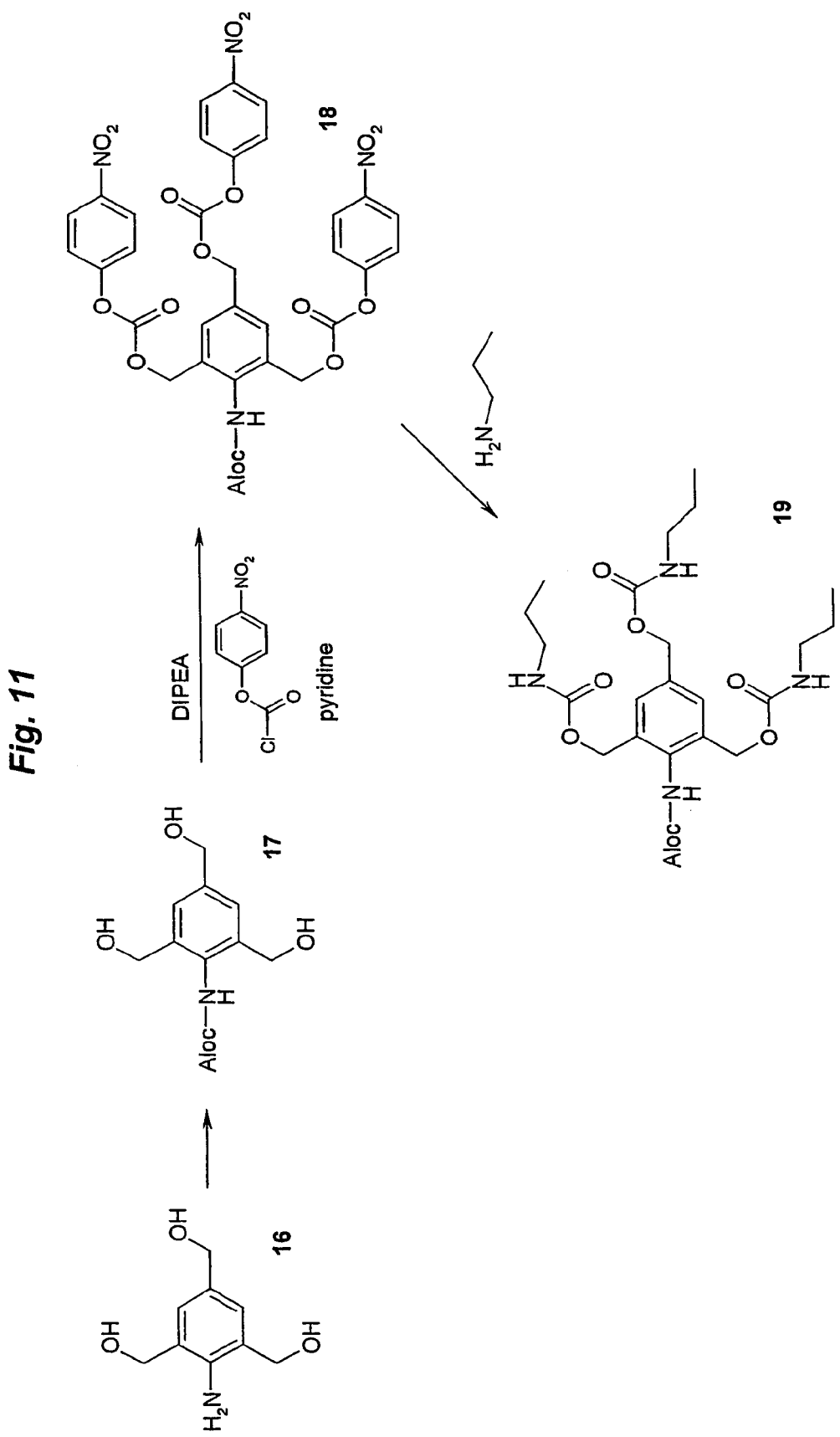
FIG. 11 shows the preparation of a model compound containing a triple release spacer and 3 propylamine leaving groups.

Protection of aminotriol 16 to give allyl N-[2,4,6-tri(hydroxymethyl)phenyl] carbamate 17 (see FIG. 11). To a solution of 1.085 g of 16 (5.92 mmol) in 20 mL dry THF under an argon atmosphere were added 1.48 mL (Aloc)$_2$O (1.5 equiv) and 200 mg HOBt (0.25 equiv). The reaction mixture was stirred for 72 hours at room temperature. THF was evaporated and the product was purified by means of column chromatography (CH$_2$Cl$_2$/MeOH 6/1) which afforded 872 mg (55%) of the desired compound 17. Mp 87° C.; $^1$H-NMR (300 MHz, CDCL$_3$/CD$_3$OD) δ 4.58-4.66 (m, 8H, 3×CH$_2$ and 2 Aloc), 5.25-5.41 (m, 2H, Aloc), 5.86-6.11 (m, 1H, Aloc), 7.35 (s, 2H, aromatic) ppm; MS (EI) m/e 249 (M–H$_2$O)$^+$; Anal. (C$_{13}$H$_{17}$NO$_5$.7/8H$_2$O) calculated C 55.17%, H 6.68%, N 4.95%, measured C 55.16%, H 6.16%, N 4.81%.

Example 6

Activation of triol 17 to give triply activated tricarbonate 18 (see FIG. 11). A solution of 837 mg of triol 17 (3.13 mmol) in dry THF was added drop wise under an argon atmosphere to a solution of 9.47 g 4-nitrophenyl chloroformate (15 equiv) and 3.8 mL pyridine (15 equiv) in dry THF. The reaction mixture was stirred for 5 hours and THF was evaporated. CH$_2$Cl$_2$ was added and the organic layer was washed with 10% aqueous citric acid and brine. The organic layer was dried over anhydrous Na$_2$SO$_4$ and evaporated. The product was purified by means of column chromatography (EtOAc/heptane 2/5) to afford 1.546 g (65%) of tricarbonate 18. Mp 46° C.; $^1$H-NMR (300 MHz, CDCL$_3$) δ 4.68 (d, 2H, J=5.7 Hz, Aloc), 5.22-5.37 (m, 8H, 3×CH$_2$ and 2 Aloc), 5.89-6.07 (m, 1H, Aloc), 7.35-7.42 (m, 6H, aromatic), 7.67 (s, 2H, aromatic), 8.26-8.30 (m, 6H, aromatic) ppm; MS (EI) m/e 763 (M+H)$^+$, 785 (M+Na)$^+$; Anal. (C$_{34}$H$_{26}$N$_4$O$_{17}$.3H$_2$O) calculated C 50.00%, H 3.95%, N 6.86%, measured C 49.99%, H 3.33%, N 6.44%.

Example 7

Coupling of propylamine to triply activated 18 to give triscarbamate 19 (see FIG. 11). To a solution of 18 (313 mg, 0.410 mmol) in dichloromethane were added propylamine (169 μL, 2.05 mmol) and Et$_3$N (286 μL, 2.05 mmol). The reaction mixture was stirred at room temperature for 16 h. Dichloromethane was added and the resulting mixture was washed with 10% citric acid, saturated sodium bicarbonate and brine, dried with anhydrous sodium sulfate, and concentrated under reduced pressure. Column chromatography (CH$_2$Cl$_2$/MeOH 20/1) gave 19 (158 mg, 74%) as a solid. $^1$H-NMR (300 MHz, CDCl$_3$) δ 0.87-0.94 (m, 9H, Me), 1.43-1.56 (m, 6H, CH$_2$C$\underline{H}_2$CH$_3$), 3.07-3.15 (m, 6H, C$\underline{H}_2$CH$_2$CH$_3$), 4.63 (d, 2H, Aloc), 5.01-5.17 (m, 8H, 2H Aloc and 6H O—CH$_2$), 5.95 (m, 1H, Aloc), 7.32 (bs, 2H, aromatic) ppm.

Example 8

Activation of nitrodiol 20 to give doubly activated 21 (see FIG. 12).: Nitrodiol 20 (130 mg, 0.621 mmol) was dissolved in 3 mL of dry THF under an argon atmosphere and the solution was cooled to 0° C. Diisopropylethylamine (DIPEA)

(865 µL, 8 equiv), 4-nitrophenyl chloroformate (751 mg, 6 equiv), and pyridine (25 µL, 0.5 equiv) were added to the solution. The reaction mixture was allowed to reach room temperature (Rt) and stirred for 16 h. Dichloromethane was added and the organic layer was washed with water, saturated sodium bicarbonate, and water. The organic layer was dried over anhydrous sodium sulfate and evaporated to dryness. The product was purified by means of column chromatography (EtOAc/heptane 2/5) to afford 280 mg (84%) of doubly activated 21. $^1$H-NMR (300 MHz, CDCl$_3$) δ 5.04 (s, 2H, CH$_2$), 5.08 (s, 2H, CH$_2$), 7.12 (s, 1H, vinylic), 7.38 (d, 2H, J=3.9 Hz, aromatic), 7.41 (d, 2H, J=3.9 Hz, aromatic), 7.51 (d, 2H, J=8.3 Hz, aromatic), 8.25-8.30 (m, 6H, aromatic) ppm; Anal. (C$_{24}$H$_{17}$N$_3$O$_{12}$) calculated C 53.44%, H 3.18%, N 7.79%, measured C 53.68%, H 3.44%, N 7.31%.

Example 9

Coupling of paclitaxel to doubly activated 21 to give 22 (see FIG. 12). Doubly activated 21 (40 mg, 0.075 mmol) was dissolved in 1 mL of dry dichloromethane and the solution was cooled to 0° C. Paclitaxel (128 mg, 2 equiv) and 4-(dimethylamino)pyridine (DMAP) (20 mg, 2.2 equiv) were added and the reaction mixture was allowed to reach Rt and was stirred for 16 h. Dichloromethane was added and the organic layer was washed with saturated sodium bicarbonate, 0.5 N potassium bisulfate, and brine, and dried over sodium sulfate. The product was purified by means of column chromatography (EtOAc) to afford 118 mg (80%) of desired product 22. $^1$H-NMR (300 MHz, CDCl$_3$) δ 1.14 (s, 6H, 17), 1.26 (s, 6H, 16), 1.68 (s, 6H, 19), 1.91 (bs, 6H, 18), 2.21 (s, 3H, 10-acetyl), 2.22 (s, 3H, 10-acetyl), 2.46 (s, 6H, 4-acetyl), 3.80 (bd, 2H, 3), 4.19 (d, 2H, 20b), 4.31 (d, 2H, 20a), 4.43 (m, 2H, 7), 4.76 (dd, 2H, CH$_2$-cinnanyl), 4.85 (s, 2H, CH$_2$-cinnamyl), 4.95 (d, 2H, 5), 5.46 (d, 1H, J=3.0 Hz, 2'), 5.49 (d, 1H, J=3.1 Hz, 2'), 5.68 (d, 2H, J=7.2 Hz, 2), 6.05 (m, 2H, 3'), 6.20-6.35 (m, 4H, 10 and 13), 6.92 (s, 1H, vinylic cinnamyl), 7.30-7.65 (m, 24H, aromatic), 7.71 (m, 4H, aromatic N-Bz), 8.12-8.16 (m, 6H, aromatic, 4H 2-Bz and 2H cinnamyl) ppm; ESI-MS m/e 1993 (M+Na)$^+$; Anal. (C$_{106}$H$_{109}$N$_3$O$_{34}$) calculated C 64.66%, H 5.58%, N 2.13%, measured C 65.02%, H 6.07%, N 1.72%.

Example 10

Coupling of aminodiol 23 to doubly activated 21 to give tetraol 24 (see FIG. 13). Doubly activated 21 (154 mg, 0.285 mmol) was dissolved in 3 mL of dry dimethylformamide (DMF) and aminodiol 23 (113 mg, 2.2 equiv), DIPEA (99 µL, 2 equiv), and a catalytic amount of hydroxybenzotriazole monohydrate (HOBt) (15 mg, 0.39 equiv) were added. The reaction mixture was stirred for 16 h. HOBt (8 mg, 0.2 equiv) was added and the reaction mixture was stirred for another 64 h. 10% 2-propanol in EtOAc was added and the organic layer was washed with water and dried over sodium sulfate. The crude product was purified by means of column chromatography (dichloromethane/MeOH 6/1) to yield tetraol 24 (72 mg, 41%). $^1$H-NMR (300 MHz, CDCl$_3$/CD$_3$OD) δ 4.31 (m, 8H, CH$_2$OH), 4.91 (s, 2H, CH$_2$OCO), 4.95 (s, 2H, CH$_2$OCO), 6.62 (s, 2H, vinylic), 6.98 (s, 1H, vinylic), 7.24 (d, 2H, J=8.6 Hz, aromatic), 7.24 (d, 2H, J=8.6 Hz, aromatic), 7.40 (m, 4H, aromatic), 7.56 (d, 2H, J=8.5 Hz, aromatic), 8.26 (d, 2H, J=8.8 Hz, aromatic) ppm; FAB-MS m/e 643 (M+Na)$^+$; Anal. (C$_{32}$H$_{33}$N$_3$O$_{10}$) calculated C 62.03%, H 5.37%, N 6.78%, measured C 62.62%, H 5.71%, N 6.18%.

Example 11

Activation of tetraol 24 to give quadruply activated 25 (see FIG. 13). Tetraol 24 (58 mg, 0.094 mmol) was dissolved in dry THF and the solution was cooled to 0° C. DIPEA (261 µL, 16 equiv), 4-nitrophenyl chloroformate (226 mg, 12 equiv), and pyridine (8 µL, 16 equiv) were added to the solution. The reaction mixture was allowed to reach Rt and was stirred for 16 h. Dry dichloromethane was added and the reaction mixture was stirred for another 24 h. Dichloromethane was added and the organic layer was washed with saturated sodium bicarbonate, 10% citric acid, and brine. The organic layer was dried over anhydrous sodium sulfate and evaporated to dryness. The product was purified by means of column chromatography (EtOAc/heptane 5/4) to afford 65 mg (54%) of quadruply activated 25. $^1$H-NMR (300 MHz, CDCl$_3$) δ 4.93 (s, 2H, CH$_2$OCONH), 4.95 (s, 2H, CH$_2$OCONH), 5.03 (s, 4H, CH$_2$OCOO), 5.07 (s, 4H, CH$_2$OCOO), 6.80-7.02 (m, 3H, vinylic), 7.28-7.50 (m, 18H, aromatic), 8.23-8.29 (m, 10H, aromatic) ppm; ESI-MS m/e 1302 (M+Na)$^+$; Anal. (C$_{60}$H$_{45}$N$_7$O$_{26}$) calculated C 56.30%, H 3.54%, N 7.66%, measured C 56.58%, H 3.74%, N 7.37%.

Example 12

Coupling of paclitaxel to quadruply activated 25 to give 26 (see FIG. 13). Quadruply activated 25 (13 mg, 0.010 mmol) was dissolved in 1 mL of dry dichloromethane and the solution was cooled to 0° C. Paclitaxel (35 mg, 4 equiv) and DMAP (5.5 mg, 4.4 equiv) were added and the reaction mixture was allowed to reach Rt and was stirred for 16 h. Dichloromethane was added and the organic layer was washed with saturated sodium bicarbonate, 0.5 N potassium bisulfate, and brine, and dried over sodium sulfate. The product was purified by means of column chromatography (EtOAc) to afford 27 mg (64%) of desired product 26. $^1$H-NMR (300 MHz, CDCl$_3$) δ 1.15 (m, 12H, 17), 1.26 (m, 12H, 16), 1.68 (bs, 12H, 19), 1.89 (m, 12H, 18), 2.17 (m, 12H, 10-acetyl), 2.42 (m, 12H, 4-acetyl), 3.80 (m, 4H, 3), 4.20 (ni, 4H, 20b), 4.29 (m, 4H, 20a), 4.40 (m, 4H, 7), 4.75-5.00 (m, 16H, 4H 5 and 12H CH$_2$-cinnamyl), 5.47 (m, 4H, 2'), 5.65 (m, 4H, 2), 5.97 (m, 4H, 3'), 6.13-6.38 (m, 8H, 10 and 13), 6.76-6.91 (m, 3H, vinylic cinnamyl), 7.23-7.65 (m, H, aromatic), 7.71 (d, 8H, aromatic N-Bz), 8.13 (m, 8H, aromatic 2-Bz), 8.23 (d, 2H, aromatic cinnamyl) ppm; ESI-MS m/e 4157 (M+H$_2$O)$^+$.

Example 13

Coupling of benzylamine to doubly activated 21 to give 27 (see FIG. 14). To a solution of 21 (50 mg, 92.7 µmol) in dichloromethane (2 mL) were added benzylamine (51 µL, 0.464 mmol) and Et$_3$N (65 µL, 0.464 mmol). The reaction mixture was stirred at room temperature for 16 h. Dichloromethane was added and the resulting mixture was washed with 10% citric acid, saturated bicarbonate and brine, dried with anhydrous sodium sulfate, and concentrated under reduced pressure. Column chromatography (CH$_2$Cl$_2$/MeOH 40/1) gave 27 (38 mg, 79.9 µmol, 86%) as a solid. $^1$H-NMR (300 MHz, CDCl$_3$) δ 4.33-4.39 (m, 4H, benzylic), 4.79 (s, 2H, spacer), 4.82 (s, 2H, spacer), 6.78 (s, 1H, alkene), 7.25-7.35 (m, 12H, aromatic), 7.42 (d, 2H, aromatic spacer), 8.18 (d, 2H, aromatic spacer) ppm.

Example 14

Figure 15:
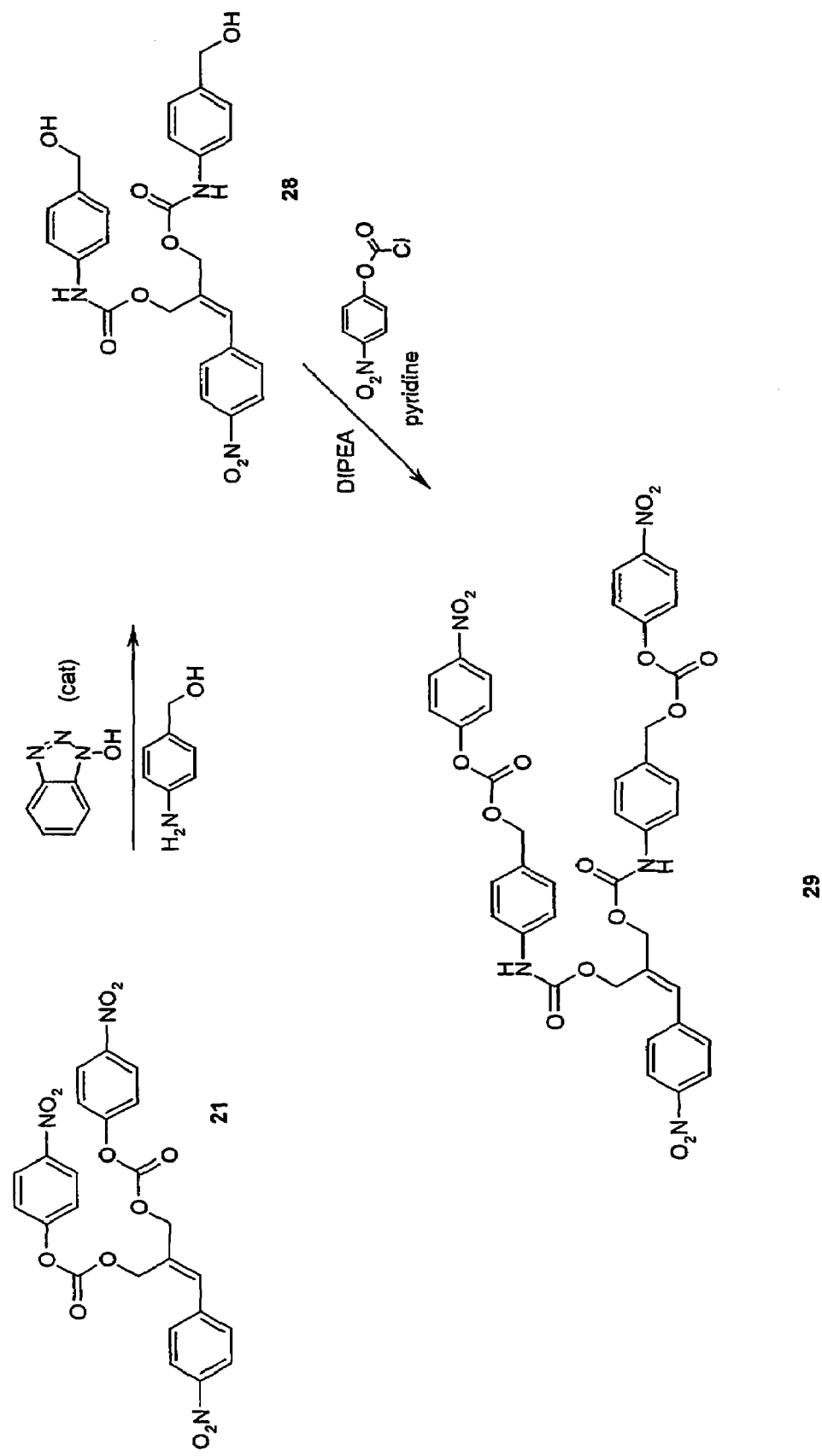
FIG. 15 shows the preparation of a doubly p-nitrophenyl carbonate activated compound containing a double release spacer coupled to two single release spacers.
Figure 16:
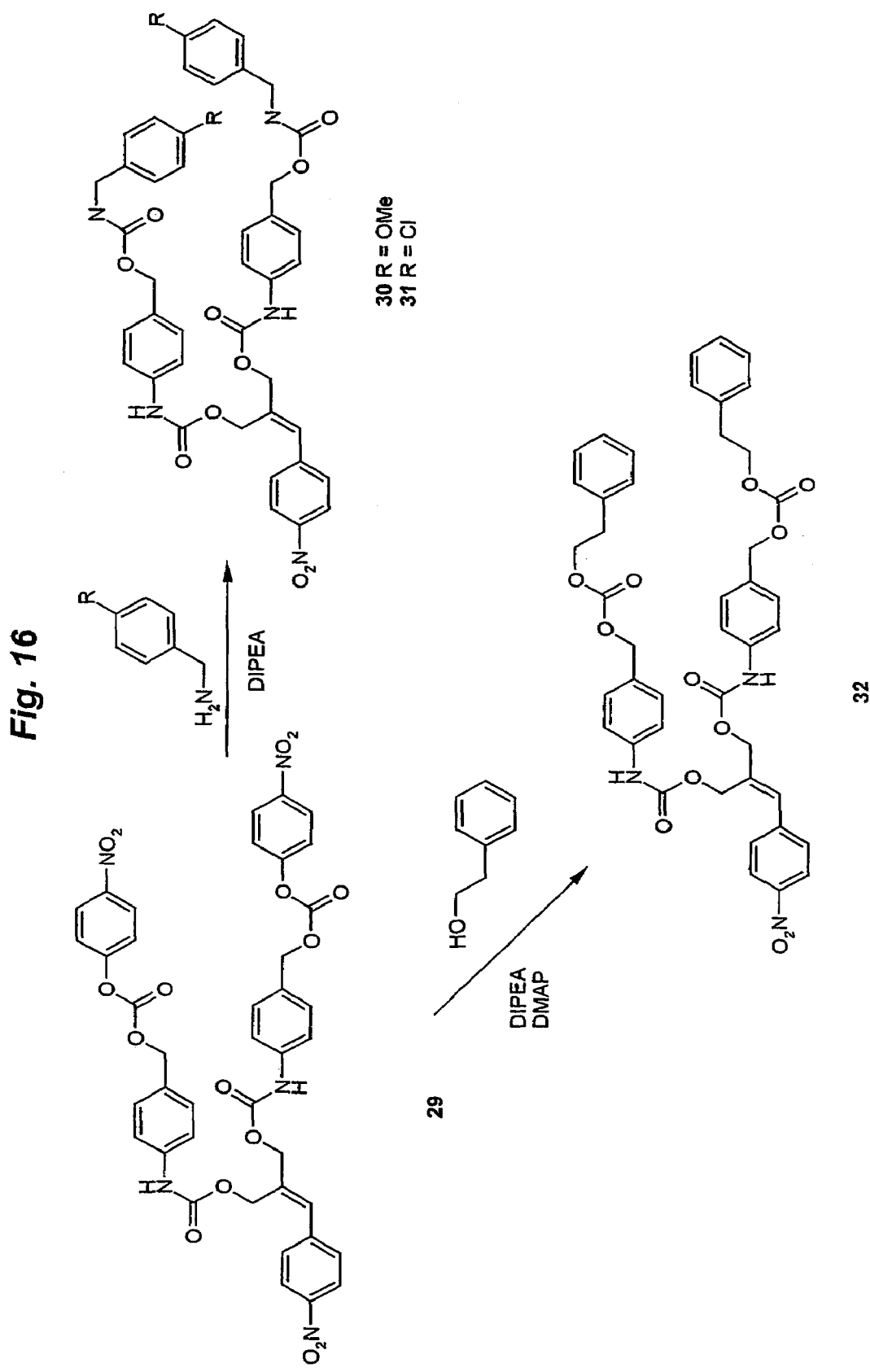
FIG. 16 shows the preparation of 3 model compounds containing a double release spacer coupled to two single release spacers.

Coupling of p-aminobenzyl alcohol to doubly activated 21 to give 28 (see FIG. 15). Compound 21 (330 mg, 0.612 mmol) was dissolved in DMF (5 mL) and p-aminobenzyl alcohol (166 mg, 1.35 mmol), DIPEA (214 µL, 1.22 mmol), and 1-hydroxybenzotriazole (24.8 mg, 0.184 mmol) were added at room temperature. The reaction mixture was stirred at room temperature for 2 days. The reaction mixture was concentrated under reduced pressure and then dissolved in ethyl acetate (75 mL). The clear solution was washed with a 10% aqueous citric acid solution and brine, dried with anhydrous sodium sulfate, filtered, and concentrated under reduced pressure. Column chromatography (chloroform/MeOH 8/1) afforded 28 (181 mg, 0.357 mmol, 58%) as a white solid after freeze-drying. $^1$H-NMR (300 MHz, CD$_3$OD/CDCl$_3$) δ 4.57 (s, 4H, CH$_2$OH), 4.89 (s, 2H, CH$_2$OC(O)R), 4.92 (s, 2H, CH$_2$OC(O)R), 6.95 (s, 1H, CH=CR$_2$), 7.25-7.54 (m, 10H, aromatic), 8.24 (d, 2H, J=8.8 Hz, aromatic) ppm; ESI-MS m/e 530 (M+Na)$^+$; Anal. (C$_{26}$H$_{25}$N$_3$O$_8$) calculated C 61.53%, H 4.97%, N 8.28%, measured C 61.60%, H 5.20%, N 7.61%.

Example 15

Activation of diol 28 with p-nitrophenyl chloroformate to give 29 (see FIG. 15). To a solution of compound 28 (160 mg, 0.315 mmol) in THF (5 mL) were added DIPEA (440 µL, 2.52 mmol), p-nitrophenyl chloroformate (381 mg, 1.89 mmol), and pyridine (12.9 µL, 0.158 mmol) at 0° C. The reaction mixture was slowly warmed to room temperature and stirred overnight. Ethyl acetate (75 mL) was added to the reaction mixture and the mixture was washed with a saturated aqueous sodium bicarbonate solution, a 10% aqueous citric acid solution, and brine. The organic fraction was dried with anhydrous sodium sulfate, filtered, and concentrated under reduced pressure. Column chromatography (EtOAc/hexanes 1/1) afforded 29 (155 mg, 0.187 mmol, 59%) as a white solid after freeze-drying. $^1$H-NMR (300 MHz, CDCl$_3$/DMSO-D$_6$) δ 4.90 (s, 2H, CH$_2$OC(O)NHR), 4.95 (s, 2H, CH$_2$OC(O)NHR), 5.23 (s, 4H, CH$_2$OC(O)OR), 6.96 (s, 1H, CH=CR$_2$), 7.34-7.56 (m, 14H, aromatic), 8.22-8.28 (m, 6H, aromatic) ppm; ESI-MS m/e 860 (M+Na)$^+$, 1697 (2M+Na)$^+$; Anal. (C$_{40}$H$_{31}$N$_5$O$_{16}$·1.5H$_2$O) calculated C 55.56%, H 3.96%, N 8.10%, measured C 55.60%, H 3.96%, N 8.30%.

Example 16

Coupling of p-methoxybenzylamine to doubly activated 29 to give 30 (see FIG. 16). To a solution of 29 (50 mg, 59.7 µmol) in 1-methyl-2-pyrrolidinone (4 mL) was added at 0° C. p-methoxybenzylamine (31 µL, 0.24 mmol) and DIPEA (3.0 µL, 18 µmol). The reaction mixture was stirred at room temperature for 15 h. A 10% solution of isopropanol in ethyl acetate (25 mL) was added and the resulting mixture was washed with water and brine, dried with anhydrous sodium sulfate, filtered, and concentrated under reduced pressure. Column chromatography (EtOAc/hexanes 1/3) gave 30 (35.0 mg, 42.0 µmol, 70%) as a white solid. $^1$H-NMR (300 MHz, CDCl$_3$/CD$_3$OD) δ 3.79 (s, 6H, OCH$_3$), 4.26 (s, 4H, NCH$_2$), 4.90 (s, 2H, CH$_2$OC(O)NHC$_6$H$_4$R), 4.94 (s, 2H, CH$_2$OC(O)NHC$_6$H$_4$R), 5.04 (s, 4H, CH$_2$OC(O)NCH$_2$R), 6.85 (d, 4H, J=8.6 Hz, aromatic), 6.96 (s, 1H, CH=CR$_2$), 7.19-7.28 (m, 8H, aromatic), 7.37-7.42 (m, 4H, aromatic), 7.53 (d, 2H, J=8.6 Hz, aromatic), 8.25 (m, 2H, aromatic) ppm; FAB-MS m/e 856 [M+Na]$^+$, 1690 [2M+Na]$^+$.

Example 17

Coupling of p-chlorobenzylamine to doubly activated 29 to give 31 (see FIG. 16). To a solution of 29 (72 mg, 86 µmol) in THF (4 mL) were added at 0° C. p-chliorobenzylaniine (42 µL, 0.34 mmol) and DIPEA (4.5 µL, 26 µmol). The reaction mixture was stirred at room temperature for 15 h. The reaction mixture was concentrated under reduced pressure and the residue was purified by colum chromatography (EtOAc/hexanes 1/1) to afford 31 (60 mg, 71.2 mmol, 83%) as a white solid after freeze-drying. $^1$H-NMR (300 MHz, CDCl$_3$/CD$_3$OD) δ 4.27 (s, 4H, NCH$_2$), 4.89 (s, 2H, CH$_2$OC(O)NHC$_6$H$_4$R), 4.94 (s, 2H, CH$_2$OC(O)NHC$_6$H$_4$R), 5.03 (s, 4H, CH$_2$OC(O)NCH$_2$R), 6.98 (s, 1H, CH=CR$_2$), 7.21-7.29 (m, 12H, aromatic), 7.40-7.44 (m, 4H, aromatic), 7.57 (d, 2H, J=8.6 Hz, aromatic), 8.25 (m, 2H, aromatic) ppm; FAB-MS m/e 864 [M+Na]$^+$.

Example 18

Coupling of phenethyl alcohol to doubly activated 29 to give 32 (see FIG. 16). To a solution of 29 (18 mg, 21 µmol) in THF (2 mL) were added at 0° C. phenethyl alcohol (10.3 µL, 85.9 µmol), DIPEA (1.9 µL, 11 µmol), and DMAP (10.5 mg, 85.9 µmol). The reaction mixture was stirred at room temperature for 15 h. The reaction mixture was concentrated under reduced pressure and the residue was purified by column chromatography (EtOAc/hexanes 1/1) to afford 32 (9.5 mg, 12 mmol, 55%) as a white solid after freeze-drying. $^1$H-NMR (300 MHz, CDCl$_3$/CD$_3$OD) δ 2.97 (t, 4H, J=7.0 Hz, CH$_2$CH$_2$Ph), 4.34 (t, 4H, J=7.0 Hz, CH$_2$CH$_2$Ph), 4.90 (s, 2H, CH$_2$OC(O)NHC$_6$H$_4$R), 4.94 (s, 2H, CH$_2$OC(O)NHC$_6$H$_4$R), 5.07 (s, 4H, CH$_2$OC(O)OR), 6.97 (s, 1H, CH=CR$_2$), 7.19-7.30 (m, 14H, aromatic), 7.39-7.44 (m, 4H, aromatic), 7.54 (d, 2H, J=8.7 Hz, aromatic), 8.25 (d, 2H, J=8.7 Hz, aromatic) ppm; FAB-MS m/e 804 [M+H]$^+$, 826 [M+Na]$^+$.

Example 19

Coupling of benzylamine to 4-nitrobenzyl chloroformate 33 to give 34 (see FIG. 17). A solution of chloroformate 33 (200 mg, 0.923 mmol) in THF was added dropwise to a mixture of benzylamine (101 µL, 0.923 mmol) and Et$_3$N (129 µL, 1 equiv) in THF at 0° C. The reaction mixture was allowed to reach room temperature and was stirred for 16 h. EtOAc was added and the organic layer was washed with 0.1 M NaOH, 10% citric acid, and brine, and dried over sodium sulfate to quantitatively yield desired product 34. $^1$H-NMR (300 MHz, CDCl$_3$) δ 4.39 (d, 2H, J=6.0 Hz, benzylic benzylamine), 5.22 (s, 2H, benzylic spacer), 7.25-7.40 (m, 5H, aromatic benzylamine), 7.50 (d, 2H, J=8.4 Hz, aromatic spacer), 8.20 (d, 2H, J=8.4 Hz, aromatic spacer) ppm.

Example 20

Proof of principle for triple elimination. Formation of benzyl alcohol upon reduction of 13 (see FIG. 19). Compound 13 was dissolved in 3 mL of MeOH/AcOH/THF (1.5/0.5/1). Zinc powder was added and the reaction mixture was stirred at Rt. After 30 min thin layer chromatography indicated disappearance of starting compound and formation of a substantial amount of benzyl alcohol. The mixture was filtered over hyflo and the residue was washed with MeOH/dichloromethane. The filtrate was concentrated in vacuo, dioxane was added, and the resulting solution was freeze-dried. $^1$H-NMR (300 MHz, CDCl$_3$/CD$_3$OD/CD$_3$CN/DMSO-D$_6$) δ 4.57 (s, 2H, benzylic), 7.28-7.36 (m, 5H, aromatic) ppm, identical with peaks observed for free benzyl alcohol in the same medium.

Example 21

Proof of principle for triple elimination. Formation of phenethyl alcohol upon reduction of 14 (see FIG. 19). Compound 14 was dissolved in 3.75 mL of MeOH/AcOH/THF (2/0.75/1). Zinc powder was added and the reaction mixture was stirred at Rt. After 1 h thin layer chromatography indicated disappearance of starting compound and formation of a substantial amount of phenethyl alcohol. The mixture was filtered over hyflo and the residue was washed with MeOH/dichloromethane. The filtrate was concentrated in vacuo, dioxane was added, and the resulting solution was freeze-dried. $^1$H-NMR (300 MHz, DMSO-D$_6$/CD$_3$OD/D$_2$O) δ 2.68 (t, 2H, CH$_2$CH$_2$Ph), 3.58 (t, 2H, CH$_2$CH$_2$Ph), 7.11-7.22 (m, 5H, aromatic) ppm, identical with peaks observed for free phenethyl alcohol in the same medium; ESI-MS m/e 122 (M)$^+$.

Example 22

Reduction of the nitro group in 15. Failure of elimination of benzylamine (see FIG. 20). Compound 15 (16 mg) was dissolved in 10 mL of MeOH/AcOH (8/2). Zinc powder was added and the reaction mixture was stirred at Rt. After 30 min, thin layer chromatography indicated disappearance of starting compound and showed complete conversion to a single product. Formation of benzylamine was not or was hardly observed. The mixture was filtered over hyflo and the residue was washed with MeOH/dichloromethane. The filtrate was concentrated in vacuo, the mixture was freeze-dried. Under a number of varied circumstances (different deuterated solvent combinations, different pH (acidic, neutral, and basic), different buffers), $^1$H-NMR did hardly show formation of free benzylamine. After 2 days, maximally 33 percent of free benzylamine was observed ($^1$H-NMR). Dissolving the reduced product in DMF did not increase amounts of released benzylamine.

Reduction of 15 using Raney Nickel/hydrazine did not lead to different results.

Example 23

Deprotection of the Aloc group from 19. Failure of elimination of propylamine (see FIG. 21). Compound 19 (36 mg, 69 µmol) was dissolved in 1 mL of CDCl$_3$. Morpholine was added (20 equiv, 120 µL, 1.38 mmol), and argon was bubbled through the solution. Then, a catalytic amount of palladium tetrakistriphenylphosphine was added. Elimination of propylamine was studied by $^1$H-NMR. After 1 h, thin layer chromatography indicated disappearance of starting compound. Under a number of varied circumstances (different deuterated solvent combinations, different pH (acidic, neutral, and basic), different buffers, in the presence of different nucleophiles), by $^1$H-NMR it was shown that maximally 33 percent of free propylamine had been formed after 2 weeks.

Example 24

Proof of principle for double elimination. Formation of paclitaxel upon reduction of 22 (see FIG. 22). Nitrocinnamyl biscarbonate 22 was dissolved in 3.5 mL of MeOH/AcOH/THF (2/0.5/1). Zinc powder was added and the reaction mixture was stirred at Rt. After 30 min thin layer chromatography indicated complete disappearance of starting compound and formation of a substantial amount of paclitaxel. The mixture was filtered over hyflo and the residue was washed with MeOH/dichloromethane. The filtrate was concentrated in vacuo, dioxane was added and the resulting solution was freeze-dried. Distinguishing peaks in the $^1$H-NMR, (300 MHz, CD$_3$OD) δ 4.19 (s, 4H, 20a and 20b), 4.32 (dd, 2H, 7), 4.74 (d, 2H, 2'), 4.99 (dd, 2H, 5), 5.65 (m, 4H, 2 and 3'), 6.16 (t, 2H, 13), 6.45 (s, 2H, 10) ppm, were identical with peaks observed for free paclitaxel in the same medium. The proton NMR spectrum did not show 2'-coupled paclitaxel; only unconjugated paclitaxel was present; FAB-MS m/e 854 (M+H)$^+$, 876 (M+Na)$^+$.

Example 25

Proof of principle for quadruple elimination. Formation of paclitaxel upon reduction of 26 (see FIG. 23). Compound 26 was dissolved in 3.25 mL MeOH/AcOH/TF (1.5/0.75/1). Zinc powder was added and the reaction mixture was stirred. After 30 min, thin layer chromatography indicated disappearance of starting compound and formation of a substantial amount of paclitaxel. After 16 h, the mixture was filtered over hyflo and the residue was washed with MeOH/dichloromethane. The filtrate was concentrated in vacuo, dioxane was added, and the resulting solution was freeze-dried. Distinguishing peaks in the $^1$H-NMR, (300 MHz, CD$_3$OD/CDCl$_3$/DMSO-D$_6$) δ 4.77 (d, 4H, 2'), 4.98 (d, 4H, 5), 5.65 (m, 8H, 2 and 3'), 6.17 (m, 4H, 13), 6.39 (s, 4H, 10) ppm, were identical with peaks observed for free paclitaxel in the same medium; ESI-MS m/e 877 (M+Na)$^+$.

Example 26

Reduction of the nitro group in 27. Failure of elimination of benzylamine (see FIG. 24). To a solution of 27 (18 mg, 38 µmol) in a 4:1 mixture of MeOH and AcOH (7.5 mL) Zinc powder was added and the reaction mixture was stirred at Rt. After 1 h, thin layer chromatography indicated disappearance of starting compound and showed complete conversion to a single product. No formation of benzylamine was observed. The mixture was filtered over hyflo and the residue was washed with MeOH/dichloromethane. The filtrate was concentrated in vacuo, dioxane was added and the mixture was freeze-dried. In a number of different deuterated solvent combinations, possessing a different pH, in some cases buffered, in the presence or absence of nucleophiles, $^1$H-NMR did not show formation of more than 50 percent of free benzylamine, even after a day.

Example 27

Reduction of the nitro group in 30. Failure of elimination of p-methoxybenzylamine (see FIG. 25). To a solution of 30 (10 mg, 12 µmol) in a 1:1 mixture of THF and methanol (2 mL) were added Raney Nickel (50% slurry in water, 0.05 mL) and hydrazine monohydrate (1.0 µL, 21 µmol). Thin layer chromatography (EtOAc/heptanes 3/1) showed complete conversion to a single product within 20 minutes. The reaction mixture was stirred overnight at room temperature. No formation of p-methoxybenzylamine was observed after night. The reaction mixture was filtered and concentrated under reduced pressure. The residue was dissolved in a 1:1 mixture of DMSO-d$_6$ and D$_2$O. $^1$H-NMR did not show any formation of free p-methoxybenzylamine after 1, 5, or 20 days. Slow decomposition of reduced 30 not involving release of p-methoxybenzylamine was observed.

Example 28

Reduction of the nitro group in 31. Failure of elimination of p-chlorobenzylamine (see FIG. 25). To a solution of 31 (10 mg, 12 μmol) in a 1:1 mixture of THF and methanol (2 mL) were added Raney Nickel (50% slurry in water, 0.05 mL) and hydrazine monohydrate (0.6 μL, 12 μmol). Thin layer cohromatography (EtOAc/heptanes 3/1) showed complete conversion to a single product within 30 minutes. The reaction mixture was filtered and concentrated under reduced pressure. The residue was dissolved in a 1:1 mixture of $CDCl_3$ and $CD_3OD$. $^1$H-NMR did not show any formation of free p-methoxybenzylamnine after 2 h, 15 h, 2 days, or 5 days. Slow decomposition of reduced 31 not involving release of p-chlorobenzylamine was observed.

Example 29

Reduction of the nitro group in 32. Formation of phenethyl alcohol (see FIG. 26). To a solution of 32 (8.0 mg, 10 μmol) in a 1:1 mixture of THF and methanol (1.5 mL) were added Raney Nickel (50% slurry in water, 0.05 mL) and hydrazine monohydrate (0.5 μL, 10 μmol). After 20 minutes, hydrazine monohydrate (0.5 μL, 10 μmol) were added. Thin layer chromatography (EtOAc/heptanes 1/1) showed complete conversion to a single product after 1 h. The reaction mixture was filtered and concentrated under reduced pressure. The residue was dissolved in a 1:1 mixture of $CDCl_3$ and $CD_3OD$ to which 10 drops of DMSO-$d_6$ were added. $^1$H-NMR showed complete release of free phenethyl alcohol. Distinguishing peaks in the $^1$H-NMR spectrum, (300 MHz, $CD_3OD/CDCl_3$/DMSO-$D_6$) δ 2.83 (t, 2H, J=7.1 Hz, $CH_2CH_2Ph$) and 3.76 (t, 2H, J=7.1 Hz, $CH_2CH_2Ph$) ppm, were identical with peaks observed for phenethyl alcohol in the same medium.

Example 30

Figure 27:
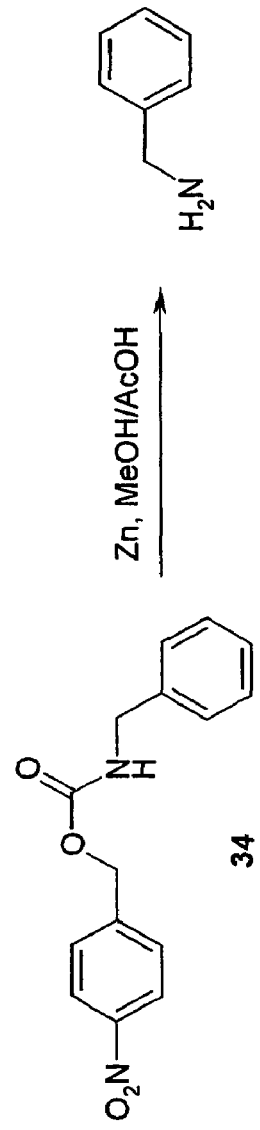
FIG. 27 shows the reduction of the nitro group in the model compound containing a benzylamine leaving group, with the concomitant liberation of benzylamine.

Proof of principle for single elimination. Formation of benzylamine upon reduction of 34 (see FIG. 27). Compound 34 (40 mg) was dissolved in 3.75 mL of MeOH/AcOH/THF (2/0.75/1). Zinc powder was added and the reaction mixture was stirred at Rt. After 100 min, thin layer chromatography indicated disappearance of starting compound and formation of a substantial amount of benzylamine. The mixture was filtered over hyflo and the residue was washed with MeOH/dichloromethane. The filtrate was concentrated in vacuo. $^1$H-NMR (300 MHz, $CD_3OD/CDCl_3$/DMSO-$D_6$) δ 3.98 (s, 2H, benzylic, liberated benzylamine), 7.34-7.43 (m, 5H, aromatic, liberated benzylamine) ppm, identical with peaks observed for free benzylamine in the same medium, indicated complete release of free benzylamine. NMR signals from conjugated benzylamine have disappeared.

Example 31

Stability of 35. Treatment of 35 with Zinc (see FIG. 28). Dibenzyl carbonate 35 (13 mg) was dissolved in 2.5 mL MeOH/THF/AcOH (1.5/0.5/0.5). Zinc powder was added and the reaction mixture was stirred at Rt for 16 h. Thin layer chromatography indicated no formation of new compounds, and indicated stability of 35. The mixture was filtered over hyflo and the residue was washed with MeOH/dichloromethane. The filtrate was concentrated in vacuo. $^1$H-NMR (300 MHz, $CDCl_3/CD_3OD/DMSO-D_6$) δ 5.07 (s, 4H, benzylic), 7.27 (m, 10H, aromatic) ppm, showed that the product was identical to starting compound; no benzyl alcohol was observed.

Example 32

Stability of 36. Treatment of 36 with Zinc (see FIG. 28). Paclitaxel-2'-carbonate 36 (3 mg) was dissolved in 2.5 mL MeOH/THF/AcOH (1.5/0.5/0.5). Zinc powder was added and the reaction mixture was stirred at Rt for 16 h. Thin layer chromatography indicated no formation of new compounds, and indicated stability of 36. The mixture was filtered over hyflo and the residue was washed with MeOH/dichloromethane. The filtrate was concentrated in vacuo. Distinguishing peaks in the $^1$H-NMR spectrum, (300 MHz, $CDCl_3/CD_3OD/DMSO-D_6$) δ 4.81 (d, 2H, J=7.2 Hz, $CH_2$ cinnamyl), 5.38 (d, 1H J=8.7 Hz, 2') ppm, showed that the product was identical to starting compound; no cinnamyl alcohol or free paclitaxel was observed.

Example 33

Cytoxicity of multiple release spacers 16 and 23. The anti-proliferative effect of the monomeric spacers was determined in vitro applying seven well-characterised human tumor cell lines and the microculture sulphorhodamine B (SRB) test. The anti-proliferative effects were determined and expressed as $ID_{50}$ values (ng/mL), which are the (pro)drug concentrations that gave 50% inhibition of cell growth when compared to control cell growth after 5 days of incubation.

Triple release monomer 16: cell lines ($ID_{50}$ values in ng/mL) MCF-7; breast cancer (>62.500). EVSA-T; breast cancer (>62.500). WIDR; colon cancer (>62.500). IGROV; ovarian cancer (>62.500). M19; melanoma (>62.500). A498; renal cancer (55867). H226; non-small cell lung cancer (>62.500).

Double release monomer 23: cell lines ($ID_{50}$ values in ng/mL): MCF-7; breast cancer (>62.500). EVSA-T; breast cancer (>62.500). WIDR; colon cancer (>62.500). IGROV; ovarian cancer (>62.500). M19; melanoma (>62.500). A498; renal cancer (56.784). H226; non-small cell lung cancer (42.406).

REFERENCES

1 Bagshawe, K. D. *Drug Dev. Res.* 1995, 34, 220.

2 Melton, R.; Connors, T.; Knox, R. J. *S.T.P. Pharma Sciences*, 1999, 13.

3 Huber, B. E.; Richards, C. A.; Krentisky, T. A. *Proc. Natl. Acad. Sci. USA*, 1991, 88, 8039.

4 Bagshawe, K. D.; Springer, C. J.; Searle, F.; Antoniw, P.; Sharma, S. K.; Melton, R. G.; Sherwood, R. F. *Br. J Cancer,* 1988, 58, 700.

5 King, H. D.; Yurgaitis, D.; Willner, D.; Firestone, R. A.; Yang, M. B.; Lasch, S. J.; Hellström, K. E.; Trail, P.A. *Biocoiyug. Chzem.*, 1999, 10, 279-288.

6 a) Kovář, M.; Strohalm, J.; Etrych, T.; Ulbrich, K.; Říhová, B. *Bioconjug. Chem.,* 2002, 13, 206-215. b) Wang, D.; Kopeckova, P.; Minko, T.; Nanayakkara, V.; Kopecek, J. *Biomacromol.,* 2000, 1, 313-319.

7 Choe, Y. H.; Conover, C. D.; Wu, D.; Royzen, M.; Gervacio, Y.; Borowski, V.; Mehlig, M.; Greenwald, R. B. *J. Contr. Rel.,* 2002, 79, 55-70.

8 Ulbrich, K.; Pechar, M.; Strohalm, J.; Subr, V.; Rihova, B. *Macromol. Symp.*, 1997, 118, 577-585.

9 a) Sun, C.; Wirsching, P.; Janda, K. M. *Bioorg. Med. Chem. Lett.*, 2002, 12, 2213-2215. b) Dubowchik, G. M.; Radia, S.; Mastalerz, H.; Walker, M. A.; Firestone, R. A.; King, H. D.; Hofstead, S. J.; Willner, D.; Lasch, S. J.; Trail, P. A. *Bioorg. Med. Chem. Lett.*, 2002, 12, 1529-1532.

10 Greenwald, R. B.; Yang, K.; Zhao, H; Conover C. D.; Lee, S.; Filpula, D. *Bioconjugate Chem.* 2003, 14, 395-403

11 Toki, B. E.; Cerveny, C. G.; Wahl, A. F.; Senter, P. D. *J. Org. Chem.*, 2002, 67, 1866-1872

12 a) Tomalia, D. A.; Naylor, A. M.; Goddard III, W. A. *Angew. Chem., Int. Ed. Engl.*, 1990, 29, 138-175. b) Newkome, G. R.; Nyak, A.; Behera, R. K.; Moorefield, C. N.; Baker, G. R. *J. Org. Chem.* 1992, 57, 358-362.

13 a) Twyman, L. J.; Beezer, A. E.; Esfand, R.; Hardy, M. J.; Mitchell, J. C. *Tet. Lett.*, 1999, 40, 1743-1746. b) Service, R. F. *Science*, 1995, 2.67, 458-459. c) Malik, N.; Wiwaftanapatapee, R.; Klopsch, R.; Lorenz, K.; Frey, H.; Weener, J. W.; Meijer, E. W.; Paulus, W.; Duncan, R. *J. Contr. Rel.*, 2000, 65, 133-148. d) Liu, M.; Fréchet, J. M. J. *Pharm. Science Techn. Today*, 1999, 2, 393-401. e) Esfand, R.; Tomalia, D. A. *Drug Discovery Today*, 2001, 6, 427-436. f) Stiriba, S.-E.; Frey, H.; Haag, R. *Angew. Chem. Int. Ed.*, 2002, 41, 1329-1334.

14 a) Ihre, H. R.; Padilla de Jésus, O. L.; Szoka, Jr., F. C.; Fréchet, J. M. J. *Bioconjug. Chem.*, 2002, 13, 443-452. b) Padilla de Jésus, O. L.; Ihre, H. R.; Gagne, L.; Fréchet, J. M. J.; Szoka, Jr., F. C. *Bioconjug. Chem.*, 2002, 13, 453-461.

15 Sideratou, Z.; Tsiourvas, D.; Paleos, C. M. *Langmuir*, 2000, 16, 1766-1769.

16 a) Battah, S. H.; Chee, C.-E.; Nakanishi, H.; Gerscher, S.; MacRobert, A. J.; Edwards, C. *Bioconjug. Chem.*, 2001, 12, 980-988. b) Smet, M.; Liao, L.-X.; Dehaen, W.; McGrath, D. V. *Org. Lett.*, 2000, 2, 511-513.

17 Seebach, D.; Herrmanm, G. F.; Lengweiler, U. D.; Bachmann, B. M.; Amrein, W. *Angew. Chem. Int. Ed. Engl.*, 1996, 35, 2795-2797.

18 Göller, R.; Vors, J.-P.; Caminade A.-M.; Majoral, J.-P. *Tet. Lett.*, 2001, 42, 3587-3590.

19 Krause, W.; Hackmann-Schlichter, N.; Maier, F. K.; Müller, R. *Top. Curr. Chem.*, 2000, 210, 261-308.

20 a) Dubowchik, G. M.; Walker, M. A. *Pharmacol. Ther.*, 1999, 83, 67-123. b) Huang, P. S.; Oliff, A. *Curr. Opin. Gen. Dev.*, 2001, 11, 104-110.

21 a) de Groot, F. M. H.; Damen, E. W. P.; Scheeren, H. W. *Curr. Med. Chem.*, 2001, 8, 1093-1122. b) Damen, E. W. P.; de Groot, P. M. H.; Scheeren, H. W. *Exp. Opin. Ther. Patents* 2001, 11, 651-666.

22 a) Houba, P. H. J.; Boven, E.; van der Meulen-Muileman, I. H.; Leenders, R. G. G.; Scheeren, J. W.; Pinedo, H. M.; Haisma, H. J. *Br. J. Cancer* 2000, 84, 1-8. b) Houba, P. H. J.; Boven, E.; van der Meulen-Muileman, I. H.; Leenders, R. G. G.; Scheeren, J. W.; Pinedo, H. M.; Haisma, H. J. *Int. J. Cancer* 2001, 91, 550-554. c) Florent, J.-C.; Dong, X.; Gaudel, G.; Mitaku, S.; Monneret, C.; Gesson, J.-P.; Jacquesy, J.-C.; Mondon, M.; Renoux, B.; Andrianomenjanahary, S.; Michel, S.; Koch, M.; Tillequin, F.; Gerken, M.; Czech, J.; Straub, R.; Bosslet, K. *J. Med. Chem.* 1998, 41, 3572-3581. d) Khan, S. R.; Denmeade, S. R. *Prostate* 2000, 45, 80-83. e) Defeo-Jones, D.; Garsky, V. M.; Wong, B. K.; Feng, D.-M.; Bolyar, T.; Haskell, K.; Kiefer, D. M.; Leander, K.; McAvoy, E.; Lumma, P.; Wai, J.; Senderak, E. T.; Motzel, S. L.; Keenan, K.; Van Zwieten, M.; Lin, J. H.; Freidinger, R.; Huff, J.; Oliff, A.; Jones, R. E. *Nature Med.* 2000, 6, 1248-1252. f) de Groot, F. M. H.; de Bart, A. C. W.; Verheijen, J. H.; Scheeren, H. W. *J. Med. Chem.*, 1999, 42, 5277-5283.

23 Ringsdorf, H. *J. Polym:. Sci., Polym. Symp.*, 1975, 51, 135-153.

24 Maeda, H.; Matsumura, Y. *Crit. Rev. Ther. Drug Carrier Systems*, 1989, 6, 193-210.

25 a) Duncan, R.; Gac-Breton, S.; Keane, R.; Musila, R.; Sat, Y. N.; Satchi, R.; Searle, F. *J. Contr. Rel.*, 2001, 74, 135-146. b) Vasey, P. A.; Kaye, S. B.; Morrison, R.; Twelves, C.; Wilson, P.; Duncan , R.; Thomson, A. H.; Murray, L. S.; Hilditch, T. E.; Murray, T.; Burtles, S.; Fraier, D.; Frigerio, E.; Cassidy, J. *Clin. Cancer Res.*, 1999, 5, 83-94.

26 a) Greenwald, R. B. *J. Contr. Rel.*, 2001, 74, 159-171. b) Greenwald, R. B.; Conover, C. D.; Choe, Y. H. *Crit. Rev. Ther. Drug Carrier Systems*, 2000, 17, 101-161.

27 Seymour, L. W. *Crit. Rev. Ther. Drug Carrier Systems*, 1992, 9, 135-187.

28 a) van Hest, J. C. M.; Delnoye, D. A. P.; Baars, M. W. P. L.; van Genderen, M. H. P.; Meijer, E. W. *Science*, 1995, 268, 1592-1595. b) Zimmerman, S. C.; Zeng, F.; Reichert, D. E. C.; Kolotuchin, S. V. *Science*, 1996, 271, 1095-1098.

29 de Groot, F. M. H.; Loos, W. J.; Koekkoek, R.; van Berkom, L. W. A.; Busscher, G. F.; Seelen, A. E.; Albrecht, C.; de Bruijn, P.; Scheeren. H. W. *J. Org. Chem.*, 2001, 66, 8815-8830.

30 a) Carl, P. L.; Chakravarty, P. K.; Katzenellenbogen, J. A. *J. Med. Chem.*, 1981, 24, 479-480. b) Wakselman, M. *New J. Chem.*, 1983, 7, 439-447.

31 a) Quilico, A.; Cardani, C.; *Gazzetta Chimica Italiana*, 1953, 83, 155-178. b) Quilico, A.; Cardani, C.; Piozzi, F. *Gazzetta Chimica Italiana*, 1953, 83, 179-191. c) Piozzi, F. *Gazzetta Chimica Italiana*, 1953, 83, 673-676.

32 Vanelle, P.; Maldonado, J.; Crozet, M. P.; Senouki, K.; Delmas, F.; Gasquet, M.; Timon-David, P. *Eur. J. Med. Chem.*, 1991, 26, 709-714.

33 De Groot, F. M. H.; Albrecht, C.; Koekkoek, R.; Beuslcer, P. H.; Scheeren, H. W. *Angew. Chem. Int. Ed.* 2003, 42, 4490-4494.

34 de Groot, F. M. H.; van Berkom, L. W. A.; Scheeren, H. W. *J. Med. Chem.*, 2000, 43, 3093-3102.

35 Remington's Pharmaceutical Science (15th ed., Mack Publishing, Easton, Pa., 1980) (incorporated by reference in its entirety for all purposes)

The invention claimed is:

1. A compound having a formula selected from

V—(W—)$_w$(X—)C((A—)$_a$Z)$_c$,

V—(W—)$_w$(X—)C(D((A—)$_a$Z)$_d$)$_c$,

V—(W—)$_w$(X—)C(D(E((A—)$_a$Z)$_e$)$_d$)$_c$, and

V—(W—)$_w$(X—)C(D(E(F((A—)$_a$Z)$_f$)$_e$)$_d$)$_c$, wherein:

V is an enzymatically removable specifier comprising an optionally protected peptide, which is optionally removable after binding to a receptor, or taken together, V—B is an oxidized form of B, wherein B is part of W or X;

each of W and X independently is a single release 1, (4+2n) electronic cascade spacer and has the formula:

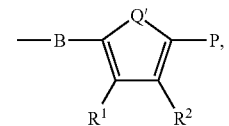

wherein

Q' is -R$^5$C=CR$^6$—;

B is selected from NR$^7$, O, and S;

P is C(R³)(R⁴)Q;
Q is —O—CO—;
A is an ω-amino aminocarbonyl cyclization elimination spacer having the formula:

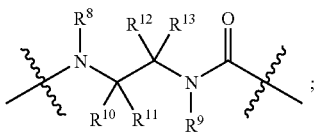

each of C, D, E, and F independently is a self-eliminating multiple release spacer or spacer system and has the formula:

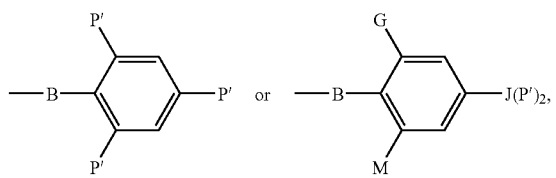

wherein
B is selected from NR¹, O, and S;
P' is C(R²)(R³)Q—(W—)$_{w(X—)x}$; wherein
  Q is —O—CO—; and
  W and X are as defined above; or
G and M are hydrogen; and
J is

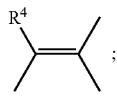

wherein R¹, R², R³, R⁴, R⁵, R⁶, and R⁷ independently are selected from H, a $C_{1-6}$ alkyl group, a $C_{3-20}$ heterocyclyl group, a $C_{5-20}$ aryl group, a $C_{1-6}$ alkoxy group, hydroxy (OH), amino (NH₂), mono-substituted amino (NR$_x$H), di-substituted amino (NR$_x^1$R$_x^2$), nitro (NO₂), halogen, CF₃, CN, CONH₂, SO₂Me, CONHMe, a cyclic $C_{1-5}$ alkylamino group, imidazolyl, a $C_{1-6}$ alkylpiperazinyl group, morpholino, thiol (SH), thioether (SR$_x$), tetrazole, carboxy (COOH), carboxylate (COOR$_x$), sulphoxy (S(=O)₂OH), sulphonate (S(=O)₂OR$_x$), sulphonyl (S(=O)₂R$_x$), sulphixy (S(=O)OH), sulphinate (S(=O)OR$_x$), sulphinyl (S(=O)R$_x$), phosphonooxy (OP(=O)(OH)₂), and phosphate (OP(=O)(OR$_x$)₂), wherein R$_x$, R$_x^1$ and R$_x^2$ are independently selected from a $C_{1-6}$ alkyl group, a $C_{3-20}$ heterocyclyl group and a $C_{5-20}$ aryl group;
R⁸ and R⁹ independently are selected from H and $C_{1-6}$ alkyl, said alkyl being optionally substituted with one or more of the following groups: hydroxy (OH), ether (OR$_x$), amino (NH₂), mono-substituted amino (NR$_x$H), di-substituted amino (NR$_x^1$R$_x^2$), nitro (NO₂), halogen, CF₃, CN, CONH₂, SO₂Me, CONHMe, cyclic $C_{1-5}$ alkylamino, imidazolyl, $C_{1-6}$ alkylpiperazinyl, morpholino, thiol (SH), thioether (SR$_x$), tetrazole, carboxy (COOH), carboxylate (COOR$_x$), sulphoxy (S(=O)₂OH), sulphonate (S(=O)₂OR$_x$), sulphonyl (S(=O)₂R$_x$), sulphixy (S(=O)OH), sulphinate (S(=O)OR$_x$), sulphinyl (S(=O)R$_x$), phosphonooxy (OP(=O)(OH)₂), and phosphate (OP(=O)(OR$_x$)₂), where R$_x$, R$_x^1$ and R$_x^2$ independently are selected from a $C_{1-6}$ alkyl group, a $C_{3-20}$ heterocyclyl group and a $C_{5-20}$ aryl group; and
R₁₀, R¹¹, R¹², and R¹³ independently are selected from, $C_{1-6}$ alkyl, $C_{3-20}$ heterocyclyl, $C_{5-20}$ aryl, $C_{1-6}$ alkoxy, hydroxy (OH), amino (NH₂), mono-substituted amino (NR$_x$H), di-substituted amino (NR$_x^1$R$_x^2$), nitro (NO₂), halogen, CF₃, CN, CONH₂, SO₂Me, CONHMe, cyclic $C_{1-5}$ alkylamino, imidazolyl, $C_{1-6}$ alkylpiperazinyl, morpholino, thiol (SH), thioether (SR$_x$), tetrazole, carboxy (COOH), carboxylate (COOR$_x$), sulphoxy (S(=O)₂OH), sulphonate (S(=O)₂OR$_x$), sulphonyl (S(=O)₂R$_x$), sulphixy (S(=O)OH), sulphinate (S(=O)OR$_x$), sulphinyl (S(=O)R$_x$), phosphonooxy (OP(=O)(OH)₂), and phosphate (OP(=O)(OR$_x$)₂), wherein R$_x$, R$_x^1$ and R$_x^2$ independently are selected from a $C_{1-6}$ alkyl group, a $C_{3-20}$ heterocyclyl group and a $C_{5-20}$ aryl group; or
alternatively, two or more of R⁸, R⁹, R¹⁰, R¹¹, R¹², and R¹³ are connected to one another to form one or more aliphatic or aromatic cyclic structures;
each Z is independently a therapeutic or diagnostic moiety;
a is 0 or 1;
c, d, e, and f are independently an integer from 2 (included) to 24 (included);
w and x are independently an integer from 0 (included) to 5 (included); and
n is an integer of 0 (included) to 10 (included).

2. The compound according to claim 1, wherein the Z groups are linked to the self-eliminating multiple release spacer or spacer system via an O, S, or aromatic N of the Z group.

3. The compound according to claim 1, wherein the Z groups are linked to the self-eliminating multiple release spacer or spacer system via an aliphatic N and wherein at least one multiple release spacer or spacer system of either generation C, D (if present), E (if present), or F (if present) is a phenol- or thiophenol-based multiple release spacer or spacer system, meaning that
  i) B=O or S for at least one multiple release spacer in said generation, or
  ii) when B=N for all multiple release spacers in said generation, at least one single release spacer is connected to at least two branches of at least one multiple release spacer in said generation, and B=O or S for at least two of said single release spacers.

4. The compound according to claim 3, wherein B=O or S for all multiple release spacers or spacer systems in said generation.

5. The compound according to claim 3, wherein the phenol- or thiophenol-based multiple release spacers are connected to either A or Z.

6. The compound according to claim 1, wherein group A is present, and Z is coupled via its hydroxyl group to A.

7. The compound of claim 1 wherein (W—)$_w$(X—)C$_c$, (W—)$_w$(X—)C(D$_d$)$_c$, (W—)$_w$(X—)C(D(E$_e$)$_d$)$_c$ or (W—)$_w$(X—)C(D(E(F$_f$)$_e$)$_d$)$_c$ is selected from the group consisting of
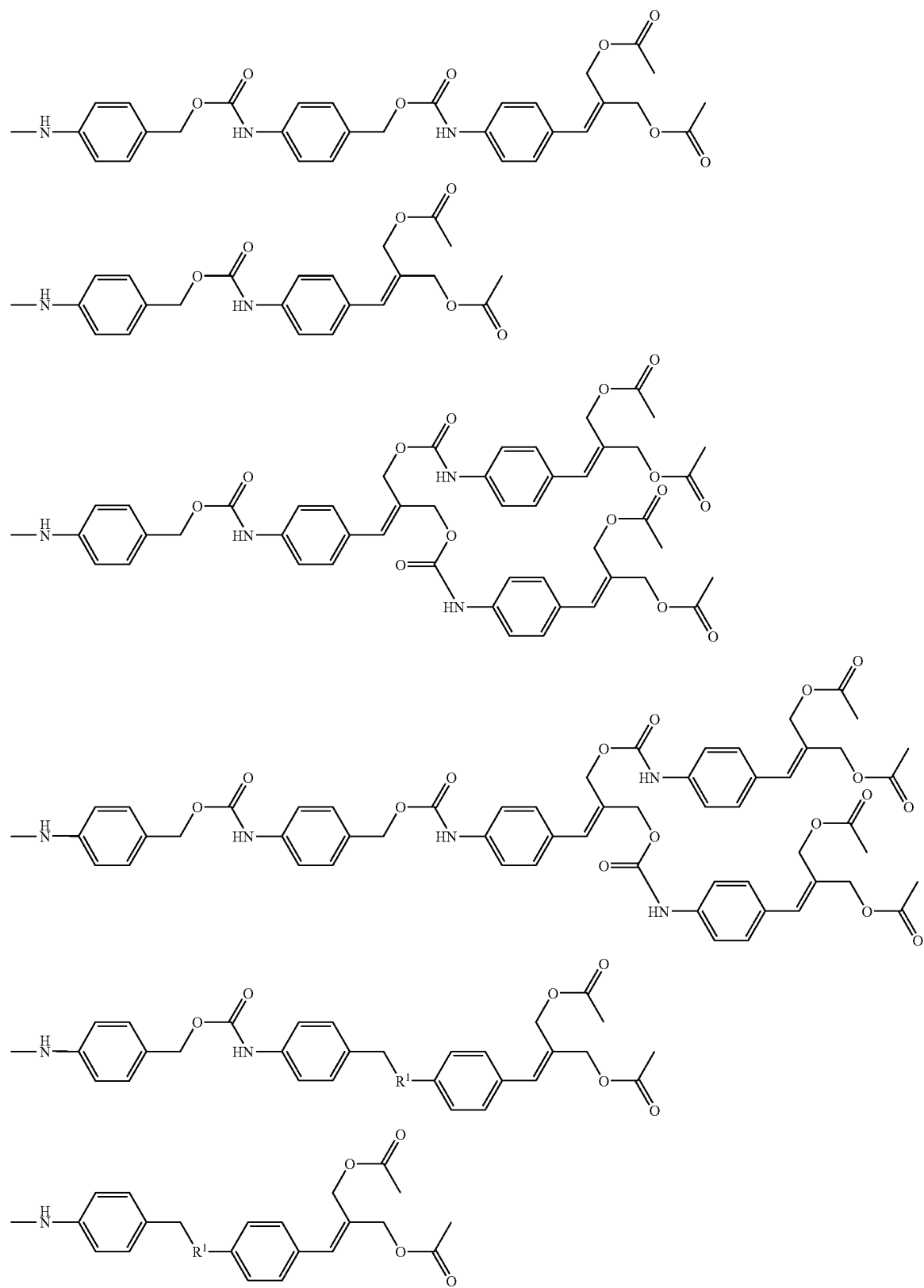

-continued
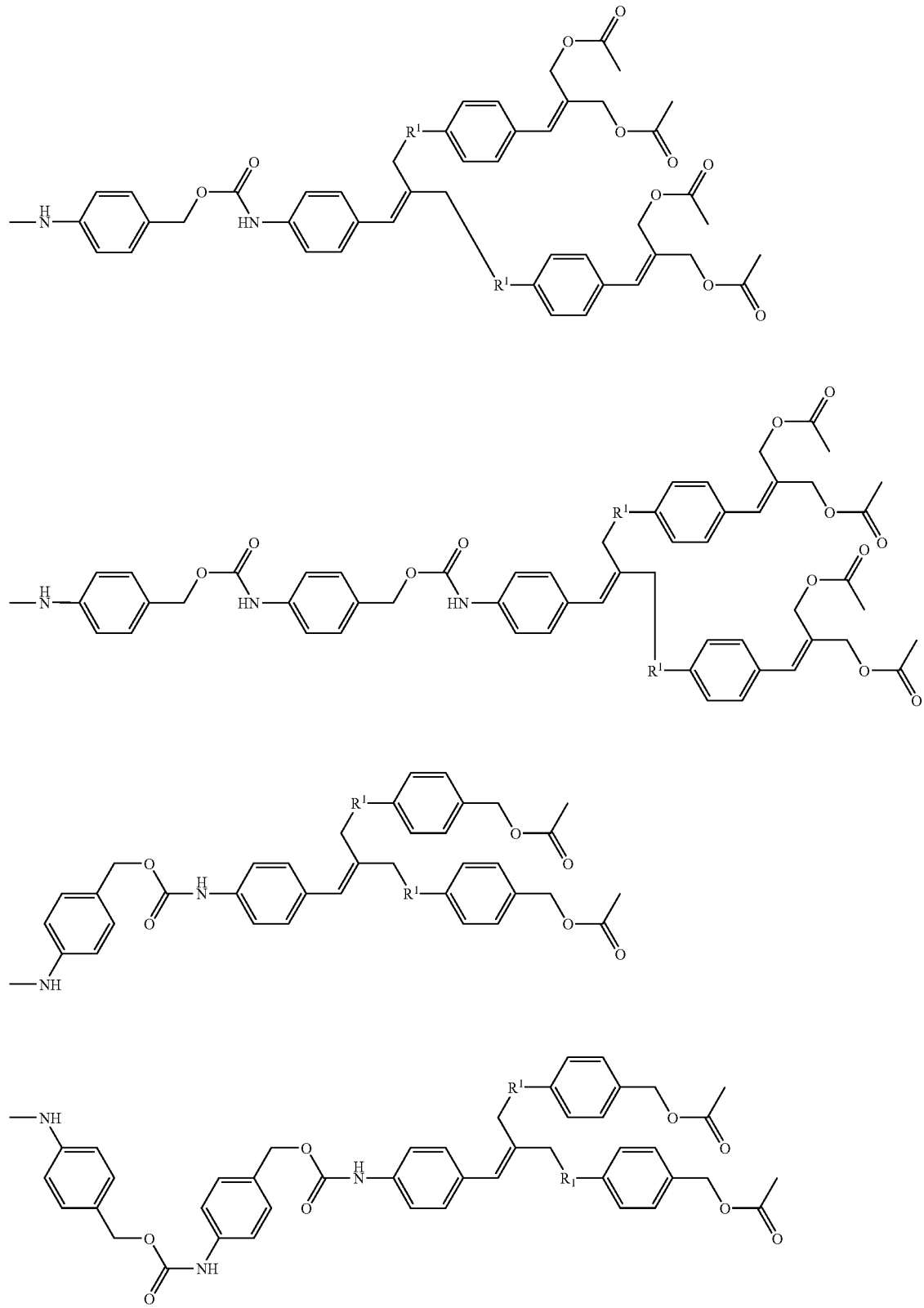

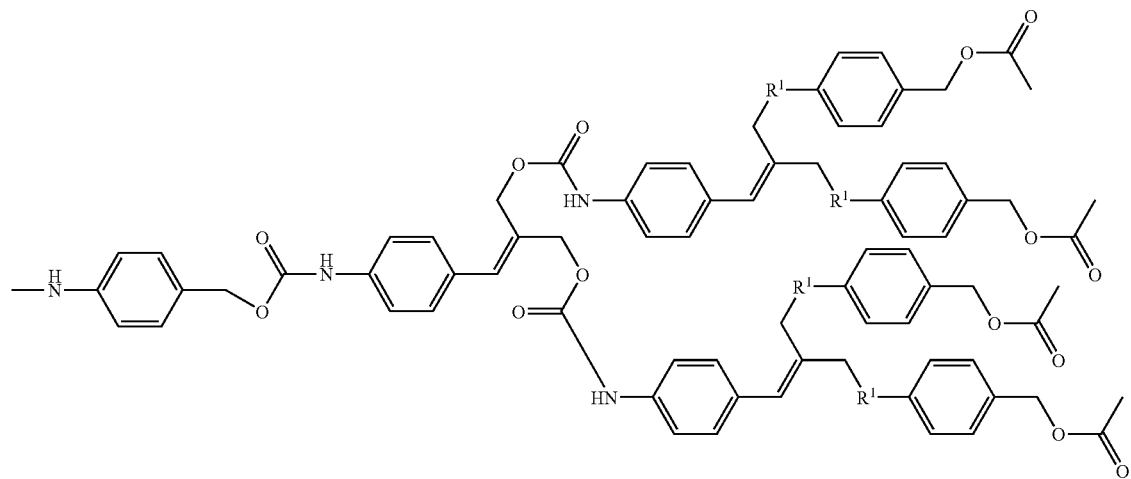
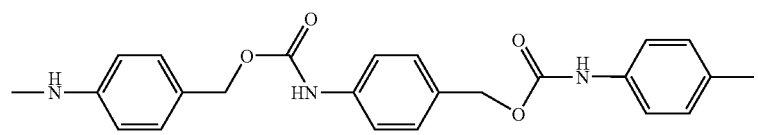
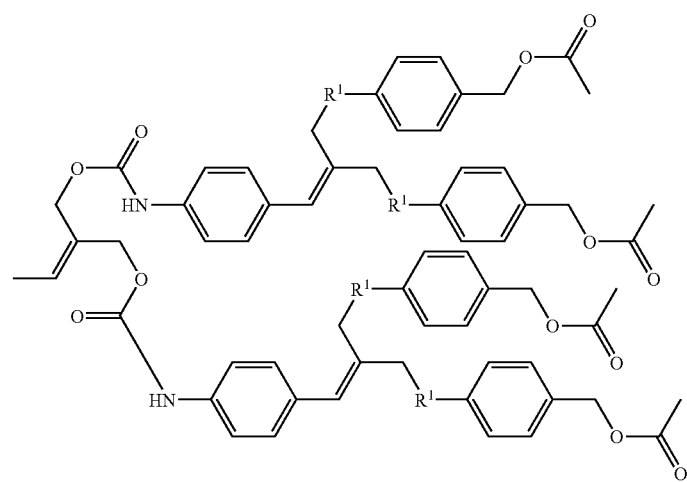
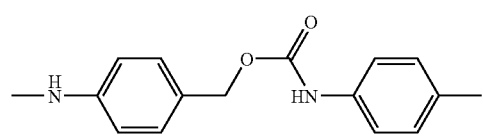

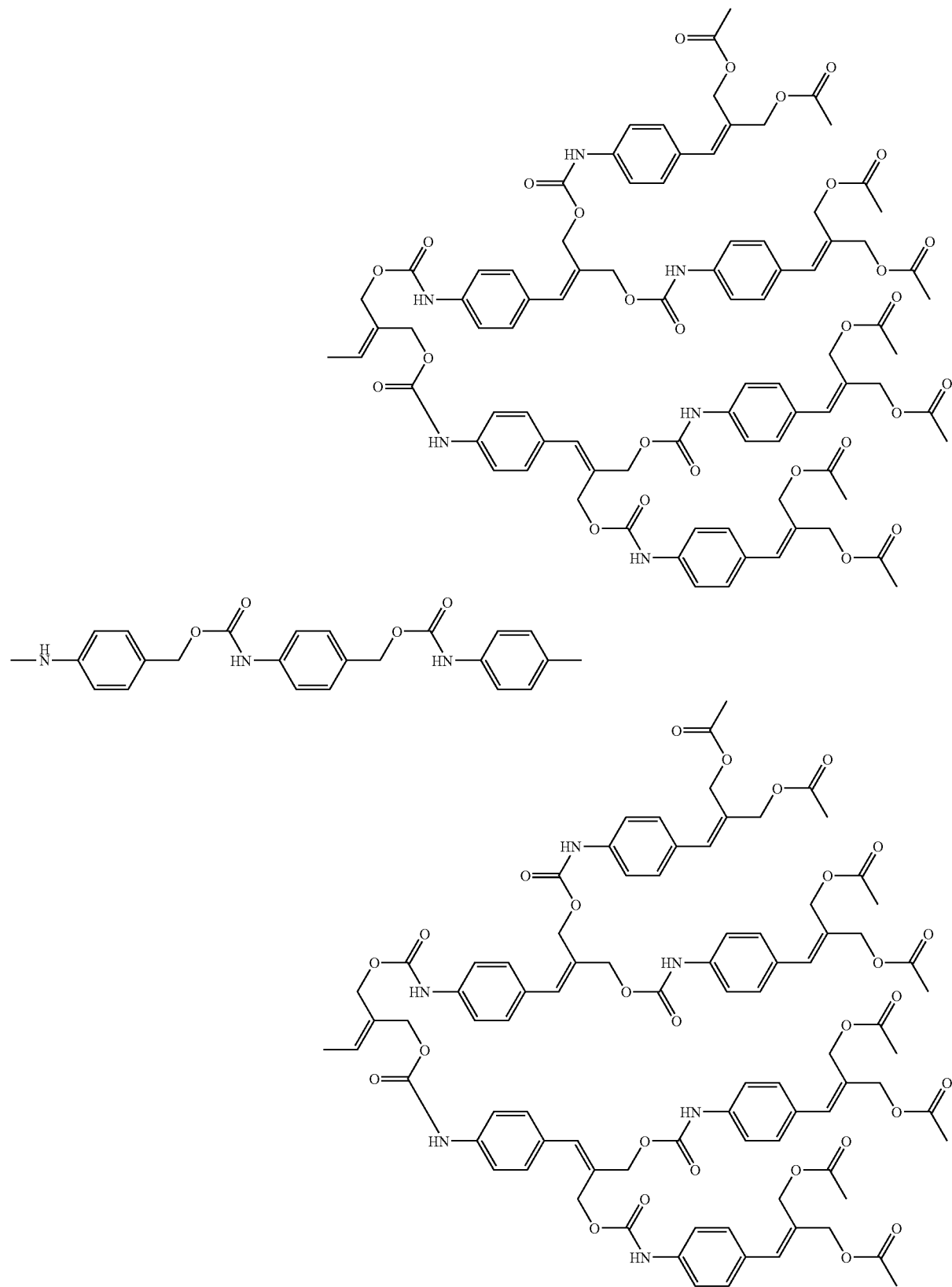

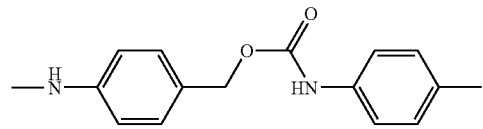
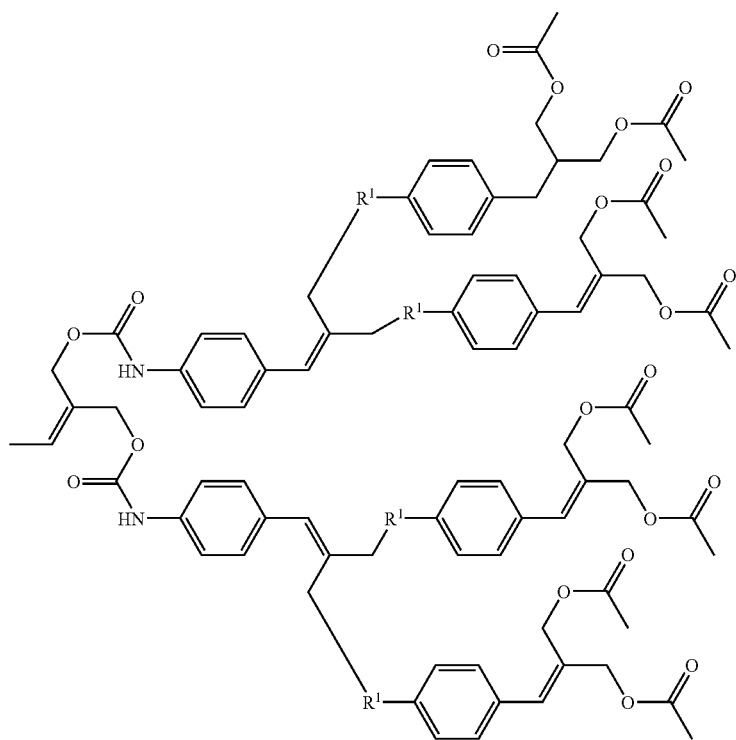
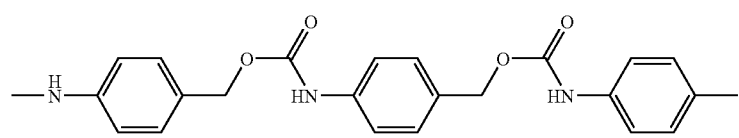

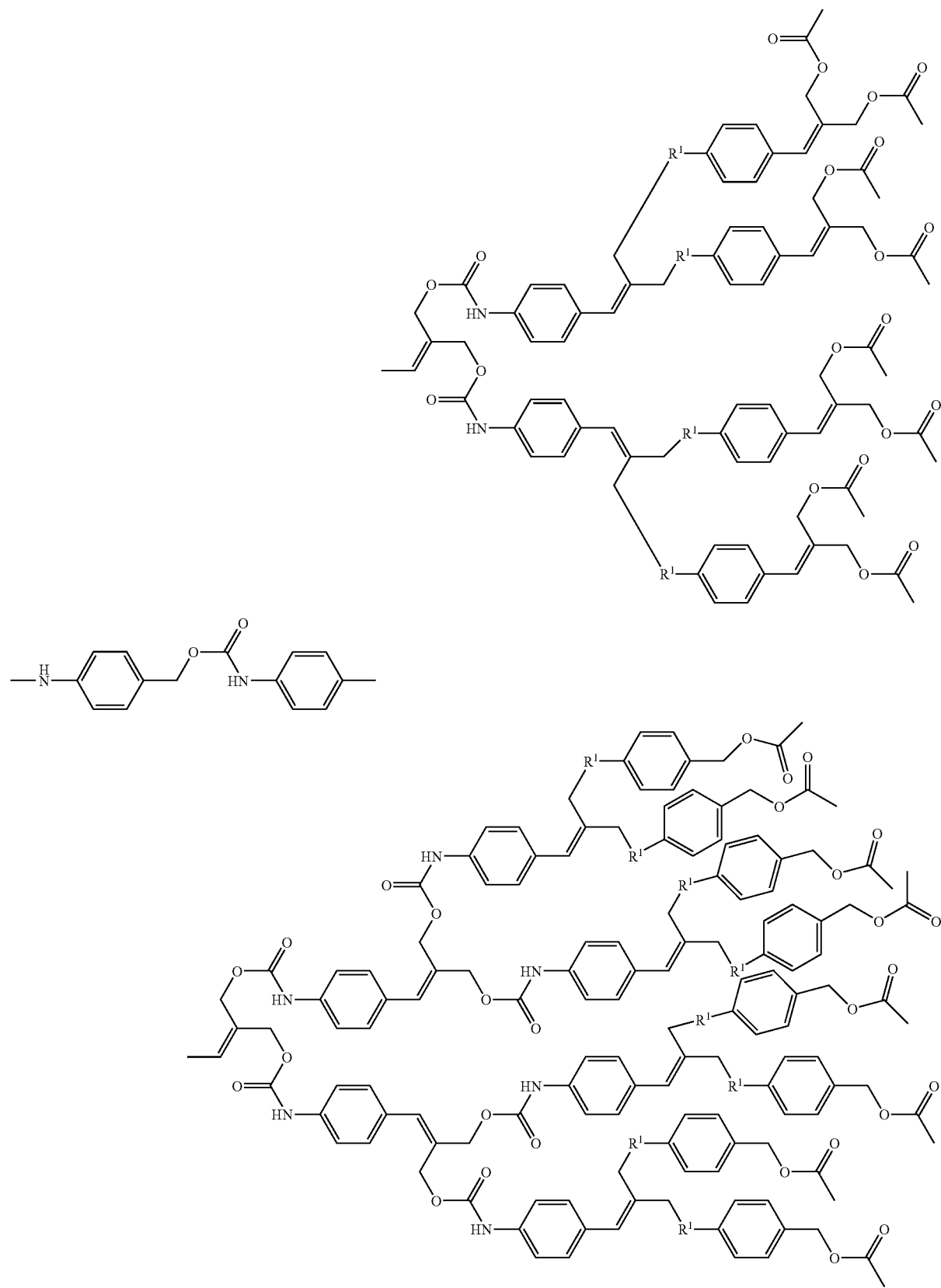

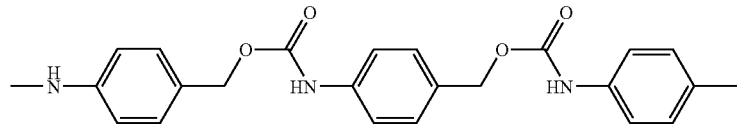
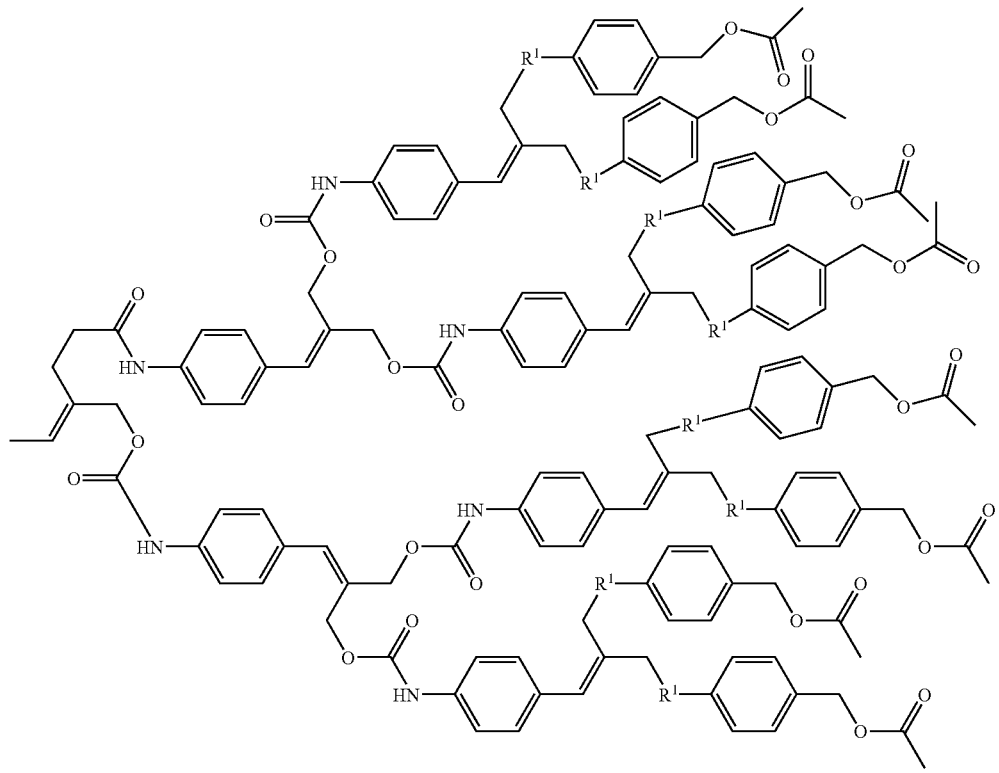
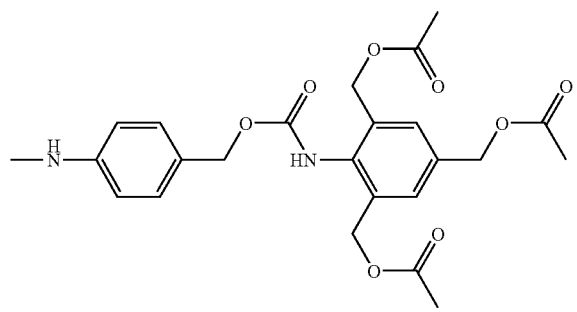
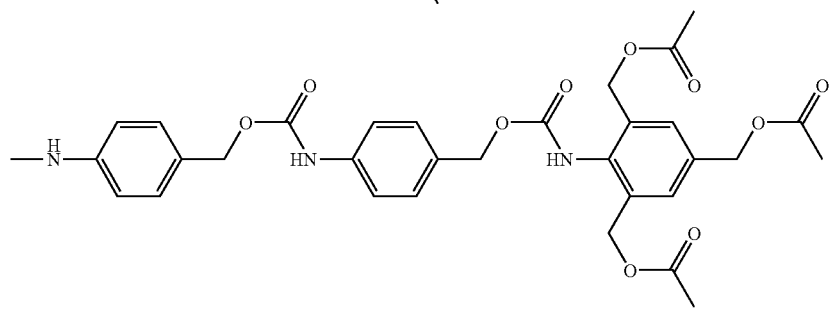

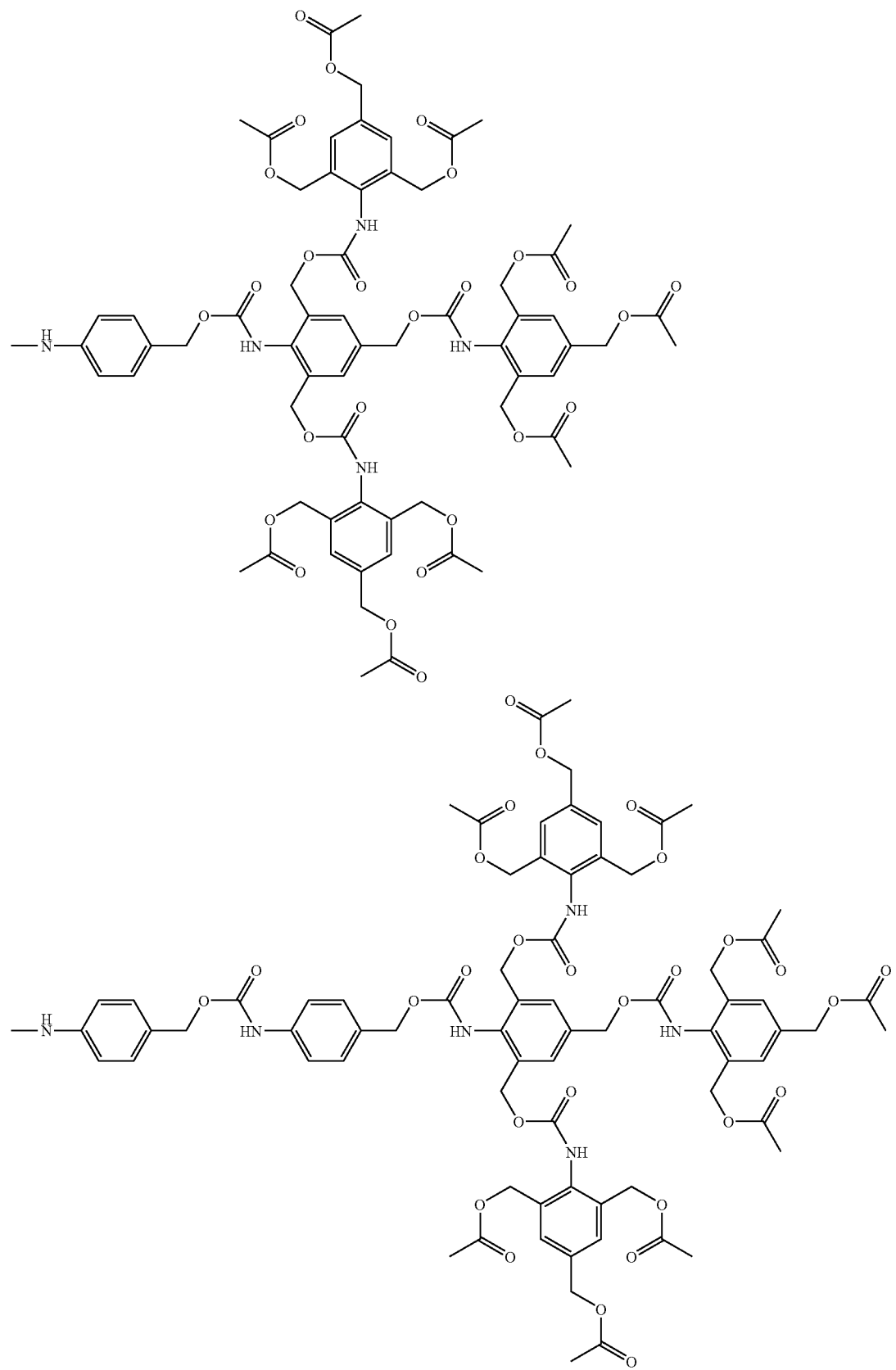

-continued
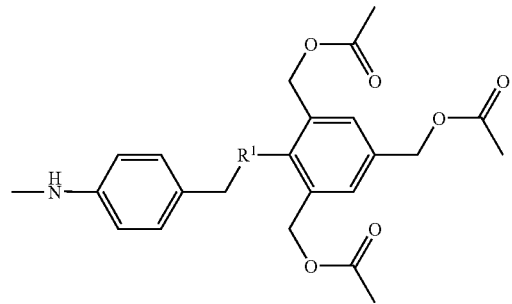
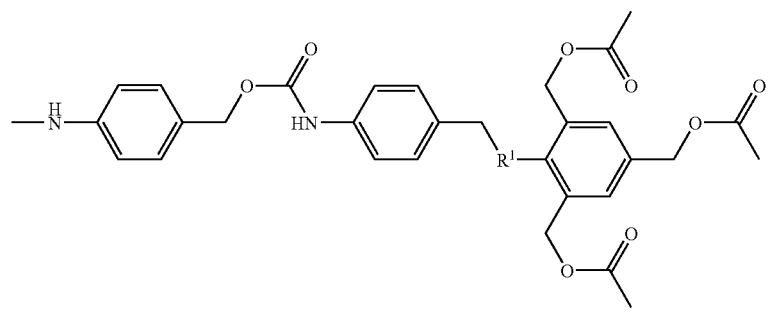
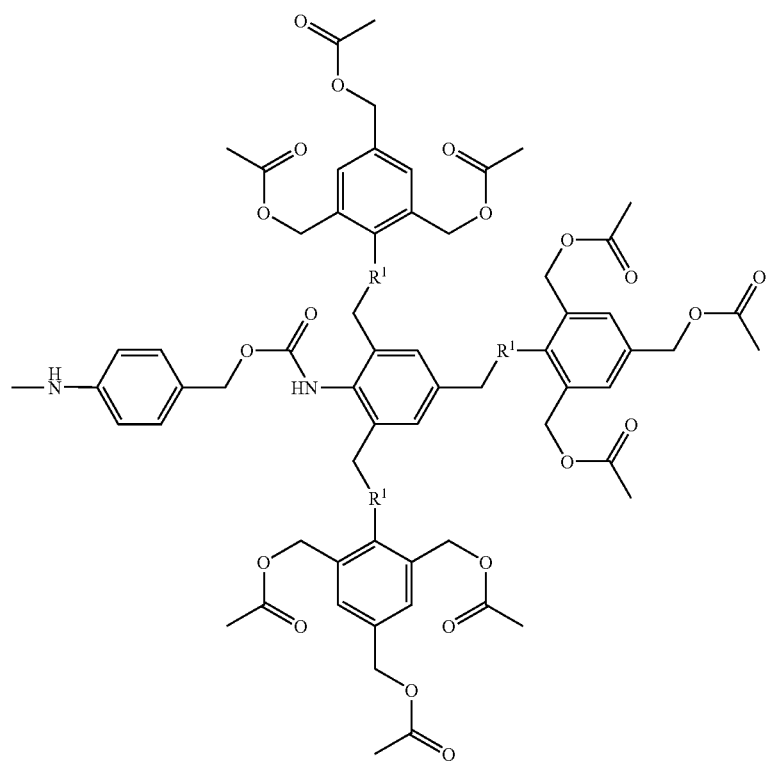

-continued
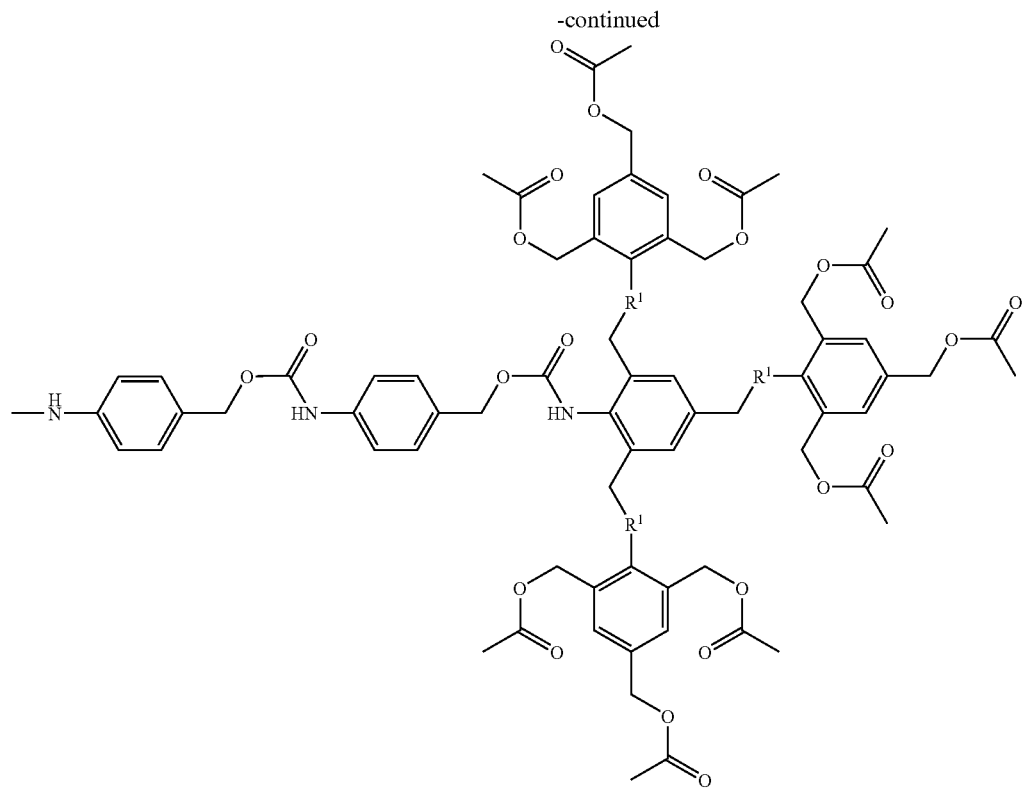
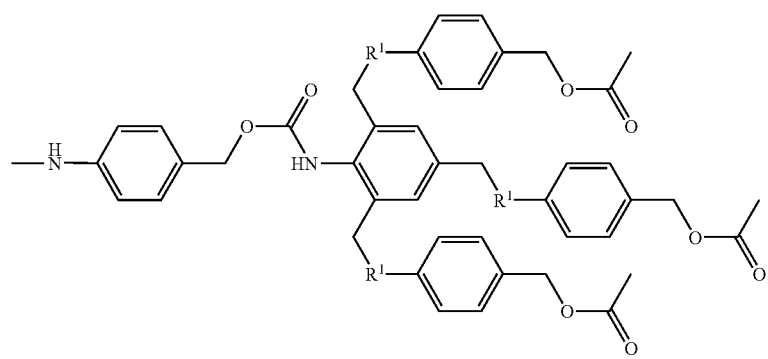
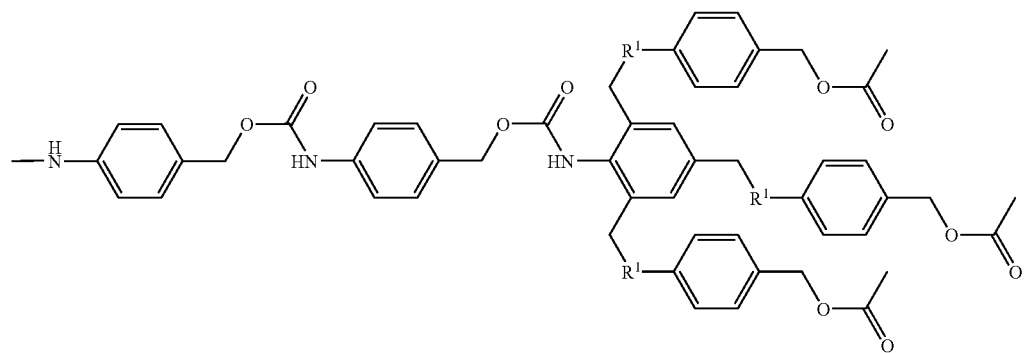
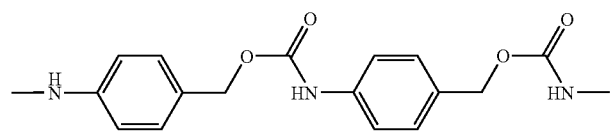

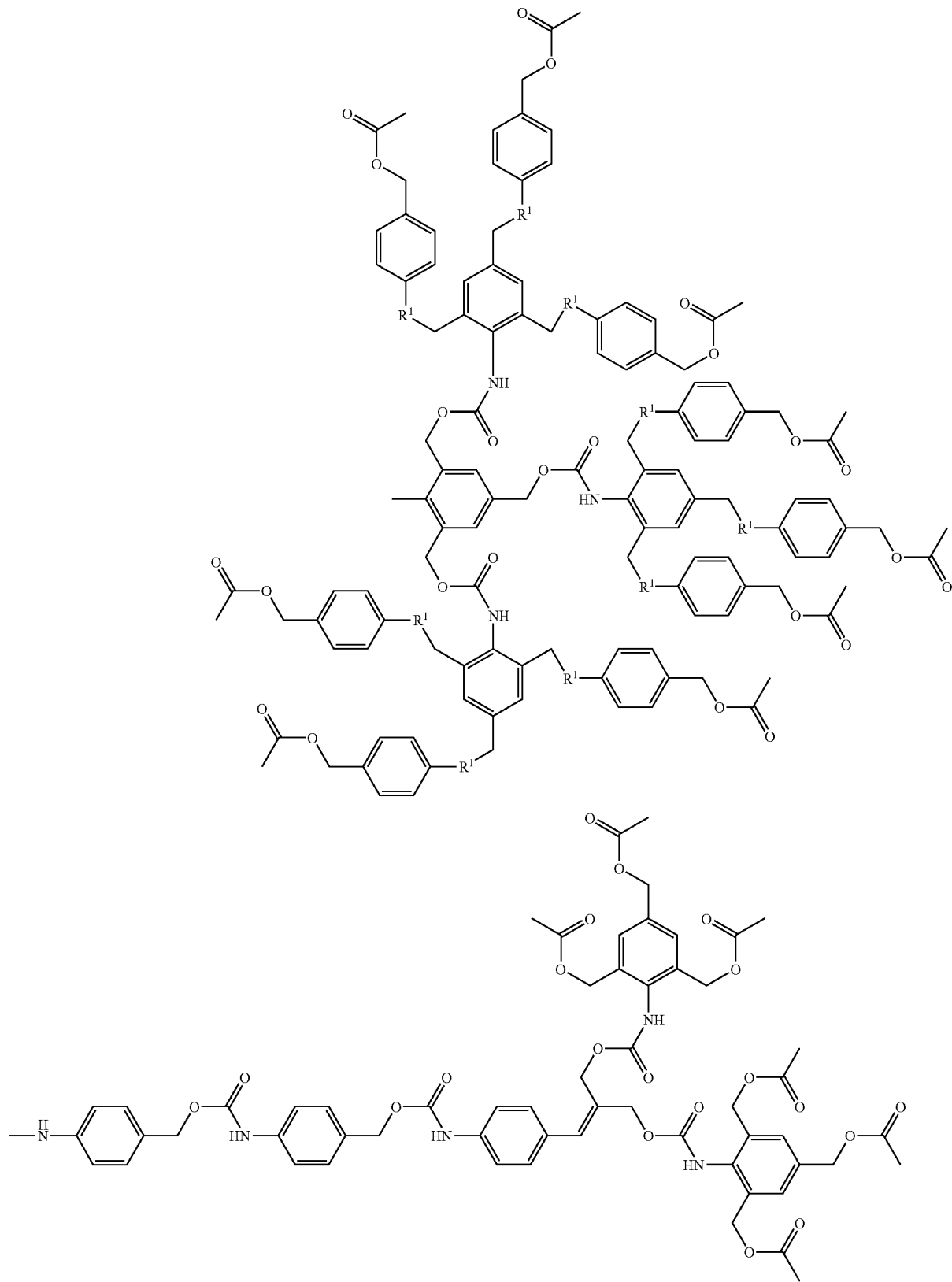

-continued
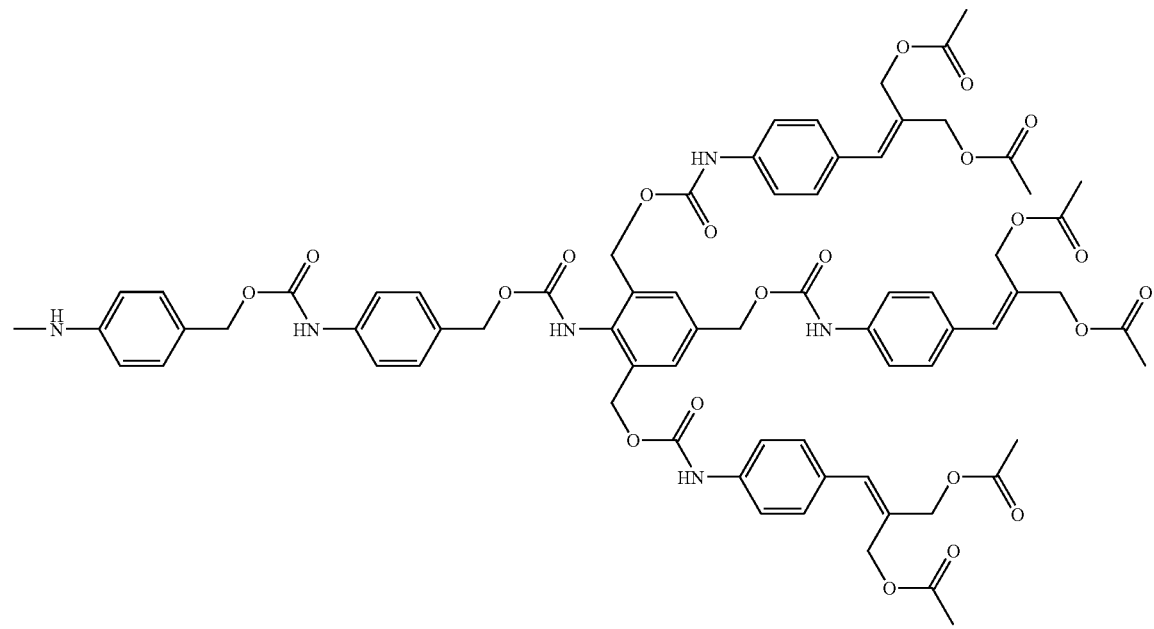
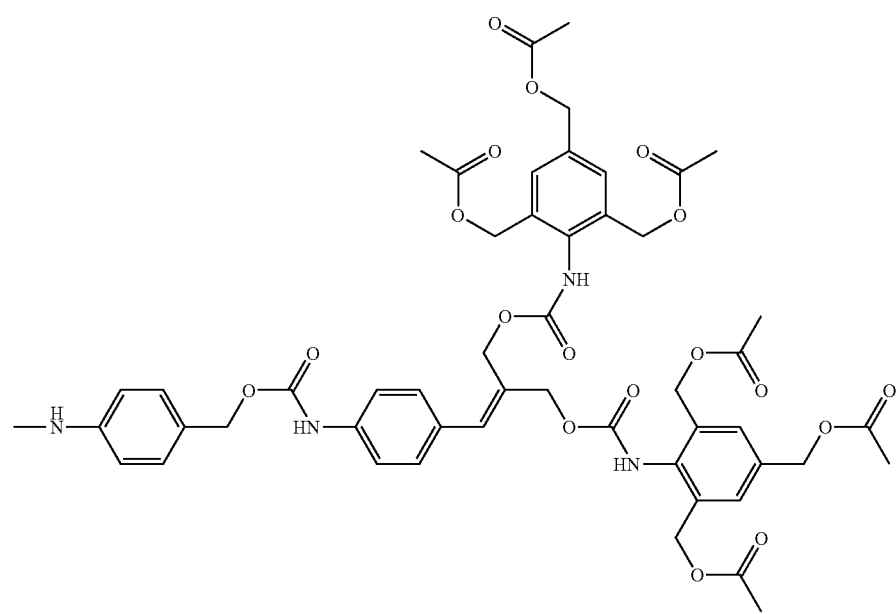

-continued
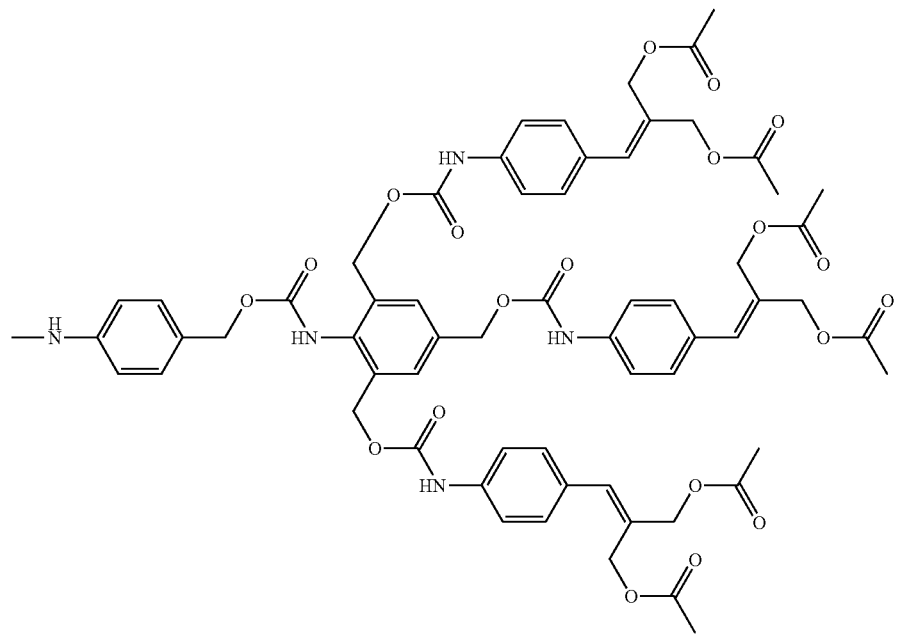
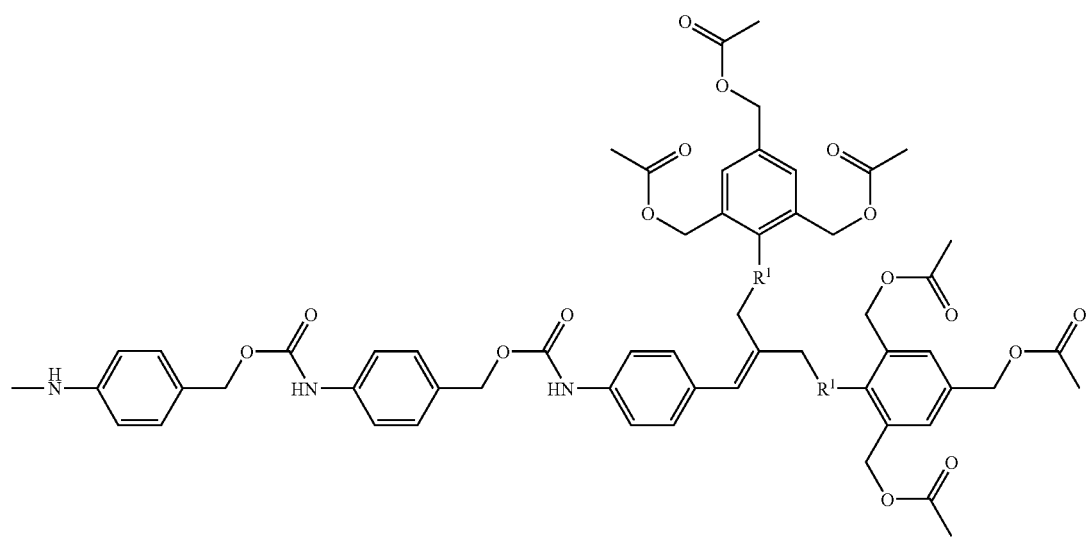

-continued
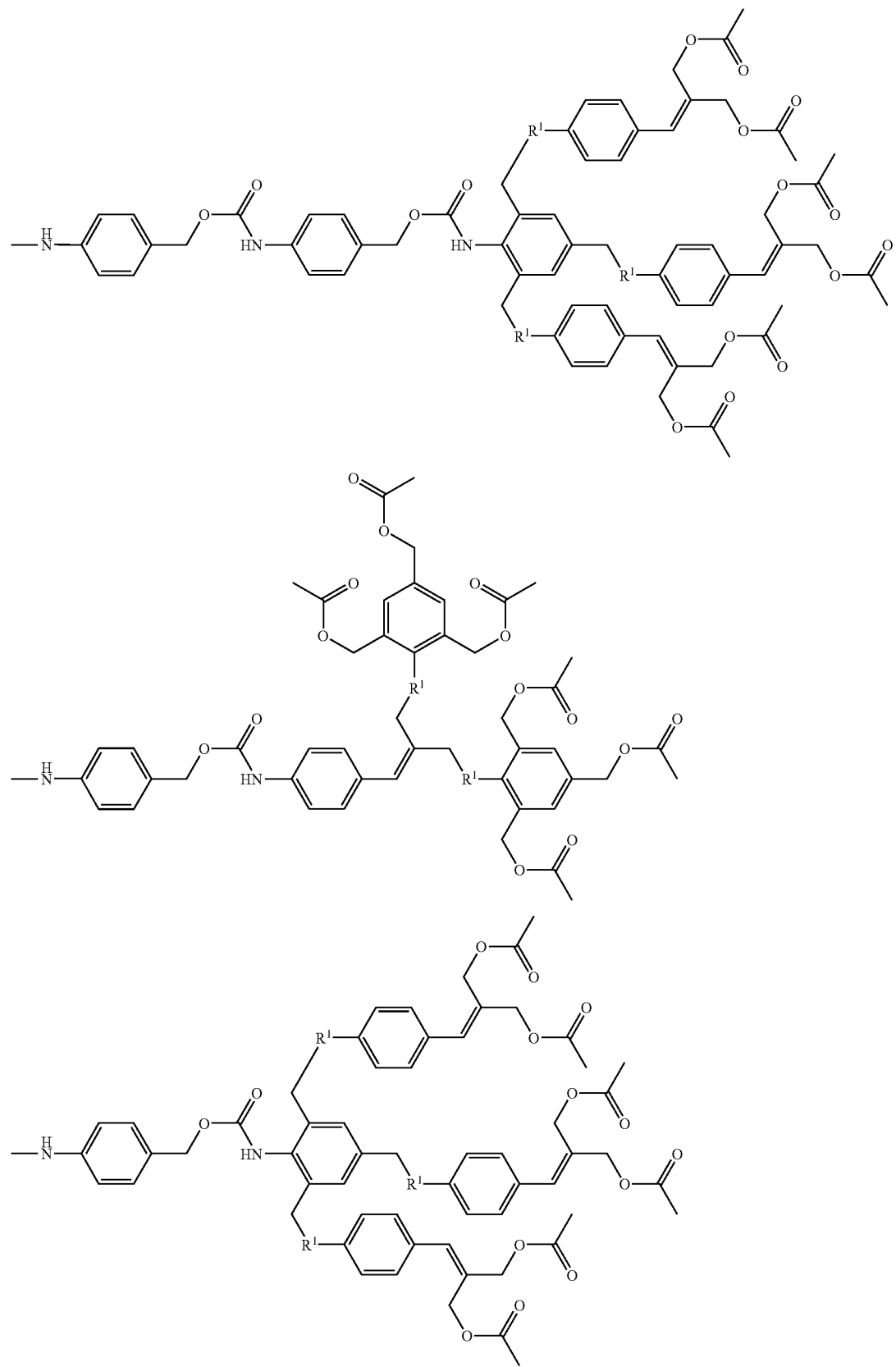

-continued
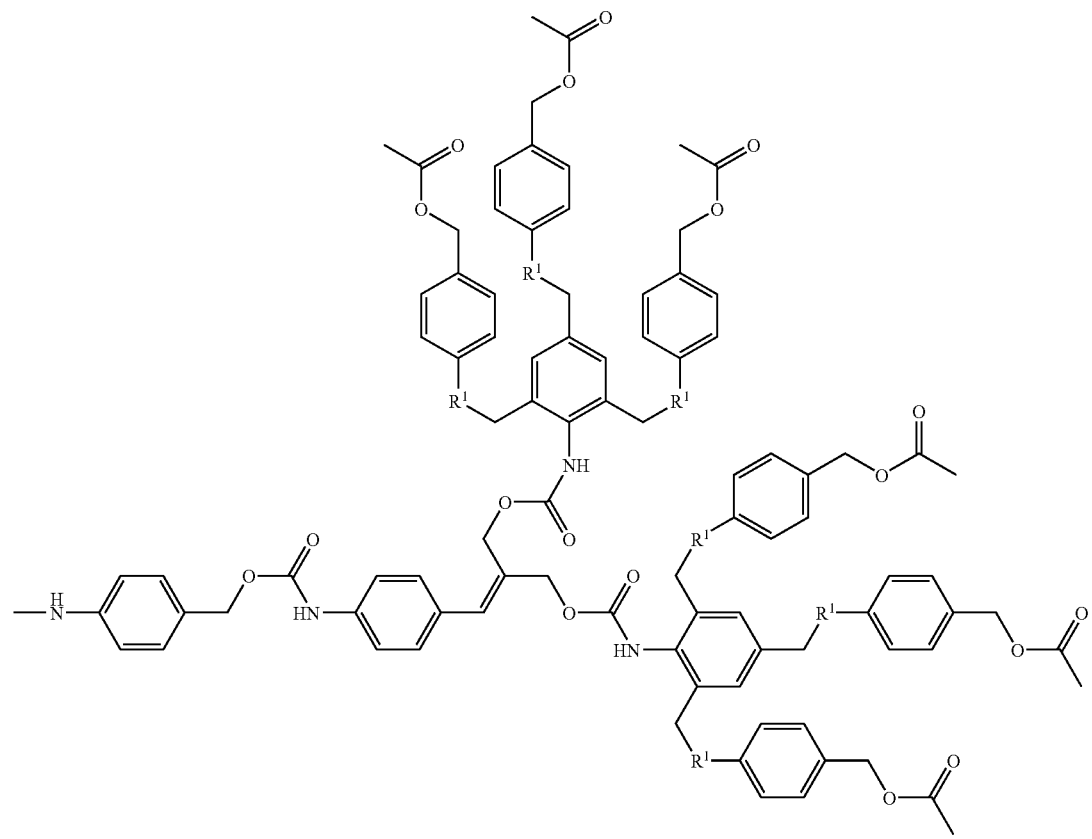
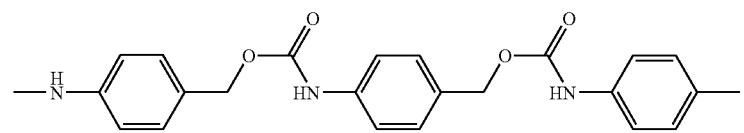

-continued
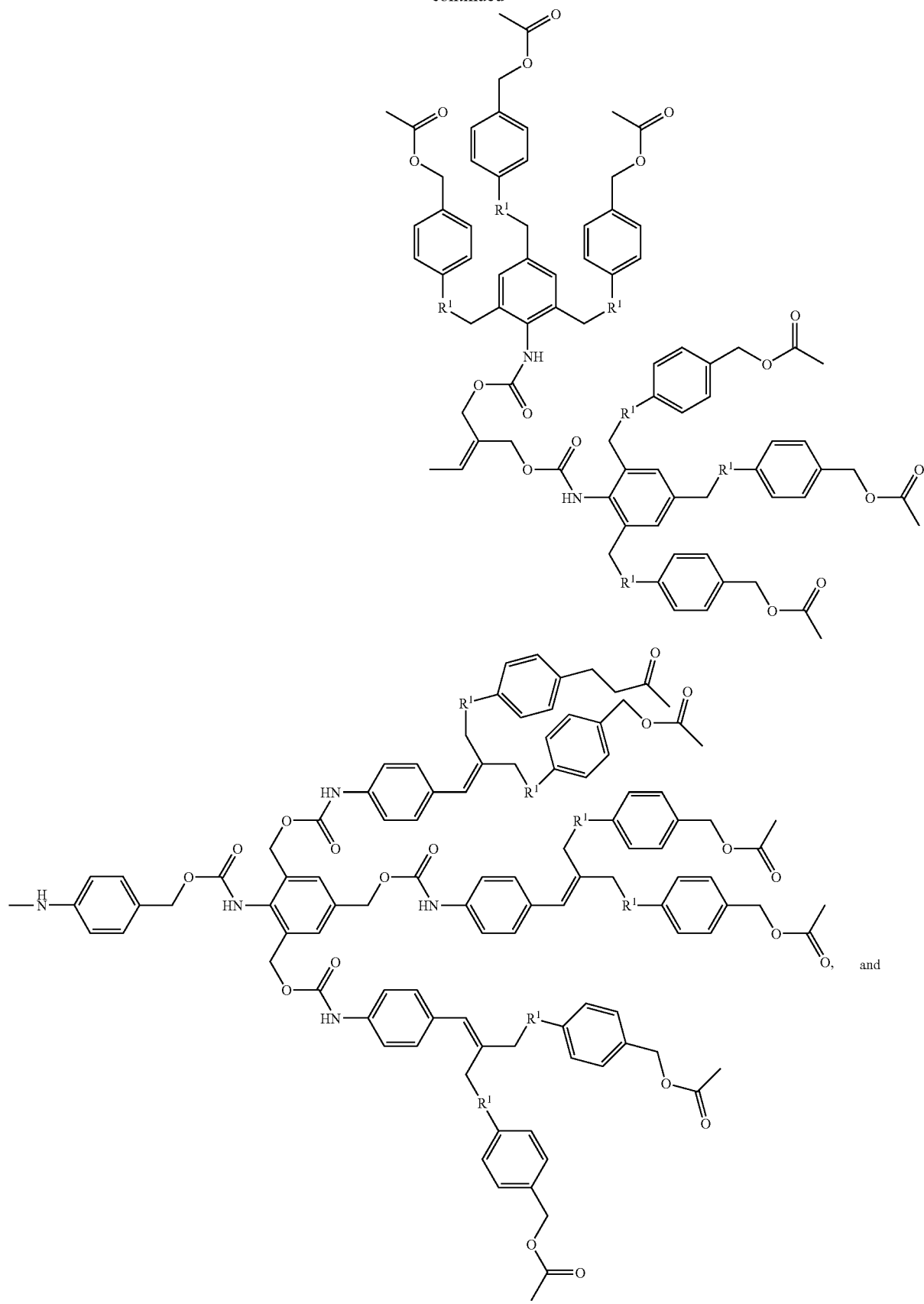

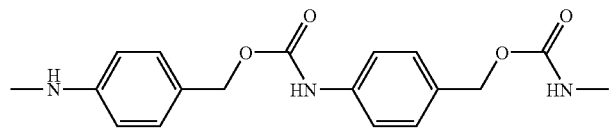

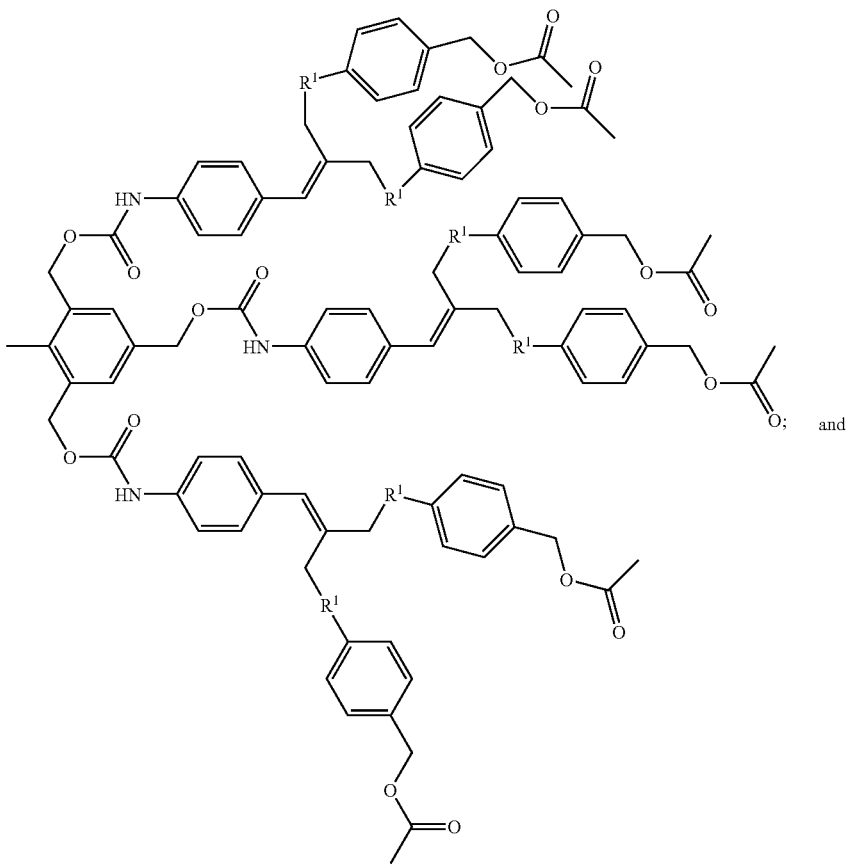

$R^1$=OC(O)O.

8. The compound according to claim 7, the compound further comprising cyclization elimination spacers A.

9. The compound according to claim 1, wherein the specifier V contains a substrate that can be cleaved by plasmin, one of the cathepsins, cathepsin B, β-glucuronidase, prostate-specific antigen (PSA), urokinase-type plasminogen activator (u-PA), a member of the family of matrix metalloproteinases, or wherein V-B is an oxidized form of B, or wherein V contains a nitro-(hetero)aromatic moiety that can be removed or transformed by reduction under hypoxic conditions or by reduction by a nitroreductase.

10. The compound according to claim 1, wherein Z is selected from an antibiotic, an anti-inflammatory agent, an anti-viral agent, and an anticancer agent.

11. The compound of claim 10, wherein Z is selected from (hydroxyl containing cytotoxic compounds) etoposide, combrestatin, camptothecin, irinotecan (CPT-11), SN-38, topotecan, 9-aminocamptothecin, 9-nitrocamptothecin, 10-hydroxycamptothecin, GG211, lurtotecan, paclitaxel, docetaxel, esperamycin, 1,8-dihydroxy-bicyclo[7.3.1] trideca-4-ene-2,6-diyne- 13-one, anguidine, doxorubicin, morpholine-doxorubicin, N-(5,5-diacetoxypentyl) doxorubicin, daunorubicin, epirubicin, idarubicin, mitoxantrone, vincristine, vinblastine, tallysomycin, bleomycin, 4-bis(2-chloroethyl)aminophenol, 4-bis(2-fluoroethyl)aminophenol, and derivatives thereof, (sulfhydryl containing compounds) esperamicin and 6-mercaptopurine, and derivatives thereof, (carboxyl containing compounds) methotrexate, aminopterin, camptothecin (ring-opened form of the lactone), chlorambucil, melphalan, butyric acid and retinoic acid, and derivatives thereof, and (aziridine amino containing or aromatic amino containing compounds) mitomycin C, mitomycin A, an anthracycline derivative containing an amine functionality with sufficient leaving group ability, mitoxantrone, 9-amino camptothecin, methotrexate, aminopterin, tallysomycin, bleomycin, actinomycin, N,N-bis(2-chloroethyl)-p-phenylenediamine, N,N-bis(2-fluoroethyl)-p-phenylenediamine, deoxycytidine, cytosine arabinoside, gemeitabine, and derivatives thereof, and (aliphatic amino containing compounds) daunorubicin, doxorubicin, epirubicin, idarubicin, N-(5,5-diacetoxypentyl)doxorubicin, an anthracycline, $N^8$-acetyl spermidine, 1-(2-chioroethyl)-1,2-dimethanesulfonyl hydrazine, or derivatives thereof.

12. The compound according to claim 11, wherein Z represents paclitaxel, docetaxel, or a derivative thereof, which is coupled to the self-eliminating multiple release spacer or spacer system via its 2'-hydroxyl group.

13. The compound according to claim 11, wherein Z represents camptothecin, irinotecan (CPT-11), SN-38, topotecan, 9-aminocamptothecin, 9-nitrocamptothecin, 10-hydroxycamptothecin, GG211, lurtotecan, or a derivative thereof, which is coupled to the self-eliminating multiple release spacer or spacer system via its 20-hydroxyl group.

14. The compound according to claim 11, wherein Z represents SN-38, topotecan, 10-hydroxycamptothecin, etoposide, 4-bis(2-chloroethyl)aminophenol, 4-bis(2-fluoroethyl) aminophenol, or a derivative thereof, which is coupled to the self-eliminating multiple release spacer or spacer system via its phenolic hydroxyl group.

15. The compound according to claim 11, wherein Z represents 9-aminocamptothecin, N,N-bis(2-chloroethyl)-p-phenylenediamine, N,N-bis(2-fluoroethyl)-p-phenylenediamine, or a derivative thereof, which is coupled to the self-eliminating multiple release spacer or spacer system via its aromatic primary amine group.

16. The compound according to claim 11, wherein Z represents daunorubicin, doxorubicin, epirubicin, idarubicin, N-(5,5-diacetoxypentyl)doxorubicin, an anthracycline, $N^8$-acetyl spermidine, 1-(2-chloroethyl)- 1,2-dimethanesulfonyl hydrazine, or derivatives thereof, which is coupled to the self-eliminating multiple release spacer or spacer system via its primary aliphatic amino group; wherein at least one multiple release spacer or spacer system of either generation C, D (if present), E (if present), or F (if present) is a phenol- or thiophenol-based multiple release spacer or spacer system, meaning that
i) B=O or S for at least one multiple release spacer in said generation, or
ii) when B=N for all multiple release spacers in said generation, at least one single release spacer is connected to at least two branches of at least one multiple release spacer in said generation, and B=O or S for at least two of said single release spacers.

17. The compound according to claim 16, wherein B=O or S for all multiple release spacers or spacer systems in said generation.

18. The compound according to claim 16, wherein the phenol- or thiophenol-based multiple release spacers are connected to either A or Z.

19. The compound according to claim 1, wherein the specifier V is a tripeptide.

20. The compound according to claim 19, wherein the tripeptide is linked via its C-terminus to the self-eliminating multiple release spacer or spacer system.

21. The compound of claim 20, wherein the C-terminal amino acid residue of the tripeptide is selected from arginine and lysine, the middle amino acid residue of the tripeptide is selected from alanine, valine, leucine, isoleucine, methionine, phenylalanine, cyclohexylglycine, tryptophan and proline, and the N-terminal amino acid residue of the tripeptide is selected from a D-amino acid residue and a protected L-amino acid residue including protected glycine.

22. The compound according to claim 21, wherein the specifier V is selected from D-alanylphenylalanyllysine, D-valylleucyllysine, D-alanylleucyllysine, D-valylphenylalanyllysine, D-valyltryptophanyllysine and D-alanyltryptophanyllysine.

23. The compound according to claim 1, wherein the specifier V is an amino-terminal capped peptide covalently linked via the C-terminus to the self-eliminating multiple release spacer or spacer system.

24. The compound according to claim 23, wherein the specifier V is selected from benzyloxycarbonylphenylalanyllysine, benzyloxycarbonylvalyllysine, D-phenylalanylphenylalanyllysine, benzyloxycarbonylvalylcitrulline, tert-butyl oxycarbonylphenylalanyllysine, benzyloxycarbonylalanylarginylarginine, benzyloxycarbonylphenylalanyl-N-tosylarginine, 2-aminoethylthiosuccinimidopropionylvalinylcitrulline, 2-aminoethylthiosuccinimidopropionyllysylphenylalanyllysine, acetylphenylalanyllysine, and benzyloxycarbonylphenylalanyl-O-benzoylthreonine.

25. The compound according to claim 1, wherein the specifier V comprises a reactive moiety that can be used to couple said compound to a targeting moiety.

26. The compound according to claim 25, wherein the reactive moiety is

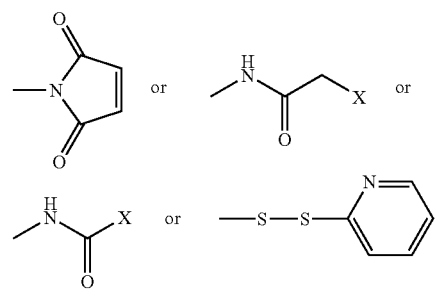

wherein X is a leaving group.

27. The compound according to claim 25, wherein the reactive moiety is selected from an N-hydroxysuccinimide ester, a p-nitrophenyl ester, a pentafluorophenyl ester, an isothiocyanate, an isocyanate, an anhydride, an acid chloride, a sulfonyl chloride, and an aldehyde.

28. The compound according to claim 25, wherein the reactive moiety is a hydrazine group or an amino group.

29. The compound according to claim 1, wherein the specifier V comprises a targeting moiety.

30. The compound according to claim 29, wherein the targeting moiety is selected from the group consisting of a protein or protein fragment, an antibody or an antibody fragment, a receptor-binding or peptide vector moiety and a polymeric or dendritic moiety.

31. A compound selected from the group consisting of
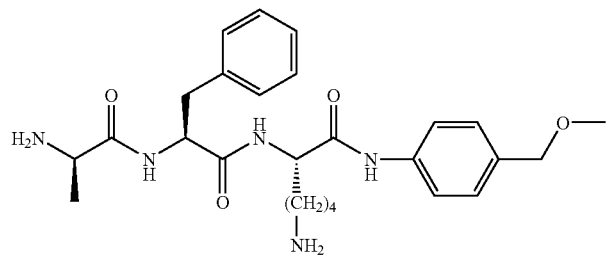
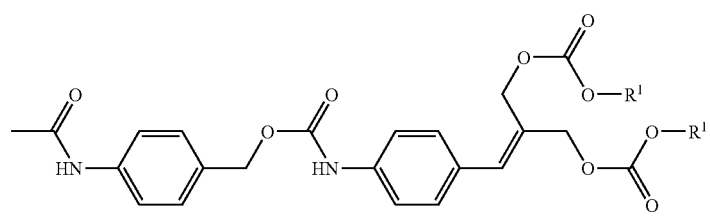
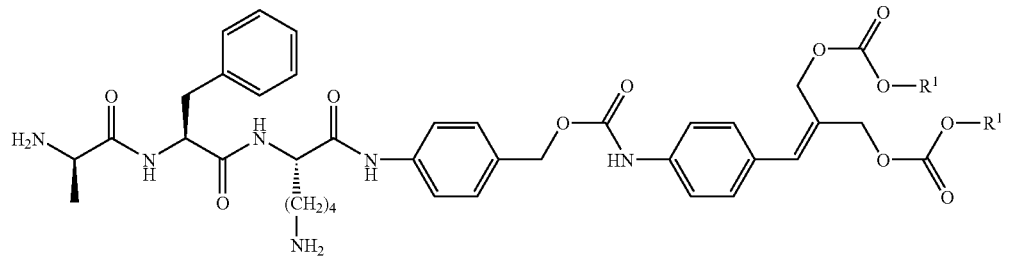
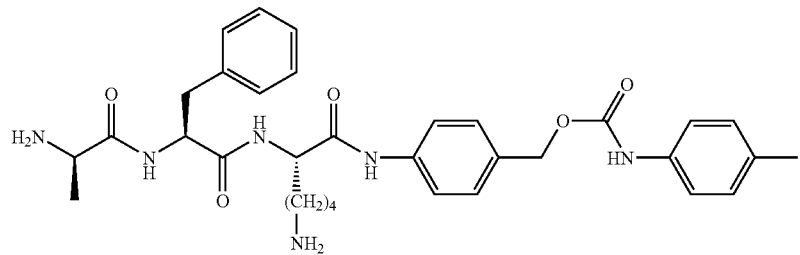
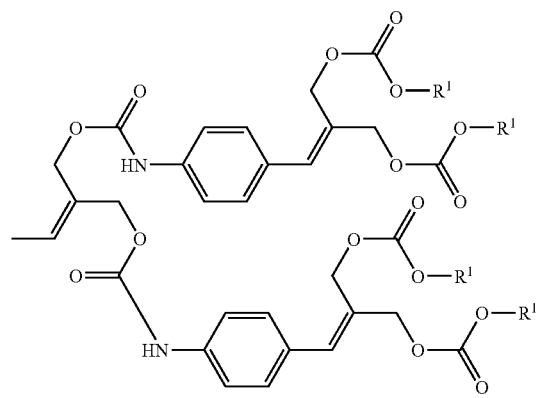
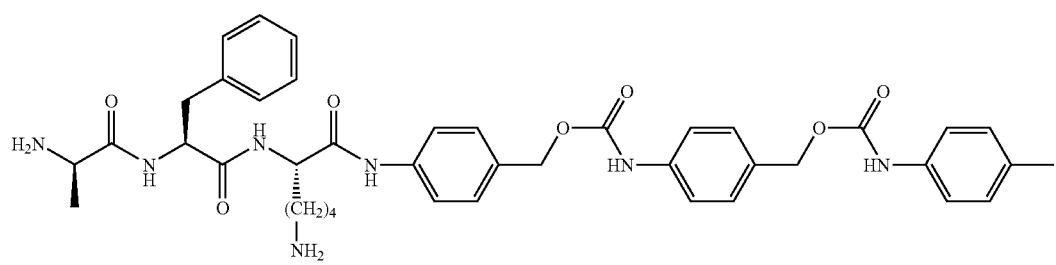

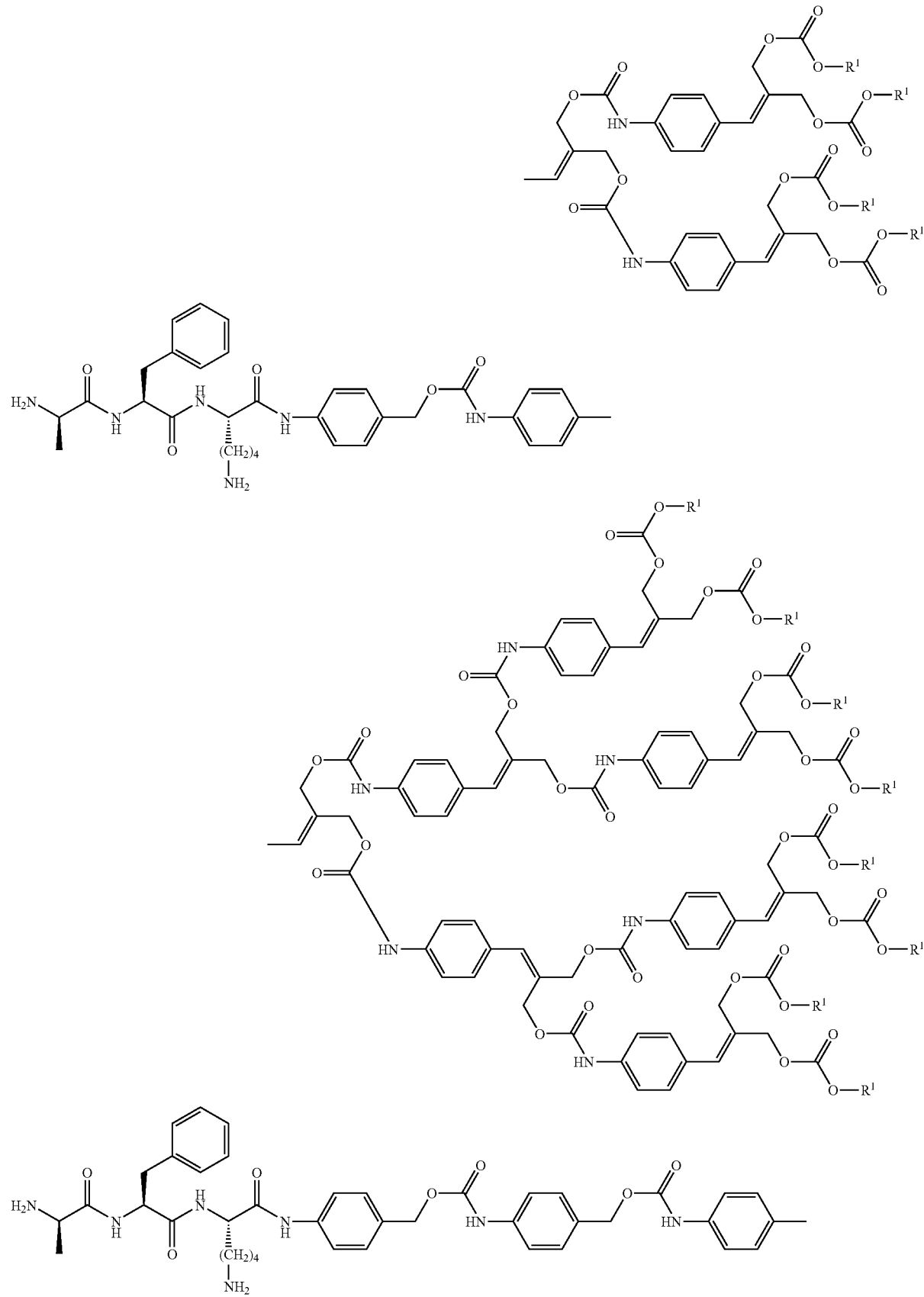

-continued
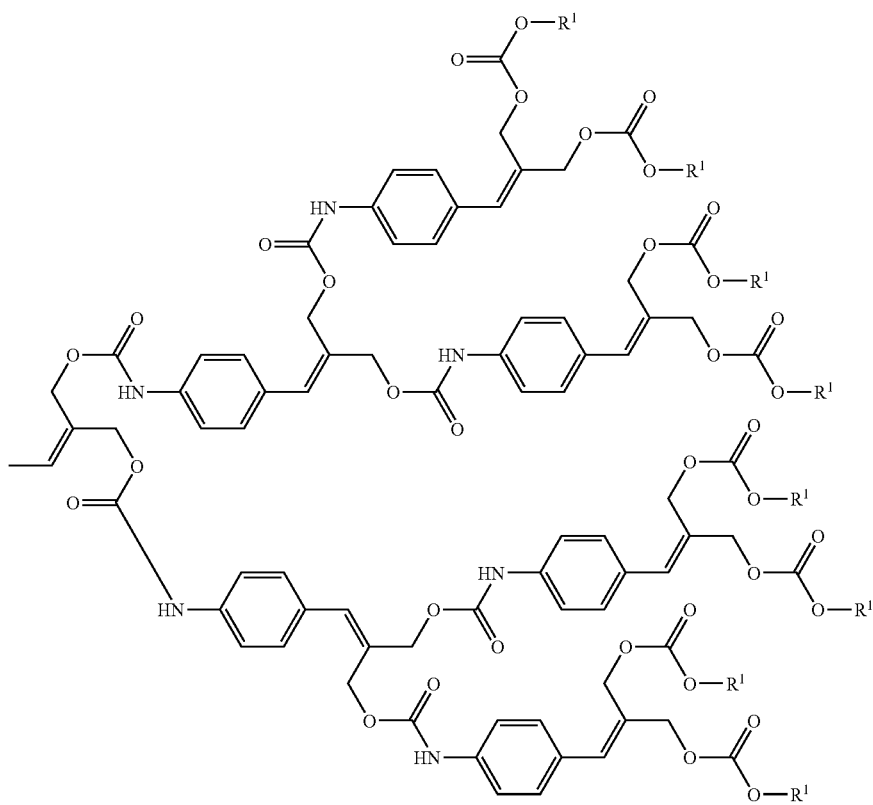
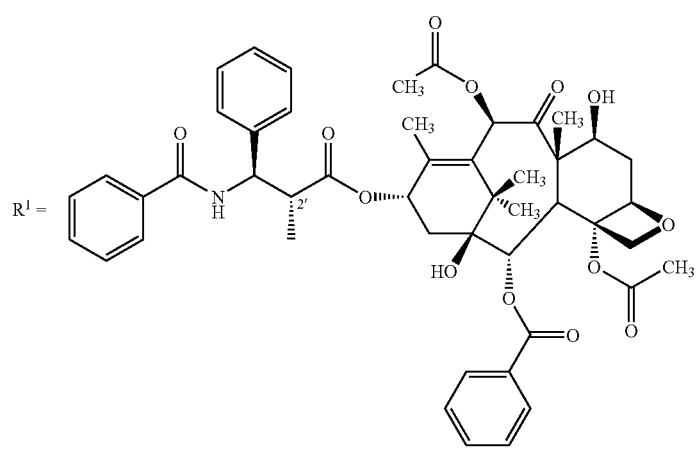
or
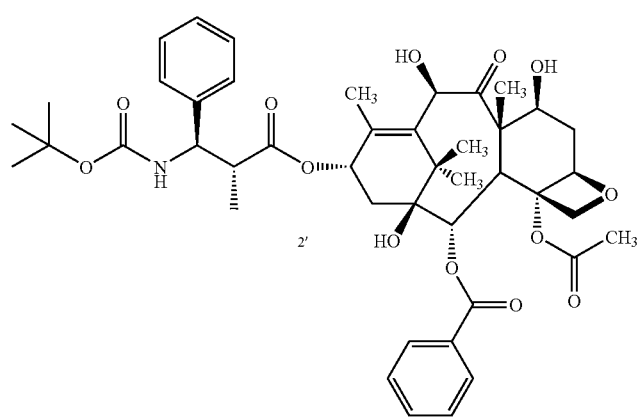

-continued
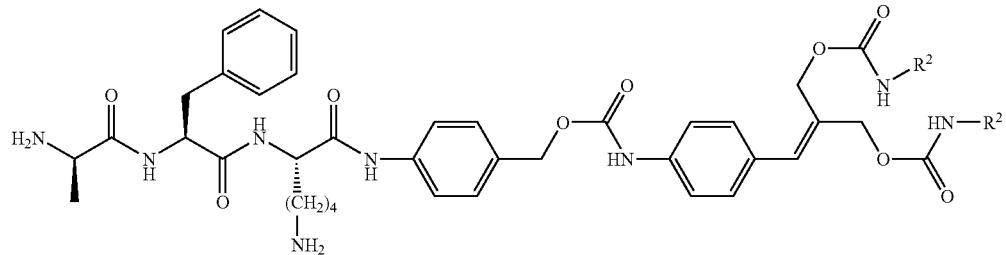
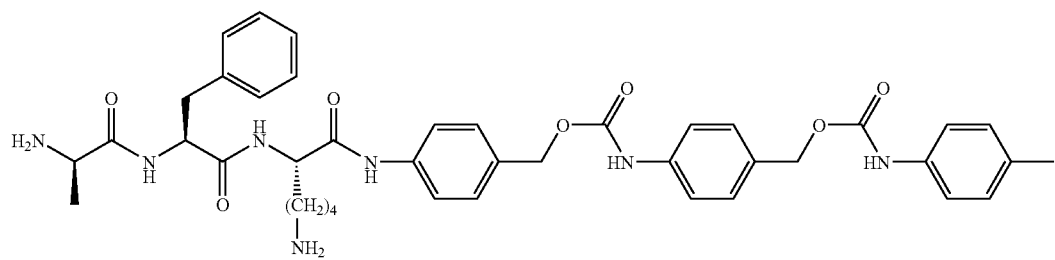
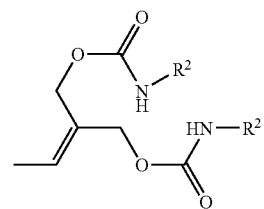
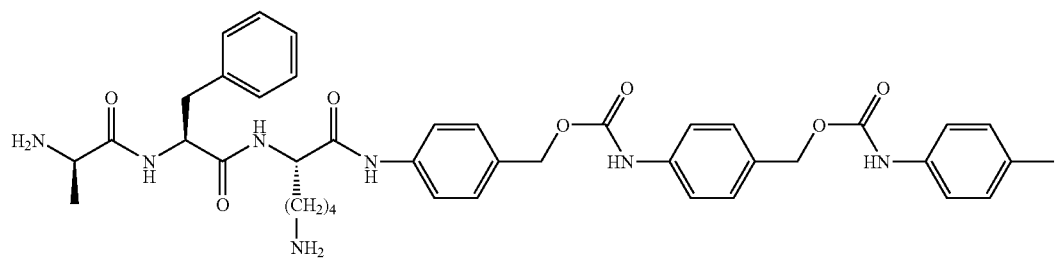
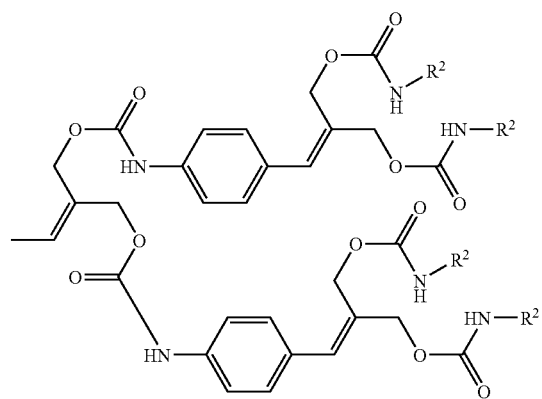
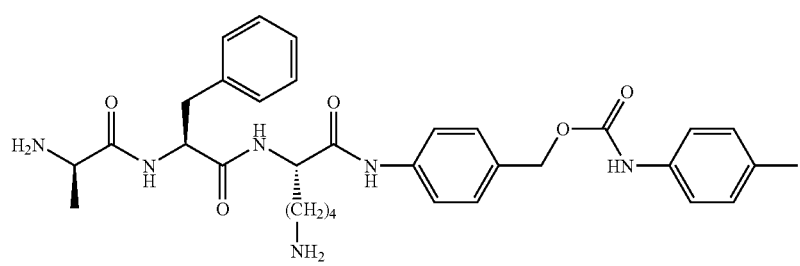

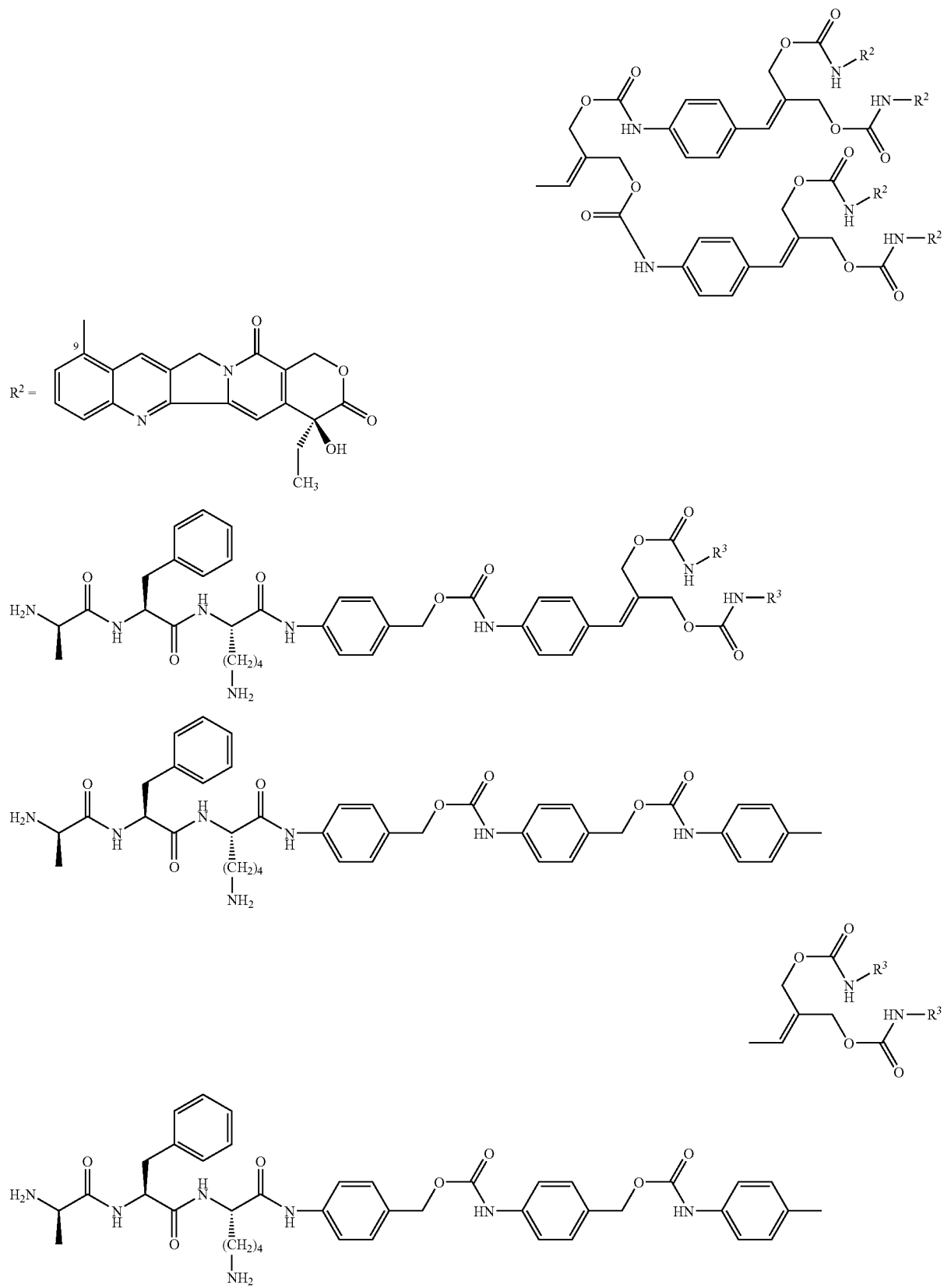

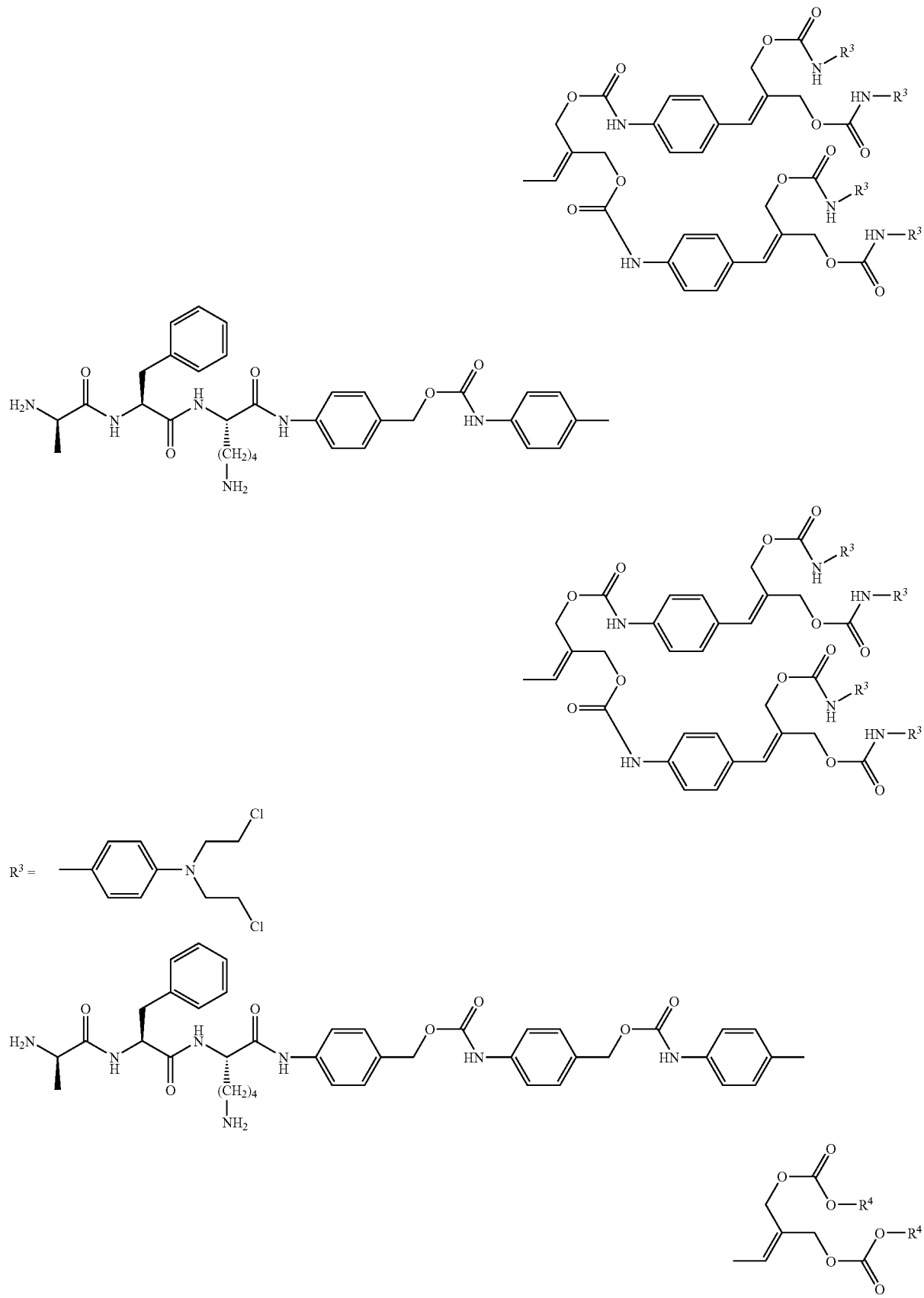

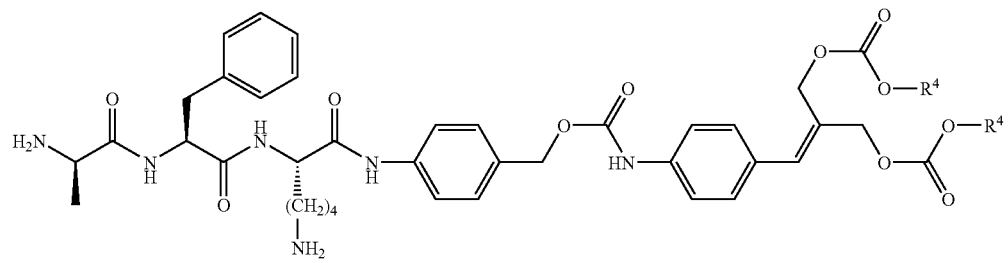
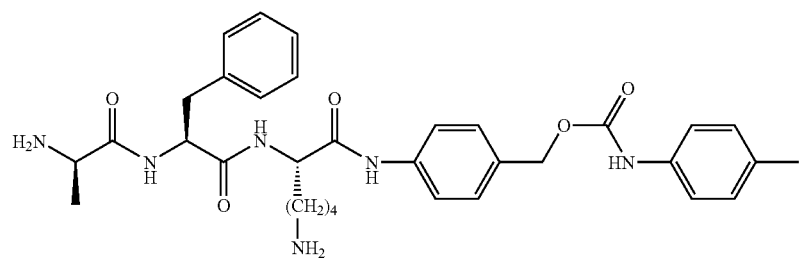
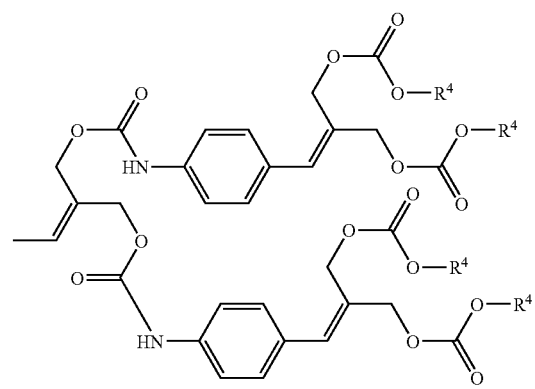
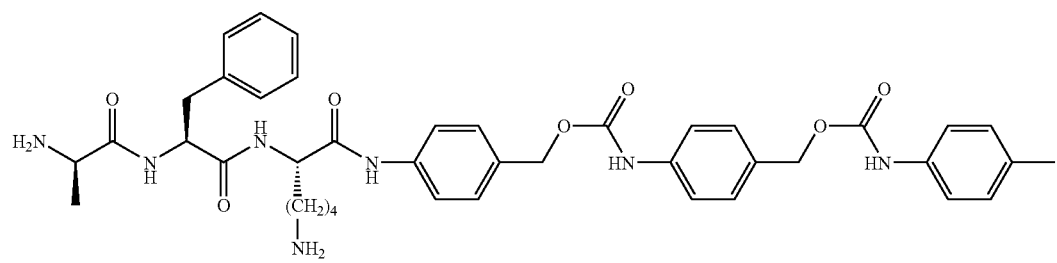
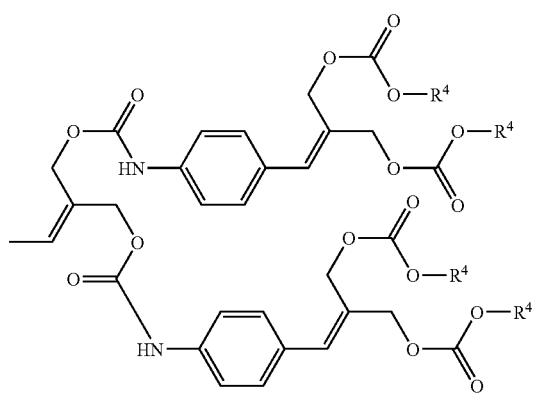

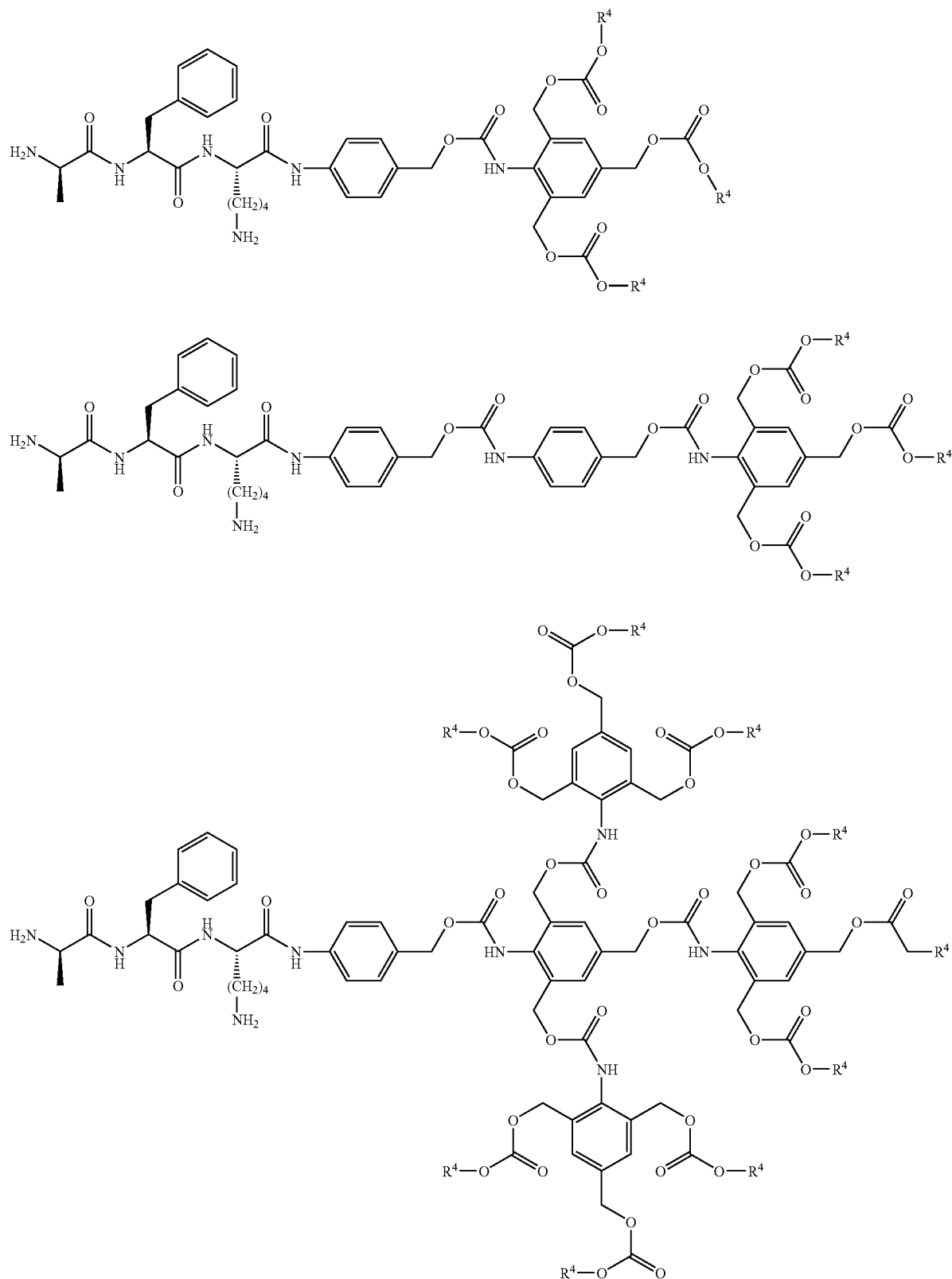

-continued
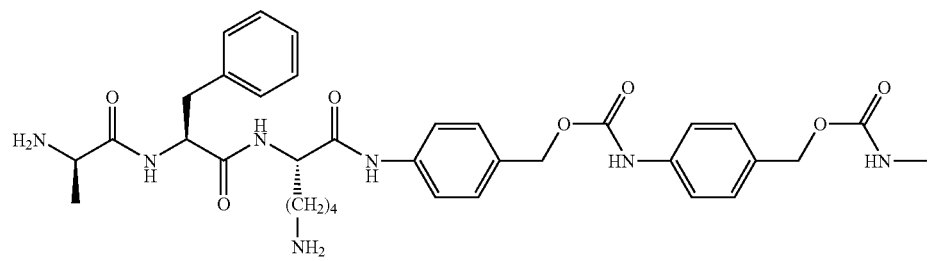
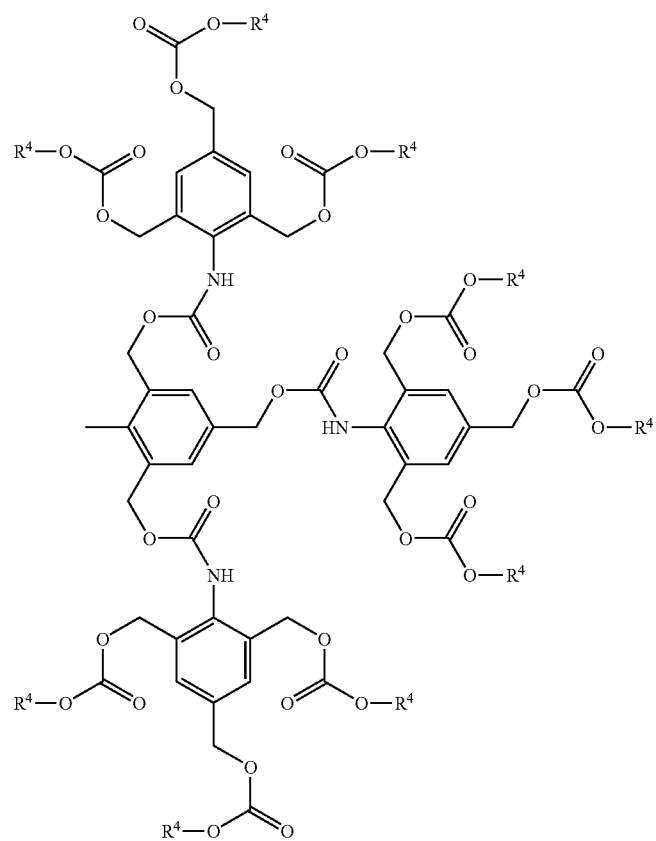
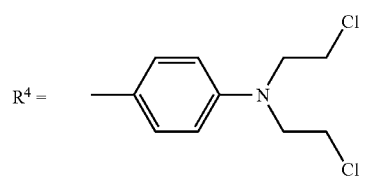
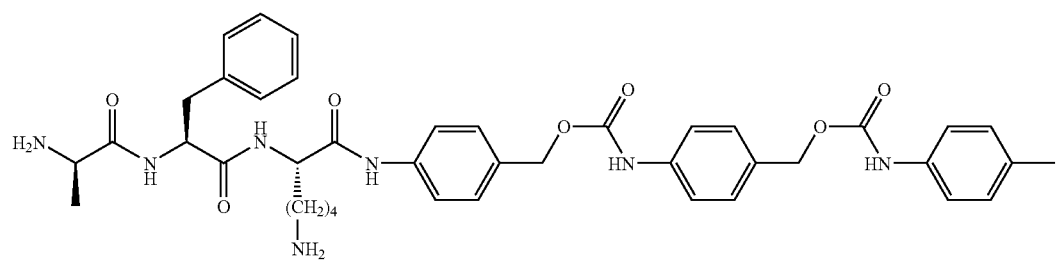

183 184
-continued
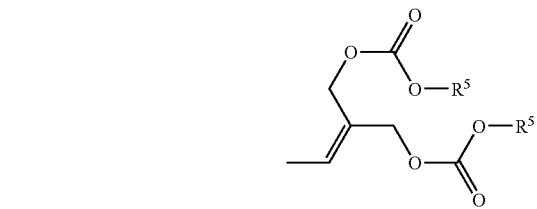
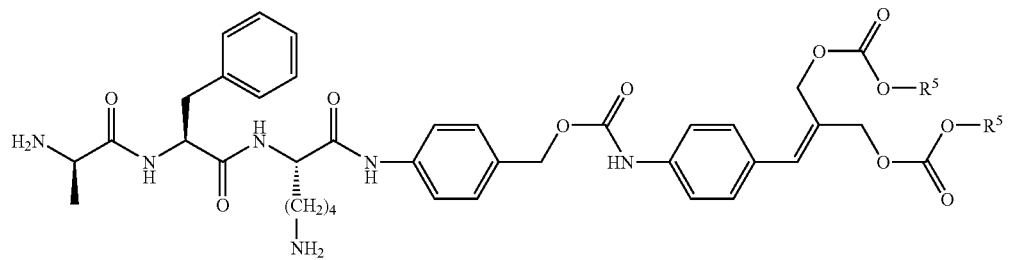
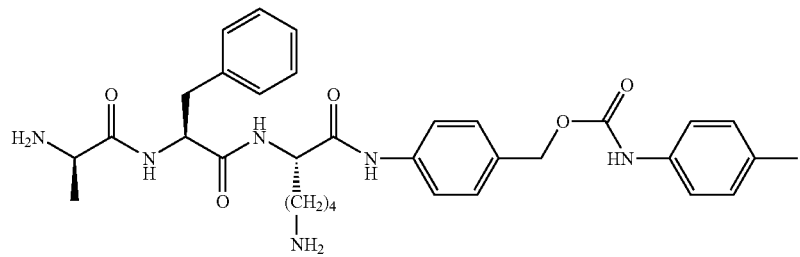
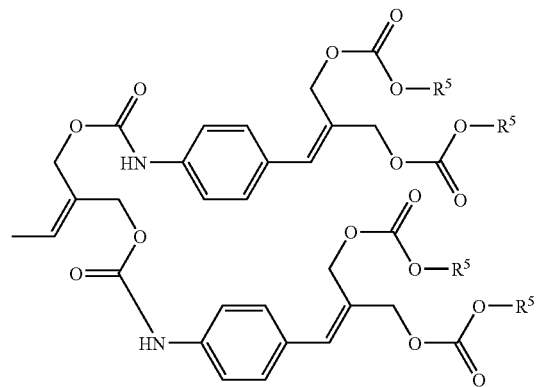
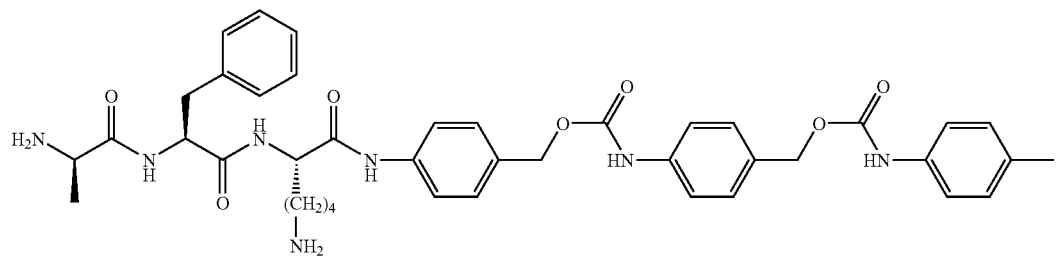

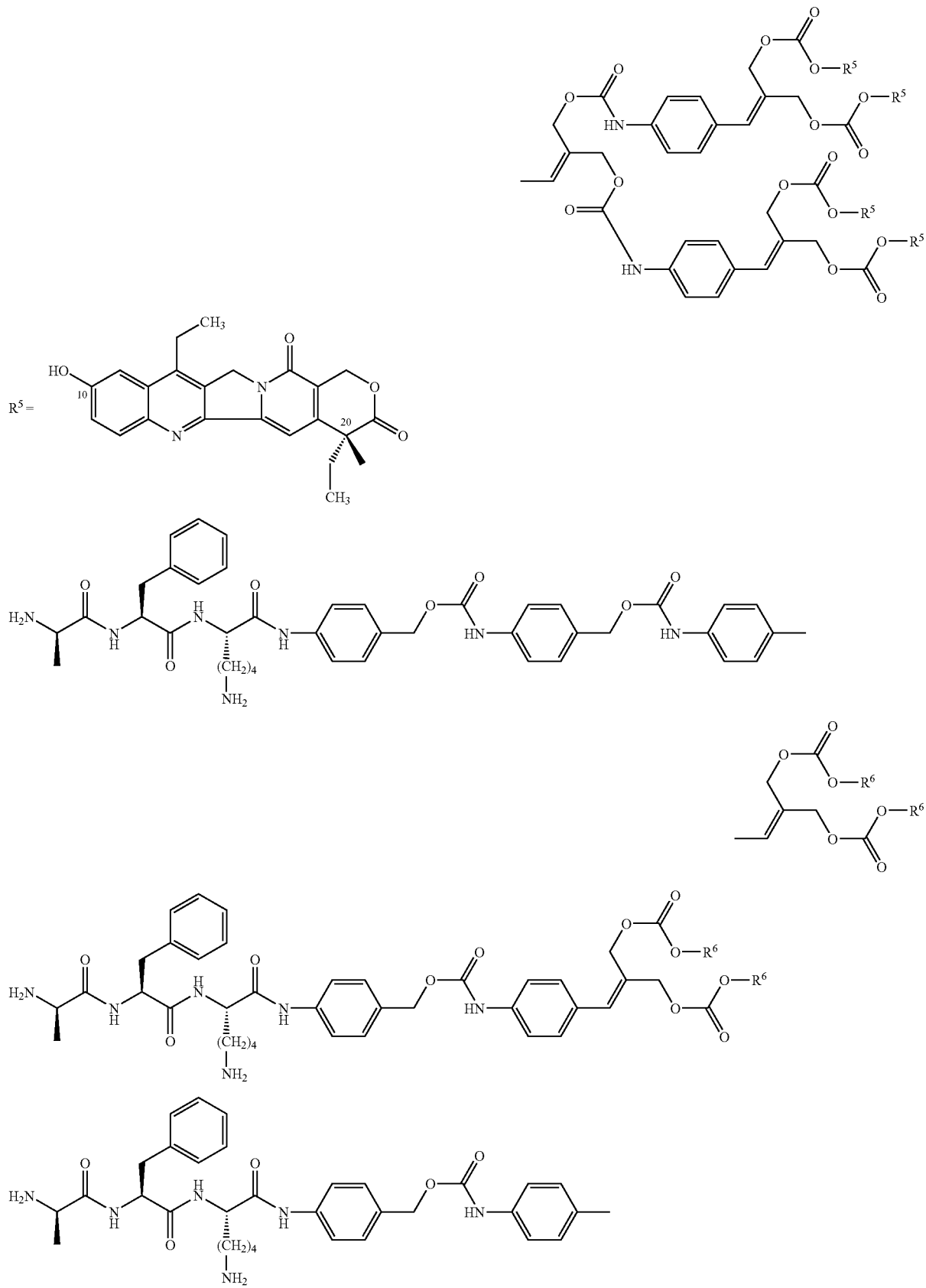

187 188
-continued
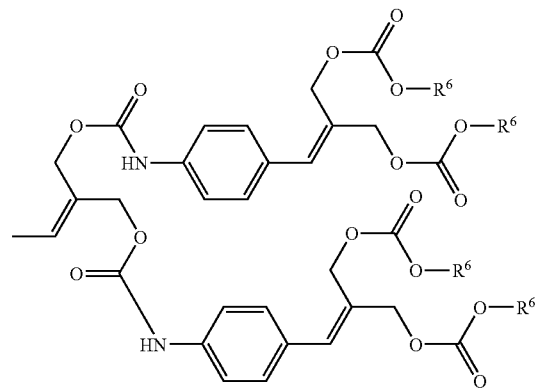
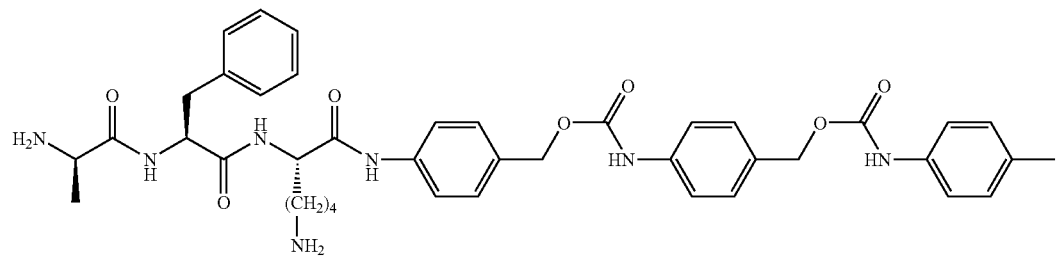
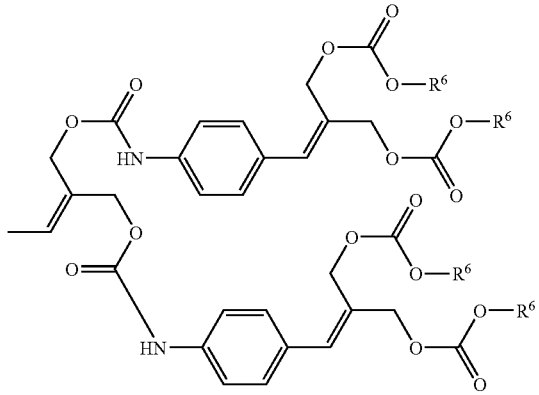
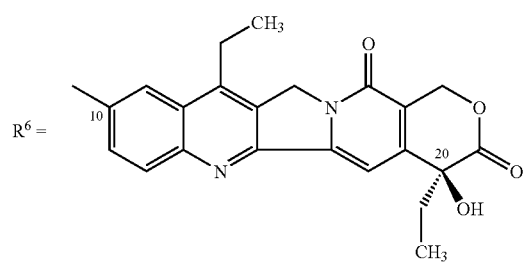
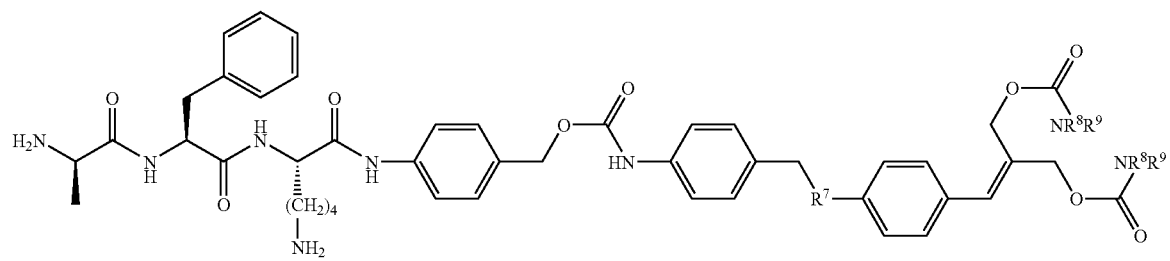

-continued
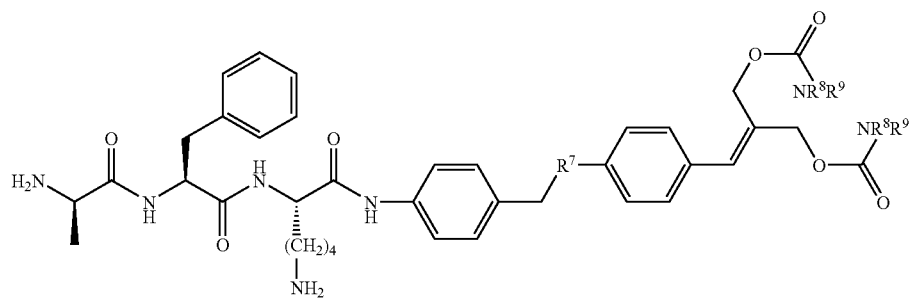
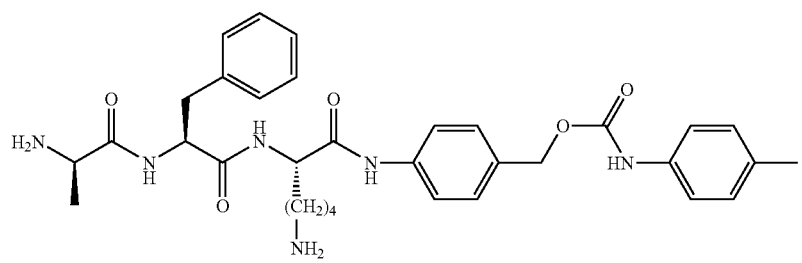
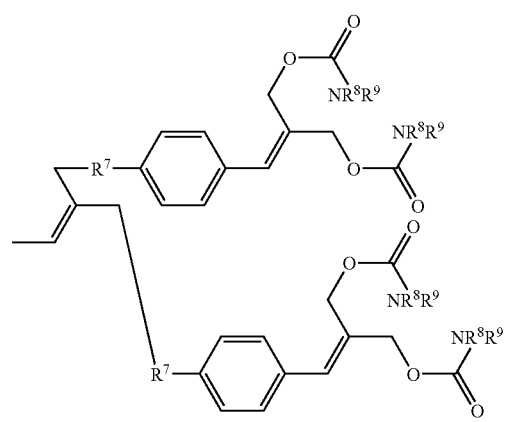
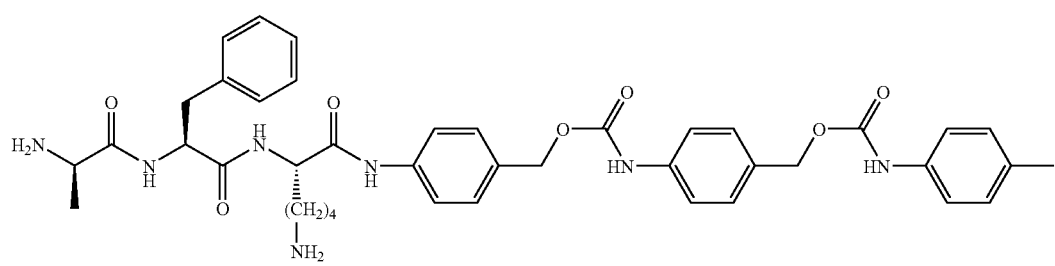
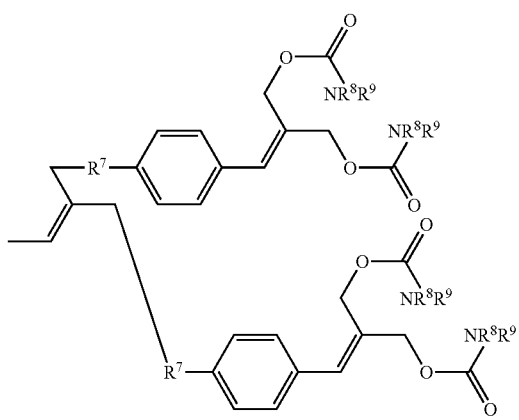

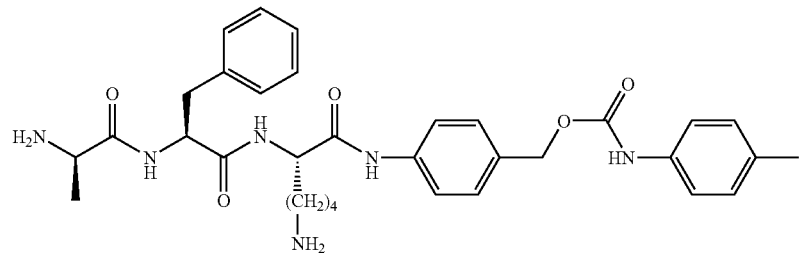
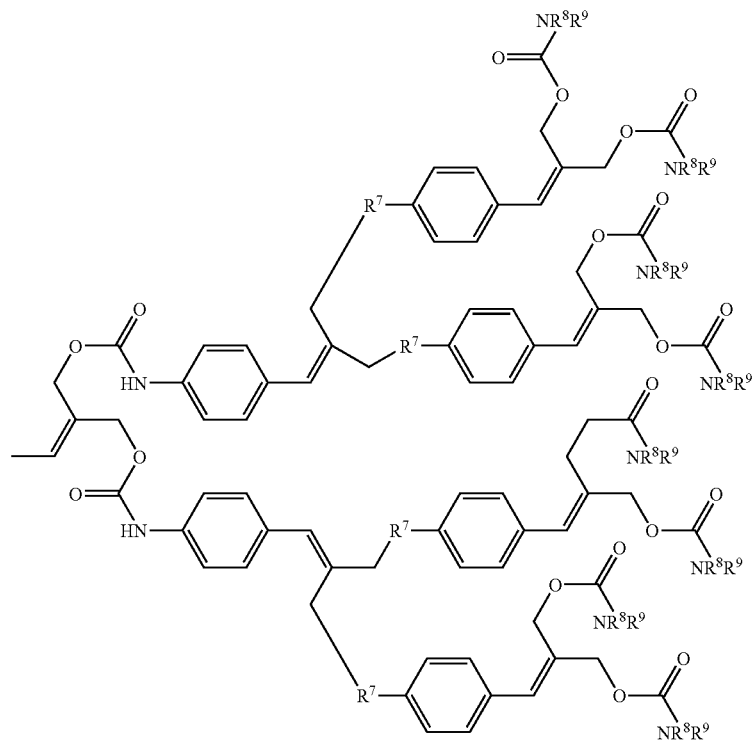
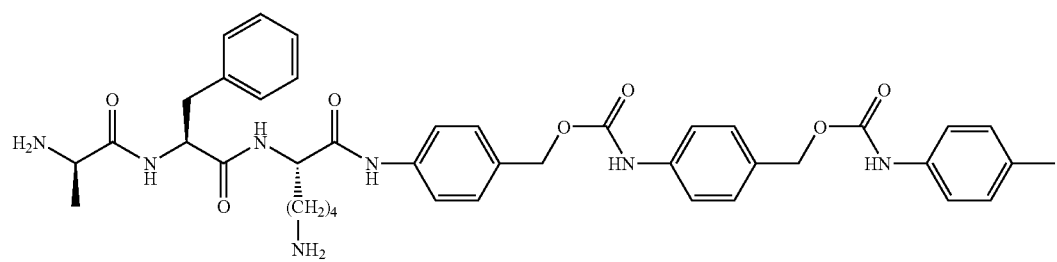

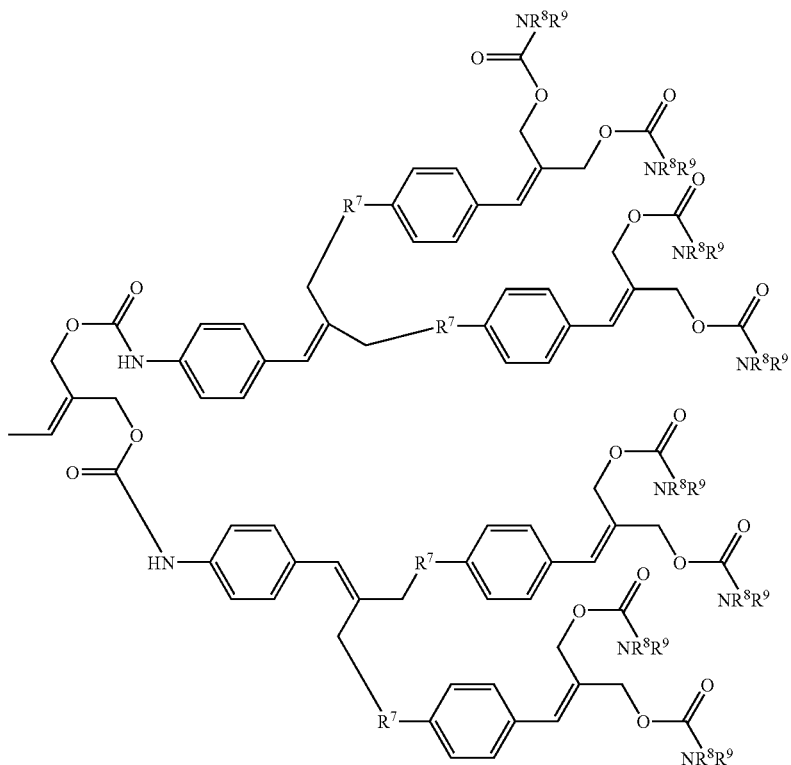
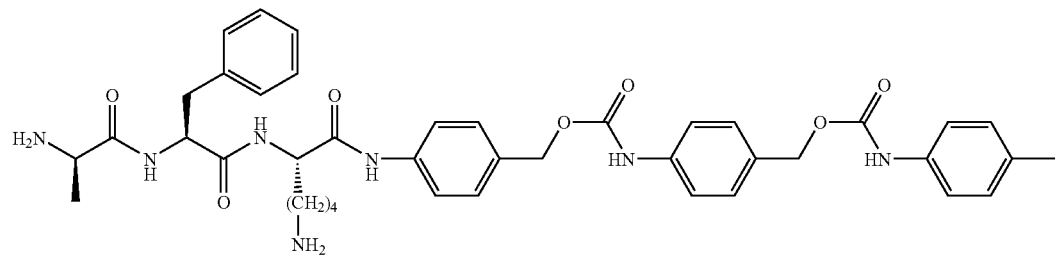
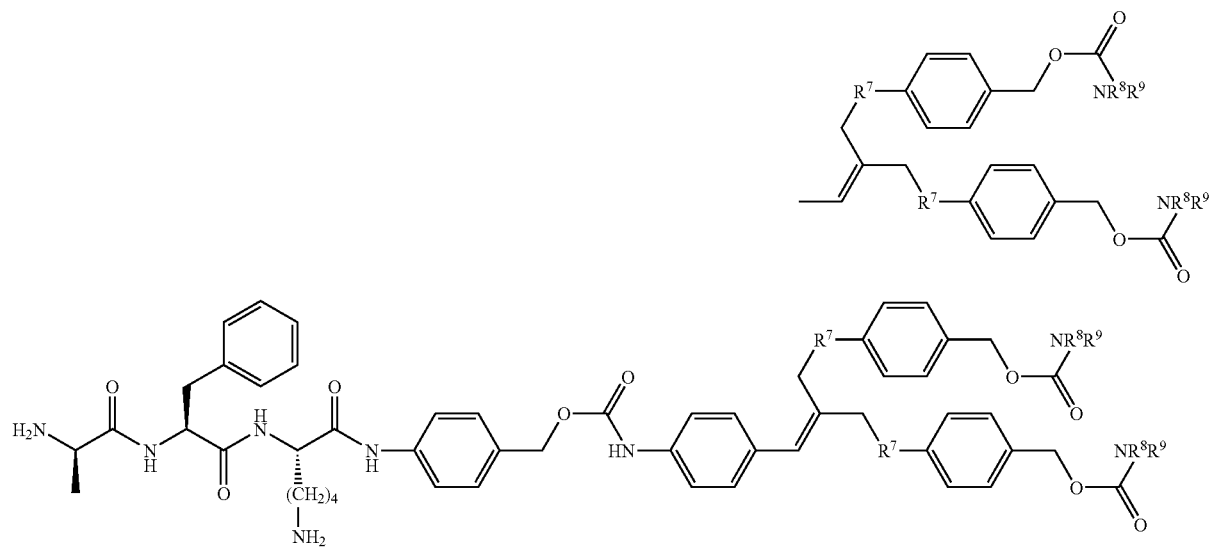

-continued
195
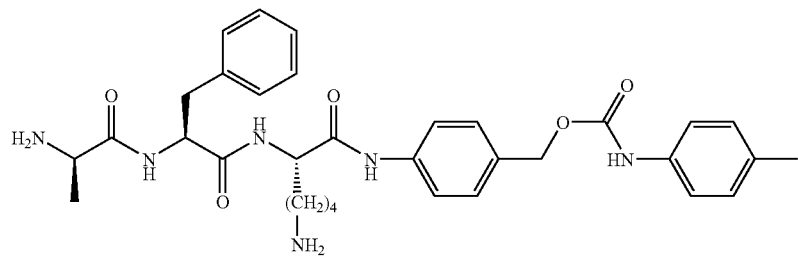
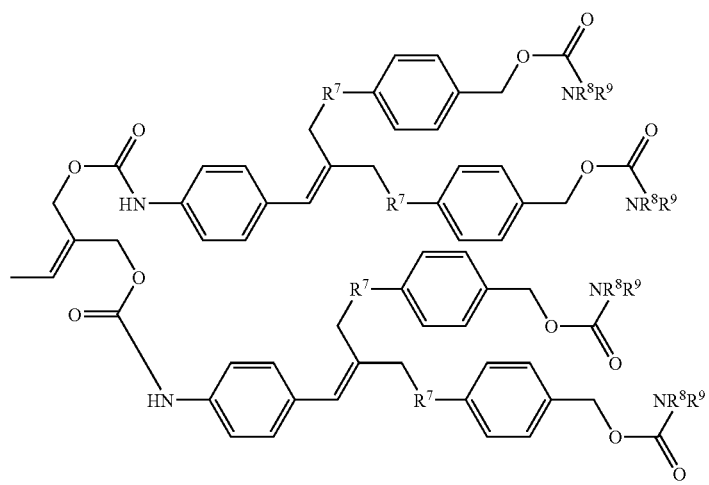
196
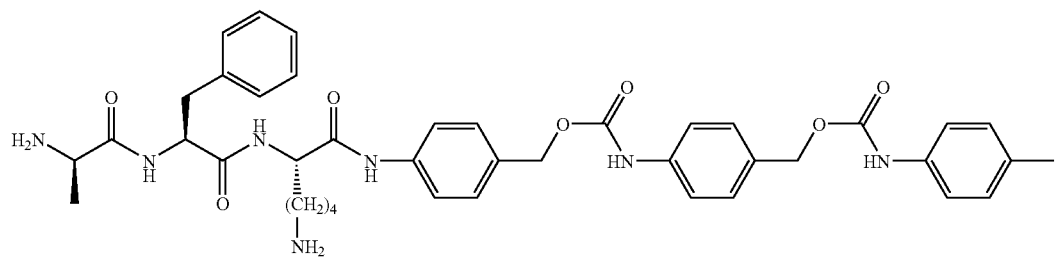
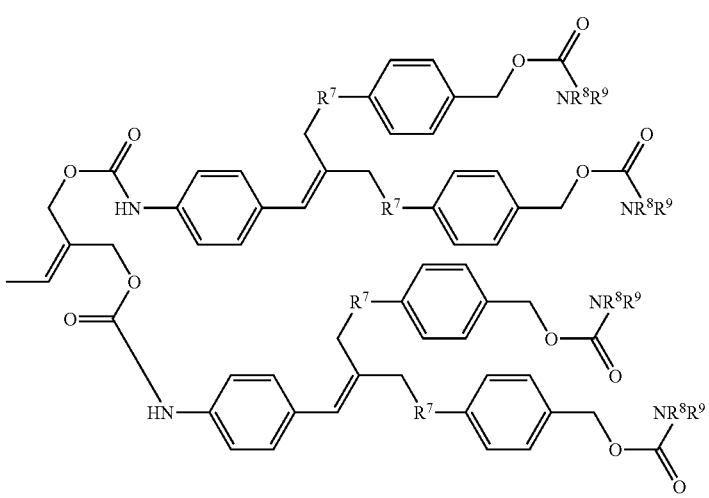

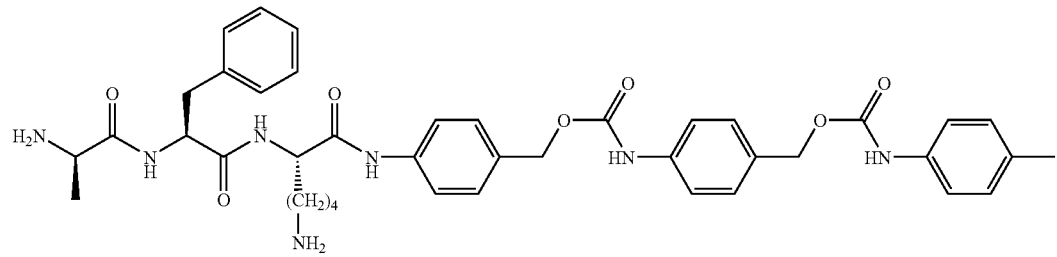
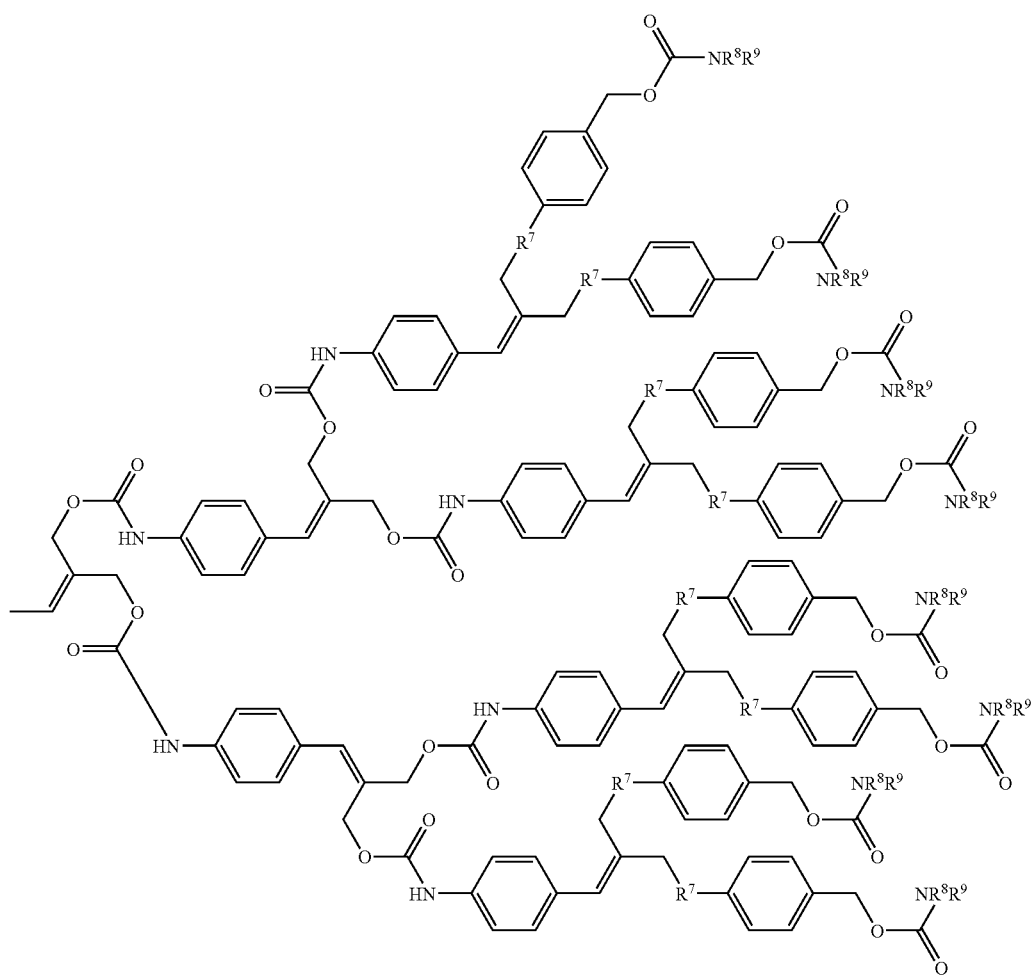
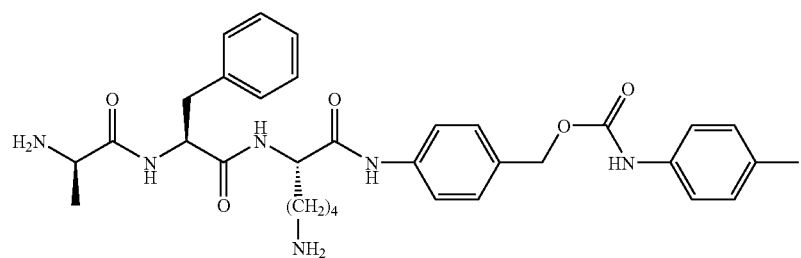

-continued
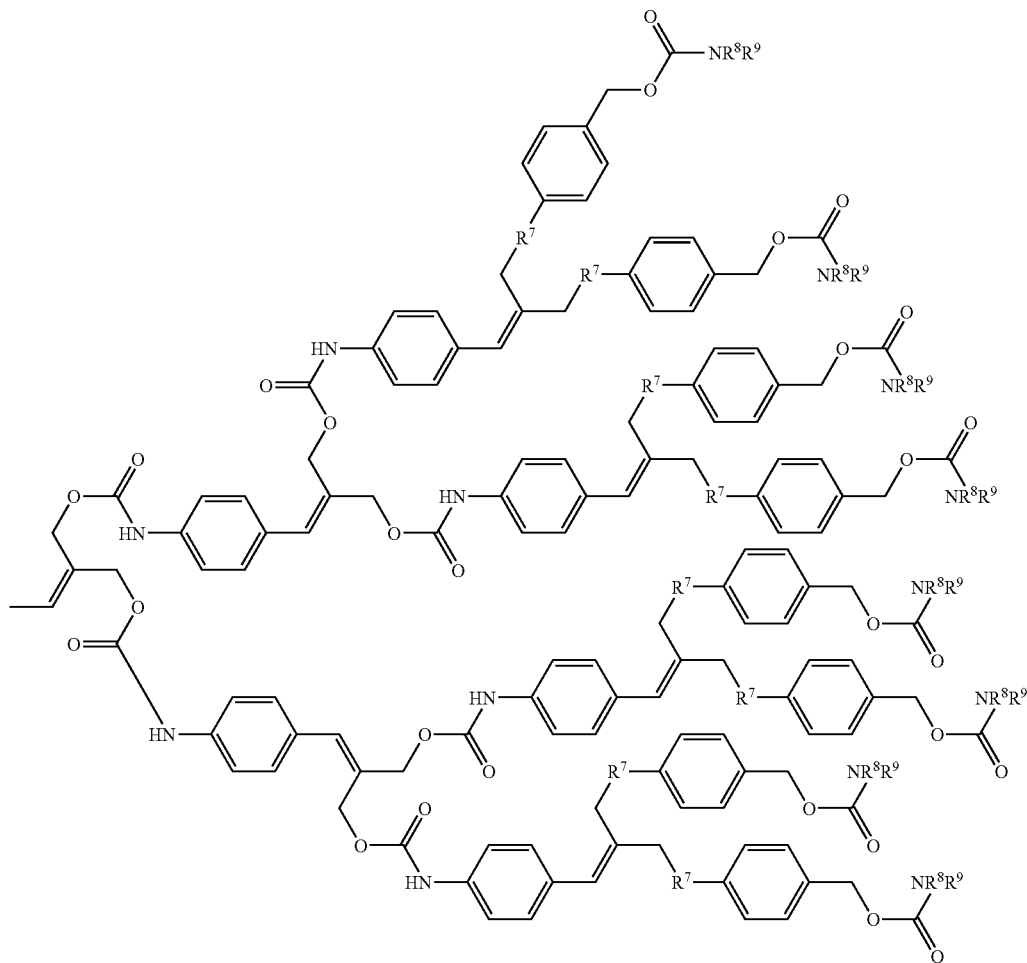
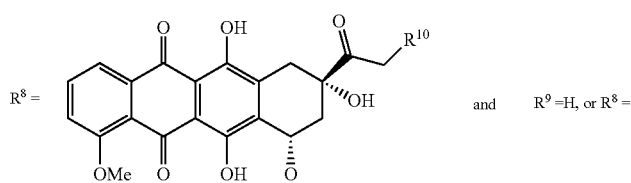
and R⁹ =H, or R⁸ =
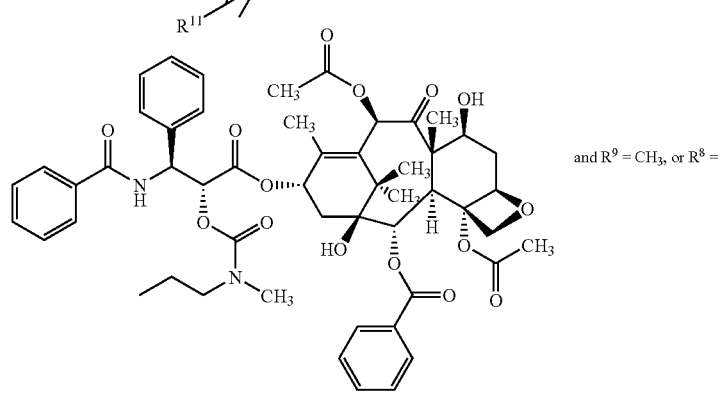
and R⁹ = CH₃, or R⁸ =

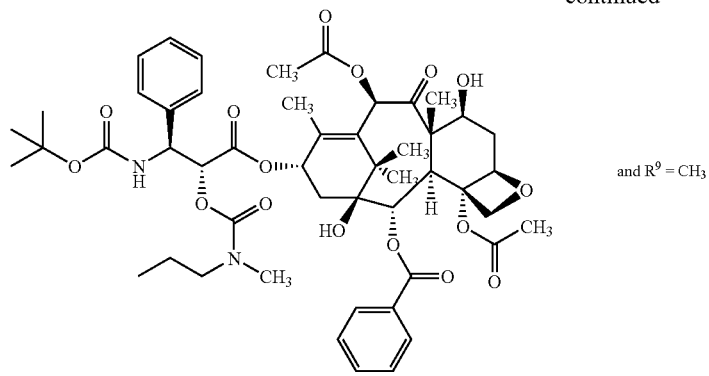

and $R^9 = CH_3$ $R^{10} = CH$ & $R^{11} = \alpha$-OH or
$R^{10} = H$ & $R^{11} = \alpha$-OH or
$R^{10} = OH$ & $R^{11} = \beta$-OH and salts thereof, wherein $R^7=OC(O)O$.

32. A diagnostic assay process, the process comprising: incubating a sample comprising an enzyme with a compound according to claim 1 to cause enzymatic cleavage of the compound, and detecting one or more molecules liberated by the enzymatic cleavage.

33. The diagnostic assay process according to claim 32, wherein the detection of the one or more molecules determines the presence or amount of the enzyme.

34. The diagnostic assay process according to claim 33, wherein the detection of the one or more molecules determines the presence or amount of a protease.

35. The diagnostic assay process according to claim 34, wherein the compound that is used comprises a substrate for said protease and one or more Z groups are detected.

36. The diagnostic assay process according to claim 34, wherein the compound that is used comprises a substrate for the enzyme, which is the product of cleavage of its pro-enzyme precursor by said protease and one or more Z groups are detected.

37. A composite structure comprising two or more compounds according to claim 1 connected with a polymeric structure.

38. The compound according to claim 1, wherein the specifier V can be removed or transformed by an enzyme that is transported to the vicinity of or inside target cells or target tissue via ADEPT, PDEPT, MDEPT, VDEPT, or GDEPT.

39. A pharmaceutical composition comprising a compound according to claim 1.

40. A process for preparing a pharmaceutical composition comprising the step of mixing a compound according to claim 1 with a pharmaceutically acceptable carrier.

* * * * *

UNITED STATES PATENT AND TRADEMARK OFFICE
CERTIFICATE OF CORRECTION

PATENT NO. : 7,705,045 B2
APPLICATION NO. : 10/534777
DATED : April 27, 2010
INVENTOR(S) : De Groot et al.

It is certified that error appears in the above-identified patent and that said Letters Patent is hereby corrected as shown below:

In claim 1, at column 127, line 27, delete "$C(R^2)(R^3)Q-(W-)_{w(X-)x}$" and replace with --$C(R^2)(R^3)Q-(W-)_w(X-)_x$--.

In claim 3, at column 128, line 45, delete "B=O" and replace with --B = O--; at column 128, line 47, delete "B=N" and replace with --B = N--; and at column 128, line 50, delete "B=O" and replace with --B = O--.

In claim 4, at column 128, line 52, delete "B=O" and replace with --B = O--.

In claim 7, at columns 147-148, insert -- 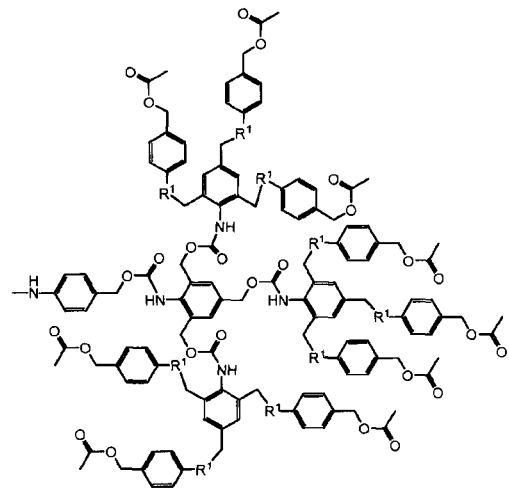 --; and at column 161, line 49, delete "$R^1$=OC(O)O" and replace with --$R^1$ = OC(O)O--.

In claim 16, at column 163, line 46, delete "B=O" and replace with --B = O--; at column 163, line 48, delete "B=N" and replace with --B = N--; and at column 163, line 51, delete "B=O" and replace with --B = O--.

In claim 17, at column 163, line 53, delete "B=O" and replace with --B = O--.

Signed and Sealed this
Sixteenth Day of August, 2011

David J. Kappos
*Director of the United States Patent and Trademark Office*

CERTIFICATE OF CORRECTION (continued)
U.S. Pat. No. 7,705,045 B2

In claim 31, at column 201, line 23, delete "$R^7=OC(O)O$" and replace with --$R^7 = OC(O)O$--.